United States Patent
Folkes et al.

(10) Patent No.: US 9,943,519 B2
(45) Date of Patent: *Apr. 17, 2018

(54) PHARMACEUTICAL COMPOUNDS

(71) Applicants: F.HOFFMANN-LA ROCHE AG, Basel (CH); GENENTECH, INC., South San Francisco, CA (US)

(72) Inventors: Adrian Folkes, Basel (CH); Stephen Shuttleworth, Basel (CH); Irina Chuckowree, Basel (CH); Sally Oxenford, Basel (CH); Nan Chi Wan, Basel (CH); Georgette Castanedo, South San Francisco, CA (US); Richard Goldsmith, South San Francisco, CA (US); Janet Gunzer-Toste, South San Francisco, CA (US); Tim Heffron, South San Francisco, CA (US); Simon Mathieu, South San Francisco, CA (US); Alan Olivero, South San Francisco, CA (US); Daniel P. Sutherlin, South San Francisco, CA (US); Bing-Yan Zhu, South San Francisco, CA (US)

(73) Assignees: Genentech, Inc., South San Francisco, CA (US); F. Hoffmann-La Roche AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/316,166

(22) Filed: Jun. 26, 2014

(65) Prior Publication Data
US 2014/0309216 A1 Oct. 16, 2014
US 2016/0152632 A9 Jun. 2, 2016

Related U.S. Application Data

(62) Division of application No. 11/789,468, filed on Apr. 24, 2007, now Pat. No. 8,802,670.

(60) Provisional application No. 60/795,048, filed on Apr. 26, 2006.

(51) Int. Cl.
| | |
|---|---|
| *C07D 413/14* | (2006.01) |
| *A61K 31/535* | (2006.01) |
| *A61K 31/5377* | (2006.01) |
| *C07D 491/04* | (2006.01) |
| *C07D 495/04* | (2006.01) |
| *A61K 31/551* | (2006.01) |
| *A61K 45/06* | (2006.01) |
| *C07D 491/048* | (2006.01) |

(52) U.S. Cl.
CPC ........ *A61K 31/5377* (2013.01); *A61K 31/551* (2013.01); *A61K 45/06* (2013.01); *C07D 491/04* (2013.01); *C07D 491/048* (2013.01); *C07D 495/04* (2013.01)

(58) Field of Classification Search
CPC .......................... A61K 31/535; C07D 413/14
See application file for complete search history.

(56) References Cited

U.S. PATENT DOCUMENTS

| | | | |
|---|---|---|---|
| 3,475,429 A | 10/1969 | Woitun et al. | |
| 3,661,908 A | 5/1972 | Woitun et al. | |
| 3,763,156 A | 10/1973 | Woitun et al. | |
| 3,838,121 A | 9/1974 | Woitun et al. | |
| 4,007,187 A | 2/1977 | Fauran et al. | |
| 4,146,716 A | 3/1979 | Cox et al. | |
| 4,196,207 A | 4/1980 | Webber et al. | |
| 6,608,053 B2 | 8/2003 | Hayakawa et al. | |
| 6,838,457 B2 | 1/2005 | Hayakawa et al. | |
| 7,037,915 B2 | 5/2006 | Hayakawa et al. | |
| 7,173,029 B2 | 2/2007 | Hayakawa et al. | |

(Continued)

FOREIGN PATENT DOCUMENTS

| | | |
|---|---|---|
| EP | 1067123 | 1/2001 |
| EP | 1277738 | 1/2003 |

(Continued)

OTHER PUBLICATIONS

Cancer and Metastasis Reviews (1998), 17(1), 91-106.*

(Continued)

*Primary Examiner* — Rebecca L Anderson
(74) *Attorney, Agent, or Firm* — Viksnins Harris Padys Malen LLP

(57) ABSTRACT

Compounds of Formulae Ia, and stereoisomers, geometric isomers, tautomers, solvates, metabolites and pharmaceutically acceptable salts thereof, are useful for inhibiting lipid kinases including PI3K, and for treating disorders such as cancer mediated by lipid kinases. Methods of using compounds of Formula Ia for in vitro, in situ, and in vivo diagnosis, prevention or treatment of such disorders in mammalian cells, or associated pathological conditions, are disclosed.

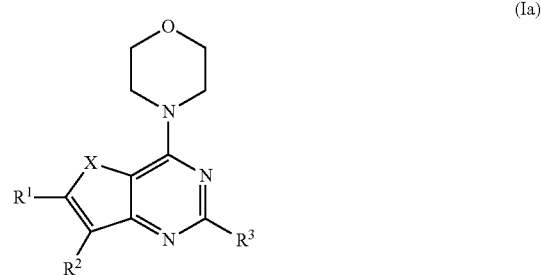

(Ia)

5 Claims, No Drawings

(56) References Cited

U.S. PATENT DOCUMENTS

| | | | |
|---|---|---|---|
| 7,750,002 B2* | 7/2010 | Shuttleworth et al. | 514/234.5 |
| 7,781,433 B2* | 8/2010 | Chuckowree et al. | 514/234.5 |
| 7,888,352 B2* | 2/2011 | Bayliss | C07D 491/04 514/234.5 |
| 8,450,315 B2* | 5/2013 | Castanedo | C07D 491/04 514/234.5 |
| 8,685,968 B2* | 4/2014 | Chuckowree et al. | 514/234.5 |
| 8,802,670 B2 | 8/2014 | Folkes et al. | |
| 8,946,217 B2* | 2/2015 | Shuttleworth et al. | 514/234.5 |
| 2003/0220365 A1 | 11/2003 | Stewart et al. | |

FOREIGN PATENT DOCUMENTS

| | | |
|---|---|---|
| GB | 1393161 | 5/1975 |
| WO | WO 2001/083456 | 11/2001 |
| WO | WO 2004/017950 | 3/2004 |
| WO | WO 2004/065391 | 8/2004 |
| WO | WO 2006/046031 | 5/2006 |
| WO | WO 2006/046035 | 5/2006 |
| WO | WO 2006/046040 | 5/2006 |
| WO | WO 2007/122410 | 11/2007 |

OTHER PUBLICATIONS

Science (1999), vol. 286, 531-537.*
Bachman et al., "The PIK3CA gene is mutated with high frequency in human breast cancers", *Cancer Biology & Therapy*, 3(8), 772-775, Aug. 2004.
Berge et al., "Pharmaceutical Salts", *Journal of Pharmaceutical Sciences*, 66(1), 1-19, Jan. 1977.
Briel et al. "Selective Nucleophilic Replacement of the Benzylsulfanyl Group in 2,4-Disulfanyl-substituted Thieno[2,3-d]pyrimidin-6-carboxylic Acid Derivatives by Secondary Amines", *Journal Heterocyclic Chem.*, 42(5), 841-846, Jul.-Aug. 2005.
Byrn et al., "Hydrates and Solvates", *Solid-State Chemistry of Drugs*, Second Edition, 233-247, 1999.
Garcia-Echeverria et al., "Drug discovery approaches targeting the PI3/Akt pathway in cancer", *Oncogene*, 27, 5511-5526, 2008.
Golub et al, "Molecular classification of cancer: class discovery and class prediction by gene expression monitoring", *Science* vol. 286, 531-537 (1999).
Kang et al., "Phosphatidylinositol 3-kinase mutations identified in human cancer are oncogenic", *PNAS*, 102(3), pp. 802-807, Jan. 18, 2005.
Lala et al., "Role of nitric oxide in tumor progression: lessons from experimental tumors", *Cancer and Metastasis Reviews* 17 (1), 91-106 (1998).
Patent Cooperation Treaty, International Search Report & Written Opinion of the International Search Authority, PCT/US2007/009866, dated Nov. 9, 2007, 14 pages.
Raynaud et al., "Biological properties of potent inhibitors of class I phophatidylinositide 3-kinases: from PI-103 through PI-540, PI-620 to the oral agent GDC-0941", *Mol. Cancer Ther.*, 8(7), 1725-1738, Jul. 2009.
Samuels et al., "High frequency of mutations of the PIK3CA gene in human cancers", *Science*, 304, 554, Apr. 23, 2004.
Shayesteh et al., "PIK3CA is implicated as an oncogene in ovarian cancer", *Nature Genetics*, 21, 99-102, Jan. 1999.
Workman et al., "Drugging the PI3 kinome", *Nature Biotechnology*, 24(7), 794-796, Jul. 2006.
Yap et al., "Targeting the PI3K-AKT-mTOR pathway: progress, pitfalls, and promises", *Current Opinion in Pharmacology*, 8, 393-412, 2008.

* cited by examiner

PHARMACEUTICAL COMPOUNDS

PRIORITY OF INVENTION

This application is a divisional application of U.S. patent application Ser. No. 11/789,468 that was filed on 24 Apr. 2007, which claims priority to U.S. Provisional Application No. 60/795,048 that was filed on 26 Apr. 2006. The entire content of the applications are hereby incorporated herein by reference.

The invention claimed herein was made as a result of activities undertaken within the scope of a joint research agreement between Piramed limited and Genentech, Inc.

FIELD OF THE INVENTION

The present invention relates to pyrimidine derivatives and their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al, 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck, 1997, Trend in Biol. Sci, 22, 267). Substrates for class I PI3Ks are PI, PI 4-phosphate (PI4P) and PI 4,5-biphosphate (PI(4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis.

There continues to be a need for class I PI3 kinase inhibitors with improved pharmacokinetic and pharmacodynamic properties. The PI3 kinase/Akt/PTEN pathway is thus an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. Nos. 6,608,056; 6,608,053; 6,838,457; 6,770,641; 6,653,320; 6,403,588; WO 2004017950; US 2004092561; WO 2004007491; WO 2004006916; WO 2003037886; US 2003149074; WO 2003035618; WO 2003034997; US 2003158212; EP 1417976; US 2004053946; JP 2001247477; JP 08175990; JP 08176070). Wortmannin analogs have PI3 kinase activity in mammals (U.S. Pat. No. 6,703,414; WO 97/15658).

SUMMARY OF THE INVENTION

It has now been found that a novel class of fused pyrimidine compounds are effective inhibitors of PI3K with drug-like physicochemical and pharmacokinetic properties. The compounds exhibit selectivity for class Ia PI3Ks over class Ib, in particular for the p110α subtype.

Accordingly, the present invention provides a compound which is a fused pyrimidine of formula (Ia) or (Ib):

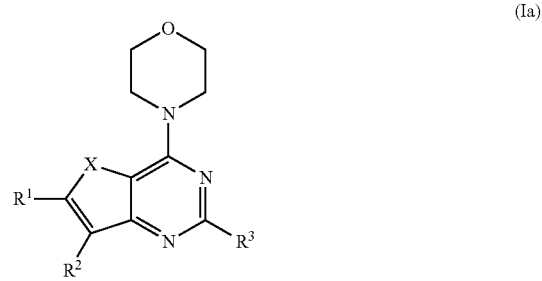

(Ia)

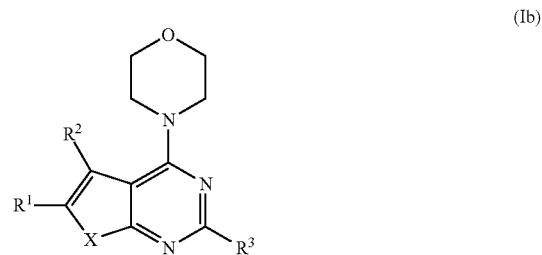

(Ib)

and stereoisomers, geometric isomers, tautomers, solvates, metabolites, and pharmaceutically acceptable salts thereof, wherein X is O or S. Groups $R^1$, $R^2$ and $R^3$ are as defined herein.

Another aspect of the invention provides a pharmaceutical composition comprising a thienopyrimidine or furanopyrimidine compound of Formulas Ia or Ib and a pharmaceutically acceptable carrier. The pharmaceutical composition may further comprise one or more additional therapeutic agents selected from anti-proliferative agents, anti-inflammatory agents, immunomodulatory agents, neurotropic factors, agents for treating cardiovascular disease, agents for treating liver disease, anti-viral agents, agents for treating blood disorders, agents for treating diabetes, and agents for treating immunodeficiency disorders.

Another aspect of the invention provides methods of inhibiting PI3 kinase activity, comprising contacting a PI3 kinase with an effective inhibitory amount of a compound of Formula Ia or Ib, or a stereoisomer, geometric isomer, tautomer, solvate, metabolite, or pharmaceutically acceptable salt or prodrug thereof.

Another aspect of the invention provides methods of preventing or treating a disease or disorder modulated by PI3 kinases, comprising administering to a mammal in need of such treatment an effective amount of a compound of Formula Ia or Ib, or a stereoisomer, geometric isomer, tautomer, solvate, metabolite, or pharmaceutically acceptable salt or prodrug thereof. Examples of such diseases, conditions and disorders include, but are not limited to, hyperproliferative disorders (e.g., cancer, including melanoma and other cancers of the skin), neurodegeneration, cardiac hypertrophy, pain, migraine, neurotraumatic diseases, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders.

Another aspect of the invention provides methods of preventing or treating a hyperproliferative disorder, comprising administering to a mammal in need of such treatment an effective amount of a compound of Formula Ia or Ib, or a stereoisomer, geometric isomer, tautomer, solvate, metabolite, or pharmaceutically acceptable salt or prodrug thereof, alone or in combination with one or more additional compounds having anti-hyperproliferative properties.

In a further aspect the present invention provides a method of using a compound of this invention to treat a disease or condition modulated by PI3 kinase in a mammal. An additional aspect of the invention is the use of a compound of this invention in the preparation of a medicament for the treatment or prevention of a disease or condition modulated by PI3 kinase in a mammal.

Another aspect of the invention includes kits comprising a compound of Formula Ia or Ib, or a stereoisomer, geometric isomer, tautomer, solvate, metabolite, or pharmaceutically acceptable salt or prodrug thereof, a container, and optionally a package insert or label indicating a treatment.

DETAILED DESCRIPTION OF THE INVENTION

Compounds of formulae Ia and Ib are regioisomers, i.e. they differ by the placement of atom X in the thienopyrimidine (X=sulphur) or furanopyrimidine (X=oxygen) fused ring system. The four possible regioisomeric forms of the ring systems encompassed by formulae Ia and Ib are:

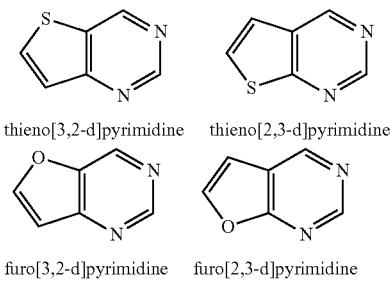

thieno[3,2-d]pyrimidine   thieno[2,3-d]pyrimidine furo[3,2-d]pyrimidine   furo[2,3-d]pyrimidine Compounds of the invention thus include both regioisomers of each of the 4-morpholino thienopyrimidine and 4-morpholino furanopyrimidine compounds of formulae (Ia), (Ia'), (Ia") and (Ia'''), and (Ib), (Ib'), (Ib") and (Ib''').

Definitions

As used herein, the terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The phrase "pharmaceutically acceptable" indicates that the substance or composition must be compatible chemically and/or toxicologically, with the other ingredients comprising a formulation, and/or the mammal being treated therewith.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitogliazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tennazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL®) (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The term "prodrug" as used in this application refers to a precursor or derivative form of a compound of the invention that is less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the PI3 kinase inhibitors disclosed herein and, optionally, a chemotherapeutic agent) to a mammal. The components of the liposome are commonly arranged in a bilayer formation, similar to the lipid arrangement of biological membranes.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

An alkyl group is a straight or branched chain saturated hydrocarbon radical which is unsubstituted or substituted. Typically it is $C_1$-$C_{20}$ alkyl, for instance $C_1$-$C_{10}$ alkyl, such as $C_1$-$C_6$ alkyl. $C_1$-$C_6$ alkyl is typically $C_1$-$C_4$ alkyl. It may be, for example, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), or 3,3-dimethyl-2-butyl (—$CH(CH_3)C(CH_3)_3$).

When an alkyl group is substituted it typically bears one or more substituents $R^{20}$ selected from halogen, alkoxy, carbocyclyl, a 5- or 6-membered saturated N-containing heterocyclic group as defined above, OH, SR, CN, nitro, $NR_2$, —COOR, —C(O)R, $S(O)_mR$ and —$CONR_2$, wherein each R is H, unsubstituted alkyl or $C_3$-$C_{10}$ cycloalkyl and m is 1 or 2. It is, for instance, a hydroxyalkyl group, a haloalkyl group or a group -alk-N($R^4$)($R^5$) wherein alk is an alkylene chain and $R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted.

Typically $R^{20}$ is selected from halogen, alkoxy, carbocyclyl, a 5- or 6-membered saturated N-containing heterocyclic group as defined above, OH, CN, $NR_2$, —COOR and —$CONR_2$, wherein each R is H or unsubstituted alkyl as defined above. It is, for instance, a haloalkyl group or a group -alk-N($R^6$)($R^5$) wherein alk is an alkylene chain and $R^4$ and $R^5$ form, together with the N atom to which they are attached, a 5- or 6-membered saturated N-containing heterocyclic group as defined above.

An alkylene group is unsubstituted or substituted, straight or branched chain saturated divalent hydrocarbon group. Typically it is $C_1$-$C_8$ alkylene, for instance $C_1$-$C_6$ alkylene. Preferably it is $C_1$-$C_4$ alkylene, for example $C_2$-$C_4$ alkylene, such as methylene, ethylene, i-propylene, n-propylene, t-butylene, s-butylene or n-butylene. It may also be pentylene, hexylene, heptylene, octylene and the various branched chain isomers thereof. When the alkylene group is substituted it is typically substituted by a group $R^{20}$ as defined above.

An alkenyl group is an unsubstituted or substituted, straight or branched chain hydrocarbon radical having one or more double bonds. Typically it is $C_2$-$C_8$ alkenyl, for instance $C_2$-$C_6$ alkenyl, such as allyl, butenyl, butadienyl, pentenyl or hexenyl. When the alkenyl group is substituted it is typically substituted by a group $R^{20}$ as defined above or by alkyl which is unsubstituted or substituted by a group $R^{20}$ as defined above.

An alkynyl group is an unsubstituted or substituted, straight or branched chain hydrocarbon radical having one or more triple bonds. Typically it is $C_2$-$C_8$ alkynyl, for instance $C_2$-$C_6$ alkynyl, such as ethynyl, propynyl or butynyl. When the alkynyl group is substituted it is typically substituted by a group $R^{20}$ as defined above or by alkyl which is unsubstituted or substituted by a group $R^{20}$ as defined above.

A haloalkyl group is an alkyl group as defined above, substituted by one or more halogen atoms. It can be a perhaloalkyl group, for instance trifluoromethyl or perfluorohexyl.

A halogen is chlorine, fluorine, bromine or iodine. It is typically bromine or iodine.

An alkoxy group is typically $C_1$-$C_6$ alkoxy, for instance $C_1$-$C_4$ alkoxy, such as methoxy, ethoxy, i-propoxy, n-propoxy, t-butoxy, n-butoxy or s-butoxy. It is unsubstituted or substituted, for instance by a group $R^{20}$ as defined above or by alkyl which is unsubstituted or substituted by a group $R^{20}$ as defined above or by alkyl which is unsubstituted or substituted by a group $R^{20}$ as defined above. Typically it is substituted by carbocyclyl, morpholino, OH, CN, $NR_2$, —COOR or —$CONR_2$, wherein each R is H or unsubstituted alkyl as defined above.

A carbocyclyl group is a non-aromatic saturated monocyclic hydrocarbon ring, typically having from 3 to 10 carbon atoms. It may be a $C_3$-$C_8$ cycloalkyl group, or $C_5$-$C_{10}$ cycloalkyl group, for instance cyclopropyl, cyclobutyl, cyclopentyl, cyclohexyl, cycloheptyl or cyclooctyl. A carbocyclyl group may be unsubstituted or substituted, for instance by a group $R^{20}$ as defined above or by alkyl which is unsubstituted or substituted by a group $R^{20}$ as defined above. Typically it is substituted by alkoxy, morpholino, OH, CN, $NR_2$, —COOR and —$CONR_2$, wherein each R is H or unsubstituted alkyl as defined above.

The term "cyclyl" as used herein denotes a $C_3$-$C_6$ cycloalkyl group, for instance cyclopropyl, cyclobutyl, cyclopentyl or cyclohexyl. In particular, cyclyl is a cyclopropyl group.

A 5- or 6-membered saturated N-containing heterocyclic group which includes 0 or 1 additional heteroatoms selected from N, S and O is unsubstituted or substituted and is typically selected from morpholine, piperidine, piperazine, pyrrolidine and thiomorpholine.

When a 5- or 6-membered saturated N-containing heterocyclic group as defined above is substituted it is typically substituted by one or more substituents, for instance 1, 2 or 3 substituents, typically by 1 or 2 substituents. Typically the substituents are selected from alkyl which is unsubstituted or substituted, alkoxy which is unsubstituted or substituted, —$NR_2$, —N(R''')-alk-OR, -alk-OR, —O-alk-OR, -alk-C(O)$NR_2$, —C(O)$NR_2$, -alk-Het, —N(R)-Het, —O-Het, —N(R)—C(O)-alk-OR, —C(O)—N(R)-alk-OR, -alk-S(O)$_2$R, —N(R)-alk-OR, -alk-NR'R'', —N(R''')—S(O)$_2$R, S(O)$_2$R''', -alk-N(R)-alk-OR, —S(O)$_2$-alk-OR, a second 5- or 6-membered saturated N-containing heterocyclic group as defined above, a 5- or 6-membered N-containing heteroaryl group which is unsubstituted or substituted and which may be fused to a benzene ring, —COOR, —$CONR_2$, oxo (=O), —$SO_2NR_2$, —$SO_2$-alk-$NR_2$ and —CO-alk-OR, wherein: alk is an alkylene chain as defined above; Het is a 5- or 6-membered N-containing heteroaryl group as defined herein which is unsubstituted or substituted; R is H or alkyl, or when two groups R are bonded to N they may form, together with the N atom, a saturated 5- or 6-membered N-containing heterocyclic group as defined herein which is unsubstituted or substituted; each of R' and R'' is independently H, alkyl or alkoxy; and R''' is alkyl which is unsubstituted or substituted, for instance by $CF_3$, $NR_2$, OR, a 5- or 6-membered saturated N-containing heterocyclic group as defined herein or a 5- or 6-membered N-containing heteroaryl group as defined herein, the said heterocyclic and heteroaryl groups being unsubstituted or substituted. It may be substituted by a group $R^{20}$ as defined above or by alkyl which is unsubstituted or substituted by a group $R^{20}$ as defined above.

Typically a 5- or 6-membered saturated N-containing heterocyclic group as defined above is substituted by a group selected from alkyl which is unsubstituted or substituted, alkoxy which is unsubstituted or substituted, a second 5- or 6-membered saturated N-containing heterocyclic group as defined above, a 5- or 6-membered N-containing heteroaryl group which is unsubstituted or substituted and which may be fused to a benzene ring, —COOR, —$CONR_2$, —CONR, oxo (=O), OH, —$NSO_2R$, —$SO_2NR_2$ or —$CO(CH_2)_nOR$ wherein R is H or alkyl, —NR'R'' wherein each of R' and R'' is independently H, alkyl or alkoxy, and —$SO_2R'''$ wherein R''' is alkyl which is unsubstituted or substituted, for instance by $NR_2$ or a 5- or 6-membered saturated N-containing heterocyclic group as defined above.

More typically a 5- or 6-membered saturated N-containing heterocyclic group is substituted by one or more substituents selected from alkyl as defined above which is unsubstituted or substituted (for instance by $R^{20}$ as defined above), haloalkyl as defined above, alkoxy as defined above which is unsubstituted or substituted, halogen, hydroxy, CN, nitro, amino, oxo (=O), and —NR'R'' wherein each of R' and R'' is independently H or alkyl.

A heteroaryl group is a heteroaryl group which contains 1, 2 3 or 4 ring nitrogen atoms and 0, 1 or 2 additional heteroatoms selected from O, N and S, which group is monocyclic or bicyclic and which is unsubstituted or substituted. It is typically a 5- to 12-membered ring. Examples of a heteroaryl group include pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine, pyrazine and isatin groups. Preferred examples include indazole, indole, pyrazole and tetrazole groups. These groups may be unsubstituted or substituted, for instance by a group $R^{20}$ as specified above or by alkyl which is unsubstituted or substituted by a group $R^{20}$ as defined above.

A 5- or 6-membered N containing heteroaryl group which may be fused to a benzene ring is typically selected from pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine and pyrazine. When such a heteroaryl group is substituted it may be substituted by a group $R^{20}$ as defined above or by alkyl which is unsubstituted or substituted by a group $R^{20}$ as defined above.

PI3 Kinase Inhibitor Compounds

The present invention provides fused pyrimidines which are 4-morpholino thienopyrimidine and furanopyrimidine compounds, and pharmaceutically acceptable salts thereof, that are potentially useful in the treatment of diseases, conditions and/or disorders modulated by PI3 kinases. The compounds may inhibit p110 isoforms including alpha, beta, gamma, and delta as pan inhibitors. The compounds may be p110 isoform selective inhibitors by selective inhibition of one of the p110 isoforms.

More specifically, the present invention provides a compound which is a fused pyrimidine of formula Ia or Ib:

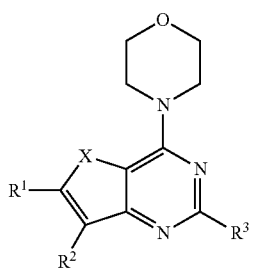

(Ia)

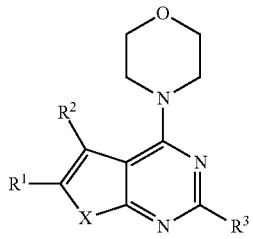

(Ib)

X is O or S;
$R^1$ is a group of formula:

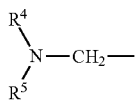

$R^2$ is H, halo or $C_1$-$C_6$ alkyl
$R^4$ and $R^5$ form, together with the N atom to which they are attached, a group selected from piperazine, piperidine, pyrrolidine, oxazolidinone, diazepan and 2,5-diaza-bicyclo[2,2,1]-heptane, which group is unsubstituted or substituted by -[(alk)$_q$-NR]$_r$—S(O)$_2$-(alk)$_q$-Z or —C(O)-(alk)$_q$-S(O)$_2$Z wherein Z is $R^{10}$ or —NR$^{11}$R$^{12}$, or by unsubstituted $C_1$-$C_6$ alkyl, hydroxyl-$C_1$-$C_6$ alkyl, oxo (=O), -(alk)$_q$-OR, —C(O)—C(R')$_2$—N(R)$_2$, —C(R)$_2$—C(O)—N(R)$_2$, —C(O)—(NR)$_q$-(alk)$_q$-OR, —C(O)-cyclyl, —C(O)R, —C(O)OR, —C(O)-Tet or —NR$^{13}$R$^{14}$;
or one of $R^4$ and $R^5$ is $C_1$-$C_6$ alkyl, -(alk)$_q$-Heterocyclyl or -(alk)$_q$-OR and the other is a piperazine, piperidine, pyrrolidine, sulphonylpyran or -(alk)$_q$-Heterocyclyl group, wherein said piperazine, piperidine, pyrrolidine, sulphonylpyran or Heterocyclyl is unsubstituted or substituted by $C_1$-$C_6$ alkyl, -(alk)$_q$-OR or —S(O)$_2$R$^{10}$;
R is H or $C_1$-$C_6$ alkyl which is unsubstituted;
each R' is, independently, H or $C_1$-$C_6$ alkyl which is unsubstituted, or the two groups R' form, together with the C atom to which they are attached, a cyclyl group;

$R^{10}$ is H, cyclyl, $C_1$-$C_6$ alkyl which is unsubstituted or $CF_3$;
$R^{11}$ and $R^{12}$ are each independently selected from H, $C_1$-$C_6$ alkyl which is unsubstituted and -(alk)$_q$-OR, or $R^{11}$ and $R^{12}$ together form, with the N atom to which they are attached, a 5- or 6-membered saturated N-containing heterocyclic group containing 0 or 1 additional heteroatoms selected from O, N and S;
$R^{13}$ and $R^{14}$ are each independently selected from $C_1$-$C_6$ alkyl, —S(O)$_2$R$^{10}$, and -(alk)$_q$-OR;
Tet is a tetrahydrofuranyl or tetrahydropyranyl group, which group is unsubstituted or substituted;
Heterocyclyl is a 5- or 6-membered saturated N-containing heterocyclic group containing 0 or 1 additional heteroatoms selected from O, N and S;
Cyclyl is a $C_3$-$C_6$ cycloalkyl group;
each q is independently 0 or 1;
r is 0 or 1;
alk is $C_1$-$C_6$ alkylene; and
$R^3$ is selected from:
(a) a group of the following formula:

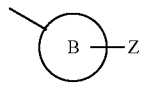

wherein B is a phenyl ring which is unsubstituted or substituted, and Z is selected from H, —OR, —SR, CH$_2$OR, —CO$_2$R, CF$_2$OH, CH(CF$_3$)OH, C(CF$_3$)$_2$OH, —(CH$_2$)$_q$OR, —(CH$_2$)$_q$NR$_2$, —C(O)N(R)$_2$, —NR$_2$, —NRC(O)R, —S(O)$_m$N(R)$_2$, —OC(O)R, OC(O)N(R)$_2$, —NRS(O)$_m$R, —NRC(O)N(R)$_2$, CN, halogen and —NO$_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2;

(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and (c) a group comprising a benzene ring which is unsubstituted or substituted and which is fused to a heteroaryl group as defined above;
or a pharmaceutically acceptable salt thereof;
with the provisos that:
(i) when X in formula (Ia) is S, then $R^3$ is other than an indole or 3-hydroxyphenyl group;
(ii) when X in formula (Ib) is S, then $R^3$ is other than an indole group;
(iii) in formula (Ia) only, when X is S and $R^2$ is H and $R^3$ is indazol-4-yl, then $R^4$ and $R^5$ do not form: (i) piperazine which is unsubstituted or substituted by a group selected from methyl, —S(O)$_2$Me, —S(O)$_2$NMe$_2$, -alk-OH, -alk-OMe, —S(O)$_2$-alk-NMe$_2$, and —S(O)$_2$-alk-morpholino; or (ii) piperidine which is substituted by a group selected from —S(O)$_2$Me, —C(O)—NR-(alk)$_q$-OR, —NMe-S(O)$_2$-Me, methyl, piperidine and —NR$^{13}$R$^{14}$ wherein one of $R^{13}$ and $R^{14}$ is -(alk)$_q$-OR.

In one embodiment the invention provides a compound which is a fused pyrimidine of formula (Ia'):

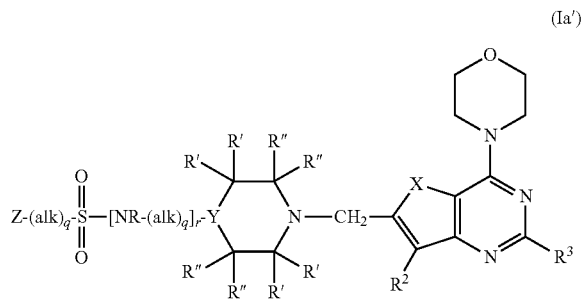

(Ia')

wherein
X is O or S;
Y is N or —CH—;
R² is H, halo or C₁-C₆ alkyl;
each R' is, independently, H, C₁-C₆ alkyl or hydroxyl-C₁-C₆ alkyl, or two groups R' on the same carbon atom form an oxo (=O) group; or when Y is N, two groups R' on different carbon atoms together form a —CH₂— bridgehead;
each R" is, independently, H or C₁-C₆ alkyl, or two groups R" on the same carbon atom form an oxo (=O) group;
Z is R¹⁰ or -(alk)$_q$-NR¹¹R¹²;
R¹⁰ is H, a C₃-C₆ cycloalkyl group, C₁-C₆ alkyl which is unsubstituted, or CF₃;
R¹¹ and R¹² are each independently selected from H, C₁-C₆ alkyl which is unsubstituted and -(alk)$_q$-OR, or R¹¹ and R¹² together form, with the N atom to which they are attached, a 5- or 6-membered saturated N-containing heterocyclic group containing 0 or 1 additional heteroatoms selected from O, N and S;
q is 0 or 1;
r is 0 or 1;
alk is C₁-C₆ alkylene; and
R³ is selected from:
(a) a group of the following formula:

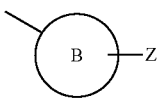

wherein B is a phenyl ring which is unsubstituted or substituted and Z is selected from H, —OR, —SR, CH₂OR, —CO₂R, CF₂OH, CH(CF₃)OH, C(CF₃)₂OH, —(CH₂)$_q$OR, —(CH₂)$_q$NR₂, —C(O)N(R)₂, —NR₂, —NRC(O)R, —S(O)$_m$N(R)₂, —OC(O)R, OC(O)N(R)₂, —NRS(O)$_m$R, —RC(O)N(R)₂, CN, halogen and —NO₂, wherein each R is independently selected from H, C₁-C₆ alkyl, C₃-C₁₀ cycloalkyl and a 5- to 12-membered aryl or heteroaryl group, the group being unsubstituted or substituted, m is 1 or 2 and q is 0, 1 or 2;
(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and
(c) a group comprising a benzene ring which is unsubstituted or substituted and which is fused to a heteroaryl group as defined above;
or a pharmaceutically acceptable salt thereof;
with the provisos that:
(i) R³ is other than an indole or 3-hydroxyphenyl group when X is S;

(ii) Z is other than a group selected from Me, -(alk)$_q$-NMe₂ and -alk-morpholino when the following are satisfied: Y is N, each of R' and R" is H, R² is H and R³ is indazol-4-yl;
(iii) Z is other than Me when the following are satisfied: Y is —CH—, each of R' and R" is H, R² is H and R³ is indazol-4-yl.

In another embodiment the invention provides a compound which is fused pyrimidine of formula (Ib'):

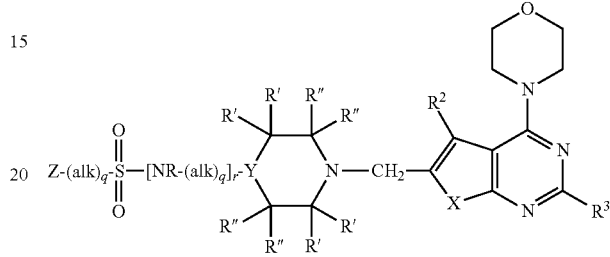

(Ib')

wherein
X is O or S;
Y is N or —CH—;
R² is H, halo or C₁-C₆ alkyl;
each R' is, independently, H, C₁-C₆ alkyl or hydroxy-C₁-C₆ alkyl, or two groups R' on the same carbon atom form an oxo (=O) group; or when Y is N, two groups R' on different carbon atoms together form a —CH₂— bridgehead;
each R" is, independently, H or C₁-C₆ alkyl, or two groups R" on the same carbon atom form an oxo (=O) group;
Z is R¹⁰ or -(alk)$_q$-NR¹¹R¹²;
R¹⁰ is H, a C₃-C₆ cycloalkyl group, C₁-C₆ alkyl which is unsubstituted, or CF₃;
R¹¹ and R¹² are each independently selected from H, C₁-C₆ alkyl which is unsubstituted and -(alk)$_q$-OR, or R¹¹ and R¹² together form, with the N atom to which they are attached, a 5- or 6-membered saturated N-containing heterocyclic group containing 0 or 1 additional heteroatoms selected from O, N and S;
q is 0 or 1;
r is 0 or 1;
alk is C₁-C₆ alkylene; and
R³ is selected from:
(a) a group of the following formula:

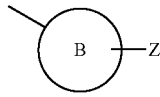

wherein B is a phenyl ring which is unsubstituted or substituted and Z is selected from H, —OR, —SR, CH₂OR, —CO₂R, CF₂OH, CH(CF₃)OH, C(CF₃)₂OH, —(CH₂)$_q$OR, —(CH₂)$_q$NR₂, —C(O)N(R)₂, —NR₂, —NRC(O)R, —S(O)$_m$N(R)₂, —OC(O)R, OC(O)N(R)₂, —NRS(O)$_m$R, —RC(O)N(R)₂, CN, halogen and —NO₂, wherein each R is independently selected from H, C₁-C₆ alkyl, C₃-C₁₀ cycloalkyl and a 5- to 12-membered aryl or heteroaryl group, the group being unsubstituted or substituted, m is 1 or 2 and q is 0, 1 or 2;

(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and (c) a group comprising a benzene ring which is unsubstituted or substituted and which is fused to a heteroaryl group as defined above;

or a pharmaceutically acceptable salt thereof.

In a yet further embodiment the invention provides a compound which is a fused pyrimidine of formula (Ia″) or (Ib″):

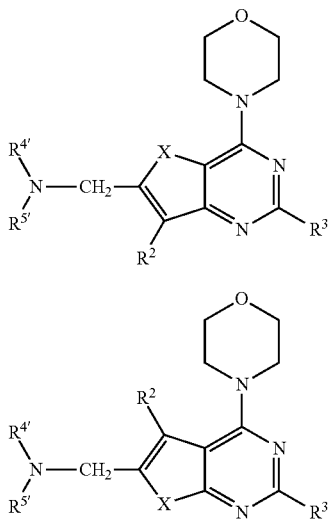

wherein
X is O or S;
$R^2$ is H, halo or $C_1$-$C_6$ alkyl;
$R^4$ is $C_1$-$C_6$ alkyl, -(alk)q-Heterocyclyl, or -(alk)$_q$-OR;
$R^5$ is a piperazine, piperidine, pyrrolidine, sulphonylpyran or -(alk)$_q$-Heterocyclyl group, wherein said piperazine, piperidine, pyrrolidine, sulphonylpyran or Heterocyclyl is unsubstituted or substituted by $C_1$-$C_6$ alkyl, -(alk)$_q$-OR or —S(O)$_2$R$^{10}$;
R is H, $C_1$-$C_6$ alkyl which is unsubstituted;
$R^{10}$ is H, a $C_3$-$C_6$ cycloalkyl group, $C_1$-$C_6$ alkyl which is unsubstituted, or $CF_3$;
Heterocyclyl is a 5- or 6-membered saturated N-containing heterocyclic group containing 0 or 1 additional heteroatoms selected from O, N and S;
q is 0 or 1;
alk is $C_1$-$C_6$ alkylene; and
$R^3$ is selected from:

(a) a group of the following formula:

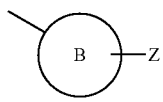

wherein B is a phenyl ring which is unsubstituted or substituted and Z is selected from H, —OR, —SR, $CH_2OR$, —$CO_2R$, $CF_2OH$, $CH(CF_3)OH$, $C(CF_3)_2OH$, —$(CH_2)_qOR$, —$(CH_2)_qNR_2$, —C(O)N(R)$_2$, —NR$_2$, —NRC(O)R, —S(O)$_m$N(R)$_2$, —OC(O)R, OC(O)N(R)$_2$, —NRS(O)$_m$R, —RC(O)N(R)$_2$, CN, halogen and —NO$_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2;

(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and (c) a group comprising a benzene ring which is unsubstituted or substituted and which is fused to a heteroaryl group as defined above;

or a pharmaceutically acceptable salt thereof;
with the provisos that:
(i) when X in formula (Ia) is S, then $R^3$ is other than an indole or 3-hydroxyphenyl group; and
(ii) when X in formula (Ib) is S, then $R^3$ is other than an indole group.

In $R^1$, the groups $R^4$ and $R^5$ typically form, together with the N atom to which they are attached, a group selected from piperidine, piperazine, pyrrolidine, oxazolidinone, diazepan and 2,5-diaza-bicyclo[2,2,1]-heptane. Typically the group formed by $R^4$ and $R^5$ is piperidine, piperazine or pyrrolidine.

The group formed by $R^4$ and $R^5$ with the N atom is unsubstituted or substituted by -[(alk)$_q$-NR]$_r$—S(O)$_2$-(alk)$_q$-Z or by unsubstituted $C_1$-$C_6$ alkyl, oxo (=O), -(alk)$_q$-OR, —C(O)—C(R)$_2$—N(R)$_2$, —C(R)$_2$—C(O)—N(R)$_2$, —C(O)—(NR)$_q$-(alk)$_q$-OR, —C(O)-cyclyl —C(O)R, —C(O)OR, or —NR$^{13}$R$^{14}$.

Alternatively, one of $R^4$ and $R^5$ is $C_1$-$C_6$ alkyl, -(alk)$_q$-Heterocyclyl or -(alk)$_q$-OR and the other is a piperazine, piperidine, pyrrolidine, sylphonylpyran or -(alk)$_q$-Heterocyclyl group, wherein said piperazine, piperidine, pyrrolidine, sulphonylpyran or Heterocyclyl group is unsubstituted or substituted by $C_1$-$C_6$ alkyl, -(alk)$_q$-OR or —S(O)$_2$R$^{10}$.

Examples of Heterocyclyl include piperidine, for instance piperidin-1-yl, piperidin-2-yl, piperidin-3-yl or piperidin-4-yl, in particular piperidin-4-yl; morpholine; and pyrrolidine, for instance pyrrolidin-2-yl or pyrrolidin-3-yl, groups.

Examples of -[(alk)$_q$-NR]$_r$—S(O)$_2$-(alk)$_q$-Z include —S(O)$_2$R$^{10}$, —S(O)$_2$-(alk)$_q$-NR$^{11}$R$^{12}$ and -(alk)$_q$-NR—S(O)$_2$R$^{10}$. Examples of —S(O)$_2$R$^{10}$ include —S(O)$_2$Me and —S(O)$_2$-cyclopropyl.

Examples of —C(O)-(alk)$_q$-S(O)$_2$Z include —C(O)—CH$_2$—S(O)$_2$Me, —C(O)—CHMe-S(O)$_2$Me and —C(O)—C(Me)$_2$-S(O)$_2$Me.

$R^{10}$ is typically H, methyl, propyl (either n-propyl or i-propyl), or $CF_3$.

Examples of —S(O)$_2$-(alk)$_q$-NR$^{11}$R$^{12}$ include —S(O)$_2$—N(Me)$_2$, —S(O)$_2$—NHMe, —S(O)$_2$—N(Me)(CH$_2$CH$_2$OMe), —S(O)$_2$—N(Me)(CH$_2$CH$_2$OH),

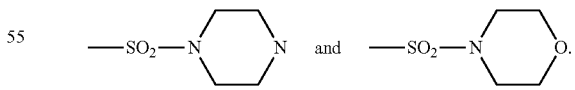

Examples of -(alk)$_q$-NR—S(O)$_2$R$^{10}$ include —CH$_2$NH(SO$_2$Me), —CH$_2$N(Me)(SO$_2$Me), —NH—SO$_2$Me and —N(Me)(SO$_2$Me).

Examples of -(alk)$_q$-OR include —OH, —OMe, —CH$_2$OH, —CH$_2$OMe, —CH$_2$CH$_2$OMe, —CH$_2$CH$_2$OH, —CH$_2$CH$_2$CH$_2$OMe and —CH$_2$CH$_2$CH$_2$OH.

Examples of —C(O)—C(R')$_2$—N(R)$_2$ include —C(O)—CH$_2$—N(Me)$_2$, —C(O)—CH$_2$—NHMe, —C(O)—CH$_2$—NH$_2$, —C(O)—CHMe-N(Me)$_2$, —C(O)—CHMe-NHMe, —C(O)—CHMe-NH$_2$, —C(O)—C(Me)$_2$-N(Me)$_2$,
—C(O)—C(Me)$_2$-NHMe, —C(O)—C(Me)$_2$-NH$_2$,
—C(O)—C(Me)$_2$-NH$_2$,

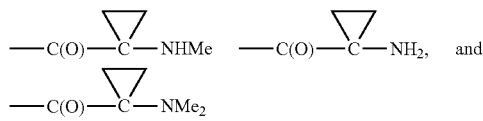

Examples of —C(R)$_2$—C(O)—N(R)$_2$ include —C(Me)$_2$-C(O)—NH$_2$, —CH$_2$—C(O)—NH$_2$, —CHMe-C(O)—NH$_2$, —C(Me)$_2$-C(O)—NHMe, —CH$_2$—C(O)—NHMe, —CHMe-C(O)—NHMe, —C(Me)$_2$-C(O)—N(Me)$_2$, —CH$_2$—C(O)—N(Me), and —CHMe-C(O)—N(Me)$_2$.

Examples of —C(O)—(NR)$_q$-(alk)$_q$-OR when each q is 1 include —C(O)—N(Me)—CH$_2$—OMe, —C(O)—N(Me)—CH$_2$—OH, —C(O)—NH—CH$_2$—OH, and —C(O)—NH—CH$_2$—OMe.

Examples of —C(O)—(NR)$_q$-(alk)$_q$-OR when one q is 0 and the other q is 1 include —C(O)—CH$_2$—OMe, —C(O)—CH(Me)-OMe, —C(O)—C(Me)$_2$-OMe, —C(O)—CH$_2$—OH, —C(O)—CH(Me)—OH, —C(O)—C(Me)$_2$-OH and —C(O)—CH(Me)-OMe.

Examples of —C(O)-cyclyl include —C(O)-(cyclopropyl).

Examples of —C(O)R include —C(O)H, —C(O)Me, —C(O)Et, and —C(O)—C(CH$_3$)$_3$.

Examples of —C(O)OR include —C(O)OH, —C(O)OMe, —C(O)OEt, and —C(O)OC(CH$_3$)$_3$.

In the definition (a) for R$^3$ the phenyl ring B is unsubstituted (apart from group Z) or substituted. When it is unsubstituted the group Z is the sole substituent. Z may be at the 2-, 3-, 4-, 5- or 6-position on the phenyl ring. Typically it is at the 2-, 3- or 4-position, more typically at the 3- or 4-position. Z is most typically other than H, such that moiety —BZ is a substituted phenyl ring. Specific examples of the group Z include —OH, —CH$_2$OH, F, Cl, 1-hydroxyethyl, —NHS(O)$_2$Me, —NC(O)Me, —S(O)$_2$NH$_2$Me and —C(O)Me.

When the phenyl ring B is substituted it typically comprises, in addition to group Z, one or more substituents selected from halo, alkyl, alkenyl, alkynyl, CN, NO$_2$, OR', SR', NR'$_2$, C(O)R', SOR', SO$_2$R', SO$_2$NR'$_2$, NC(O)R' and CO$_2$R', wherein each R' is independently H or C$_1$-C$_6$ alkyl.

In definition (b) for R$^3$ the heteroaryl group is unsubstituted or substituted. It is typically selected from indazole, indole, pyridine, pyrimidine, benzimidazole, quinoline, isoquinoline, imidazole and pyrazole, each of which is linked via any available ring C or N atom. For instance, an indazole group may be linked as indazol-4-yl, indazol-5-yl or indazol-6-yl. Pyrimidine may be linked as pyrimidin-1-yl, pyrimidine-2-yl, pyrimidin-3-yl or pyrimidin-4-yl. Pyridine may be linked as pyridin-1-yl, pyridine-2-yl, pyridine-3-yl or pyridine-4-yl. Benzimidazole may be linked via N as benzimidazol-1-yl. Quinoline may be linked as quinolin-3-yl or quinolin-4-yl. Isoquinoline may be linked as isoquinolin-3-yl or isoquinolin-4-yl. Imidazole may be linked via N as imidazol-1-yl If the heteroaryl group is substituted it may be substituted by one or more substituents selected from a group Z, R$^{20}$ as defined above, alkyl which is unsubstituted or substituted by a R$^{20}$ as defined above, any group specified above as an additional substituent on the phenyl ring B, and an oxo group (=O). Typically, if substituted, the heteroaryl group is substituted by OH, OMe, NH$_2$, NMe$_2$, F or Cl. In one embodiment the heteroaryl group is unsubstituted.

In definition (c) for R$^3$ the benzene ring is unsubstituted or substituted. If it is substituted it may be substituted by one or more substituents selected from a group Z, R$^{20}$ as defined above, alkyl which is unsubstituted or substituted by R$^{20}$ as defined above, and any of the groups specified above as an additional substituent on the phenyl ring B. The heteroaryl group to which the benzene ring is fused is itself unsubstituted or substituted, for instance by a group Z, R$^{20}$ or alkyl which is unsubstituted or substituted by a group R$^{20}$ as defined above; by any group specified above as an option for an additional substituent on the phenyl ring B; or by an oxo group (=O). In one embodiment both the benzene ring and the heteroaryl group are unsubstituted.

Groups included in definitions (b) and (c) for R$^3$ as defined above include the following structures:

1 i

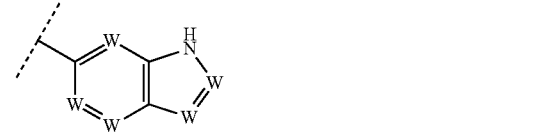

1 ii

1 iii

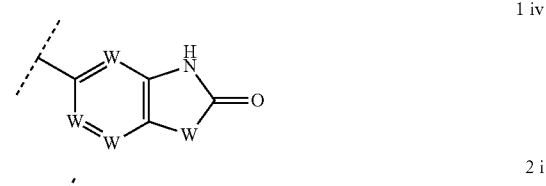

1 iv

2 i

2 ii

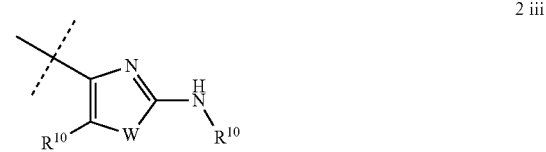

2 iii

-continued
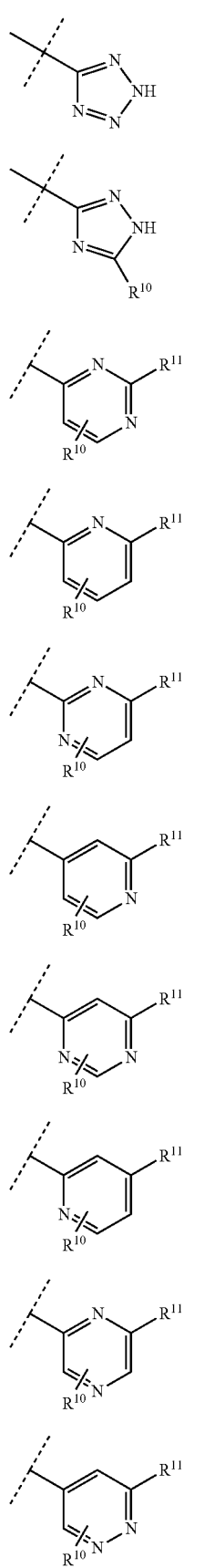
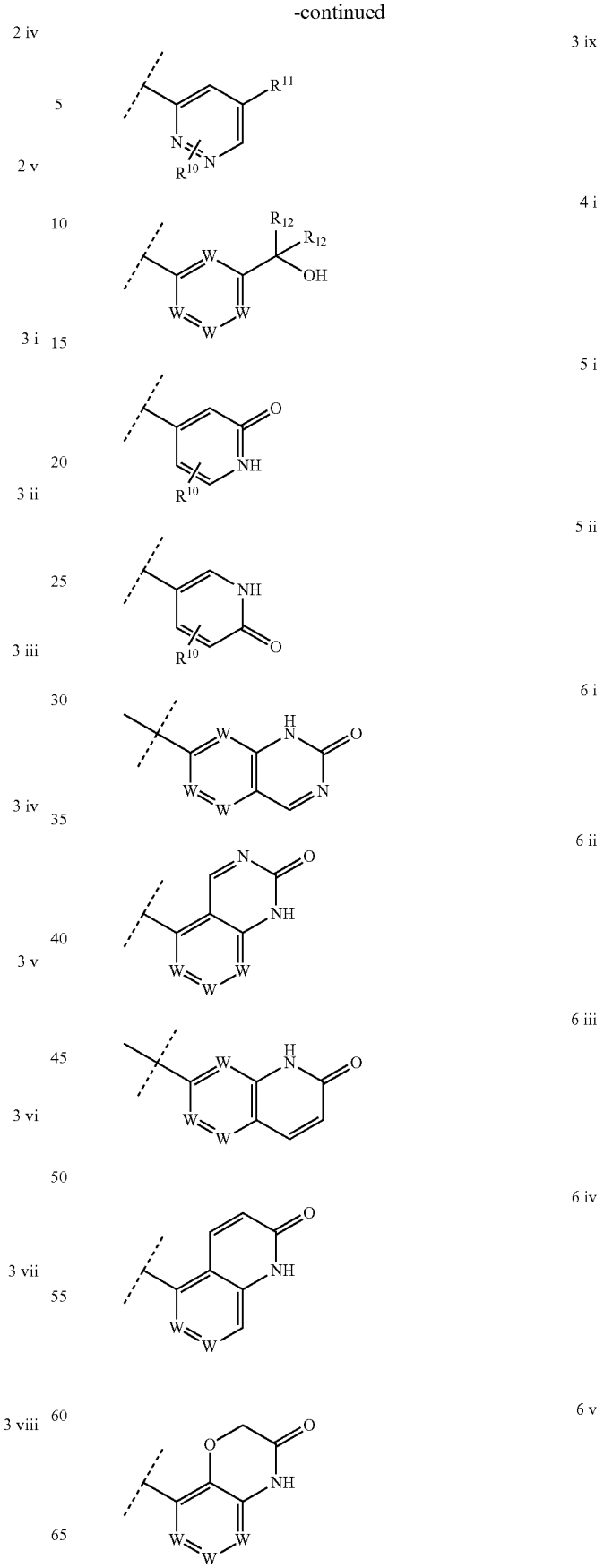

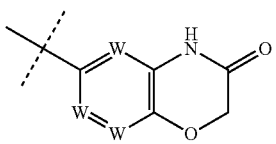

6 vi wherein each $R^{10}$ is independently selected from H, $C_1$-$C_6$ alkyl, $C_1$-$C_6$ alkoxy, $C_1$-$C_6$ acyl, —C(O)NR'R", —S(O)$_t$NR'R", aryl, heteroaryl, sulphonyl and halogen, wherein R' and R" are each independently H or $C_1$-$C_6$ alkyl and t is 1 or 2;

each $R^{11}$ is independently selected from —$OR^{10}$ and —N($R^{10}$)$_2$, wherein $R^{10}$ is as defined above;

each $R^{12}$ is independently H, F or $CF_3$;

each W is independently selected from $CR^{10}$ and N, wherein $R^{10}$ is as defined above; and W' is selected from O, S and $NR^{12}$ wherein $R^{12}$ is as defined above.

Typical examples of $R^3$ include

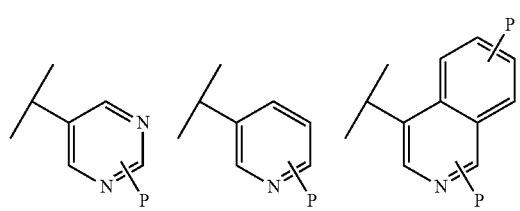

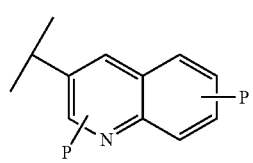

wherein P is selected from H, —OR, —$NR_2$, —CN, halo and $C_1$-$C_6$ alkyl.

Typically in compounds of the invention, $R^3$ takes definition (a) or (b) as defined above.

In one aspect the invention provides a compound which is a fused pyrimidine of formula (Ia''') or (Ib'''):

(Ia''')

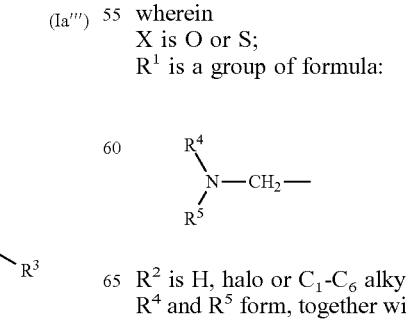

(Ib''')

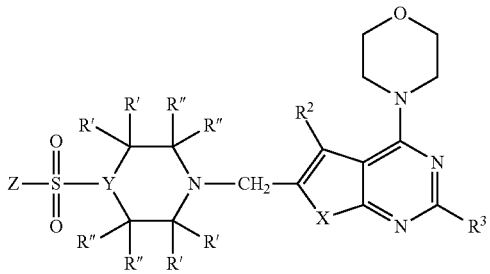

wherein
$R^2$, $R^3$, X, Y, Z, R' and R" are as defined above for formulae (Ia') and (Ib');
or a pharmaceutically acceptable salt thereof;
with the provisos that, in formula (Ia''') only:
(i) $R^3$ is other than an indole or 3-hydroxyphenyl group when X is S;
(ii) Z is other than a group selected from Me, -(alk)$_q$-NMe$_2$ and -alk-morpholino when the following are satisfied: Y is N, each of R' and R" is H, $R^2$ is H and $R^3$ is indazol-4-yl; and
(iii) Z is other than Me when the following are satisfied: Y is —CH—, each of R' and R" is H, $R^2$ is H and $R^3$ is indazol-4-yl.

In one aspect the invention provides a compound which is a fused pyrimidine of formula (Ia) or (Ib):

(Ia)

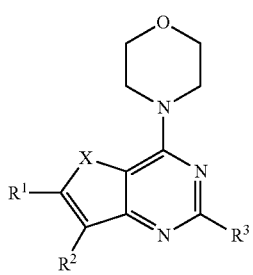

(Ib)

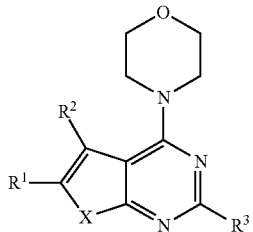

wherein
X is O or S;
$R^1$ is a group of formula:

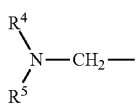

$R^2$ is H, halo or $C_1$-$C_6$ alkyl
$R^4$ and $R^5$ form, together with the N atom to which they are attached, a group selected from piperazine, piperidine, pyrrolidine, oxazolidinone, diazepan and 2,5-diaza-bicyclo[2,2,1]-heptane, which group is unsubstituted or substituted by -[(alk)$_q$-NR]$_r$—S(O)$_2$-(alk)$_q$-Z or —C(O)-(alk)$_q$-S(O)$_2$Z wherein Z is R$^{10}$ or —NR$^{11}$R$^{12}$, or by unsubstituted C$_1$-C$_6$ alkyl, hydroxyl-C$_1$-C$_6$ alkyl, oxo (═O), -(alk)$_q$-OR, —C(O)—C(R')$_2$—N(R)$_2$, —C(R)$_2$—C(O)—N(R)$_2$, —C(O)—(NR)$_q$-(alk)$_q$-OR, —C(O)-cyclyl, —C(O)R, —C(O)OR, —C(O)-Tet or
—NR$^{13}$R$^{14}$, with the proviso that, in formula (Ia) only, when X is S and R$^2$ is H and R$^3$ is indazol-4-yl, said group is other than (i) piperazine which is unsubstituted or substituted by a group selected from methyl, —S(O)$_2$Me, —S(O)$_2$NMe$_2$, -alk-OH, -alk-OMe, —S(O)$_2$-alk-NMe$_2$, and —S(O)$_2$-alk-morpholino; and (ii) piperidine which is substituted by a group selected from —S(O)$_2$Me, —C(O)—NR-(alk)$_q$-OR, —NMe-S(O)$_2$-Me, methyl, piperidine and —NR$^{13}$R$^{14}$ wherein one of R$^{13}$ and R$^{14}$ is -(alk)$_q$-OR;
or one of R$^4$ and R$^5$ is C$_1$-C$_6$ alkyl, -(alk)$_q$-Heterocyclyl or -(alk)$_q$-OR and the other is a piperazine, piperidine, pyrrolidine, sulphonylpyran or -(alk)$_q$-Heterocyclyl group, wherein said piperazine, piperidine, pyrrolidine, sulphonylpyran or Heterocyclyl is unsubstituted or substituted by C$_1$-C$_6$ alkyl, -(alk)$_q$-OR or —S(O)$_2$R$^{10}$;
R is H or C$_1$-C$_6$ alkyl which is unsubstituted;
each R' is, independently, H or C$_1$-C$_6$ alkyl which is unsubstituted, or the two groups R' form, together with the C atom to which they are attached, a cyclyl group;
R$^{10}$ is H, C$_1$-C$_6$ alkyl which is unsubstituted or CF$_3$;
R$^{11}$ and R$^{12}$ are each independently selected from H, C$_1$-C$_6$ alkyl which is unsubstituted and -(alk)$_q$-OR, or R$^{11}$ and R$^{12}$ together form, with the N atom to which they are attached, a 5- or 6-membered saturated N-containing heterocyclic group containing 0 or 1 additional heteroatoms selected from O, N and S;
R$^{13}$ and R$^{14}$ are each independently selected from C$_1$-C$_6$ alkyl, —S(O)$_2$R$^{10}$, and -(alk)$_q$-OR;
Tet is a tetrahydrofuranyl or tetrahydropyranyl group, which group is unsubstituted or substituted;
Heterocyclyl is a 5- or 6-membered saturated N-containing heterocyclic group containing 0 or 1 additional heteroatoms selected from O, N and S;
Cyclyl is a C$_3$-C$_6$ cycloalkyl group;
each q is independently 0 or 1;
r is 0 or 1;
alk is C$_1$-C$_6$ alkylene; and
R$^3$ is selected from:
(a) a group of the following formula:

wherein B is a phenyl ring which is unsubstituted or substituted and Z is selected from H, —OR, —SR, CH$_2$OR, —CO$_2$R, CF$_2$OH, CH(CF$_3$)OH, C(CF$_3$)$_2$OH, —(CH$_2$)$_q$OR, —(CH$_2$)$_q$NR$_2$, —C(O)N(R)$_2$, —NR$_2$, —NRC(O)R, —S(O)$_m$N(R)$_2$, —OC(O)R, OC(O)N(R)$_2$, —NRS(O)$_m$R, —NRC(O)N(R)$_2$, CN, halogen and —NO$_2$, wherein each R is independently selected from H, C$_1$-C$_6$ alkyl, C$_3$-C$_{10}$ cycloalkyl and a 5- to 12-membered aryl or heteroaryl group, the group being unsubstituted or substituted, m is 1 or 2 and q is 0, 1 or 2;
(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and
(c) a group comprising a benzene ring which is unsubstituted or substituted and which is fused to a heteroaryl group as defined above;
or a pharmaceutically acceptable salt thereof;
with the provisos that:
(i) when X in formula (Ia) is S, then R$^3$ is other than an indole or 3-hydroxyphenyl group; and
(ii) when X in formula (Ib) is S, then R$^3$ is other than an indole group.
In one aspect the invention provides a compound which is a fused pyrimidine of formula (Ia')

(Ia')

wherein
X is O or S;
Y is N or —CH—;
R$^2$ is H, halo or C$_1$-C$_6$ alkyl;
each R' is, independently, H, C$_1$-C$_6$ alkyl or hydroxyl-C$_1$-C$_6$ alkyl, or two groups R' on the same carbon atom form an oxo (═O) group; or when Y is N, two groups R' on different carbon atoms together form a —CH$_2$— bridgehead;
each R" is, independently, H or C$_1$-C$_6$ alkyl, or two groups R" on the same carbon atom form an oxo (═O) group;
Z is R$^{10}$ or -(alk)$_q$-NR$^{11}$R$^{12}$;
R$^{10}$ is H, C$_1$-C$_6$ alkyl which is unsubstituted, or CF$_3$;
R$^{11}$ and R$^{12}$ are each independently selected from H, C$_1$-C$_6$ alkyl which is unsubstituted and -(alk)$_q$-OR, or R$^{11}$ and R$^{12}$ together form, with the N atom to which they are attached, a 5- or 6-membered saturated N-containing heterocyclic group containing 0 or 1 additional heteroatoms selected from O, N and S;
q is 0 or 1;
alk is C$_1$-C$_6$ alkylene; and
and R$^3$ is selected from:
(a) a group of the following formula:

wherein B is a phenyl ring which is unsubstituted or substituted and Z is selected from H, —OR, —SR, CH$_2$OR, —CO$_2$R, CF$_2$OH, CH(CF$_3$)OH, C(CF$_3$)$_2$OH, —(CH$_2$)$_q$OR, —(CH$_2$)$_q$NR$_2$, —C(O)N(R)$_2$, —NR$_2$, —NRC(O)R, —S(O)$_m$N(R)$_2$, —OC(O)R, OC(O)N(R)$_2$, —NRS(O)$_m$R, —NRC(O)N(R)$_2$, CN, halogen and —NO$_2$, wherein each R is independently selected from H, C$_1$-C$_6$ alkyl, C$_3$-C$_{10}$ cycloalkyl and a 5- to 12-membered aryl or heteroaryl group, the group being unsubstituted or substituted, m is 1 or 2 and q is 0, 1 or 2;

(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and (c) a group comprising a benzene ring which is unsubstituted or substituted and which is fused to a heteroaryl group as defined above;

or a pharmaceutically acceptable salt thereof;
with the provisos that:
(i) $R^3$ is other than an indole or 3-hydroxyphenyl group when X is S;
(ii) Z is other than a group selected from Me, -(alk)$_q$-NMe$_2$ and -alk-morpholino when the following are satisfied: Y is N, each of R' and R" is H, $R^2$ is H and $R^3$ is indazol-4-yl;
(iii) Z is other than Me when the following are satisfied: Y is —CH—, each of R' and R" is H, $R^2$ is H and $R^3$ is indazol-4-yl.

In one aspect the invention provides a compound which is fused pyrimidine of formula (Ib'):

(Ib')

wherein
X is O or S;
Y is N or —CH—;
$R^2$ is H, halo or $C_1$-$C_6$ alkyl;
each R' is, independently, H, $C_1$-$C_6$ alkyl or hydroxy-$C_1$-$C_6$ alkyl, or two groups R' on the same carbon atom form an oxo (=O) group; or when Y is N, two groups R' on different carbon atoms together form a —CH$_2$— bridgehead;
each R" is, independently, H or $C_1$-$C_6$ alkyl, or two groups R" on the same carbon atom form an oxo (=O) group;
Z is $R^{10}$ or -(alk)$_q$-NR$^{11}$R$^{12}$;
$R^{10}$ is H, $C_1$-$C_6$ alkyl which is unsubstituted, or CF$_3$;
$R^{11}$ and $R^{12}$ are each independently selected from H, $C_1$-$C_6$ alkyl which is unsubstituted and -(alk)$_q$-OR, or $R^{11}$ and $R^{12}$ together form, with the N atom to which they are attached, a 5- or 6-membered saturated N-containing heterocyclic group containing 0 or 1 additional heteroatoms selected from O, N and S;
q is 0 or 1;
alk is $C_1$-$C_6$ alkylene; and
and $R^3$ is selected from:
(a) a group of the following formula:

wherein B is a phenyl ring which is unsubstituted or substituted and Z is selected from H, —OR, —SR, CH$_2$OR, —CO$_2$R, CF$_2$OH, CH(CF$_3$)OH, C(CF$_3$)$_2$OH, —(CH$_2$)$_q$OR, —(CH$_2$)$_q$NR$_2$, —C(O)N(R)$_2$, —NR$_2$, —NRC(O)R, —S(O)$_m$N(R)$_2$, —OC(O)R, OC(O)N(R)$_2$, —NRS(O)$_m$R, —NRC(O)N(R)$_2$, CN, halogen and —NO$_2$, wherein each R is independently selected from H, $C_1$-$C_6$ alkyl, $C_3$-$C_{10}$ cycloalkyl and a 5- to 12-membered aryl or heteroaryl group, the group being unsubstituted or substituted, m is 1 or 2 and q is 0, 1 or 2;

(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and (c) a group comprising a benzene ring which is unsubstituted or substituted and which is fused to a heteroaryl group as defined above;

or a pharmaceutically acceptable salt thereof.

In one aspect the invention provides a compound which is a fused pyrimidine of formula (Ia") or (Ib"):

(Ia")

(Ib")

wherein
X is O or S;
$R^2$ is H, halo or $C_1$-$C_6$ alkyl;
$R^4$ is $C_1$-$C_6$ alkyl, -(alk)$_q$-Heterocyclyl, or -(alk)$_q$-OR;
$R^5$ is a piperazine, piperidine, pyrrolidine, sulphonylpyran or -(alk)$_q$-Heterocyclyl group, wherein said piperazine, piperidine, pyrrolidine, sulphonylpyran or Heterocyclyl group is unsubstituted or substituted by $C_1$-$C_6$ alkyl, -(alk)$_q$-OR or —S(O)$_2$R$^{10}$;
R is H, $C_1$-$C_6$ alkyl which is unsubstituted;
$R^{10}$ is H, $C_1$-$C_6$ alkyl which is unsubstituted, or CF$_3$;
Heterocyclyl is a 5- or 6-membered saturated N-containing heterocyclic group containing 0 or 1 additional heteroatoms selected from O, N and S;
q is 0 or 1;
alk is $C_1$-$C_6$ alkylene; and
and $R^3$ is selected from:
(a) a group of the following formula:

wherein B is a phenyl ring which is unsubstituted or substituted and Z is selected from H, —OR, —SR, CH$_2$OR, —CO$_2$R, CF$_2$OH, CH(CF$_3$)OH, C(CF$_3$)$_2$OH, —(CH$_2$)$_q$OR, —(CH$_2$)$_m$NR$_2$, —C(O)N(R)$_2$, —NR$_2$, —NRC(O)R, —S(O)$_m$N(R)$_2$, —OC(O)R, OC(O)N(R)$_2$, —NRS(O)$_m$R, —NRC(O)N(R)$_2$, CN, halogen and —NO$_2$, wherein each R is independently selected from H, C$_1$-C$_6$ alkyl, C$_3$-C$_{10}$ cycloalkyl and a 5- to 12-membered aryl or heteroaryl group, the group being unsubstituted or substituted, m is 1 or 2 and q is 0, 1 or 2;

(b) a heteroaryl group which contains 1, 2, 3 or 4 ring nitrogen atoms and 0, 1 or 2 additional heteroatoms selected from O and S, which group is monocyclic or bicyclic and which is unsubstituted or substituted; and (c) a group comprising a benzene ring which is unsubstituted or substituted and which is fused to a heteroaryl group as defined above;

or a pharmaceutically acceptable salt thereof;

with the provisos that:

(i) when X in formula (Ia") is S, then R$^3$ is other than an indole or 3-hydroxyphenyl group; and (ii) when X in formula (Ib") is S, then R$^3$ is other than an indole group.

Specific examples of compounds of the invention include:

TABLE 1a

| Compound No. | Structure | Name |
| --- | --- | --- |
| 1 | 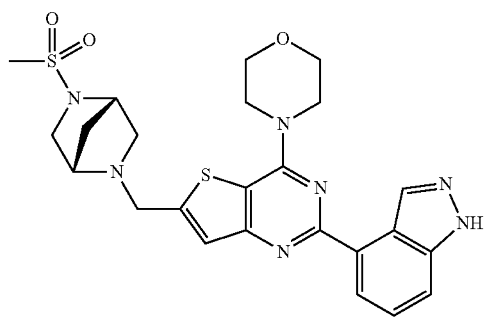 [SMILES: CS(=O)(=O)N1C[C@@H]2C[C@H]1CN2Cc1cc2nc(-c3cccc4[nH]ncc34)nc(N3CCOCC3)c2s1] | (1S,4S)-2-((2-(1H-indazol-4-yl)-4-morpholinothieno[3,2-d]pyrimidin-6-yl)methyl)-5-methylsulfonyl-2,5-diaza-bicyclo[2.2.1]heptane |
| 2 | 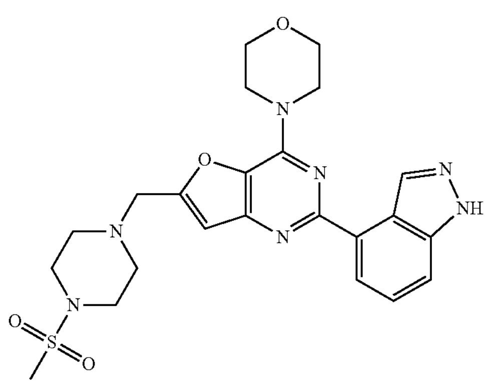 [SMILES: CS(=O)(=O)N1CCN(Cc2cc3nc(-c4cccc5[nH]ncc45)nc(N4CCOCC4)c3o2)CC1] | 2-(1H-indazol-4-yl)-6-((4-methylsulfonylpiperazin-1-yl)methyl)-4-morpholinofuro[3,2-d]pyrimidine |
| 3 | 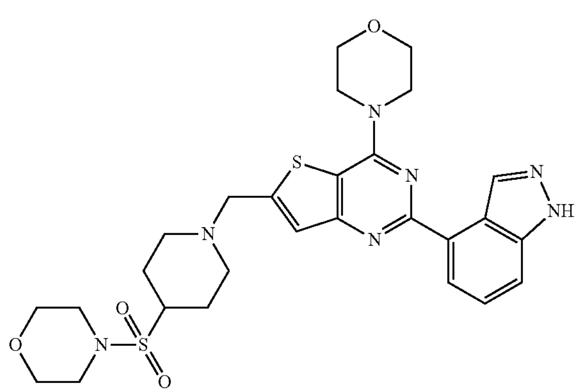 [SMILES: O=S(=O)(C1CCN(Cc2cc3nc(-c4cccc5[nH]ncc45)nc(N4CCOCC4)c3s2)CC1)N1CCOCC1] | 2-(1H-indazol-4-yl)-6-((4-(N-morpholino)sulfonylpiperazin-1-yl)methyl)-4-morpholinothieno[3,2-d]pyrimidine |

TABLE 1a-continued

| Compound No. | Structure | Name |
|---|---|---|
| 4. | 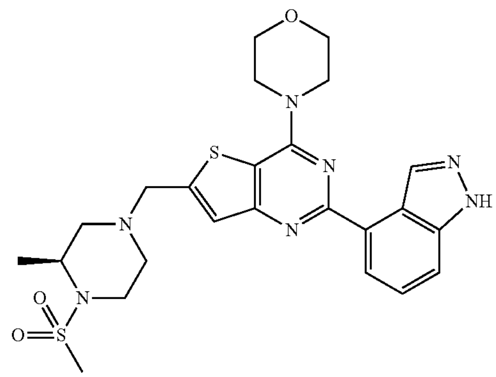 [SMILES: C[C@H]1CN(Cc2cc3nc(-c4cccc5[nH]ncc45)nc(N4CCOCC4)c3s2)CCN1S(C)(=O)=O] | 2-(1H-indazol-4-yl)-6-(((3S,5R)-3-methyl-4-methylsulfonylpiperazin-1-yl)methyl)-4-morpholinothieno[3,2-d]pyrimidine |
| 5. | 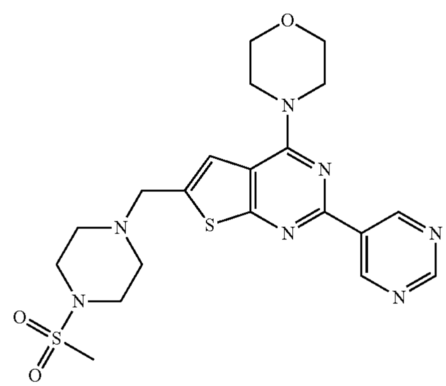 [SMILES: CS(=O)(=O)N1CCN(Cc2cc3c(N4CCOCC4)nc(-c4cncnc4)nc3s2)CC1] | 6-((4-methylsulfonylpiperazin-1-yl)methyl)-4-morpholino-2-(pyrimidin-5-yl)thieno[2,3-d]pyrimidine |
| 6. | 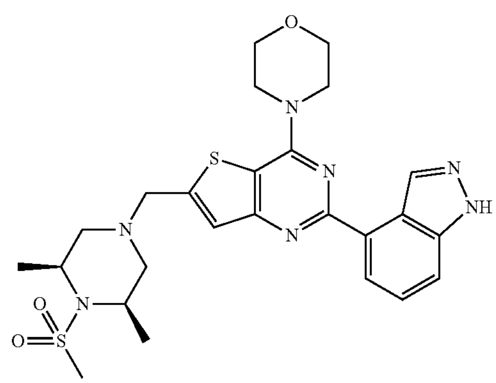 [SMILES: C[C@@H]1CN(Cc2cc3nc(-c4cccc5[nH]ncc45)nc(N4CCOCC4)c3s2)C[C@H](C)N1S(C)(=O)=O] | 2-(1H-indazol-4-yl)-6-(((3S,5R)-3,5-dimethyl-4-methylsulfonylpiperazin-1-yl)methyl)-4-morpholinothieno[3,2-d]pyrimidine |
| 7. | 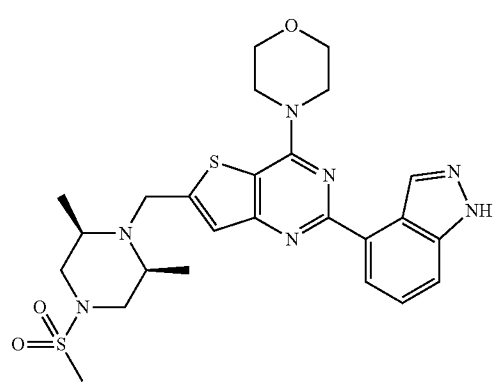 [SMILES: C[C@@H]1CN(S(C)(=O)=O)C[C@H](C)N1Cc1cc2nc(-c3cccc4[nH]ncc34)nc(N3CCOCC3)c2s1] | 6-(((2R,6S)-4-methylsulfonyl-2,6-dimethylpiperazin-1-yl)methyl)-2-(1H-indazol-4-yl)-4-morpholinothieno[3,2-d]pyrimidine |

TABLE 1a-continued

| Compound No. | Structure | Name |
|---|---|---|
| 8. | 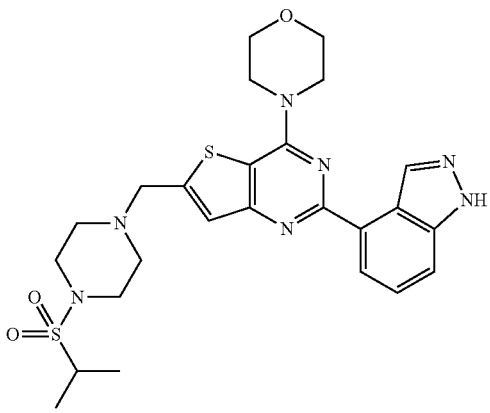 [SMILES: CC(C)S(=O)(=O)N1CCN(Cc2cc3nc(-c4cccc5[nH]ncc45)nc(N4CCOCC4)c3s2)CC1] | 6-(((2R,6S)-4-isopropylsulfonyl-2,6-dimethylpiperazin-1-yl)methyl)-2-(1H-indazol-4-yl)-4-morpholinothieno[3,2-d]pyrimidine |
| 9. | 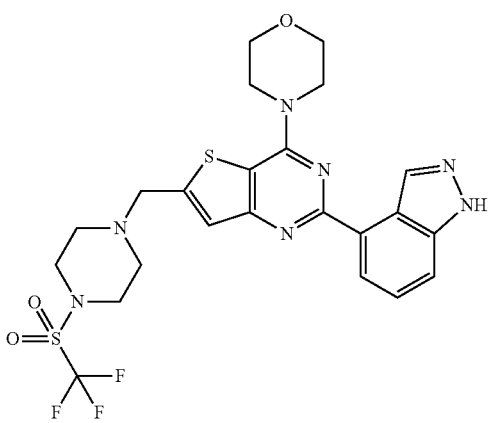 [SMILES: O=S(=O)(N1CCN(Cc2cc3nc(-c4cccc5[nH]ncc45)nc(N4CCOCC4)c3s2)CC1)C(F)(F)F] | 6-(((2R,6S)-4-trifluoromethylsulfonyl-2,6-dimethylpiperazin-1-yl)methyl)-2-(1H-indazol-4-yl)-4-morpholinothieno[3,2-d]pyrimidine |
| 10. | 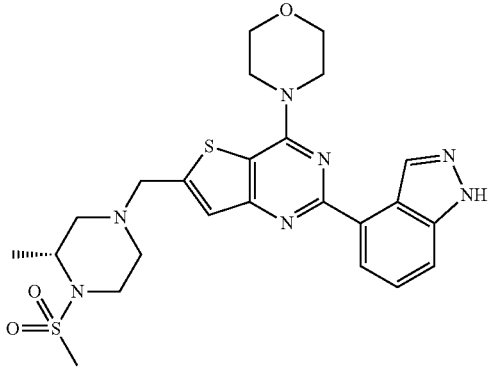 [SMILES: C[C@@H]1CN(Cc2cc3nc(-c4cccc5[nH]ncc45)nc(N4CCOCC4)c3s2)CCN1S(C)(=O)=O] | 6-(((R)-4-methylsulfonyl-3-methylpiperazin-1-yl)methyl)-2-(1H-indazol-4-yl)-4-morpholinothieno[3,2-d]pyrimidine |
| 11. | 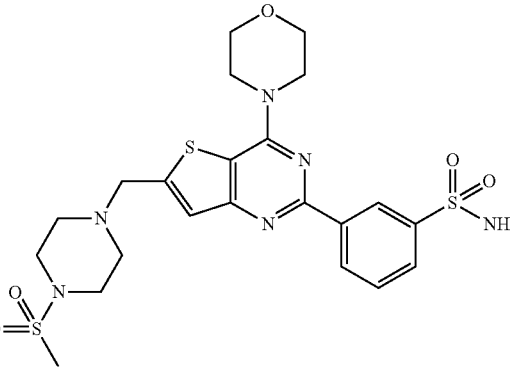 | 3-(6-((4-methylsulfonylpiperazin-1-yl)methyl)-4-morpholinothieno[3,2-d]pyrimidin-2-yl)benzenesulfonamide |

TABLE 1a-continued

| Compound No. | Structure | Name |
|---|---|---|
| 12. | 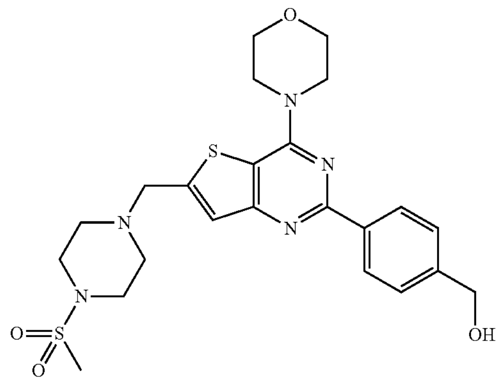 [SMILES: CS(=O)(=O)N1CCN(Cc2cc3nc(-c4ccc(CO)cc4)nc(N4CCOCC4)c3s2)CC1] | (4-(6-((4-methylsulfonylpiperazin-1-yl)methyl)-4-morpholinothieno[3,2-d]pyrimidin-2-yl)phenyl)methanol |
| 13. | 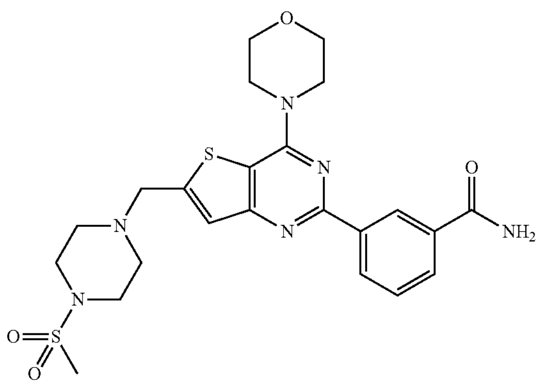 [SMILES: CS(=O)(=O)N1CCN(Cc2cc3nc(-c4cccc(C(N)=O)c4)nc(N4CCOCC4)c3s2)CC1] | 3-(6-((4-methylsulfonylpiperazin-1-yl)methyl)-4-morpholinothieno[3,2-d]pyrimidin-2-yl)benzamide |
| 14. | 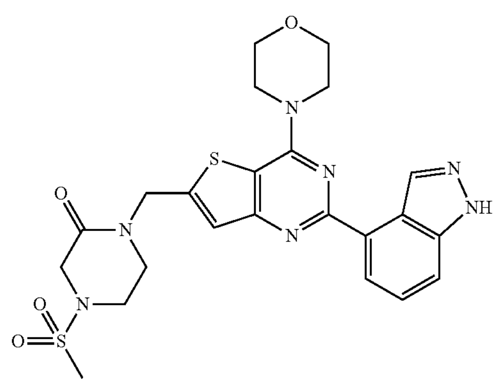 [SMILES: CS(=O)(=O)N1CCN(Cc2cc3nc(-c4cccc5[nH]ncc45)nc(N4CCOCC4)c3s2)C(=O)C1] | 1-((2-(1H-indazol-4-yl)-4-morpholinothieno[3,2-d]pyrimidin-6-yl)methyl)-4-methylsulfonylpiperazin-2-one |
| 15. | 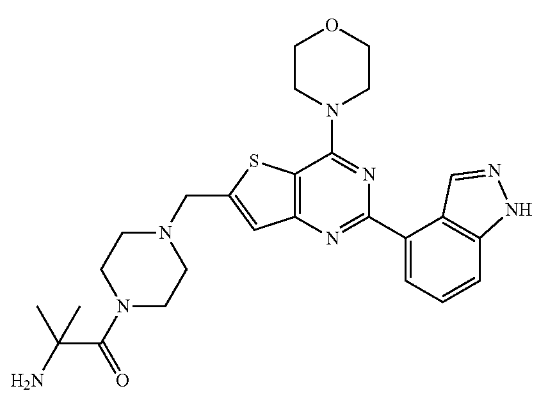 [SMILES: CC(C)(N)C(=O)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)-2-amino-2-methylpropan-1-one |

TABLE 1a-continued

| Compound No. | Structure | Name |
|---|---|---|
| 16. | 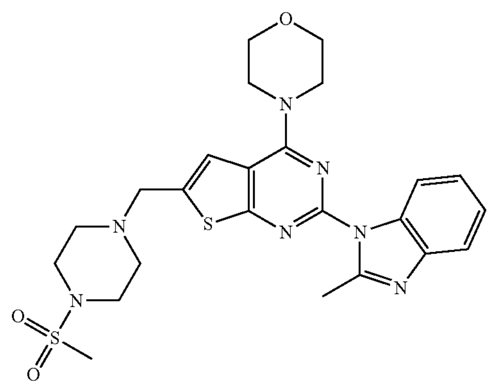 [SMILES: Cc1nc2ccccc2n1-c1nc(N2CCOCC2)c2cc(CN3CCN(S(C)(=O)=O)CC3)sc2n1] | 2-(2-methyl-1H-benzo[d]imidazol-1-yl)-6-((4-methylsulfonylpiperazin-1-yl)methyl)-4-morpholinothieno[2,3-d]pyrimidine |
| 17. | 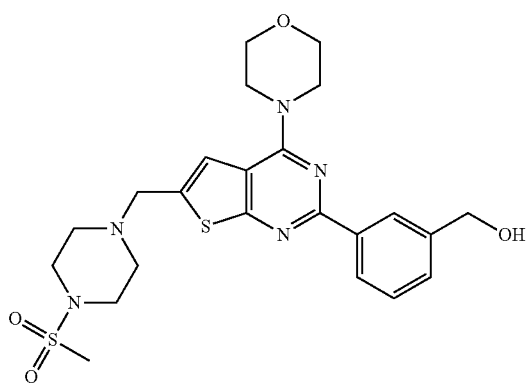 [SMILES: CS(=O)(=O)N1CCN(Cc2cc3c(N4CCOCC4)nc(-c4cccc(CO)c4)nc3s2)CC1] | (3-(6-((4-methylpiperazin-1-yl)methyl)-4-morpholinothieno[2,3-d]pyrimidin-2-yl)phenyl)methanol |
| 18. | 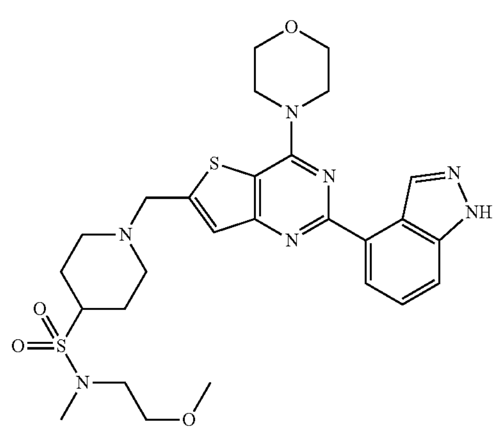 [SMILES: COCCN(C)S(=O)(=O)C1CCN(Cc2cc3nc(-c4cccc5[nH]ncc45)nc(N4CCOCC4)c3s2)CC1] | 2-(1H-indazol-4-yl)-6-((4-N-methyl-N-methoxyethylaminosulfonylpiperidin-1-yl)methyl)-4-morpholinothieno[3,2-d]pyrimidine |

TABLE 1a-continued

| Compound No. | Structure | Name |
|---|---|---|
| 19. | 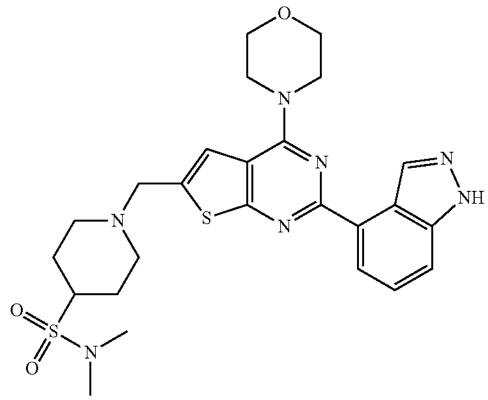 [SMILES: CN(C)S(=O)(=O)C1CCN(Cc2cc3c(N4CCOCC4)nc(-c4cccc5[nH]ncc45)nc3s2)CC1] | 2-(1H-indazol-4-yl)-6-((4-N,N-dimethylaminosulfonylpiperidin-1-yl)methyl)-4-morpholinothieno[2,3-d]pyrimidine |
| 20. | 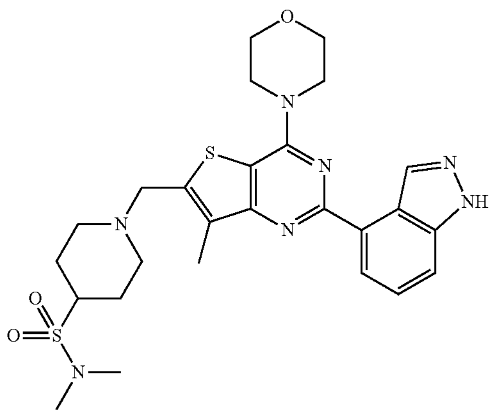 [SMILES: Cc1c(CN2CCC(S(=O)(=O)N(C)C)CC2)sc2c(N3CCOCC3)nc(-c3cccc4[nH]ncc34)nc12] | 2-(1H-indazol-4-yl)-6-((4-N,N-dimethylaminosulfonylpiperidin-1-yl)methyl)-7-methyl-4-morpholinothieno[3,2-d]pyrimidine |
| 21. | 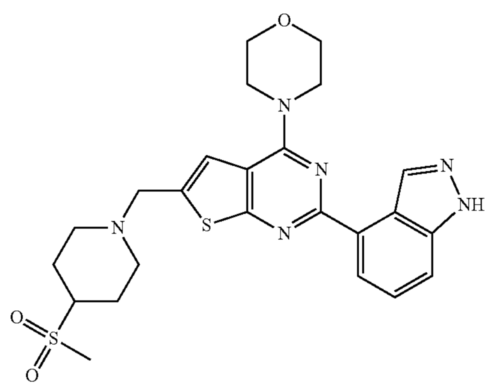 [SMILES: CS(=O)(=O)C1CCN(Cc2cc3c(N4CCOCC4)nc(-c4cccc5[nH]ncc45)nc3s2)CC1] | 2-(1H-indazol-4-yl)-6-((4-methylsulfonylpiperidin-1-yl)methyl)-4-morpholinothieno[2,3-d]pyrimidine |
| 22. | 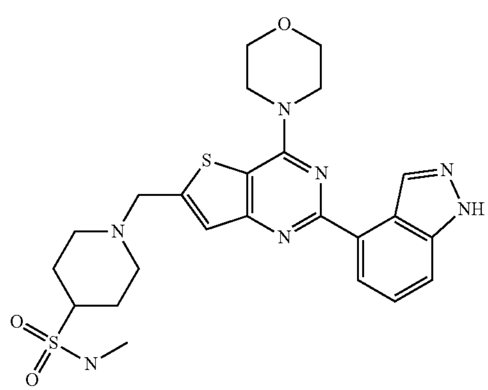 [SMILES: CNS(=O)(=O)C1CCN(Cc2cc3nc(-c4cccc5[nH]ncc45)nc(N4CCOCC4)c3s2)CC1] | 2-(1H-indazol-4-yl)-6-((4-N-methylaminosulfonylpiperidin-1-yl)methyl)-4-morpholinothieno[3,2-d]pyrimidine |

TABLE 1a-continued

| Compound No. | Structure | Name |
|---|---|---|
| 23. | 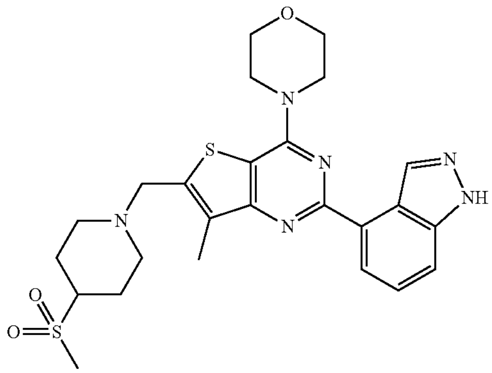 [SMILES: Cc1c(CN2CCC(S(C)(=O)=O)CC2)sc2c(N3CCOCC3)nc(-c3cccc4[nH]ncc34)nc12] | 2-(1H-indazol-4-yl)-7-methyl-6-((4-(methylsulfonyl)piperidin-1-yl)methyl)-4-morpholinothieno[3,2-d]pyrimidine |
| 24. | 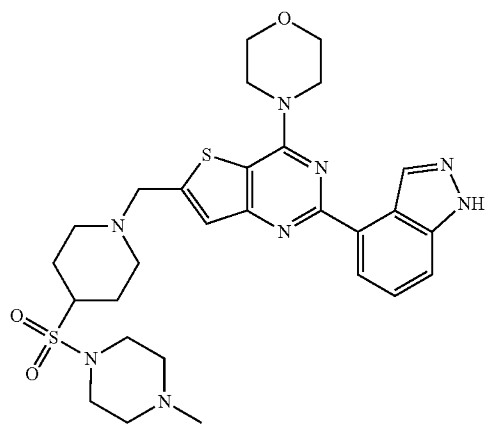 [SMILES: CN1CCN(S(=O)(=O)C2CCN(Cc3cc4nc(-c5cccc6[nH]ncc56)nc(N5CCOCC5)c4s3)CC2)CC1] | 2-(1H-indazol-4-yl)-6-((4-N-4-methylpiperazinosulfonylpiperidin-1-yl)methyl)-4-morpholinothieno[3,2-d]pyrimidine |
| 25. | 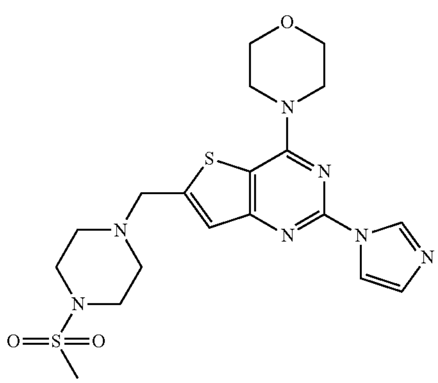 [SMILES: CS(=O)(=O)N1CCN(Cc2cc3nc(-n4ccnc4)nc(N4CCOCC4)c3s2)CC1] | 2-(1H-imidazol-1-yl)-6-((4-methylsulfonylpiperazin-1-yl)methyl)-4-morpholinothieno[3,2-d]pyrimidine |
| 26. | 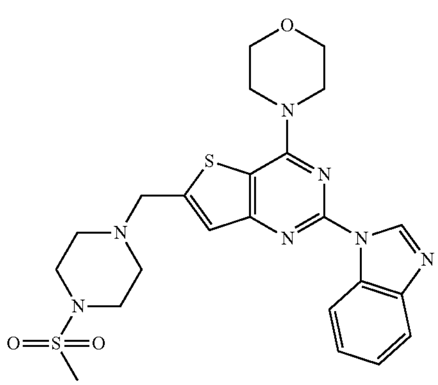 [SMILES: CS(=O)(=O)N1CCN(Cc2cc3nc(-n4cnc5ccccc54)nc(N4CCOCC4)c3s2)CC1] | 2-(1H-benzo[d]imidazol-1-yl)-6-((4-methylsulfonylpiperazin-1-yl)methyl)-4-morpholinothieno[3,2-d]pyrimidine |

TABLE 1a-continued

| Compound No. | Structure | Name |
|---|---|---|
| 27. | 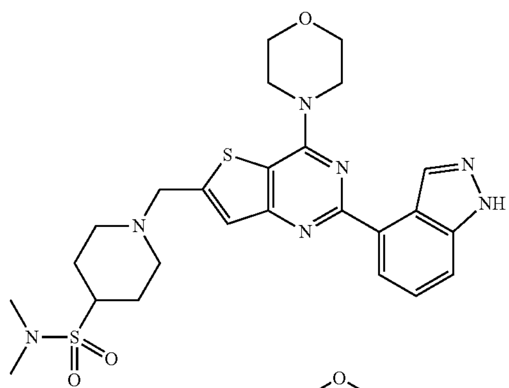 [SMILES: CN(C)S(=O)(=O)C1CCN(Cc2cc3nc(-c4cccc5[nH]ncc45)nc(N4CCOCC4)c3s2)CC1] | 2-(1H-indazol-4-yl)-6-((4-N,N-dimethylaminosulfonylpiperidin-1-yl)methyl)-4-morpholinothieno[3,2-d]pyrimidine |
| 28. | 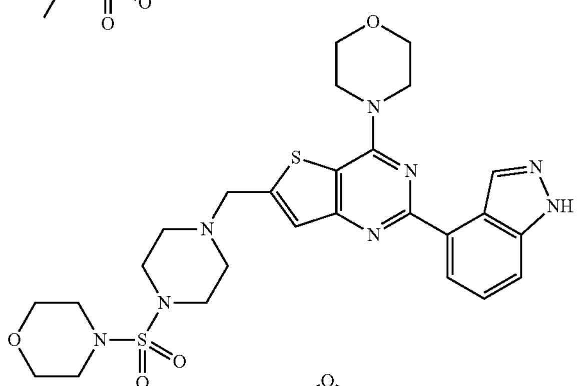 | 2-(1H-indazol-4-yl)-6-((4-N-morpholinosulfonylpiperazin-1-yl)methyl)-4-morpholinothieno[3,2-d]pyrimidine |
| 29. | 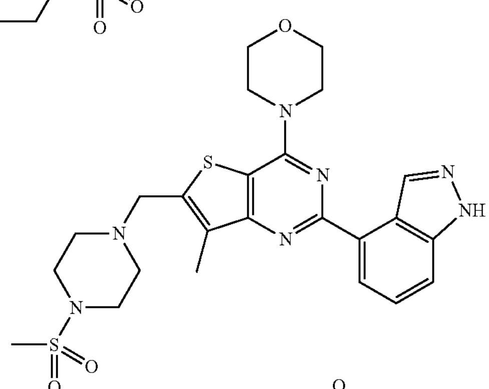 | 2-(1H-indazol-4-yl)-7-methyl-6-((4-(methylsulfonyl)piperazin-1-yl)methyl)-4-morpholinothieno[3,2-d]pyrimidine |
| 30. | 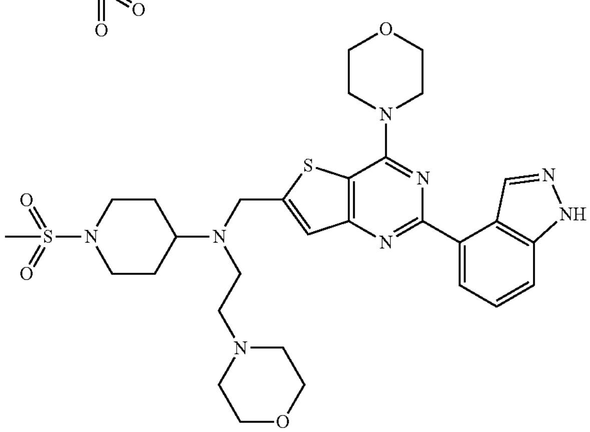 | N-((2-(1H-indazol-4-yl)-4-morpholinothieno[3,2-d]pyrimidin-6-yl)methyl)-1-methylsulfonyl-N-(2-morpholinoethyl)piperidin-4-amine |

TABLE 1a-continued

| Compound No. | Structure | Name |
|---|---|---|
| 31. | 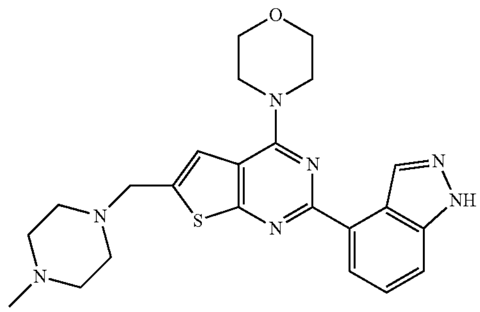 [SMILES: CN1CCN(Cc2cc3c(N4CCOCC4)nc(-c4cccc5[nH]ncc45)nc3s2)CC1] | 2-(1H-indazol-4-yl)-6-((4-methylpiperazin-1-yl)methyl)-4-morpholinothieno[2,3-d]pyrimidine |
| 32. | 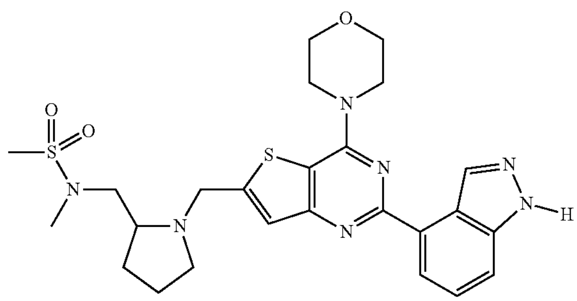 [SMILES: CN(CC1CCCN1Cc1cc2nc(-c3cccc4[nH]ncc34)nc(N3CCOCC3)c2s1)S(C)(=O)=O] | (1-((2-(1H-indazol-4-yl)-4-morpholinothieno[3,2-d]pyrimidin-6-yl)methyl)pyrrolidin-2-yl)-N-methylsulfonylmethanamine |
| 33. | 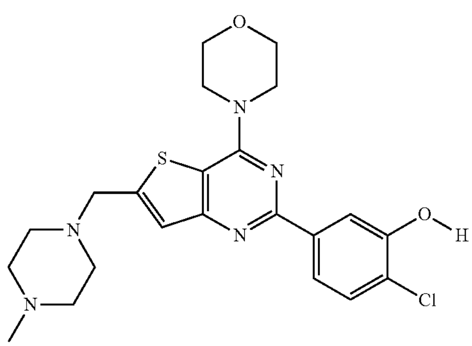 [SMILES: CN1CCN(Cc2cc3nc(-c4ccc(Cl)c(O)c4)nc(N4CCOCC4)c3s2)CC1] | 2-chloro-5-(6-((4-methylpiperazin-1-yl)methyl)-4-morpholinothieno[3,2-d]pyrimidin-2-yl)phenol |
| 34. | 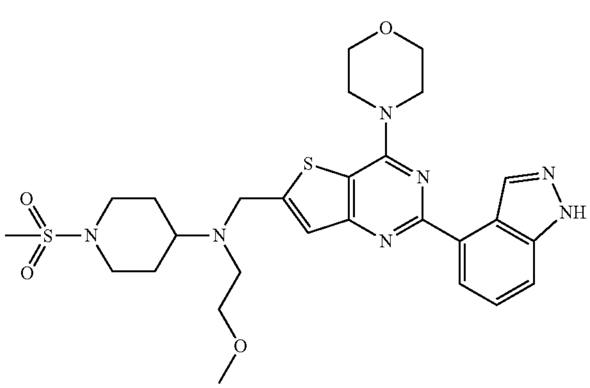 [SMILES: COCCN(Cc1cc2nc(-c3cccc4[nH]ncc34)nc(N3CCOCC3)c2s1)C1CCN(S(C)(=O)=O)CC1] | N-((2-(1H-indazol-4-yl)-4-morpholinothieno[3,2-d]pyrimidin-6-yl)methyl)-N-(2-methoxyethyl)-1-methylsulfonylpiperidin-4-amine |

TABLE 1a-continued

| Compound No. | Structure | Name |
|---|---|---|
| 35. | 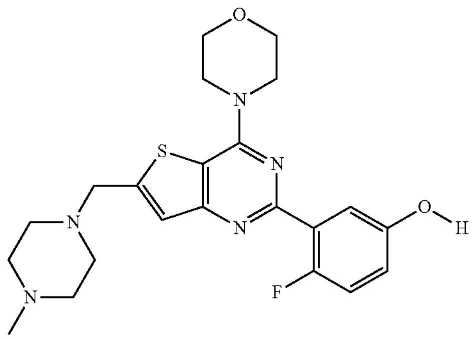 [SMILES: CN1CCN(Cc2cc3nc(-c4cc(O)ccc4F)nc(N4CCOCC4)c3s2)CC1] | 4-fluoro-3-(6-((4-methylpiperazin-1-yl)methyl)-4-morpholinothieno[3,2-d]pyrimidin-2-yl)phenol |
| 36. | 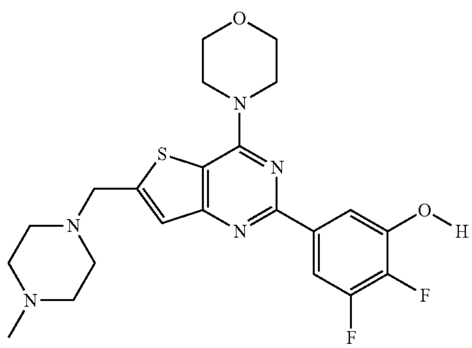 [SMILES: CN1CCN(Cc2cc3nc(-c4cc(O)c(F)c(F)c4)nc(N4CCOCC4)c3s2)CC1] | 2,3-difluoro-5-(6-((4-methylpiperazin-1-yl)methyl)-4-morpholinothieno[3,2-d]pyrimidin-2-yl)phenol |
| 37. | 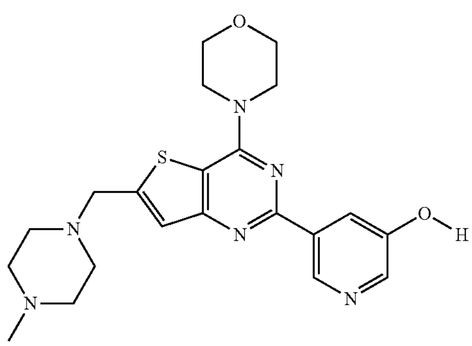 [SMILES: CN1CCN(Cc2cc3nc(-c4cncc(O)c4)nc(N4CCOCC4)c3s2)CC1] | 5-(6-((4-methylpiperazin-1-yl)methyl)-4-morpholinothieno[3,2-d]pyrimidin-2-yl)pyridin-3-ol |
| 38. | 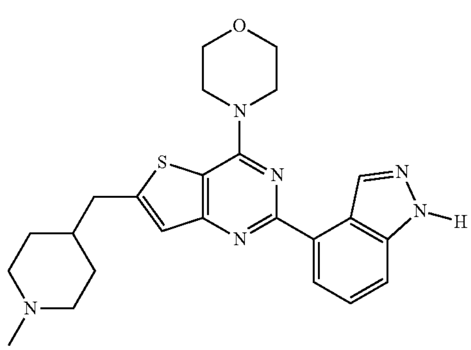 [SMILES: CN1CCC(Cc2cc3nc(-c4cccc5[nH]ncc45)nc(N4CCOCC4)c3s2)CC1] | 2-(1H-indazol-4-yl)-6-((1-methylpiperidin-4-yl)methyl)-4-morpholinothieno[3,2-d]pyrimidine |

TABLE 1a-continued

| Compound No. | Structure | Name |
|---|---|---|
| 39. | 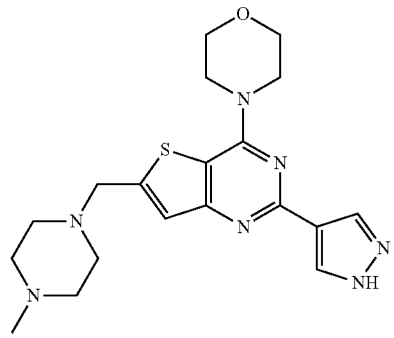 [SMILES: CN1CCN(Cc2cc3nc(-c4cn[nH]c4)nc(N4CCOCC4)c3s2)CC1] | 6-((4-methylpiperazin-1-yl)methyl)-4-morpholino-2-(1H-pyrazol-4-yl)thieno[3,2-d]pyrimidine |
| 40. | 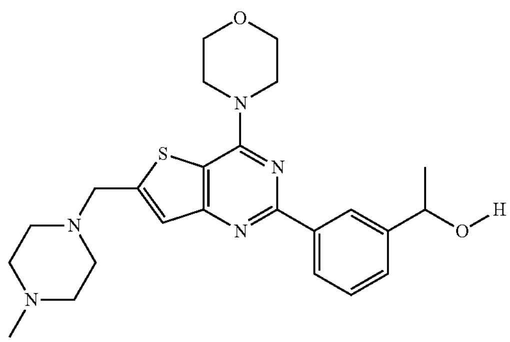 [SMILES: CC(O)c1cccc(-c2nc(N3CCOCC3)c3sc(CN4CCN(C)CC4)cc3n2)c1] | 1-(3-(6-((4-methylpiperazin-1-yl)methyl)-4-morpholinothieno[3,2-d]pyrimidin-2-yl)phenyl)ethanol |
| 41. | 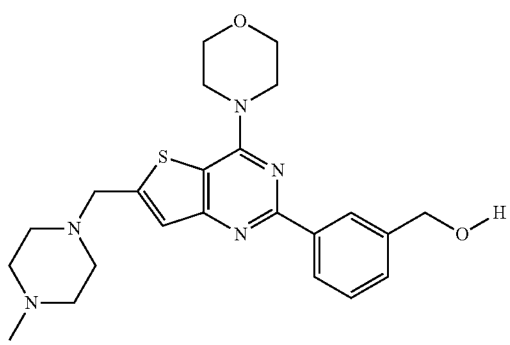 [SMILES: CN1CCN(Cc2cc3nc(-c4cccc(CO)c4)nc(N4CCOCC4)c3s2)CC1] | (3-(6-((4-methylpiperazin-1-yl)methyl)-4-morpholinothieno[3,2-d]pyrimidin-2-yl)phenyl)methanol |
| 42. | 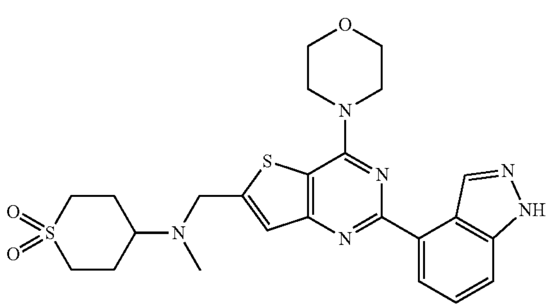 [SMILES: CN(Cc1cc2nc(-c3cccc4[nH]ncc34)nc(N3CCOCC3)c2s1)C1CCS(=O)(=O)CC1] | N-((2-(1H-indazol-4-yl)-4-morpholinothieno[3,2-d]pyrimidin-6-yl)methyl)-tetrahydro-N-methyl-2H-sulfonylpyran-4-amine |

TABLE 1a-continued
| Compound No. | Structure | Name |
|---|---|---|
| 43. | 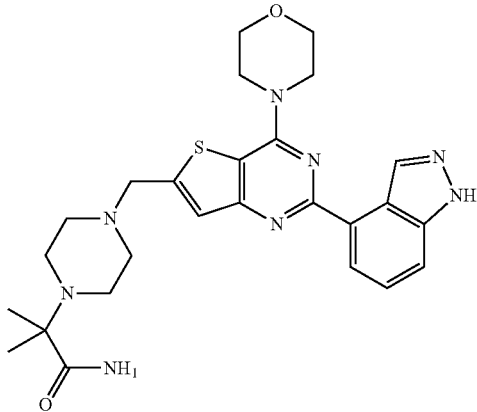 [SMILES: CC(C)(C(N)=O)N1CCN(Cc2cc3nc(-c4cccc5[nH]ncc45)nc(N4CCOCC4)c3s2)CC1] | 2-(4-((2-(1H-indazol-4-yl)-4-morpholinothieno[3,2-d]pyrimidin-6-yl)methyl)piperazin-1-yl)-2-methylpropanamide |
| 44. | 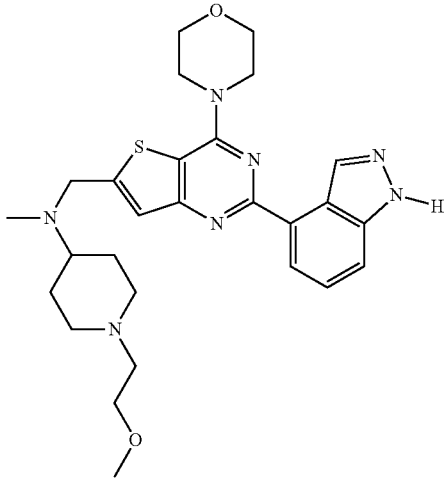 [SMILES: COCCN1CCC(N(C)Cc2cc3nc(-c4cccc5[nH]ncc45)nc(N4CCOCC4)c3s2)CC1] | N-((2-(1H-indazol-4-yl)-4-morpholinothieno[3,2-d]pyrimidin-6-yl)methyl)-1-(2-methoxyethyl)-N-methylpiperidin-4-amine |
| 45. | 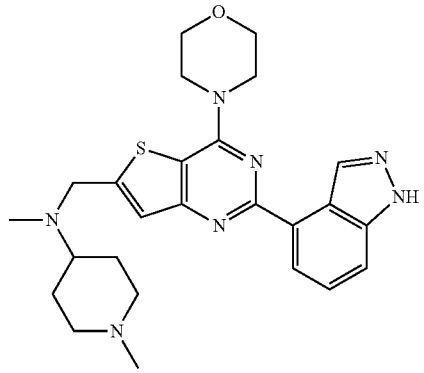 [SMILES: CN1CCC(N(C)Cc2cc3nc(-c4cccc5[nH]ncc45)nc(N4CCOCC4)c3s2)CC1] | N-((2-(1H-indazol-4-yl)-4-morpholinothieno[3,2-d]pyrimidin-6-yl)methyl)-N,1-dimethylpiperidin-4-amine |

TABLE 1a-continued

| Compound No. | Structure | Name |
|---|---|---|
| 46. | 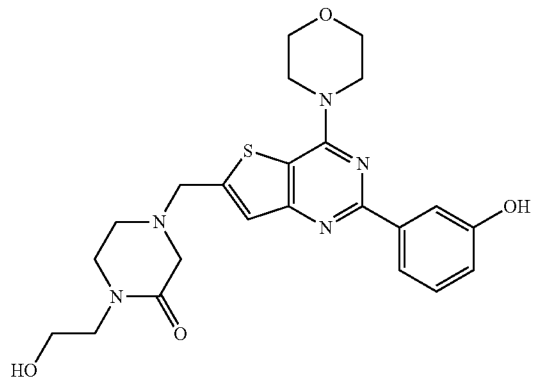 [SMILES: O=C1CN(Cc2cc3nc(-c4cccc(O)c4)nc(N4CCOCC4)c3s2)CCN1CCO] | 1-(2-hydroxyethyl)-4-((2-(3-hydroxyphenyl)-4-morpholinothieno[3,2-d]pyrimidin-6-yl)methyl)piperazin-2-one |
| 47. | 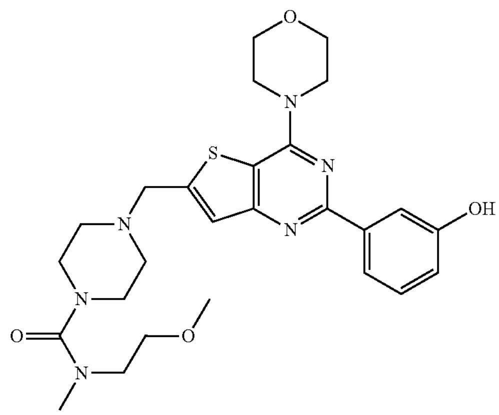 [SMILES: COCCN(C)C(=O)N1CCN(Cc2cc3nc(-c4cccc(O)c4)nc(N4CCOCC4)c3s2)CC1] | 4-((2-(3-hydroxyphenyl)-4-morpholinothieno[3,2-d]pyrimidin-6-yl)methyl)-N-(2-methoxyethyl)-N-methylpiperazine-1-carboxamide |
| 48. | 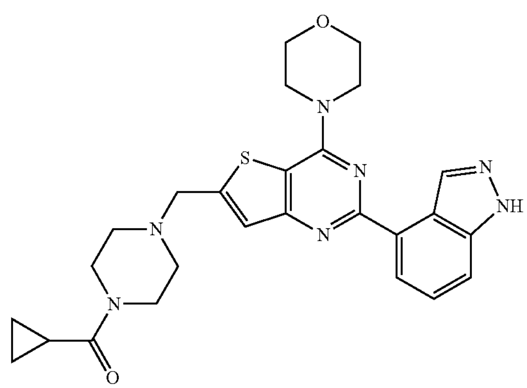 [SMILES: O=C(C1CC1)N1CCN(Cc2cc3nc(-c4cccc5[nH]ncc45)nc(N4CCOCC4)c3s2)CC1] | (4-((2-(1H-indazol-4-yl)-4-morpholinothieno[3,2-d]pyrimidin-6-yl)methyl)piperazin-1-yl)(cyclopropyl)methanone |
| 49. | 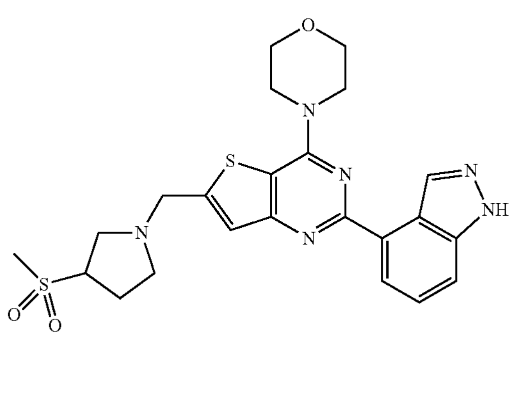 [SMILES: CS(=O)(=O)C1CCN(Cc2cc3nc(-c4cccc5[nH]ncc45)nc(N4CCOCC4)c3s2)C1] | 2-(1H-indazol-4-yl)-6-((3-(methylsulfonyl)pyrrolidin-1-yl)methyl)-4-morpholinothieno[3,2-d]pyrimidine |

TABLE 1a-continued

| Compound No. | Structure | Name |
|---|---|---|
| 50. | 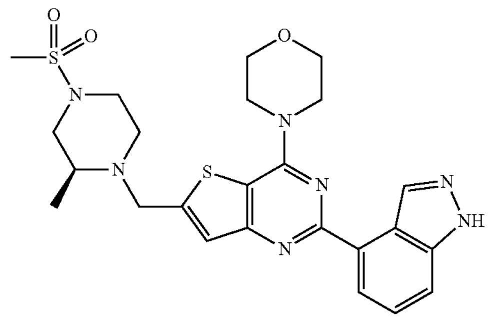 [SMILES: C[C@H]1CN(S(C)(=O)=O)CCN1Cc1cc2nc(-c3cccc4[nH]ncc34)nc(N3CCOCC3)c2s1] | 2-(1H-indazol-4-yl)-6-(((S)-2-methyl-4-methylsulfonylpiperazin-1-yl)methyl)-4-morpholinothieno[3,2-d]pyrimidine |
| 51. | 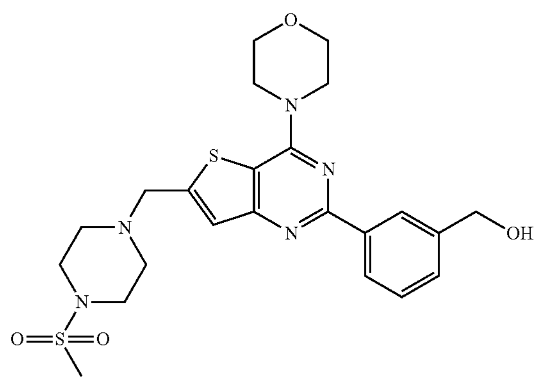 [SMILES: CS(=O)(=O)N1CCN(Cc2cc3nc(-c4cccc(CO)c4)nc(N4CCOCC4)c3s2)CC1] | (3-(6-((4-methylsulfonylpiperazin-1-yl)methyl)-4-morpholinothieno[3,2-d]pyrimidin-2-yl)phenyl)methanol |
| 52. | 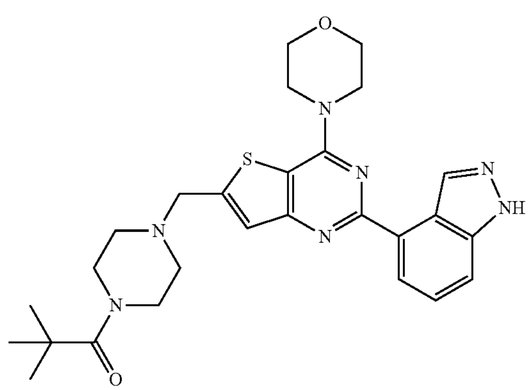 [SMILES: CC(C)(C)C(=O)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)-2,2-dimethylpropan-1-one |
| 53. | 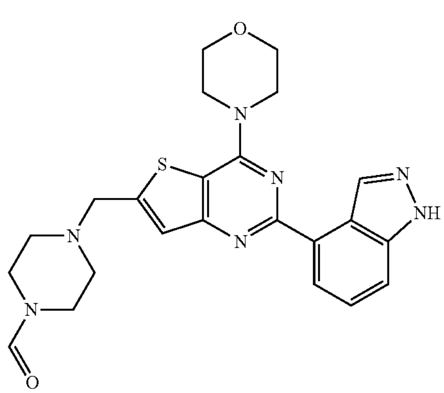 [SMILES: O=CN1CCN(Cc2cc3nc(-c4cccc5[nH]ncc45)nc(N4CCOCC4)c3s2)CC1] | 4-((2-(1H-indazol-4-yl)-4-morpholinothieno[3,2-d]pyrimidin-6-yl)methyl)piperazine-1-carbaldehyde |

TABLE 1a-continued

| Compound No. | Structure | Name |
|---|---|---|
| 54. | 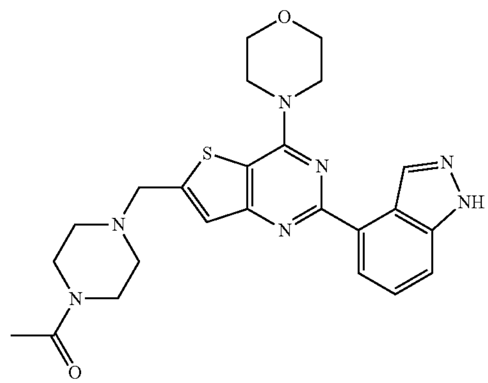 [SMILES: CC(=O)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)ethanone |
| 55. | 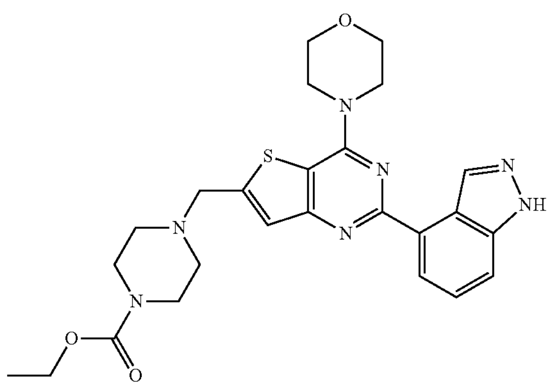 [SMILES: CCOC(=O)N1CCN(Cc2cc3nc(-c4cccc5[nH]ncc45)nc(N4CCOCC4)c3s2)CC1] | ethyl 4-((2-(1H-indazol-4-yl)-4-morpholinothieno[3,2-d]pyrimidin-6-yl)methyl)piperazine-1-carboxylate |
| 56. | 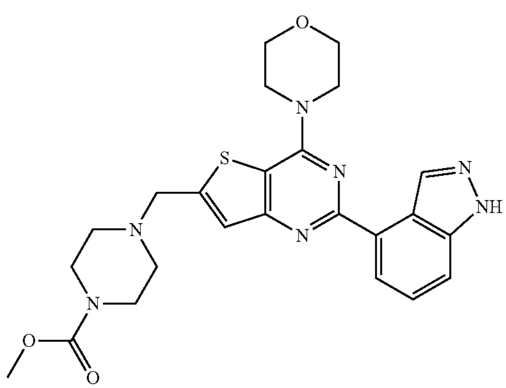 [SMILES: COC(=O)N1CCN(Cc2cc3nc(-c4cccc5[nH]ncc45)nc(N4CCOCC4)c3s2)CC1] | methyl 4-((2-(1H-indazol-4-yl)-4-morpholinothieno[3,2-d]pyrimidin-6-yl)methyl)piperazine-1-carboxylate |
| 57. | 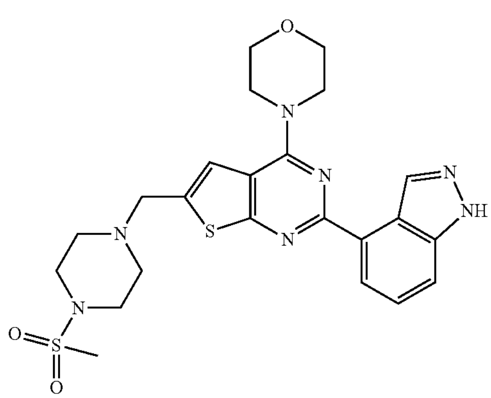 [SMILES: CS(=O)(=O)N1CCN(Cc2cc3c(N4CCOCC4)nc(-c4cccc5[nH]ncc45)nc3s2)CC1] | 2-(1H-indazol-4-yl)-6-((4-methylsulfonylpiperazin-1-yl)methyl)-4-morpholinothieno[2,3-d]pyrimidine |

TABLE 1a-continued

| Compound No. | Structure | Name |
|---|---|---|
| 58. | 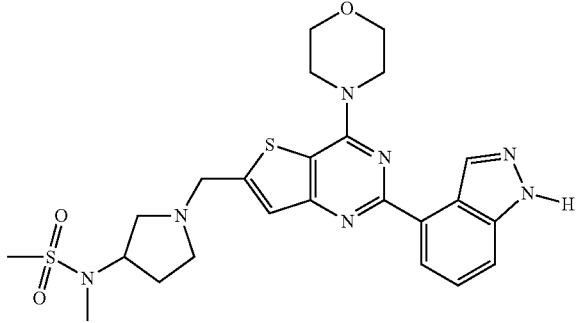 [SMILES: CN(C1CCN(Cc2cc3nc(-c4cccc5[nH]ncc45)nc(N4CCOCC4)c3s2)C1)S(C)(=O)=O] | 1-((2-(1H-indazol-4-yl)-4-morpholinothieno[3,2-d]pyrimidin-6-yl)methyl)-N-methyl-N-methylsulfonylpyrrolidin-3-amine |
| 59. | 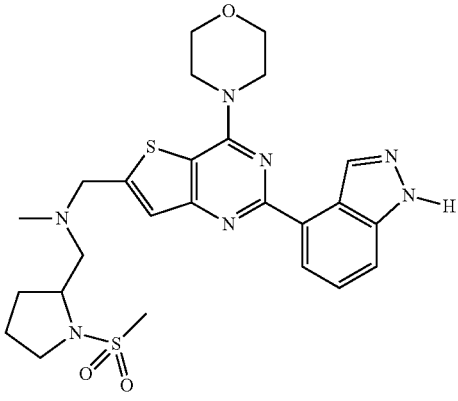 [SMILES: CN(Cc1cc2nc(-c3cccc4[nH]ncc34)nc(N3CCOCC3)c2s1)CC1CCCN1S(C)(=O)=O] | N-((2-(1H-indazol-4-yl)-4-morpholinothieno[3,2-d]pyrimidin-6-yl)methyl)-N-methyl(1-methylsulfonylpyrrolidin-2-yl)methanamine |
| 60. | 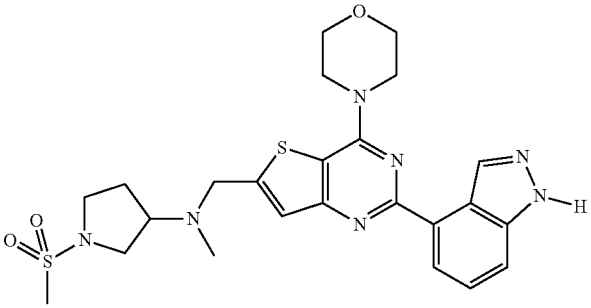 [SMILES: CN(Cc1cc2nc(-c3cccc4[nH]ncc34)nc(N3CCOCC3)c2s1)C1CCN(S(C)(=O)=O)C1] | N-((2-(1H-indazol-4-yl)-4-morpholinothieno[3,2-d]pyrimidin-6-yl)methyl)-N-methyl-(1-methylsulfonylpyrrolidin)-3-amine |
| 61. | 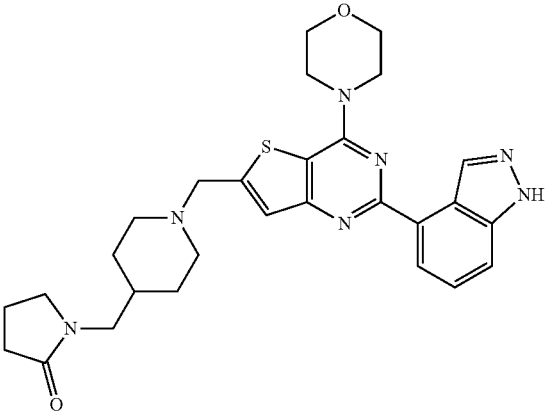 [SMILES: O=C1CCCN1CC1CCN(Cc2cc3nc(-c4cccc5[nH]ncc45)nc(N4CCOCC4)c3s2)CC1] | 1-((1-((2-(1H-indazol-4-yl)-4-morpholinothieno[3,2-d]pyrimidin-6-yl)methyl)piperidin-4-yl)methyl)pyrrolidin-2-one |

TABLE 1a-continued

| Compound No. | Structure | Name |
|---|---|---|
| 62. | 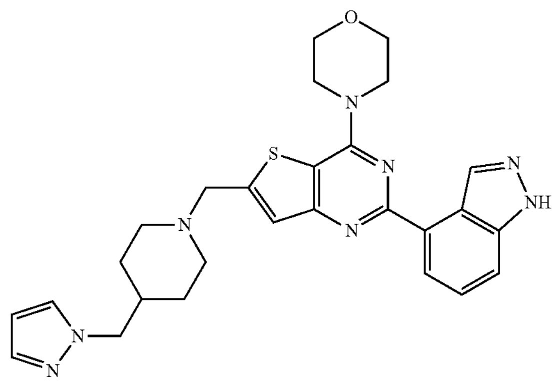 [SMILES: c1cc(-c2nc(N3CCOCC3)c3sc(CN4CCC(Cn5cccn5)CC4)cc3n2)c2cn[nH]c2c1] | 6-((4-((1H-pyrazol-1-yl)methyl)piperidin-1-yl)methyl)-2-(1H-indazol-4-yl)-4-morpholinothieno[3,2-d]pyrimidine |
| 63. | 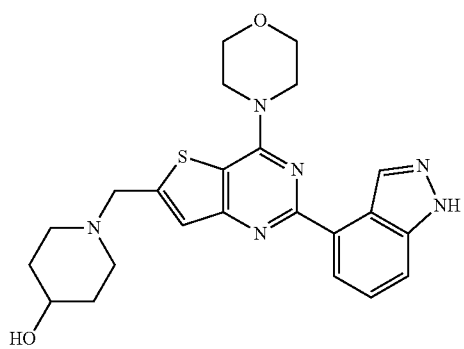 [SMILES: OC1CCN(Cc2cc3nc(-c4cccc5[nH]ncc45)nc(N4CCOCC4)c3s2)CC1] | 1-((2-(1H-indazol-4-yl)-4-morpholinothieno[3,2-d]pyrimidin-6-yl)methyl)piperidin-4-ol |
| 64. | 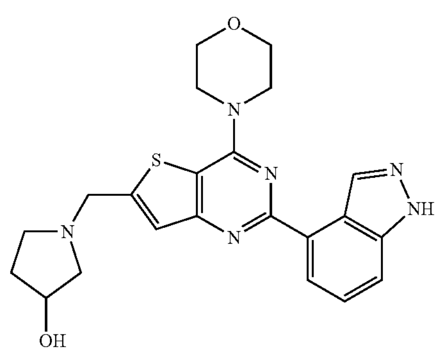 [SMILES: OC1CCN(Cc2cc3nc(-c4cccc5[nH]ncc45)nc(N4CCOCC4)c3s2)C1] | 1-((2-(1H-indazol-4-yl)-4-morpholinothieno[3,2-d]pyrimidin-6-yl)methyl)pyrrolidin-3-ol |
| 65. | 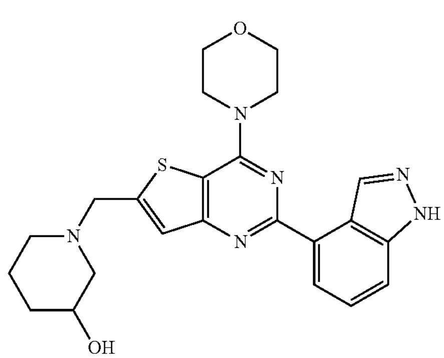 [SMILES: OC1CCCN(Cc2cc3nc(-c4cccc5[nH]ncc45)nc(N4CCOCC4)c3s2)C1] | 1-((2-(1H-indazol-4-yl)-4-morpholinothieno[3,2-d]pyrimidin-6-yl)methyl)piperidin-3-ol |

TABLE 1a-continued

| Compound No. | Structure | Name |
|---|---|---|
| 66. | 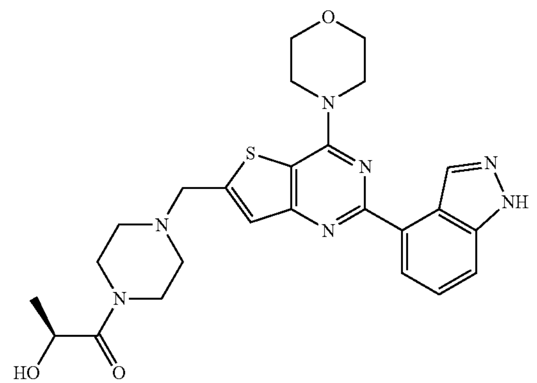 [SMILES: C[C@H](O)C(=O)N1CCN(Cc2cc3nc(-c4cccc5[nH]ncc45)nc(N4CCOCC4)c3s2)CC1] | (S)-1-(4-((2-(1H-indazol-4-yl)-4-morpholinothieno[3,2-d]pyrimidin-6-yl)methyl)piperazin-1-yl)-2-hydroxypropan-1-one |
| 67. | 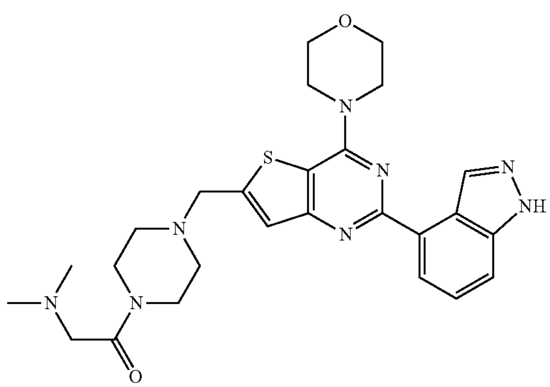 [SMILES: CN(C)CC(=O)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)-2-(dimethylamino)ethanone |
| 68. | 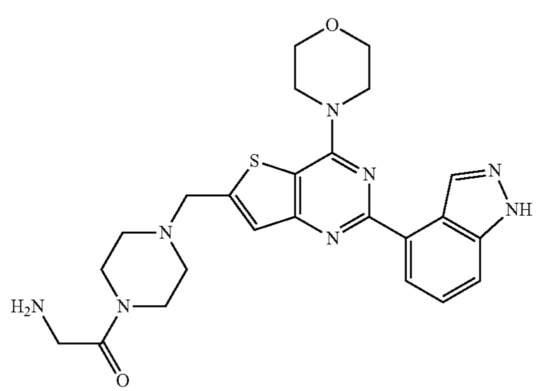 [SMILES: NCC(=O)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)-2-aminoethanone |
| 69. | 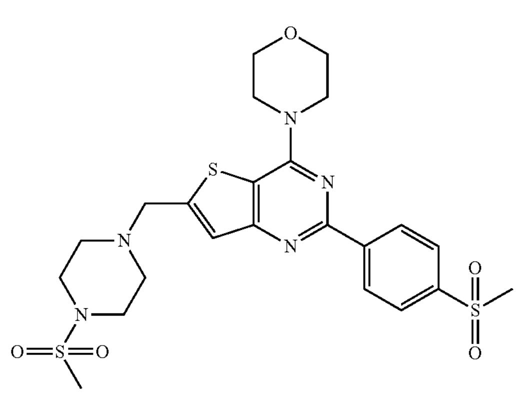 [SMILES: CS(=O)(=O)c1ccc(-c2nc(N3CCOCC3)c3sc(CN4CCN(S(C)(=O)=O)CC4)cc3n2)cc1] | 6-((4-methylsulfonylpiperazin-1-yl)methyl)-2-(4-(methylsulfonyl)phenyl)-4-morpholinothieno[3,2-d]pyrimidine |

TABLE 1a-continued

| Compound No. | Structure | Name |
|---|---|---|
| 70. | 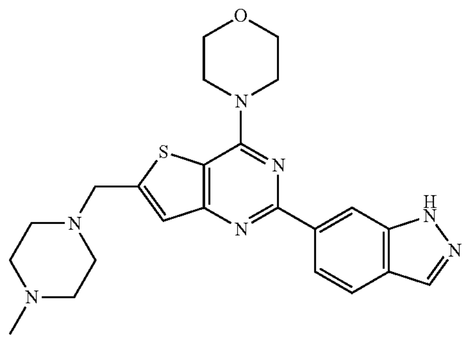 [SMILES: CN1CCN(Cc2cc3nc(-c4ccc5cn[nH]c5c4)nc(N4CCOCC4)c3s2)CC1] | 2-(1H-indazol-6-yl)-6-((4-methylpiperazin-1-yl)methyl)-4-morpholmothieno[3,2-d]pyrimidine |
| 71. | 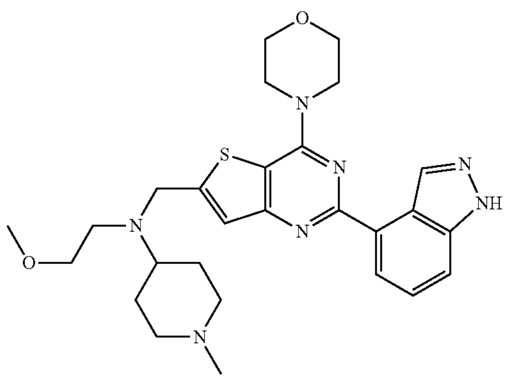 [SMILES: COCCN(Cc1cc2nc(-c3cccc4[nH]ncc34)nc(N3CCOCC3)c2s1)C1CCN(C)CC1] | N-((2-(1H-indazol-4-yl)-4-morpholinothieno[3,2-d]pyrimidin-6-yl)methyl)-N-(2-methoxyethyl)-1-methylpiperidin-4-amine |
| 72. | 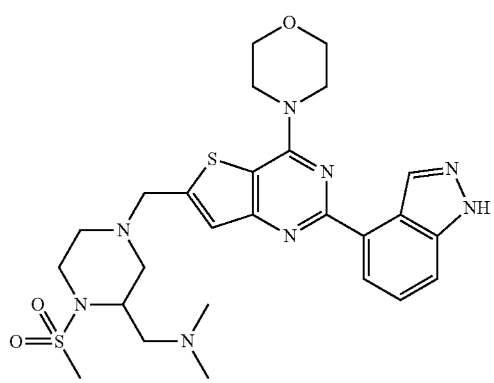 [SMILES: CN(C)CC1CN(Cc2cc3nc(-c4cccc5[nH]ncc45)nc(N4CCOCC4)c3s2)CCN1S(C)(=O)=O] | (4-((2-(1H-indazol-4-yl)-4-morpholinothieno[3,2-d]pyrimidin-6-yl)methyl)-1-methylsulfonylpiperazin-2-yl)-N,N-dimethylmethanamine |
| 73. | 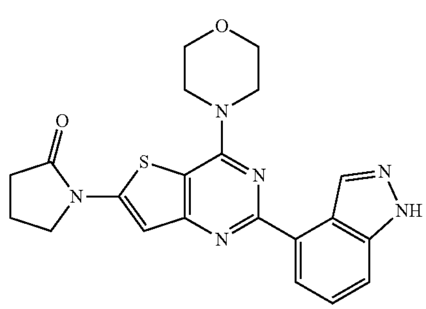 [SMILES: O=C1CCCN1c1cc2nc(-c3cccc4[nH]ncc34)nc(N3CCOCC3)c2s1] | 1-(2-(1H-indazol-4-yl)-4-morpholinothieno[3,2-d]pyrimidin-6-yl)pyrrolidin-2-one |

TABLE 1a-continued

| Compound No. | Structure | Name |
|---|---|---|
| 74. | 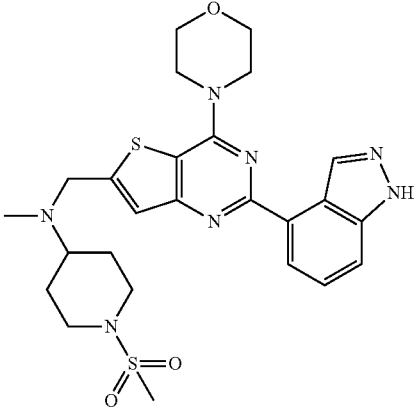 [SMILES: CN(Cc1cc2nc(-c3cccc4[nH]ncc34)nc(N3CCOCC3)c2s1)C1CCN(S(C)(=O)=O)CC1] | N-((2-(1H-indazol-4-yl)-4-morpholinothieno[3,2-d]pyrimidin-6-yl)methyl)-N,1-dimethylpiperidin-4-amine |
| 75. | 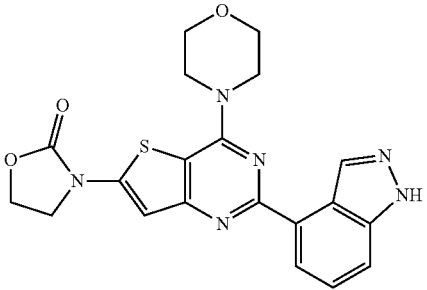 [SMILES: O=C1OCCN1c1cc2nc(-c3cccc4[nH]ncc34)nc(N3CCOCC3)c2s1] | 3-(2-(1H-indazol-4-yl)-4-morpholinothieno[3,2-d]pyrimidin-6-yl)oxazolidin-2-one |
| 76. | 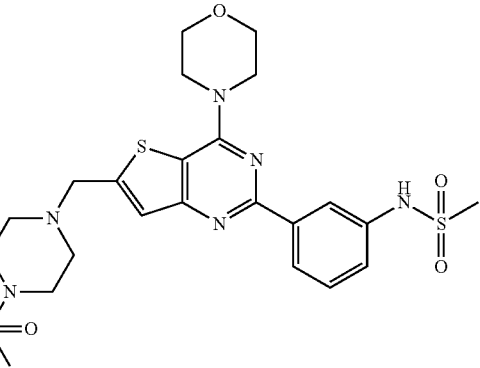 | 3-(6-((4-methylsulfonylpiperazin-1-yl)methyl)-4-morpholinothieno[3,2-d]pyrimidin-2-yl)benzenemethylsulfonylamine |
| 77. | 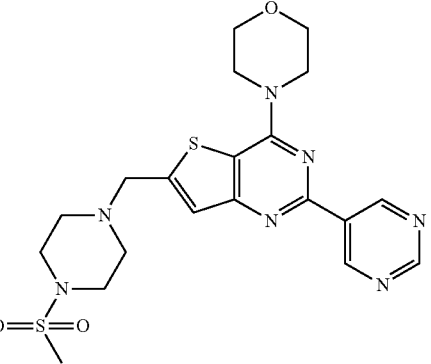 | 6-((4-methylsulfonylpiperazin-1-yl)methyl)-4-morpholino-2-(pyrimidin-5-yl)thieno[3,2-d]pyrimidine |

TABLE 1a-continued

| Compound No. | Structure | Name |
|---|---|---|
| 78. | 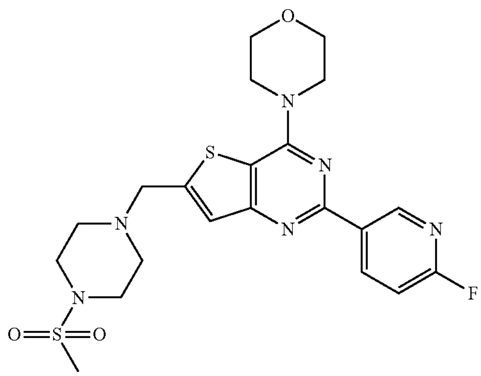 [SMILES: CS(=O)(=O)N1CCN(Cc2cc3nc(-c4ccc(F)nc4)nc(N4CCOCC4)c3s2)CC1] | 2-(6-fluoropyridin-3-yl)-6-((4-methylsulfonylpiperazin-1-yl)methyl)-4-morpholinothieno[3,2-d]pyrimidine |
| 79. | 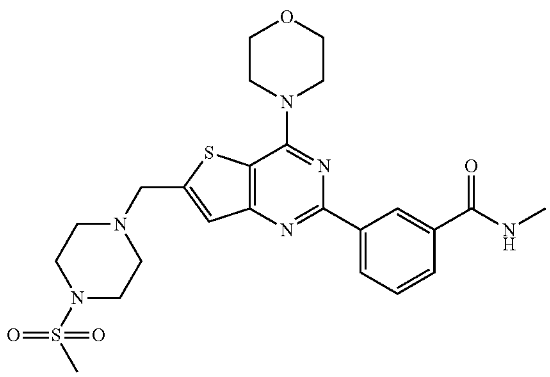 [SMILES: CNC(=O)c1cccc(-c2nc(N3CCOCC3)c3sc(CN4CCN(S(C)(=O)=O)CC4)cc3n2)c1] | N-methyl-3-(6-((4-melhylsulfonylpiperazin-1-yl)methyl)-4-morpholinothieno[3,2-d]pyrimidin-2-yl)benzamide |
| 80. | 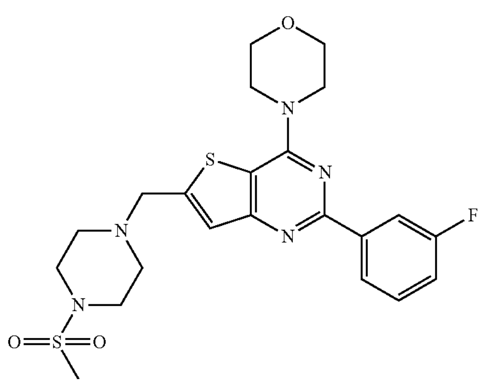 [SMILES: CS(=O)(=O)N1CCN(Cc2cc3nc(-c4cccc(F)c4)nc(N4CCOCC4)c3s2)CC1] | 2-(3-fluorophenyl)-6-((4-methylpiperazin-1-yl)methyl)-4-morpholinothieno[3,2-d]pyrimidme |
| 81. | 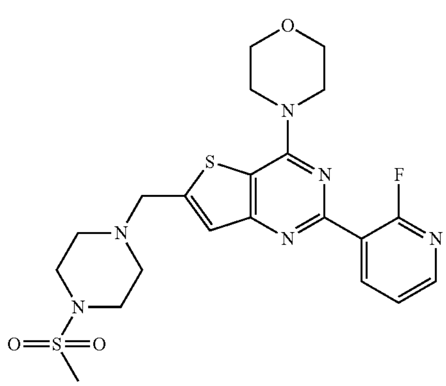 [SMILES: CS(=O)(=O)N1CCN(Cc2cc3nc(-c4cccnc4F)nc(N4CCOCC4)c3s2)CC1] | 2-(2-fluoropyridin-3-yl)-6-((4-methylsulfonylpiperazin-1-yl)methyl)-4-morpholinothieno[3,2-d]pyrimidine |

TABLE 1a-continued

| Compound No. | Structure | Name |
|---|---|---|
| 82. | 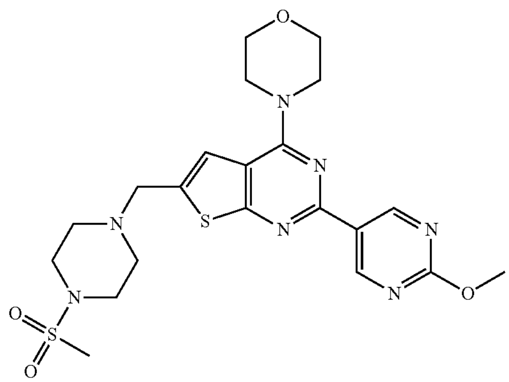 [SMILES: COc1ncc(-c2nc(N3CCOCC3)c3cc(CN4CCN(S(C)(=O)=O)CC4)sc3n2)cn1] | 6-(4-Methanesulfonyl-piperazin-1-ylmethyl)-2-(2-methoxy-pyrimidin-5-yl)-4-morpholin-4-yl-thieno[2,3-d]pyrimidine |
| 83. | 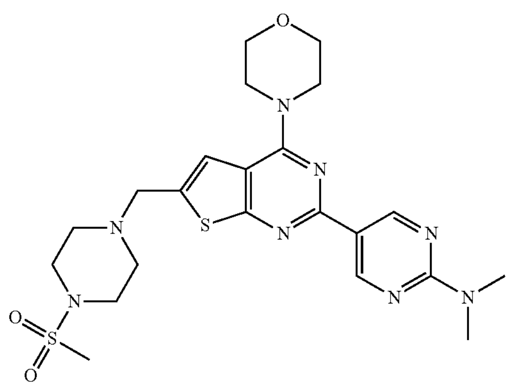 [SMILES: CN(C)c1ncc(-c2nc(N3CCOCC3)c3cc(CN4CCN(S(C)(=O)=O)CC4)sc3n2)cn1] | {5-[6-(4-Methanesulfonyl-piperazin-1-ylmethyl)-4-morpholin-4-yl-thieno[2,3-d]pyrimidin-2-yl]-pyrimidin-2-yl}-dimethyl-amine |
| 84. | 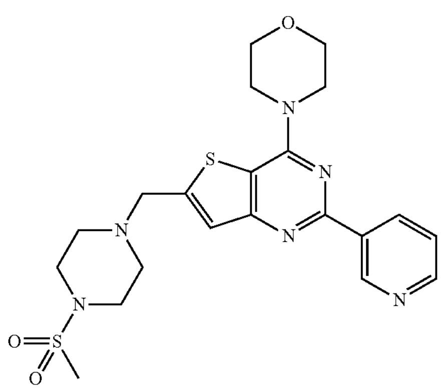 [SMILES: CS(=O)(=O)N1CCN(Cc2cc3nc(-c4cccnc4)nc(N4CCOCC4)c3s2)CC1] | 6-(4-Methanesulfonyl-piperazin-1-ylmethyl)-4-morpholin-4-yl-2-pyridin-3-yl-thieno[3,2-d]pyrimidine |
| 85. | 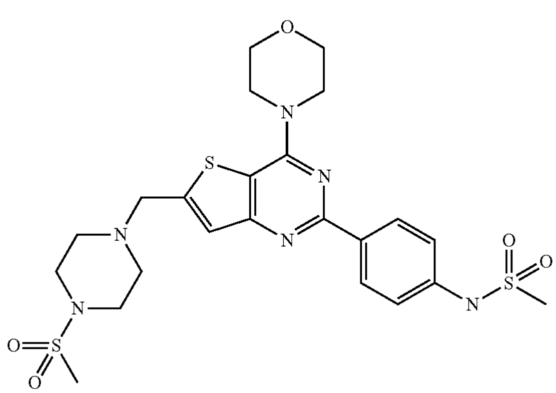 [SMILES: CS(=O)(=O)Nc1ccc(-c2nc(N3CCOCC3)c3sc(CN4CCN(S(C)(=O)=O)CC4)cc3n2)cc1] | N-{4-[6-(4-Methanesulfonyl-piperazin-1-ylmethyl)-4-morpholin-4-yl-thieno[3,2-d]pyrimidin-2-yl]-phenyl}-methanesulfonamide |

TABLE 1a-continued

| Compound No. | Structure | Name |
| --- | --- | --- |
| 86. | 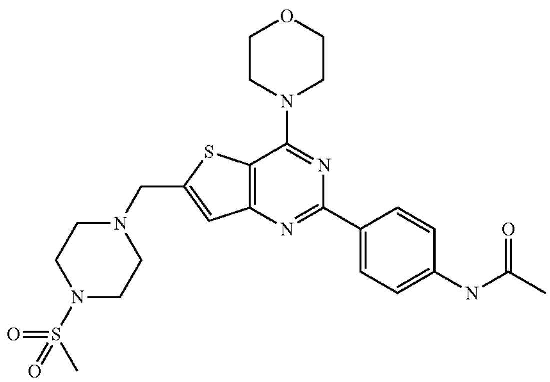 [SMILES: CC(=O)Nc1ccc(-c2nc(N3CCOCC3)c3sc(CN4CCN(S(C)(=O)=O)CC4)cc3n2)cc1] | N-4-[6-(4-Methanesulfonyl-piperazin-1-ylmethyl)-4-morpholin-4-yl-thieno[3,2-d]pyrimidin-2-yl]-phenyl}-acetamide |
| 87. | 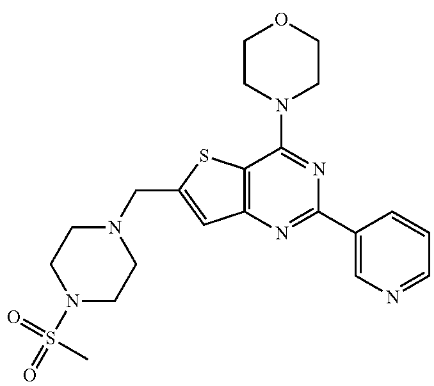 [SMILES: CS(=O)(=O)N1CCN(Cc2cc3nc(-c4cccnc4)nc(N4CCOCC4)c3s2)CC1] | 6-(4-Methanesulfonyl-piperazin-1-ylmethyl)-4-morpholin-4-yl-2-pyridin-3-yl-thieno[2,3-d]pyrimidine |
| 88. | 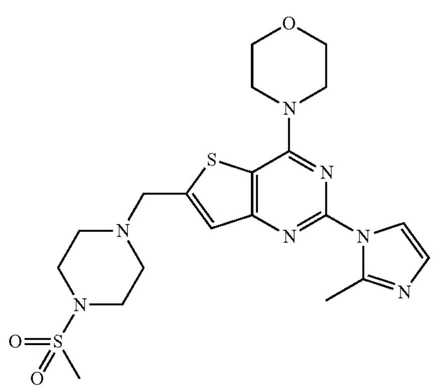 [SMILES: Cc1nccn1-c1nc(N2CCOCC2)c2sc(CN3CCN(S(C)(=O)=O)CC3)cc2n1] | 6-(4-Methanesulfonyl-piperazin-1-ylmethyl)-2-(2-methyl-imidazol-1-yl)-4-morpholin-4-yl-thieno[3,2-d]pyrimidine |
| 89. | 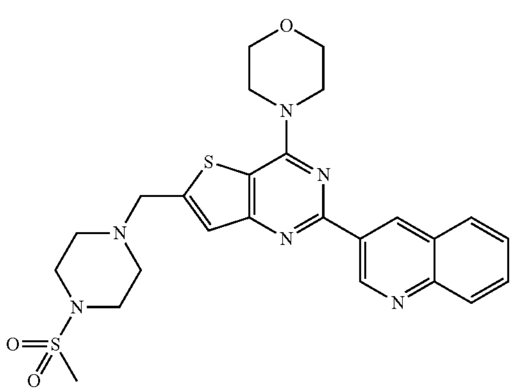 [SMILES: CS(=O)(=O)N1CCN(Cc2cc3nc(-c4cnc5ccccc5c4)nc(N4CCOCC4)c3s2)CC1] | 3-[6-(4-Methanesulfonyl-piperazin-1-ylmethyl)-4-morpholin-yl-thieno[3,2-d]pyrimidin-2-yl]-quinoline |

TABLE 1a-continued

| Compound No. | Structure | Name |
|---|---|---|
| 90. | 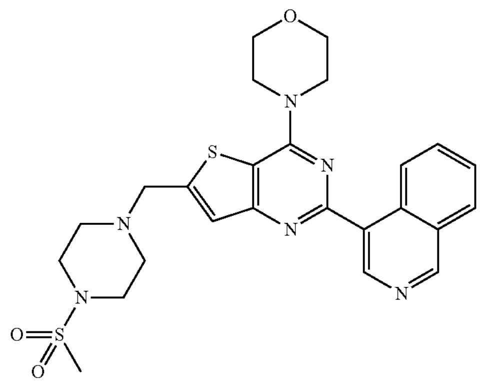 [SMILES: CS(=O)(=O)N1CCN(Cc2cc3nc(-c4cncc5ccccc45)nc(N4CCOCC4)c3s2)CC1] | 4-[6-(4-Methanesulfonyl-piperazin-1-ylmethyl)-4-morpholin-4-yl-thieno[3,2-d]pyrimidin-2-yl]-isoquinoline |
| 91. | 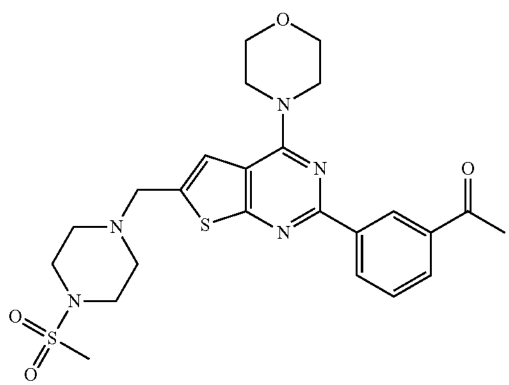 [SMILES: CC(=O)c1cccc(-c2nc(N3CCOCC3)c3cc(CN4CCN(S(C)(=O)=O)CC4)sc3n2)c1] | 1-{3-[6-(4-Methanesulfonyl-piperazin-1-ylmethyl)-4-morpholin-4-yl-thieno[2,3-d]pyrimidin-2-yl]-phenyl}-ethanone |
| 92. | 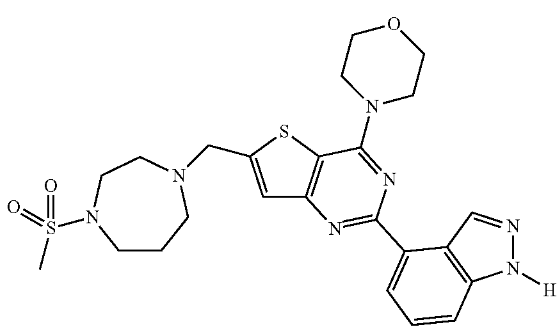 [SMILES: CS(=O)(=O)N1CCCN(Cc2cc3nc(-c4cccc5[nH]ncc45)nc(N4CCOCC4)c3s2)CC1] | 2-(1H-Indazol-4-yl)-6-(4-methanesulfonyl-[1,4]diazepan-1-ylmethyl)-4-morpholin-4-yl-thieno[3,2-d]pyrimidine |
| 93. | 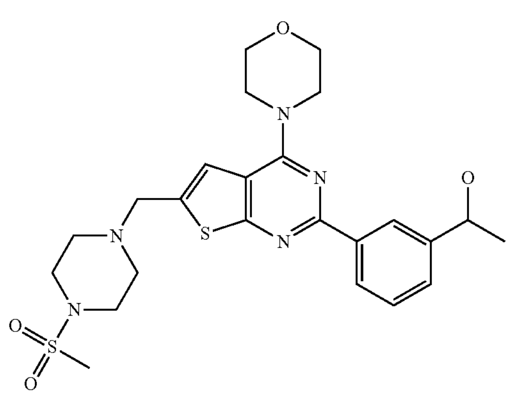 [SMILES: CC(O)c1cccc(-c2nc(N3CCOCC3)c3cc(CN4CCN(S(C)(=O)=O)CC4)sc3n2)c1] | 1-{3-[6-(4-Methanesulfonyl-piperazin-1-ylmethyl)-4-morpholin-4-yl-thieno[2,3-d]pyrimidin-2-yl]-phenyl}-ethanol |

TABLE 1a-continued

| Compound No. | Structure | Name |
|---|---|---|
| 94. | 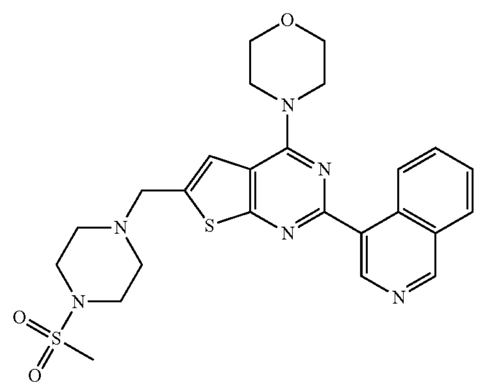 [SMILES: CS(=O)(=O)N1CCN(Cc2cc3c(N4CCOCC4)nc(-c4cncc5ccccc45)nc3s2)CC1] | 4-[6-(4-Methanesulfonyl-piperazin-1-ylmethyl)-4-morpholin-4-yl-thieno[2,3-d]pyrimidin-2-yl]-isoquinoline |
| 95. | 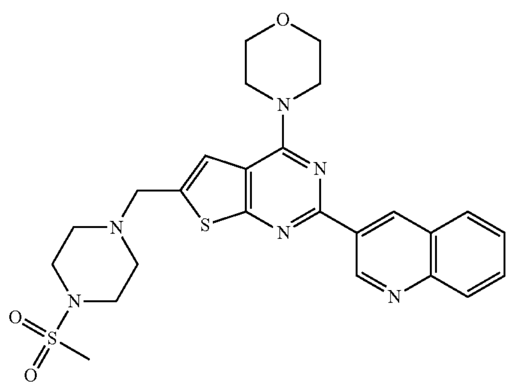 [SMILES: CS(=O)(=O)N1CCN(Cc2cc3c(N4CCOCC4)nc(-c4cnc5ccccc5c4)nc3s2)CC1] | 3-[6-(4-Methanesulfonyl-piperazin-1-ylmethyl)-4-morpholin-4-yl-thieno[2,3-d]pyrimidin-2-yl]-quinoline |
| 96. | 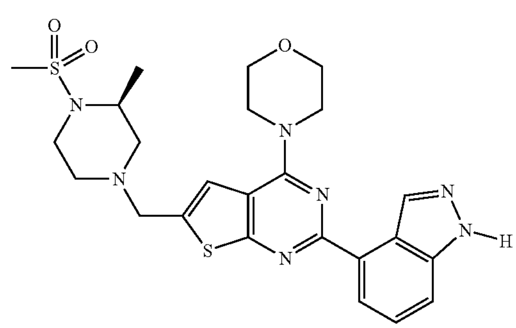 [SMILES: C[C@H]1CN(Cc2cc3c(N4CCOCC4)nc(-c4cccc5[nH]ncc45)nc3s2)CCN1S(C)(=O)=O] | 2-(1H-Indazol-4-yl)-6-((S)-4-methanesulfonyl-3-methyl-piperazin-1-ylmethyl)-4-morpholin-4-yl-thieno[2,3-d]pyrimidine |
| 97. | 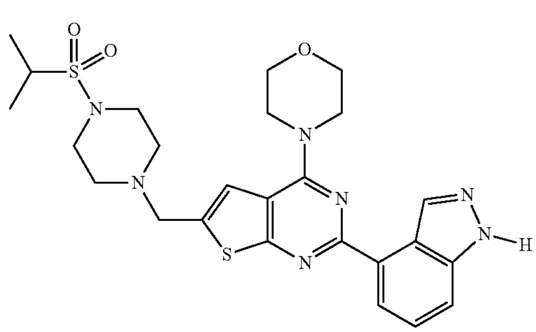 [SMILES: CC(C)S(=O)(=O)N1CCN(Cc2cc3c(N4CCOCC4)nc(-c4cccc5[nH]ncc45)nc3s2)CC1] | 2-(1H-Indazol-4-yl)-4-morpholin-4-yl-6-[4-(propane-2-sulfonyl)-piperazin-1-ylmethyl]-thieno[2,3-d]pyrimidine |

TABLE 1a-continued

| Compound No. | Structure | Name |
| --- | --- | --- |
| 98. | 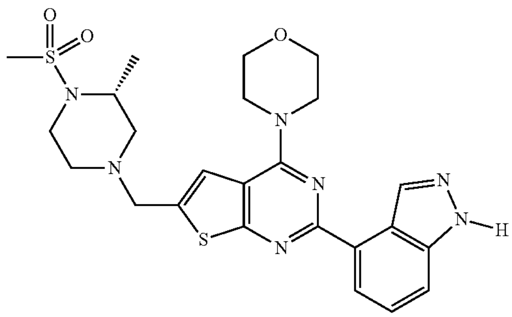 [SMILES: C[C@@H]1CN(Cc2cc3c(N4CCOCC4)nc(-c4cccc5[nH]ncc45)nc3s2)CCN1S(C)(=O)=O] | 2-(1H-Indazol-4-yl)-6-((R)-4-methanesulfonyl-3-methyl-piperazin-1-ylmethyl)-4-morpholin-4-yl-thieno[2,3-d]pyrimidine |
| 99. | 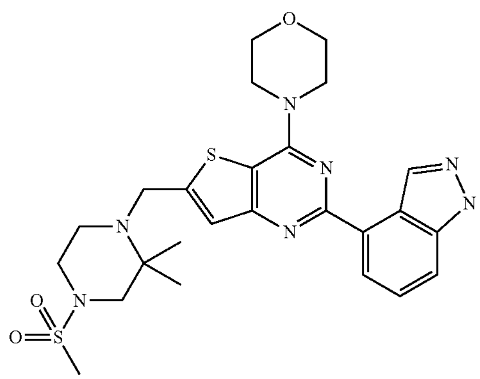 [SMILES: CC1(C)CN(S(C)(=O)=O)CCN1Cc1cc2nc(-c3cccc4[nH]ncc34)nc(N3CCOCC3)c2s1] | 2-(1H-Indazol-4-yl)-6-(4-methanesulfonyl-2,2-dimethyl-piperazin-1-ylmethyl)-4-morpholin-4-yl-thieno[3,2-d]pyrimidine |
| 100. | 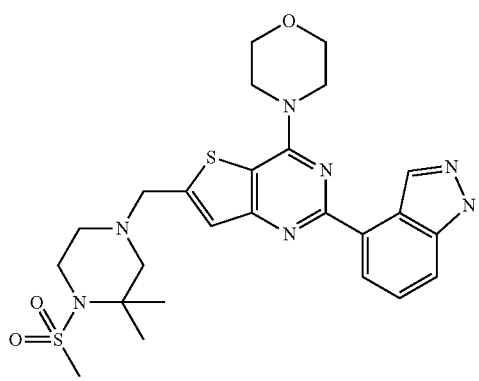 [SMILES: CC1(C)CN(Cc2cc3nc(-c4cccc5[nH]ncc45)nc(N4CCOCC4)c3s2)CCN1S(C)(=O)=O] | 2-(1H-Indazol-4-yl)-6-(4-methanesulfonyl-3,3-dimethyl-piperazin-1-ylmethyl)-4-morpholin-4-yl-thieno[3,2-d]pyrimidine |
| 101. | 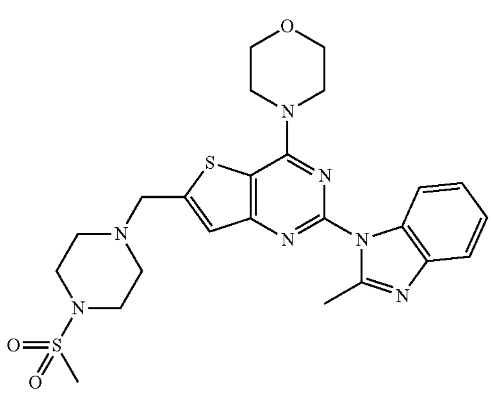 [SMILES: Cc1nc2ccccc2n1-c1nc(N2CCOCC2)c2sc(CN3CCN(S(C)(=O)=O)CC3)cc2n1] | 6-(4-Methanesulfonyl-piperazin-1-ylmethyl)-2-(2-methyl-benzoimidazol-1-yl)-4-morpholin-4-yl-thieno[3,2-d]pyrimidine |

TABLE 1a-continued

| Compound No. | Structure | Name |
|---|---|---|
| 102. | 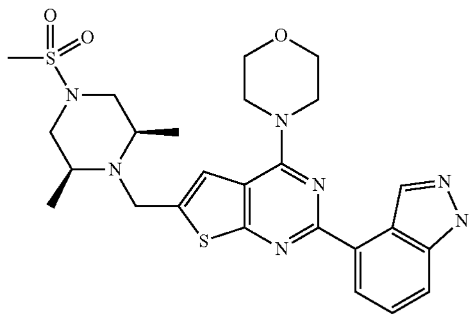 [SMILES: C[C@@H]1CN(S(C)(=O)=O)C[C@H](C)N1Cc1cc2c(N3CCOCC3)nc(-c3cccc4[nH]ncc34)nc2s1] | 2-(1H-Indazol-4-yl)-6-((2S,6R)-4-methanesulfonyl-2,6-dimethyl-piperazin-1-ylmethyl)-4-morpholin-4-yl-thieno[2,3-d]pyrimidine |
| 103 | 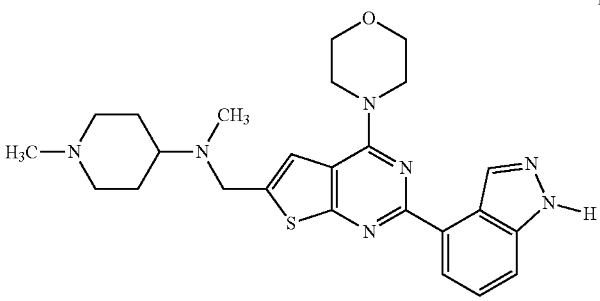 | [2-(1H-Indazol-4-yl)-4-morpholin-4-yl-thieno[2,3-d]pyrimidin-6-ylmethyl]-methyl-(1-methyl-piperidin-4-yl)-amine |
| 104 | 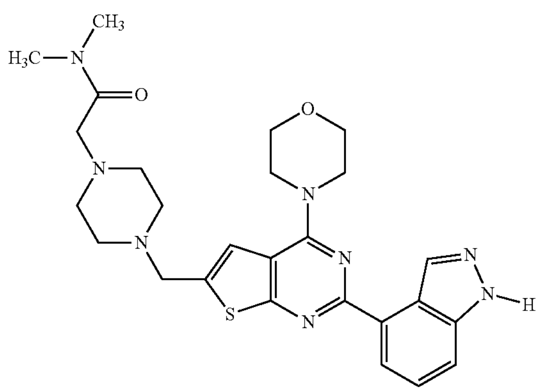 [SMILES: CN(C)C(=O)CN1CCN(Cc2cc3c(N4CCOCC4)nc(-c4cccc5[nH]ncc45)nc3s2)CC1] | 2-{4-[2-(1H-Indazol-4-yl)-4-morpholin-4-yl-thieno[2,3-d]pyrimidin-6-ylmethyl]-piperazin-1-yl}-N,N-dimethyl-acetamide |
| 105 | 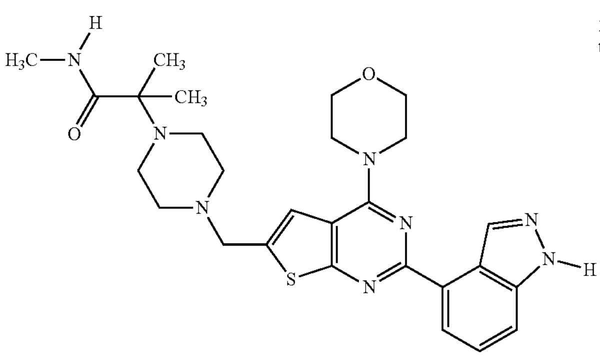 | 2-{4-[2-(1H-Indazol-4-yl)-4-morpholin-4-yl-thieno[2,3-d]pyrimidin-6-ylmethyl]-piperazin-1-yl}-N-methyl-isobutyramide |

TABLE 1a-continued

| Compound No. | Structure | Name |
| --- | --- | --- |
| 106 | 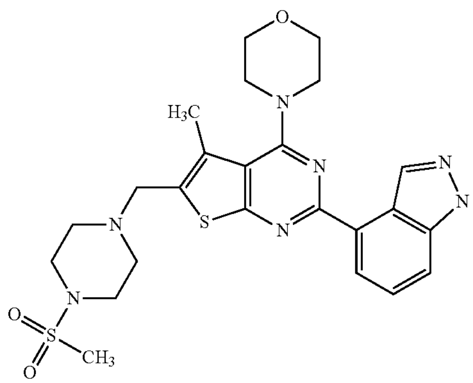 [SMILES: Cc1c(CN2CCN(S(C)(=O)=O)CC2)sc2nc(-c3cccc4[nH]ncc34)nc(N3CCOCC3)c12] | 2-(1H-Indazol-4-yl)-6-(4-methanesulfonyl-piperazin-1-ylmethyl)-5-methyl-4-morpholin-4-yl-thieno[2,3-d]pyrimidine |
| 107 | 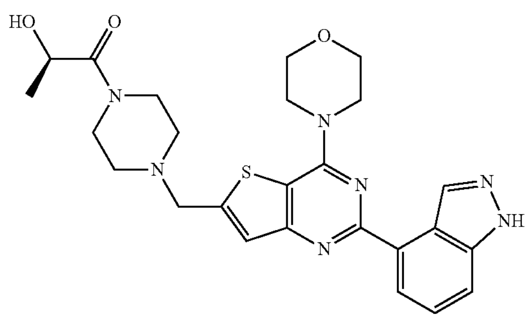 [SMILES: C[C@@H](O)C(=O)N1CCN(Cc2cc3nc(-c4cccc5[nH]ncc45)nc(N4CCOCC4)c3s2)CC1] | (R)-1-(4-((2-(1H-indazol-4-yl)-4-morpholinothieno[3,2-d]pyrimidin-6-yl)methyl)piperazin-1-yl)-2-hydroxypropan-1-one |
| 108 | 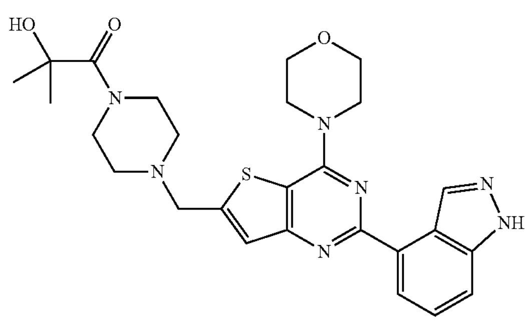 [SMILES: CC(C)(O)C(=O)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)-2-hydroxy-2-methylpropan-1-one |
| 109 | 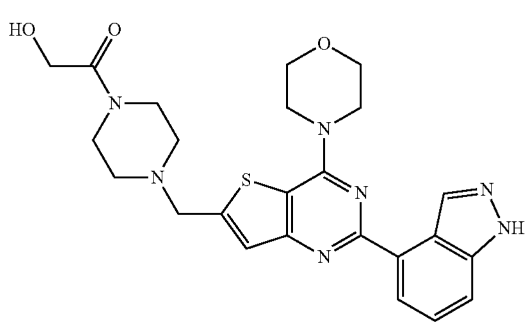 [SMILES: O=C(CO)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)-2-hydroxyethanone |

TABLE 1a-continued

| Compound No. | Structure | Name |
|---|---|---|
| 110 | 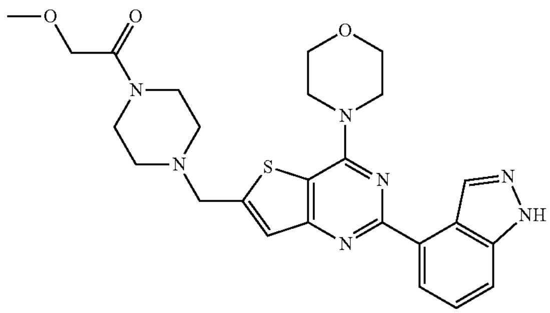 [SMILES: COCC(=O)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)-2-methoxyethanone |
| 111 | 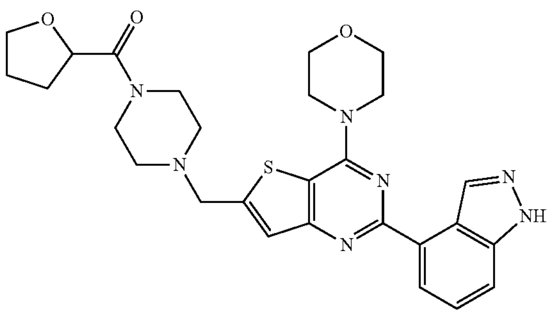 [SMILES: O=C(C1CCCO1)N1CCN(Cc2cc3nc(-c4cccc5[nH]ncc45)nc(N4CCOCC4)c3s2)CC1] | (4-((2-(1H-indazol-4-yl)-4-morpholinothieno[3,2-d]pyrimidin-6-yl)methyl)piperazin-1-yl)(tetrahydrofuran-2-yl)methanone |
| 112 | 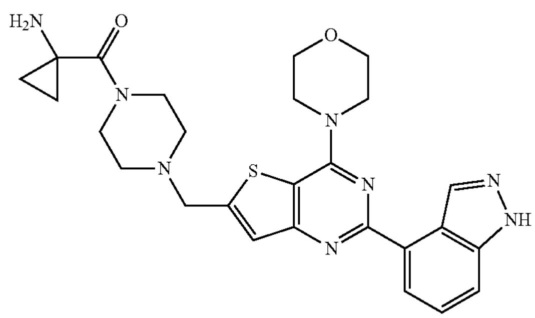 [SMILES: NC1(C(=O)N2CCN(Cc3cc4nc(-c5cccc6[nH]ncc56)nc(N5CCOCC5)c4s3)CC2)CC1] | (4-((2-(1H-indazol-4-yl)-4-morpholinothieno[3,2-d]pyrimidin-6-yl)methyl)piperazin-1-yl)(1-aminocyclopropyl)methanone |
| 113 | 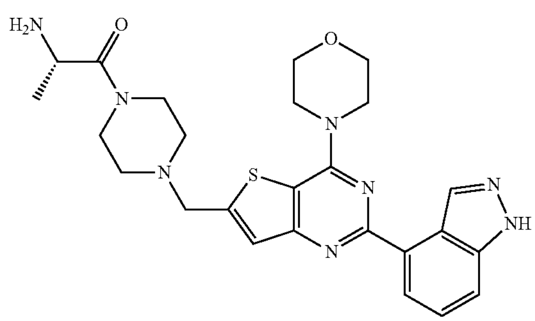 [SMILES: C[C@H](N)C(=O)N1CCN(Cc2cc3nc(-c4cccc5[nH]ncc45)nc(N4CCOCC4)c3s2)CC1] | (S)-1-(4-((2-(1H-indazol-4-yl)-4-morpholinothieno[3,2-d]pyrimidin-6-yl)methyl)piperazin-1-yl)-2-aminopropan-1-one |
| 114 | 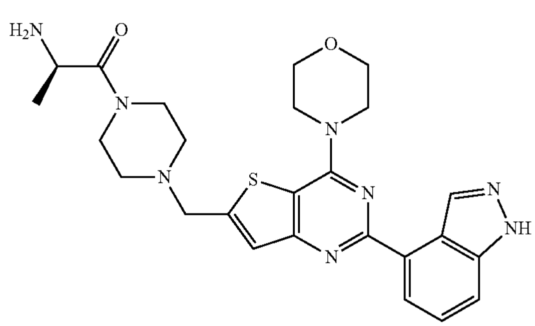 [SMILES: C[C@@H](N)C(=O)N1CCN(Cc2cc3nc(-c4cccc5[nH]ncc45)nc(N4CCOCC4)c3s2)CC1] | (R)-1-(4-((2-(1H-indazol-4-yl)-4-morpholinothieno[3,2-d]pyrimidin-6-yl)methyl)piperazin-1-yl)-2-aminopropan-1-one |

TABLE 1a-continued

| Compound No. | Structure | Name |
|---|---|---|
| 115 | 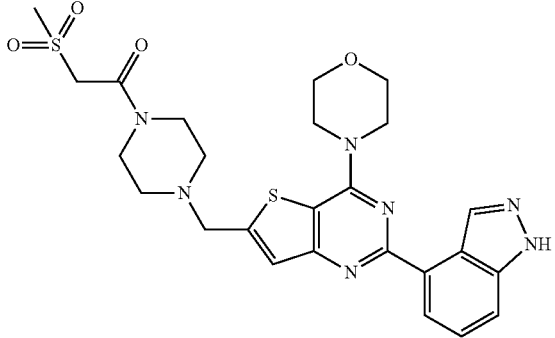 [SMILES: CS(=O)(=O)CC(=O)N1CCN(Cc2cc3nc(-c4cccc5[nH]ncc45)nc(N4CCOCC4)c3s2)CC1] | 1-(4-((2-(1H-indazol-4-yl)-4-morpholinothieno[3,2-d]pyrimidin-6-yl)methyl)piperazin-1-yl)-2-(methylsulfonyl)ethanone |
| 116 | 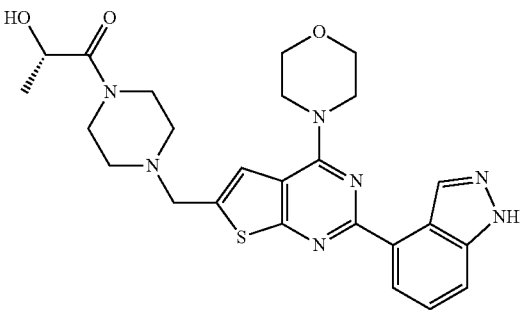 [SMILES: C[C@H](O)C(=O)N1CCN(Cc2cc3c(N4CCOCC4)nc(-c4cccc5[nH]ncc45)nc3s2)CC1] | (S)-1-(4-((2-(1H-indazol-4-yl)-4-morpholinothieno[2,3-d]pyrimidin-6-yl)methyl)piperazin-1-yl)-2-hydroxypropan-1-one |
| 117 | 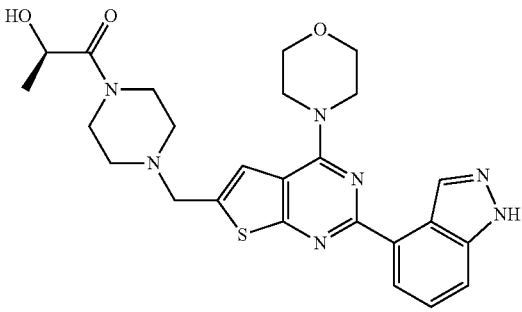 [SMILES: C[C@@H](O)C(=O)N1CCN(Cc2cc3c(N4CCOCC4)nc(-c4cccc5[nH]ncc45)nc3s2)CC1] | (R)-1-(4-((2-(1H-indazol-4-yl)-4-morpholinothieno[2,3-d]pyrimidin-6-yl)methyl)piperazin-1-yl)-2-hydroxypropan-1-one |
| 118 | 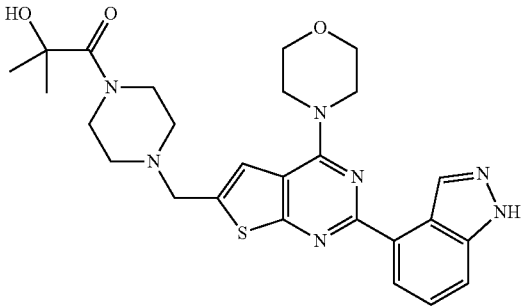 [SMILES: CC(C)(O)C(=O)N1CCN(Cc2cc3c(N4CCOCC4)nc(-c4cccc5[nH]ncc45)nc3s2)CC1] | 1-(4-((2-(1H-indazol-4-yl)-4-morpholinothieno[2,3-d]pyrimidin-6-yl)methyl)piperazin-1-yl)-2-hydroxy-2-methylpropan-1-one |

TABLE 1a-continued

| Compound No. | Structure | Name |
|---|---|---|
| 119 | 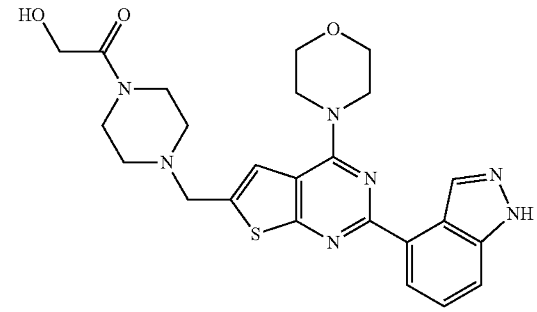 [SMILES: O=C(CO)N1CCN(Cc2cc3c(N4CCOCC4)nc(-c4cccc5[nH]ncc45)nc3s2)CC1] | 1-(4-((2-(1H-indazol-4-yl)-4-morpholinothieno[2,3-d]pyrimidin-6-yl)methyl)piperazin-1-yl)-2-hydroxyethanone |
| 120 | 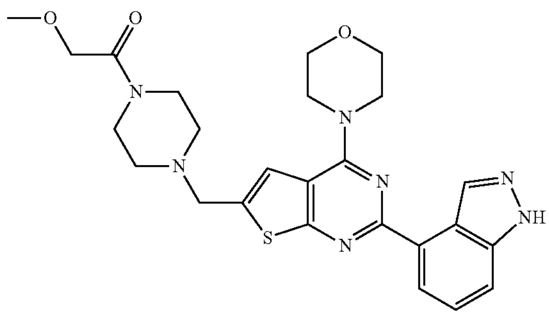 [SMILES: COCC(=O)N1CCN(Cc2cc3c(N4CCOCC4)nc(-c4cccc5[nH]ncc45)nc3s2)CC1] | 1-(4-((2-(1H-indazol-4-yl)-4-morpholinothieno[2,3-d]pyrimidin-6-yl)methyl)piperazin-1-yl)-2-methoxyethanone |
| 121 | 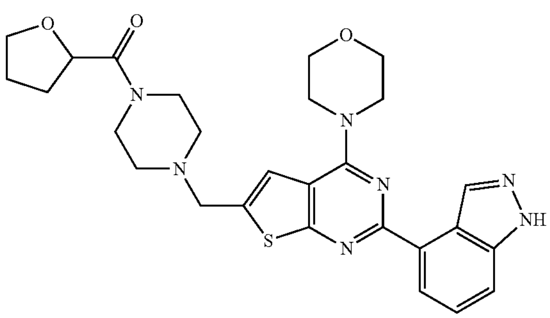 [SMILES: O=C(C1CCCO1)N1CCN(Cc2cc3c(N4CCOCC4)nc(-c4cccc5[nH]ncc45)nc3s2)CC1] | (4-((2-(1H-indazol-4-yl)-4-morpholinothieno[2,3-d]pyrimidin-6-yl)methyl)piperazin-1-yl)(tetrahydrofuran-2-yl)methanone |
| 122 | 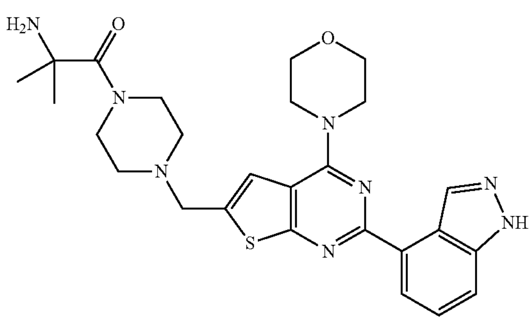 [SMILES: CC(C)(N)C(=O)N1CCN(Cc2cc3c(N4CCOCC4)nc(-c4cccc5[nH]ncc45)nc3s2)CC1] | 1-(4-((2-(1H-indazol-4-yl)-4-morpholinothieno[2,3-d]pyrimidin-6-yl)methyl)piperazin-1-yl)-2-amino-2-methylpropan-1-one |
| 123 | 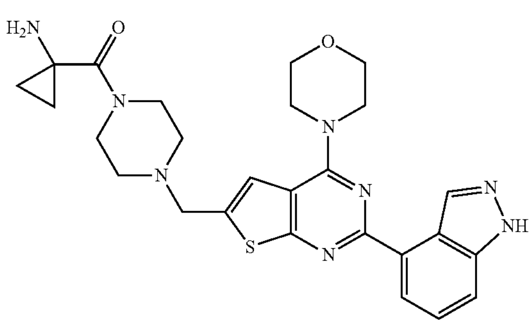 [SMILES: NC1(C(=O)N2CCN(Cc3cc4c(N5CCOCC5)nc(-c5cccc6[nH]ncc56)nc4s3)CC2)CC1] | (4-((2-(1H-indazol-4-yl)-4-morpholinothieno[2,3-d]pyrimidin-6-yl)methyl)piperazin-1-yl)(1-aminocyclopropyl)methanone |

TABLE 1a-continued

| Compound No. | Structure | Name |
|---|---|---|
| 124 | 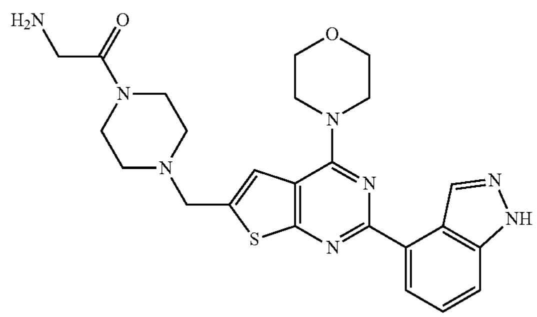 [SMILES: NCC(=O)N1CCN(Cc2cc3c(N4CCOCC4)nc(-c4cccc5[nH]ncc45)nc3s2)CC1] | 1-(4-((2-(1H-indazol-4-yl)-4-morpholinothieno[2,3-d]pyrimidin-6-yl)methyl)piperazin-1-yl)-2-aminoethanone |
| 125 | 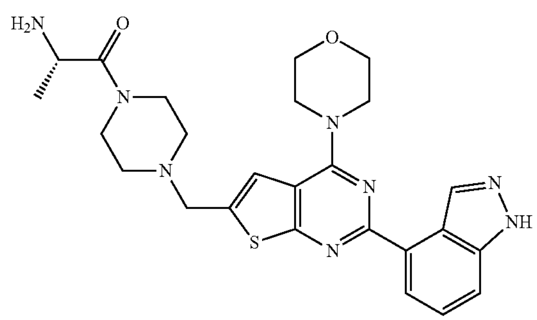 [SMILES: C[C@H](N)C(=O)N1CCN(Cc2cc3c(N4CCOCC4)nc(-c4cccc5[nH]ncc45)nc3s2)CC1] | (S)-1-(4-((2-(1H-indazol-4-yl)-4-morpholinothieno[2,3-d]pyrimidin-6-yl)methyl)piperazin-1-yl)-2-aminopropan-1-one |
| 126 | 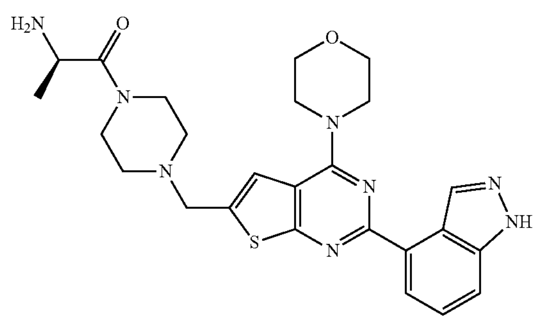 [SMILES: C[C@@H](N)C(=O)N1CCN(Cc2cc3c(N4CCOCC4)nc(-c4cccc5[nH]ncc45)nc3s2)CC1] | (R)-1-(4-((2-(1H-indazol-4-yl)-4-morpholinothieno[2,3-d]pyrimidin-6-yl)methyl)piperazin-1-yl)-2-aminopropan-1-one |
| 127 | 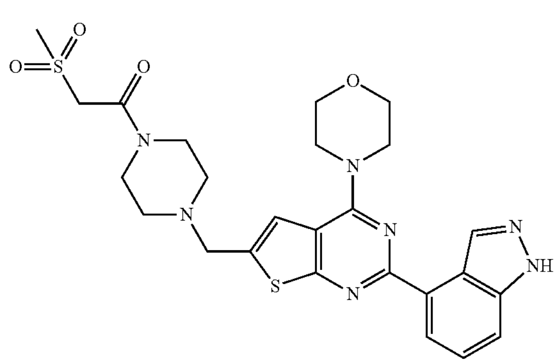 [SMILES: CS(=O)(=O)CC(=O)N1CCN(Cc2cc3c(N4CCOCC4)nc(-c4cccc5[nH]ncc45)nc3s2)CC1] | 1-(4-((2-(1H-indazol-4-yl)-4-morpholinothieno[2,3-d]pyrimidin-6-yl)methyl)piperazin-1-yl)-2-(methylsulfonyl)ethanone |

TABLE 1b

| Compound No. | Structure | Name |
|---|---|---|
| 128 | 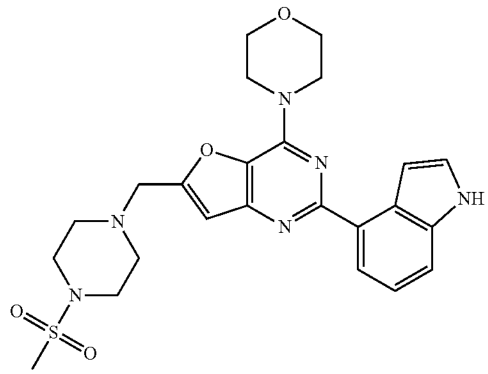 | 2-(1H-indol-4-yl)-6-((4-methylsulfonylpiperazin-1-yl)methyl)-4-morpholinofuro[3,2-d]pyrimidine |
| 129 | 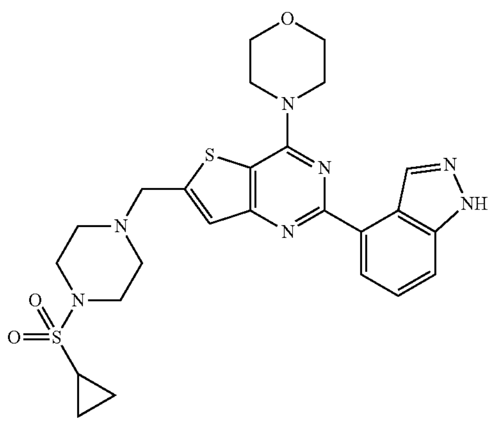 [SMILES: O=S(=O)(C1CC1)N1CCN(Cc2cc3nc(-c4cccc5[nH]ncc45)nc(N4CCOCC4)c3s2)CC1] | 2-(1H-indazol-4-yl)-6-((4-methylsulfonylpiperazin-1-yl)methyl)-4-morpholinothieno[3,2-d]pyrimidine |
| 130 | 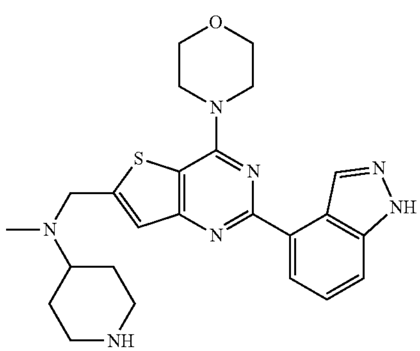 [SMILES: CN(Cc1cc2nc(-c3cccc4[nH]ncc34)nc(N3CCOCC3)c2s1)C1CCNCC1] | N-((2-(1H-indazol-4-yl)-4-morpholinothieno[3,2-d]pyrimidin-6-yl)methyl)-N-methylpiperidin-4-amine |
| 131 | 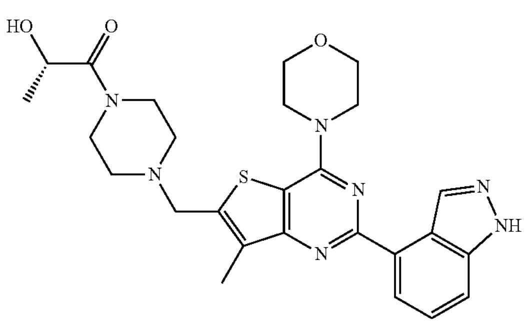 [SMILES: Cc1c(CN2CCN(C(=O)[C@H](C)O)CC2)sc2c(N3CCOCC3)nc(-c3cccc4[nH]ncc34)nc12] | (S)-1-(4-((2-(1H-indazol-4-yl)-7-methyl-4-morpholinothieno[3,2-d]pyrimidin-6-yl)methyl)piperazin-1-yl)-2-hydroxyl)ropan-1-one |

TABLE 1b-continued

| Compound No. | Structure | Name |
|---|---|---|
| 132 | 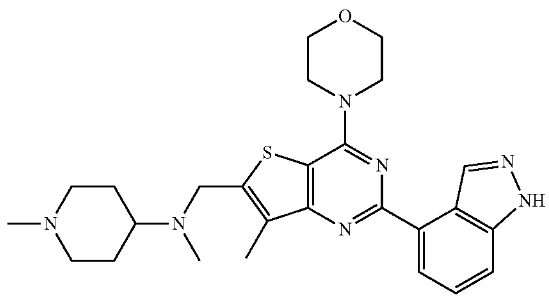 [SMILES: Cc1c(CN(C)C2CCN(C)CC2)sc2c(N3CCOCC3)nc(-c3cccc4[nH]ncc34)nc12] | N-((2-(1H-indazol-4-yl)-7-methyl-4-morpholinothieno[3,2-d]pyrimidin-6-yl)methyl)-N,1-dimethylpiperidin-4-amine |
| 133 | 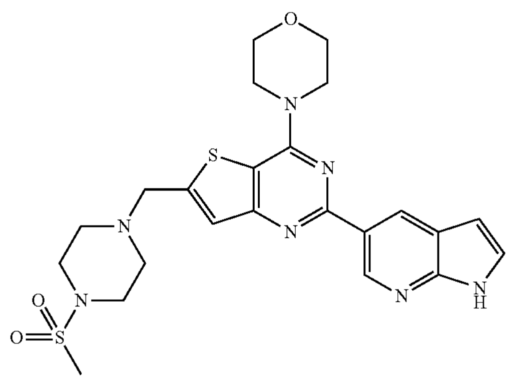 [SMILES: CS(=O)(=O)N1CCN(Cc2cc3nc(-c4cnc5[nH]ccc5c4)nc(N4CCOCC4)c3s2)CC1] | 6-((4-methylsulfonylpiperazin-1-yl)methyl)-4-morpholino-2-(1H-pyrrolo[2,3-b]pyridin-5-yl)thieno[3,2-d]pyrimidine |
| 134 | 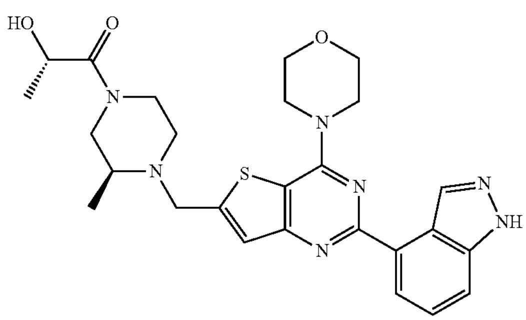 [SMILES: C[C@H](O)C(=O)N1CCN(Cc2cc3nc(-c4cccc5[nH]ncc45)nc(N4CCOCC4)c3s2)[C@@H](C)C1] | (S)-1-((S)-4-((2-(1H-indazol-4-yl)-4-morpholinothieno[3,2-d]pyrimidin-6-yl)methyl)-3-methylpiperazin-1-yl)-2-hydroxypropan-1-one |
| 135 | 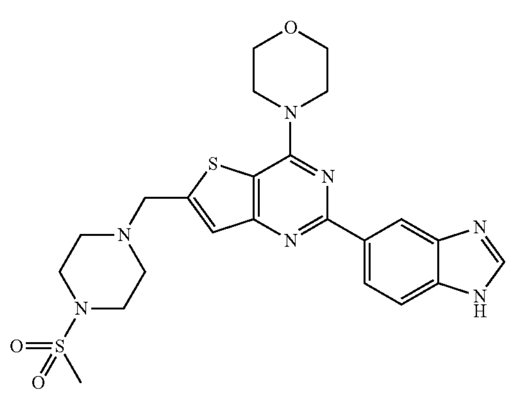 [SMILES: CS(=O)(=O)N1CCN(Cc2cc3nc(-c4ccc5[nH]cnc5c4)nc(N4CCOCC4)c3s2)CC1] | 2-(1H-benzo[d]imidazol-5-yl)-6-((4-methylpiperazin-1-yl)methyl)-4-morpholinothieno[3,2-d]pyrimidine |

TABLE 1b-continued

| Compound No. | Structure | Name |
|---|---|---|
| 136 | 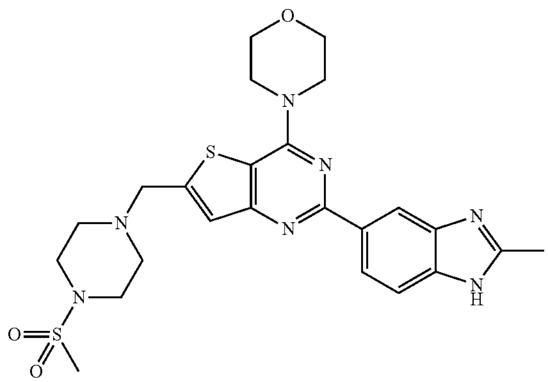 [SMILES: Cc1nc2cc(-c3nc(N4CCOCC4)c4sc(CN5CCN(S(C)(=O)=O)CC5)cc4n3)ccc2[nH]1] | 2-(2-methyl-1H-benzo[d]imidazol-5-yl)-6-((4-methylsulfonylpiperazin-1-yl)methyl)-4-morpholinothieno[3,2-d]pyrimidine |
| 137 | 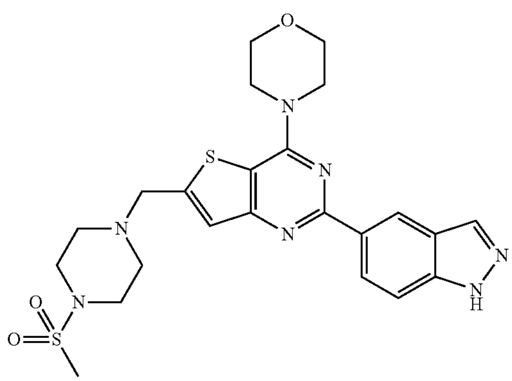 [SMILES: CS(=O)(=O)N1CCN(Cc2cc3nc(-c4ccc5[nH]ncc5c4)nc(N4CCOCC4)c3s2)CC1] | 2-(1H-indazol-5-yl)-6-((4-methylsulfonylpiperazin-1-yl)methyl)-4-morpholinothieno[3,2-d]pyrimidine |
| 138 | 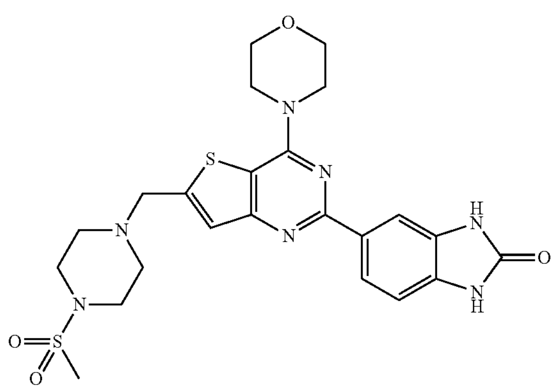 [SMILES: CS(=O)(=O)N1CCN(Cc2cc3nc(-c4ccc5[nH]c(=O)[nH]c5c4)nc(N4CCOCC4)c3s2)CC1] | 5-(6-((4-methylsulfonylpiperazin)1-yl)methyl)-4-morpholinothieno[3,2-d]pyrimidin-2-yl)-1H-benzo[d]imidazol-2(3H)-one |
| 139 | 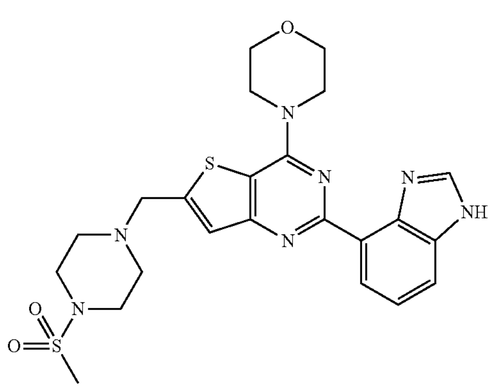 [SMILES: CS(=O)(=O)N1CCN(Cc2cc3nc(-c4cccc5[nH]cnc45)nc(N4CCOCC4)c3s2)CC1] | 2-(1H-benzo[d]imidazol-4-yl)-6-((4-methylsulfonylpiperazin)1-yl)methyl)-4-morpholinothieno[3,2-d]pyrimidine |

TABLE 1b-continued

| Compound No. | Structure | Name |
|---|---|---|
| 140 | 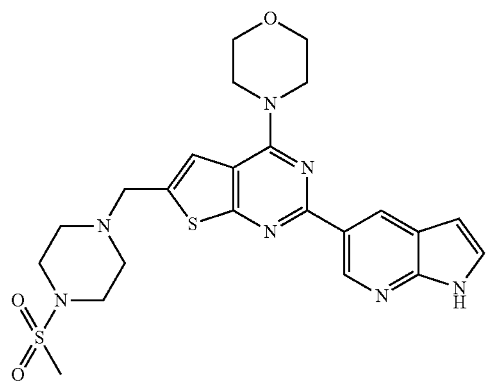 [SMILES: CS(=O)(=O)N1CCN(Cc2cc3c(N4CCOCC4)nc(-c4cnc5[nH]ccc5c4)nc3s2)CC1] | 6-((4-methylsulfonylpiperazin)1-yl)methyl)-4-morpholino-2-(1H-pyrrolo[2,3-b]pyridin)5-yl)thieno[2,3-d]pyrimidine |
| 141 | 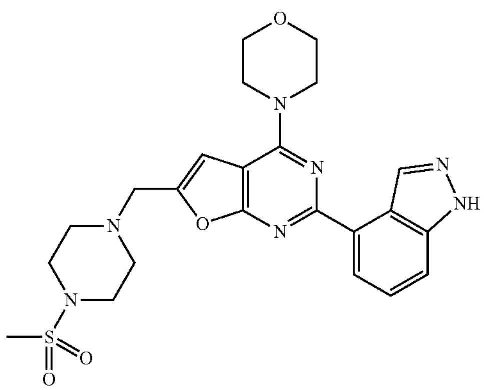 [SMILES: CS(=O)(=O)N1CCN(Cc2cc3c(N4CCOCC4)nc(-c4cccc5[nH]ncc45)nc3o2)CC1] | 2-(1H-indazol-4-yl)-6-((4-methylsulfonylpiperazin-1-yl)methyl)-4-morpholinofuro[2,3-d]pyrimidine |
| 142 | | 6-((4-methylsulfonylpiperazin)1-yl)methyl)-4-morpholino-2-(1H-pyrrolo[2,3-b]pyridin)5-yl)furo[3,2-d]pyrimidine |
| 143 | 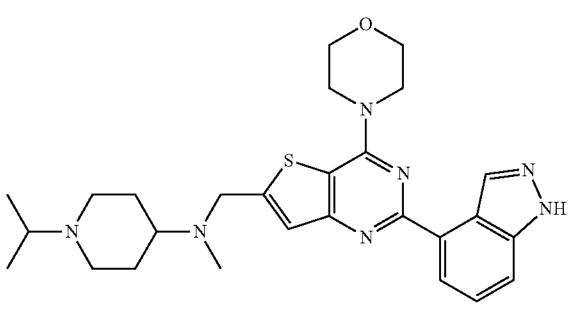 [SMILES: CC(C)N1CCC(N(C)Cc2cc3nc(-c4cccc5[nH]ncc45)nc(N4CCOCC4)c3s2)CC1] | N-((2-(1H-indazol-4-yl)-4-morpholinothieno[3,2-d]pyrimidin-6-yl)methyl)-1-isopropyl-N-methylpiperidin-4-amine |
| 144 | | 6-(6-((4-methylsulfonylpiperazin)1-yl)methyl)-4-morpholinothieno[3,2-d]pyrimidin-2-yl)-3H-imidazo[4,5-b]pyridine |

TABLE 1b-continued

| Compound No. | Structure | Name |
|---|---|---|
| 145 | 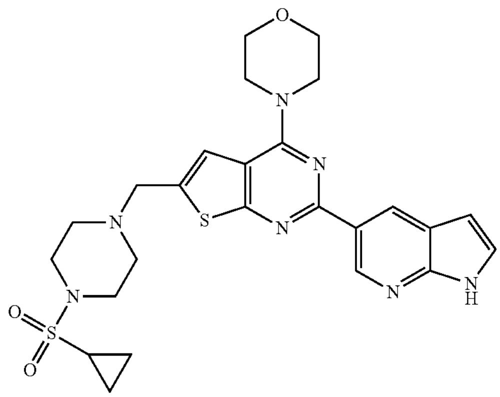 [SMILES: O=S(=O)(C1CC1)N1CCN(Cc2cc3c(N4CCOCC4)nc(-c4cnc5[nH]ccc5c4)nc3s2)CC1] | 6((4-isopropylsulfonylpiperazin-1-yl)methyl)-4-morpholino-2-(1H-pyrrolo[2,3-b]pyridin-5-yl)thieno[2,3-d]pyrimidine |
| 146 | 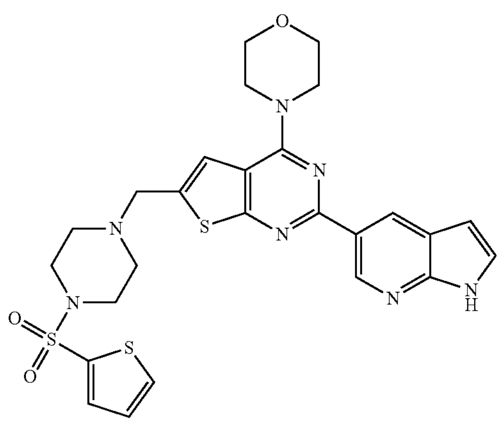 [SMILES: O=S(=O)(c1cccs1)N1CCN(Cc2cc3c(N4CCOCC4)nc(-c4cnc5[nH]ccc5c4)nc3s2)CC1] | 6-((4-(2-thiophen)sulfonylpiperazin-1-yl)methyl)-4-morpholino-2-(1H-pyrrolo[2,3-b]pyridin-5-yl)thieno[2,3-d]pyrimidine |
| 147 | 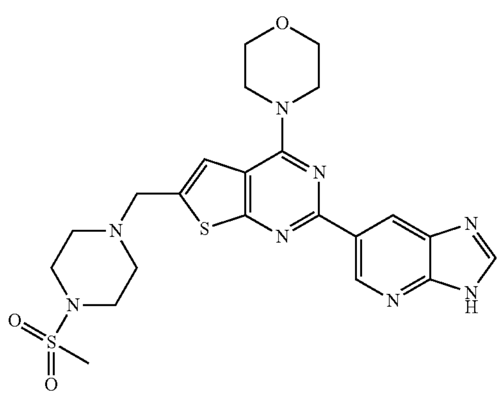 [SMILES: CS(=O)(=O)N1CCN(Cc2cc3c(N4CCOCC4)nc(-c4cnc5[nH]cnc5c4)nc3s2)CC1] | 6-(6-((4-methylsulfonylpiperazin)1-yl)methyl)-4-morpholinothieno[2,3-d]pyrimidin-2-yl)-3H-imidazo[4,5-b]pyridine |
| 148 | 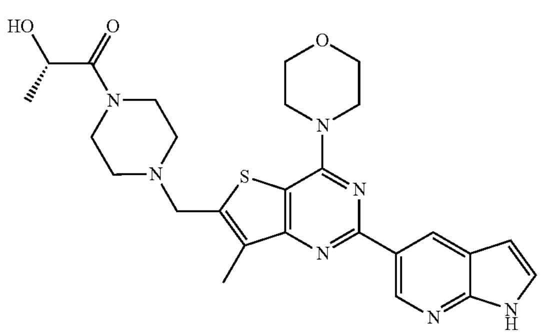 [SMILES: Cc1c(CN2CCN(C(=O)[C@H](C)O)CC2)sc2c(N3CCOCC3)nc(-c3cnc4[nH]ccc4c3)nc12] | (S)-2-hydroxy-1-(4-((7-methyl-4-morpholino-2-(1H-pyrrolo[2,3-b]pyridin-5-yl)thieno[3,2-d]pyrimidin-6-yl)methyl)piperazin-1-yl)propan-1-one |

TABLE 1b-continued

| Compound No. | Structure | Name |
|---|---|---|
| 149 | 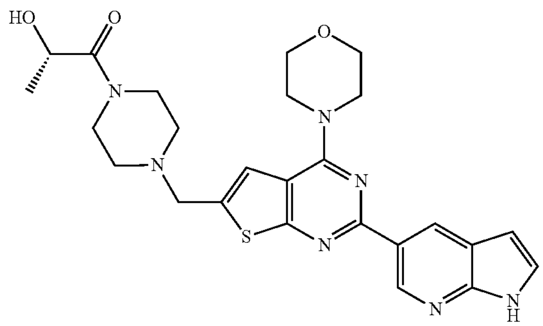 [SMILES: C[C@H](O)C(=O)N1CCN(Cc2cc3c(N4CCOCC4)nc(-c4cnc5[nH]ccc5c4)nc3s2)CC1] | (S)-2-hydroxy-1-(4-((4-morpholino-2-(1H-pyrrolo[2,3-b]pyridin-5-yl)thieno[2,3-d]pyrimidin-6-yl)methyl)piperazin-1-yl)propan-1-one |
| 150 | 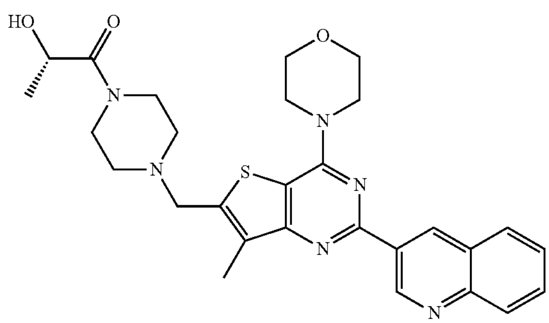 [SMILES: Cc1c(CN2CCN(C(=O)[C@H](C)O)CC2)sc2c(N3CCOCC3)nc(-c3cnc4ccccc4c3)nc12] | (S)-2-hydroxy-1-(4-((7-methyl-4-morpholino-2-(quinolin-3-yl)thieno[3,2-d]pyrimidin-6-yl)methyl)piperazin-1-yl)propan-1-one |
| 151 | 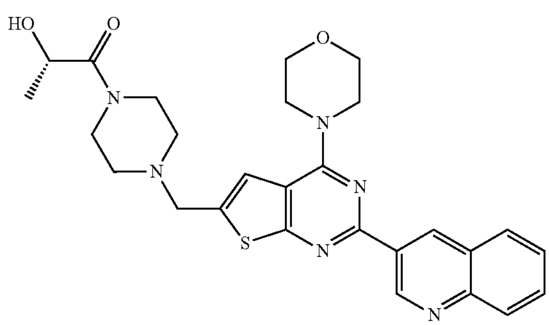 [SMILES: C[C@H](O)C(=O)N1CCN(Cc2cc3c(N4CCOCC4)nc(-c4cnc5ccccc5c4)nc3s2)CC1] | (S)-2-hydroxy-1-(4-((4-morpholino-2-(quinolin-3-yl)thieno[2,3-d]pyrimidin-6-yl)methyl)piperazin-1-yl)propan-1-one |
| 152 | 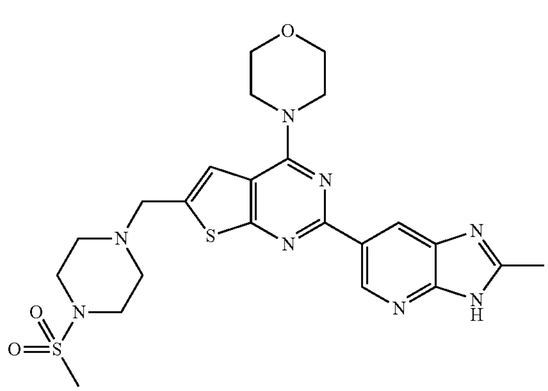 [SMILES: Cc1nc2cc(-c3nc(N4CCOCC4)c4cc(CN5CCN(S(C)(=O)=O)CC5)sc4n3)cnc2[nH]1] | 2-methyl-6-(6-((4-methylsulfonylpiperazin-1-yl)methyl)-4-morpholinothieno[2,3-d]pyrimidin-2-yl)-3H-imidazo[4,5-b]pyridine |

| Compound No. | Structure | Name |
|---|---|---|
| 153 | 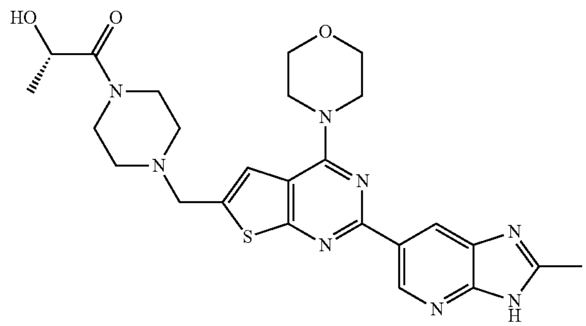 [SMILES: Cc1nc2cc(-c3nc(N4CCOCC4)c4cc(CN5CCN(C(=O)[C@H](C)O)CC5)sc4n3)cnc2[nH]1] | (S)-2-hydroxy-1-(4-((2-(2-methyl-3H-imidazo[4,5-b]pyridin-6-yl)-4-morpholinothieno[2,3-d]pyrimidin-6-yl)methyl)piperazin-1-yl)propan-1-one |
| 154 | 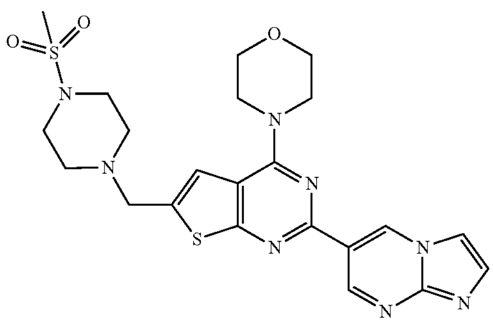 [SMILES: CS(=O)(=O)N1CCN(Cc2cc3c(N4CCOCC4)nc(-c4cnc5nccn5c4)nc3s2)CC1] | 6-(6-((4-methylsulfonylpiperazin-1-yl)methyl)-4-morpholinothieno[2,3-d]pyrimidin-2-yl)imidazo[1,2-a]pyrimidine |
| 155 | 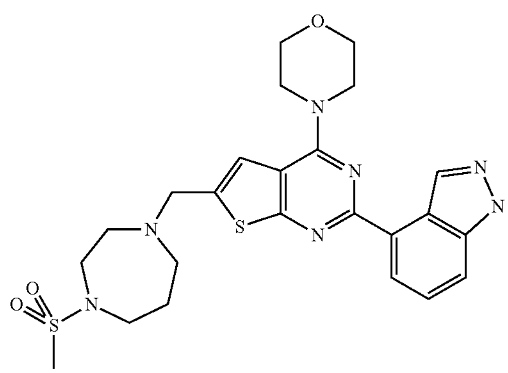 [SMILES: CS(=O)(=O)N1CCCN(Cc2cc3c(N4CCOCC4)nc(-c4cccc5[nH]ncc45)nc3s2)CC1] | 2-(1H-Indazol-4-yl)-6-(4-methanesulfonyl-[1,4]diazepan-1-ylmethyl)-4-morpholin-4-yl-thieno[2,3-d]pyrimidine |
| 156 | 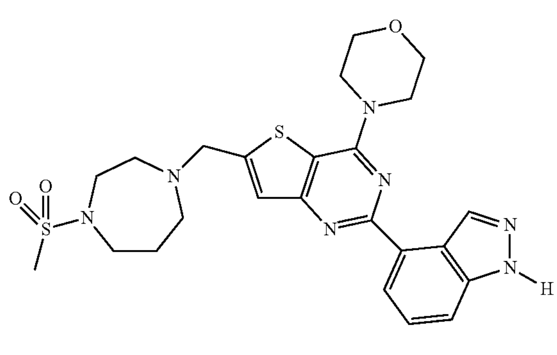 [SMILES: CS(=O)(=O)N1CCCN(Cc2cc3nc(-c4cccc5[nH]ncc45)nc(N4CCOCC4)c3s2)CC1] | 2-(1H-Indazol-4-yl)-6-(4-methanesulfonyl-1,4]diazepan-1-ylmethyl)-4-morpholin-4-yl-thieno[3,2-d]pyrimidine |

TABLE 1b-continued

| Compound No. | Structure | Name |
|---|---|---|
| 157 | 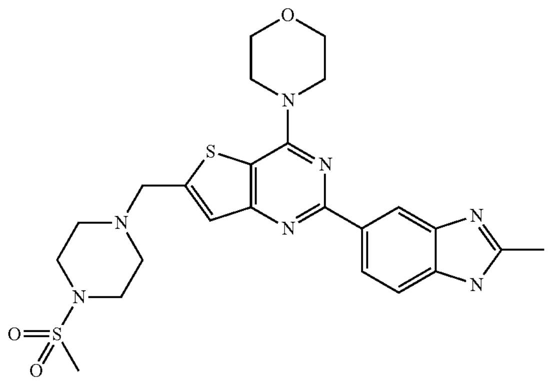 [SMILES: Cc1nc2cc(-c3nc(N4CCOCC4)c4sc(CN5CCN(S(C)(=O)=O)CC5)cc4n3)ccc2[nH]1] | 6-(4-Methanesulfonyl-piperazin-1-ylmethyl)-2-(2-methyl-1H-benzoimidazol-5-yl)-4-morpholin-4-yl-thieno[3,2-d]pyrimidine |
| 158 | 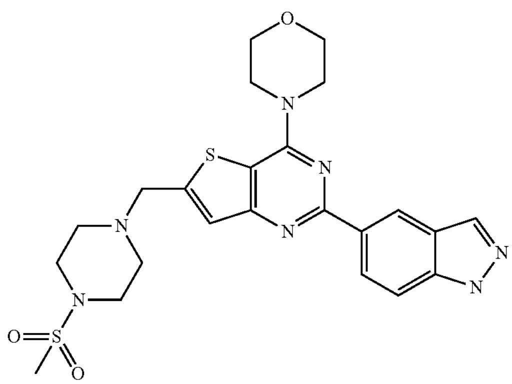 [SMILES: CS(=O)(=O)N1CCN(Cc2cc3nc(-c4ccc5[nH]ncc5c4)nc(N4CCOCC4)c3s2)CC1] | 2-(1H-Indazol-5-yl)-6-(4-methanesulfonyl-piperazin-1-ylmethyl)-4-morpholin-4-yl-thieno[3,2-d]pyrimidine |
| 159 | 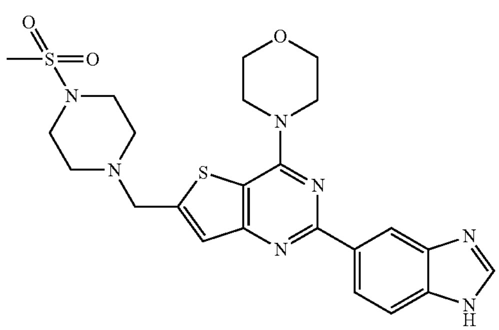 [SMILES: CS(=O)(=O)N1CCN(Cc2cc3nc(-c4ccc5[nH]cnc5c4)nc(N4CCOCC4)c3s2)CC1] | 2-(1H-benzo[d]imidazol-5-yl)-6-((4-(methylsulfonyl)piperazin-1-yl)methyl)-4-morpholinothieno[2,3-d]pyrimidine |
| 160 | 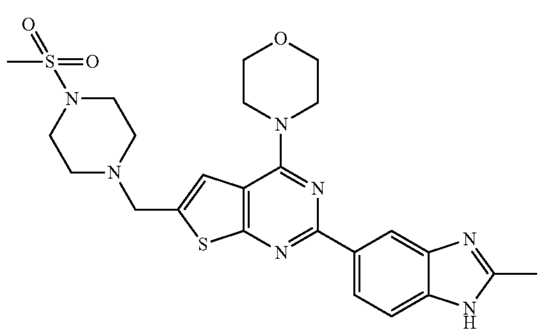 | 2-(2-methyl-1H-benzo[d]imidazol-5-yl)-6-((4-(methylsulfonyl)piperazin-1-yl)methyl)-4-morpholinothieno[2,3-d]pyrimidine |

TABLE 1b-continued

| Compound No. | Structure | Name |
|---|---|---|
| 161 | 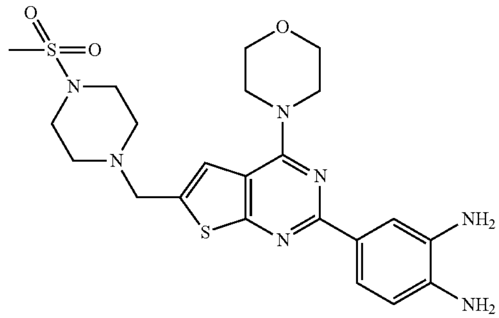 [SMILES: CS(=O)(=O)N1CCN(Cc2cc3c(N4CCOCC4)nc(-c4ccc(N)c(N)c4)nc3s2)CC1] | 4-(6-((4-(methylsulfonyl)piperazin-1-yl)methyl)-4-morpholinothieno[2,3-d]pyrimidin-2-yl)benzene-1,2-diamine |
| 162 | 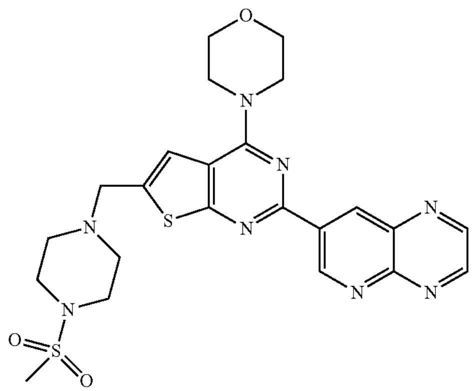 [SMILES: CS(=O)(=O)N1CCN(Cc2cc3c(N4CCOCC4)nc(-c4cnc5nccnc5c4)nc3s2)CC1] | 4-(6-((4-(methylsulfonyl)piperazin-1-yl)methyl)-2-(pyrido[2,3-b]pyrazin-7-yl)thieno[2,3-d]pyrimidin-4-yl)morpholine |
| 163 | 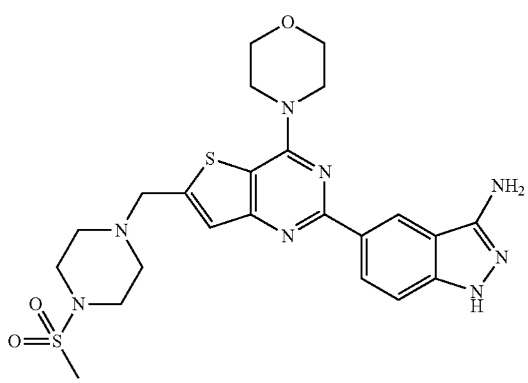 [SMILES: CS(=O)(=O)N1CCN(Cc2cc3nc(-c4ccc5[nH]nc(N)c5c4)nc(N4CCOCC4)c3s2)CC1] | 5-(6-((4-(methylsulfonyl)piperazin-1-yl)methyl)-4-morpholinothieno[3,2-d]pyrimidin-2-yl)-1H-indazol-3-amine |
| 164 | 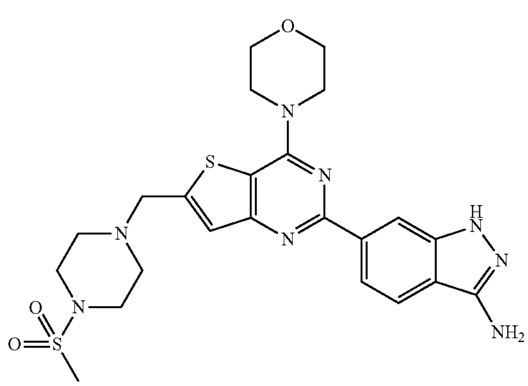 [SMILES: CS(=O)(=O)N1CCN(Cc2cc3nc(-c4ccc5c(N)n[nH]c5c4)nc(N4CCOCC4)c3s2)CC1] | 6-(6-((4-(methylsulfonyl)piperazin-1-yl)methyl)-4-morpholinothieno[3,2-d]pyrimidin-2-yl)-1H-indazol-3-amine |

TABLE 1b-continued

| Compound No. | Structure | Name |
|---|---|---|
| 165 | 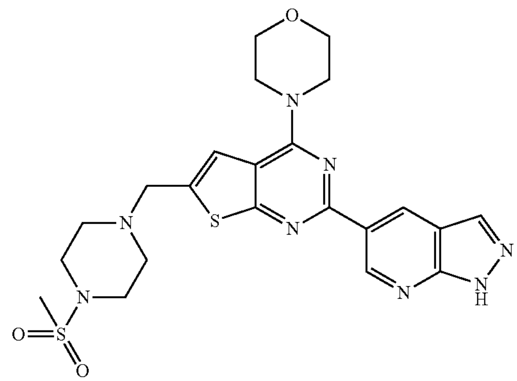 [SMILES: CS(=O)(=O)N1CCN(Cc2cc3c(N4CCOCC4)nc(-c4cnc5[nH]ncc5c4)nc3s2)CC1] | 4-(6-((4-(methylsulfonyl)piperazin-1-yl)methyl)-2-(1H-pyrazolo[3,4-b]pyridin-5-yl)thieno[2,3-d]pyrimidin-4-yl)morpholine |
| 166 | 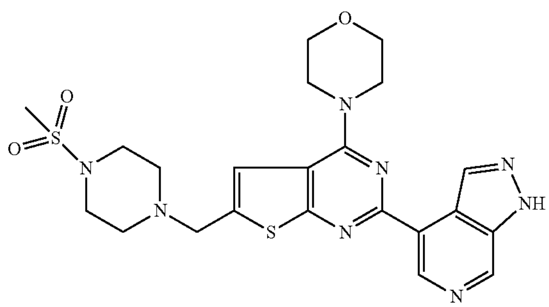 [SMILES: CS(=O)(=O)N1CCN(Cc2cc3c(N4CCOCC4)nc(-c4cncc5[nH]ncc45)nc3s2)CC1] | 4-(6-((4-(methylsulfonyl)piperazin-1-yl)methyl)-2-(1H-pyrazolo[3,4-c]pyridin-4-yl)thieno[2,3-d]pyrimidin-4-yl)morpholine |
| 167 | 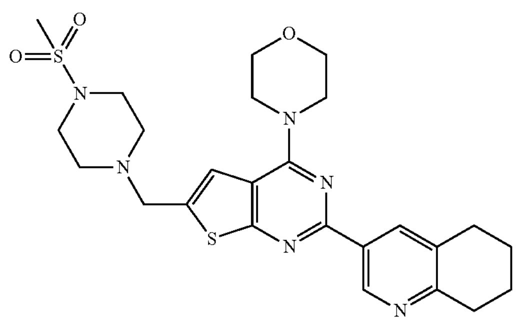 [SMILES: CS(=O)(=O)N1CCN(Cc2cc3c(N4CCOCC4)nc(-c4cnc5c(c4)CCCC5)nc3s2)CC1] | 4-(6-((4-(methylsulfonyl)piperazin-1-yl)methyl)-2-(5,6,7,8-tetrahydroquinolin-3-yl)thieno[2,3-d]pyrimidin-4-yl)morpholine |
| 168 | 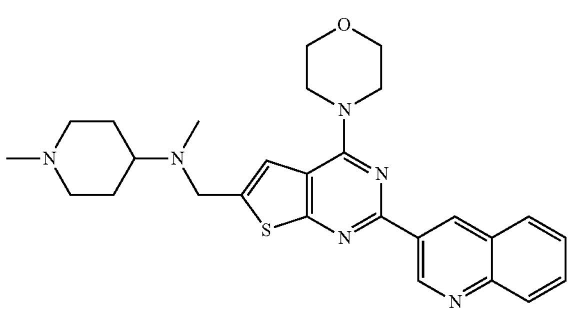 [SMILES: CN1CCC(N(C)Cc2cc3c(N4CCOCC4)nc(-c4cnc5ccccc5c4)nc3s2)CC1] | N,1-dimethyl-N-((4-morpholino-2-(quinolin-3-yl)thieno[2,3-d]pyrimidin-6-yl)methyl)piperidin-4-amine |

TABLE 1b-continued

| Compound No. | Structure | Name |
|---|---|---|
| 169 | (structure) | (S)-2-hydroxy-1-(4-((7-methyl-2-(2-methyl-1H-imidazo[4,5-b]pyridin-6-yl)-4-morpholinothieno[3,2-d]pyrimidin-6-yl)methyl)piperazin-1-yl)propan-1-one | and the pharmaceutically acceptable salts thereof.

The Formula Ia and Ib compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula Ia and Ib compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined. The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^{3}H$ and $^{14}C$) are useful in compound and/or substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The compounds of the invention may exist in the form of geometrical isomers or tautomers depending on the kinds of substituent groups, and these isomers in separated forms or mixtures thereof may be used in the present invention. Where the compounds have asymmetric carbon atoms, optical isomer forms may exist based on such carbon atoms. All of the mixtures and the isolated forms of these optical isomers may be used in the present invention.

A suitable synthetic strategy for producing compounds of the invention as defined above employs the precursor carboxaldehyde of formula (IIa) or (IIb):

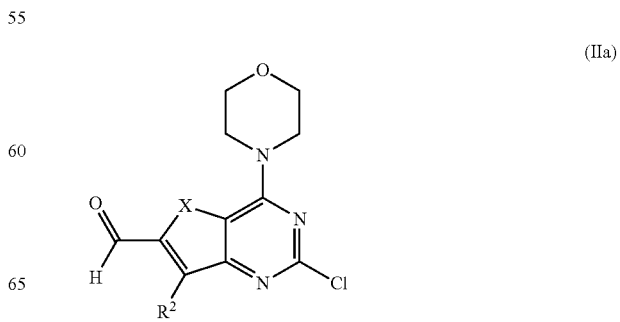

(IIa)

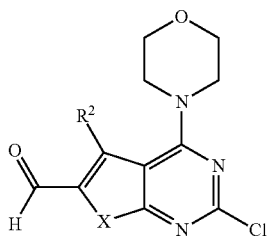
(IIb)

wherein X and R² are as defined above. Starting from this precursor the synthesis comprises performing, in either order, a palladium-mediated (Suzuki-type) cross-coupling reaction and a reductive amination. The process comprises:

(a) treating a compound of formula (IIa) or (IIb):

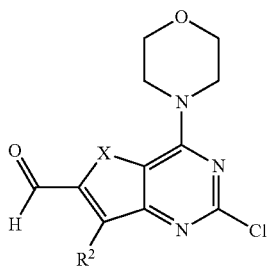
(IIa)

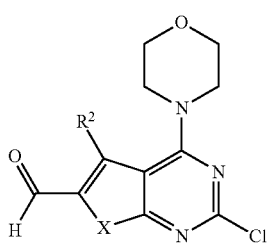
(IIb)

wherein X and R² are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst; and treating the resulting compound of formula (IIIa or (IIIb):

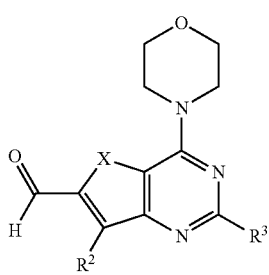
(IIIa)

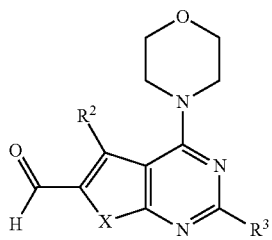
(IIIb)

wherein X, R² and R³ are as defined above, with an amine of formula $NHR^4R^5$ in which $R^4$ and $R^5$ are as defined above, in the presence of a suitable reducing agent; or (b) treating a compound of formula (IIIa) or (IIIb) as defined above with an amine of formula $NHR^4R^5$ wherein $R^4$ and $R^5$ are as defined above, in the presence of a suitable reducing agent; and treating the resulting compound of formula (IVa) or (IVb):

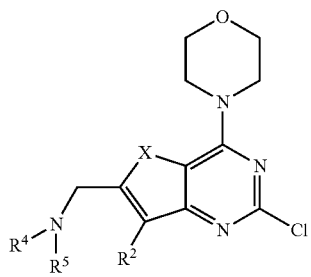
(IVa)

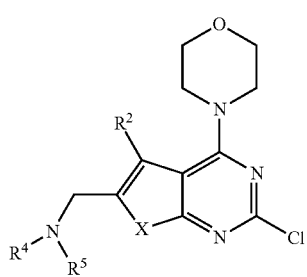
(IVb)

wherein X, R², R⁴ and R⁵ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

Accordingly, the present invention provides a process for producing a compound of the invention as defined above, which process comprises treating a compound of formula (IIIa or (IIIb):

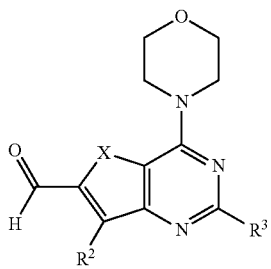

(IIIa)

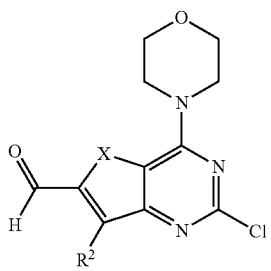

(IIIb)

wherein X, R² and R³ are as defined above, with an amine of formula NHR⁴R⁵ in which R⁴ and R⁵ are as defined above, in the presence of a suitable reducing agent.

The process may further comprise producing the compound of formula (IIIa) or (IIIb) by treating a compound of formula (IIa) or (IIb):

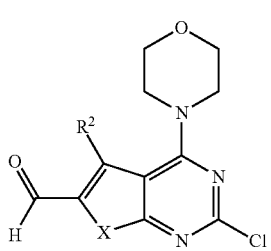

wherein X and R² are as defined above, ith a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

The invention further provides a process for producing a compound of the invention as defined above, which process comprises treating a compound of formula (IVa) or (IVb):

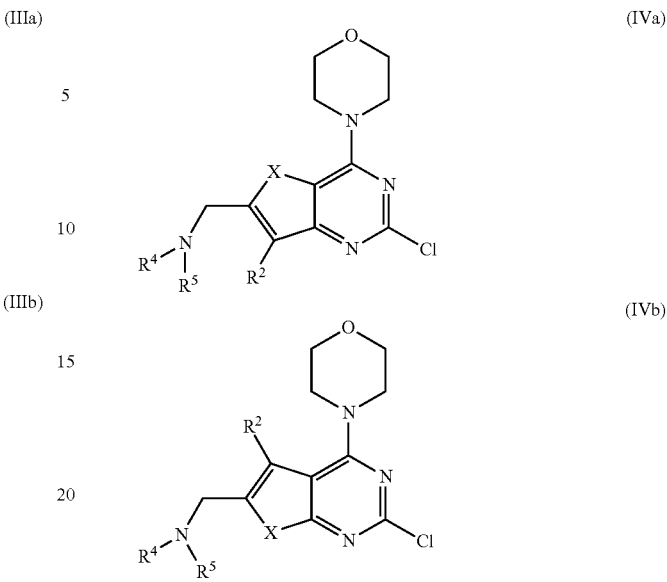

wherein X, R², R⁴ and R⁵ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

The process may further comprise producing the compound of formula (IVa) or (IVb) by treating a compound of formula (IIa or (IIb):

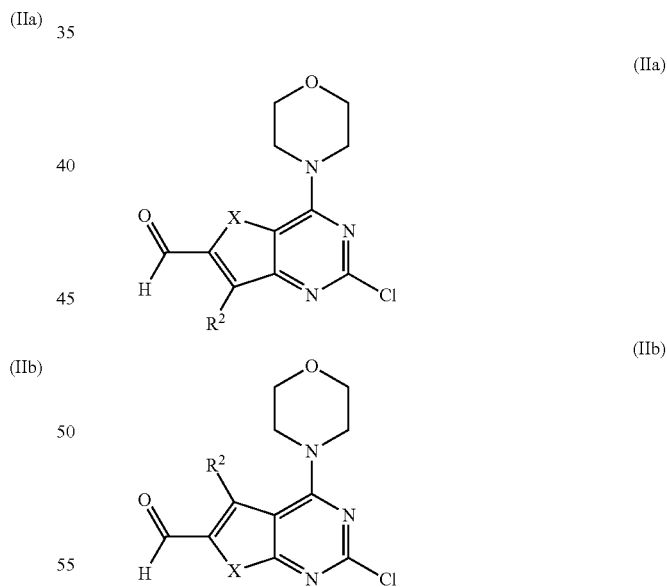

wherein X and R² are as defined above, with an amine of formula NHR⁴R⁵ in which R⁴ and R⁵ are as defined above, in the presence of a suitable reducing agent.

Both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, for instance $NaBH(OAc)_3$, $NaBH_4$ or $NaCNBH_4$, in particular $NaBH(OAc)_3$.

Compounds of formula (Ia) or (Ib) in which $R^3$ is a 3- or 4-hydroxyphenyl group may be produced by a process which comprises:

(a) treating a compound of formula (Va) or (Vb):

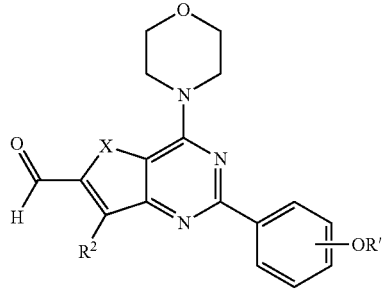
(Va)

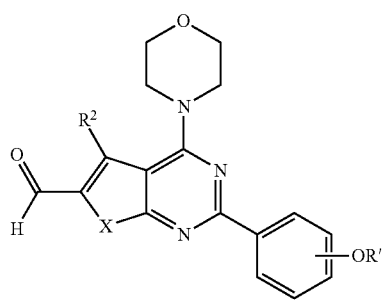
(Vb)

wherein OR' is bonded at position 3 or 4 of the phenyl ring to which it is attached, R' is a hydroxy protecting group and X and $R^2$ are as defined above, with an amine of formula $NHR^4R^5$ wherein $R^4$ and $R^5$ are as defined above, in the presence of a suitable reducing agent; and (b) removing the hydroxy protecting group.

The reducing agent is typically a borohydride, for instance as specified above.

Examples of hydroxy protecting groups are known in the art, for instance as described in "Protective Groups for Organic Chemistry", Third Edition, T. W. Greene and P. G. M. Wuts, John Wiley & Sons, 1999. For instance, a hydroxy group can be protected as an acetal, a substituted acetal, an ester, a xanthate, an ether or a silyl ether. The acetal is preferably tetrahydropyran. The silyl ether is preferably trimethylsilyl ether, t-butyl dimethylsilyl ether, triiso-propylsilyl ether or t-butyldiphenyl-silyl ether. These protecting groups are removed by conventional techniques.

A compound of formula (Va) or (Vb) as defined above may be produced by a process which comprises treating a compound of formula (VIa) or (VIb):

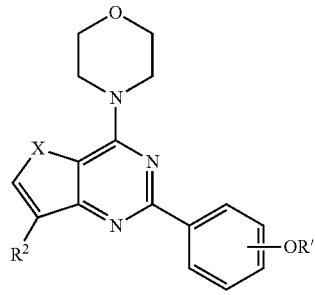
(VIa)

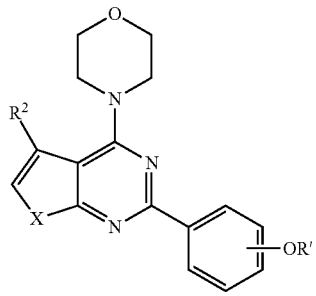
(VIb)

wherein X, $R^2$ and R' are as defined above, with a lithiating agent followed by N,N'-dimethylformamide (DMF). The reaction is typically conducted by adding a solution of the lithiating agent in a non-polar organic solvent, for instance a hydrocarbon solvent such as hexane, to a suspension of the compound of formula (VI) in an organic solvent such as tetrahydrofuran (THF). If THF is used the addition takes place at a low temperature, of about −78° C. The lithiating agent is typically an alkyllithium, for instance n-butyllithium.

A compound of formula (VIa) or (VIb) as defined above may be produced by a process which comprises treating a compound of formula (VIIa) or (VIIb):

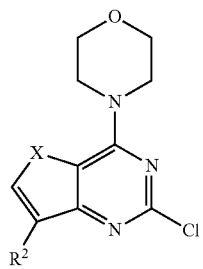
(VIIa)

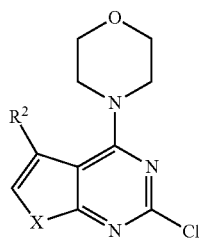
(VIIb)

wherein X and $R^2$ are as defined above, with a boronic acid of formula (VIII):

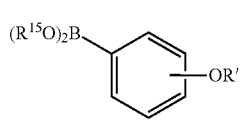
(VIII)

wherein R' and $R^{15}$ are as defined above, in the presence of a palladium catalyst. The reaction is conducted under conventional conditions for a Suzuki-type cross-coupling reaction, for instance as described above.

A fused pyrmidine of the invention may be converted into a pharmaceutically acceptable salt, and a salt may be converted into the free compound, by conventional methods. The phrase "pharmaceutically acceptable salt" as used herein, refers to pharmaceutically acceptable organic or inorganic salts of a compound of the invention.

Examples of pharmaceutically acceptable salts include salts with inorganic acids such as hydrochloric acid, hydrobromic acid, hydroiodic acid, sulphuric acid, nitric acid and phosphoric acid; and organic acids such as methanesulfonic acid, benzenesulphonic acid, formic acid, acetic acid, trifluoroacetic acid, propionic acid, oxalic acid, malonic acid, succinic acid, fumaric acid, maleic acid, lactic acid, malic acid, tartaric acid, citric acid, ethanesulfonic acid, aspartic acid and glutamic acid.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

Typically the salt is a mesylate, a hydrochloride, a phosphate, a benzenesulphonate or a sulphate. Most typically the salt is a mesylate or a hydrochloride.

The salts, for instance salts with any of the inorganic or organic acids mentioned above, may be mono-salts or bis-salts. Thus, for example, the mesylate salt may be the mono-mesylate or the bis-mesylate.

A fused pyrimidine of the invention and its salts may exist as a solvate or a hydrate. A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

Biological Activity

Compounds of the present invention have been found in biological tests to be inhibitors of PI3 kinase. Determination of the activity of PI3 kinase activity of a compound of the present invention is possible by a number of direct and indirect detection methods. Certain exemplary compounds described herein were prepared, characterized, and assayed for their PI3K binding activity (Example 7). Certain exemplary compounds of the invention had PI3K binding activity $IC_{50}$ values less than 50 uM.

The compounds of the present invention may inhibit p110 catalytic subunit isoforms including alpha, beta, gamma, and delta as pan inhibitors. Certain compounds of the invention may be p110 isoform selective inhibitors by selectively inhibiting one of one of the p110 isoforms; alpha, beta, gamma, or delta. A p110 selective inhibitor may mitigate the risk of toxicity due to potential toxicities associated with inhibiting the other p110 isoforms. Certain compounds of the invention may be p110 isoform pan inhibitors by possessing significant binding to two or more of the p110 isoforms.

Binding of compounds of the invention from above Tables 1a and 1b to purified preparations of p110 isoforms alpha, beta, delta, and gamma was measured by a Scintillation Proximity Assay (SPA) to determine binding activity ($IC_{50}$ μMol) and selectivity of binding of beta, delta, and gamma isoforms relative to alpha (Example 8). These values are expressed in Table 2.

A compound of the present invention may be used as an inhibitor of PI3 kinase, in particular of a class Ia PI3 kinase. The compounds are typically selective for class Ia kinases over class Ib and typically exhibit a 20-fold selectivity for class Ia over class Ib PI3 kinases. In particular the compounds ae selective for the p110alpa isoform.

Accordingly, a compound of the present invention can be used to treat a disease or disorder arising from abnormal cell growth, function or behaviour. Such abnormal cell growth, function or behaviour is typically associated with PI3 kinase. Examples of such diseases and disorders are discussed by Drees et al in Expert Opin. Ther. Patents (2004) 14(5):703-732. These include cancer, immune disorders, cardiovascular disease, viral infection, inflammation, metabolism/endocrine disorders and neurological disorders. Examples of metabolism/endocrine disorders include diabetes and obesity.

Examples of cancers which the present compounds can be used to treat include leukaemia, brain tumours, renal cancer, gastric cancer and cancer of the skin, bladder, breast, uterus, lung, colon, prostate, ovary and pancreas. A human or animal patient suffering from an immune disorder, cancer, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of Formula Ia or Ib and a pharmaceutically acceptable carrier, adjuvant, or vehicle, wherein said compound of Formula Ia or Ib is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

In addition to possessing biochemical potency a compound of the invention exhibits physicochemical and pharmacokinetic properties which makes it particularly well adapted for drug use. This is shown for instance in the results of the biological assays described in Example 5 which follows. In particular the compound possesses high aqueous solubility at physiological pH; the solubility is greater than 100 µM. High solubility at physiological pH is desirable since it promotes bioavailability.

The compound also possesses high metabolic stability, as shown in particular by the hepatocyte clearance assay described in Example 2 in which the compound was shown to have low hepatocyte clearance. Low hepatocyte clearance correlates with a low rate of liver metabolism. It can therefore be seen that the compound of the present invention possess improved physicochemical and pharmacokinetic properties whilst retaining biochemical potency as an inhibitor of PI3 kinase.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

Typically a dose to treat human patients may range from about 10 mg to about 1000 mg of a compound of the invention. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

A compound is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

F) Vaginally, in the form of pessaries, tampons, creams, gels, pastes, foams or spray formulations containing in addition to the active ingredient such carriers as are known in the art to be appropriate.

Sustained-release preparations of a compound of the invention may be prepared. Suitable examples of sustained-release preparations include semipermeable matrices of solid hydrophobic polymers containing a compound of Formula Ia or Ib, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(–)-3-hydroxybutyric acid.

A compound of the invention may be employed alone or in combination with other therapeutic agents for the treatment of a disease or disorder described herein, such as a hyperproliferative disorder (e.g., cancer). In certain embodiments, a compound of the invention is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of the invention such that they do not adversely affect each other. Such compounds are suitably present in combination in amounts that are effective for the purpose intended. In one embodiment, a composition of this invention comprises a compound of the invention, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The invention will be further described in the Examples which follow:

EXAMPLE 1A

General Synthetic Procedures

The following general procedures A, B and C are referred to in the subsequent Examples and Reference Examples:
A) Suzuki Coupling Substituted 2-chloro-4-morpholinothieno[3,2-d]pyrimidine or 2-chloro-4-morpholinothieno[2,3-d]pyrimidine was combined with 1.5 equivalents of 4-(4,4,5,5-tertamethyl-1,3,2-dioxaborolan-2-yl)1H-indazole (alternatively, a variety of boronic acids or boronic esters can be used in place of the indazole boronic ester indicated) and dissolved in 3.0 equivalents of sodium carbonate as a 1 molar solution in water and an equal volume of acetonitrile. In some cases potassium acetate was used in place of sodium carbonate to adjust the pH of the aqueous layer. The reaction was then heated to between 140-150° C. under pressure in a Biotage Optimizer microwave reactor (Biotage, Inc.) for 10 to 30 minutes. The contents were extracted with ethyl acetate. After evaporation of the organic layer the product was purified on silica or by reverse phase HPLC.

B) Amide Coupling

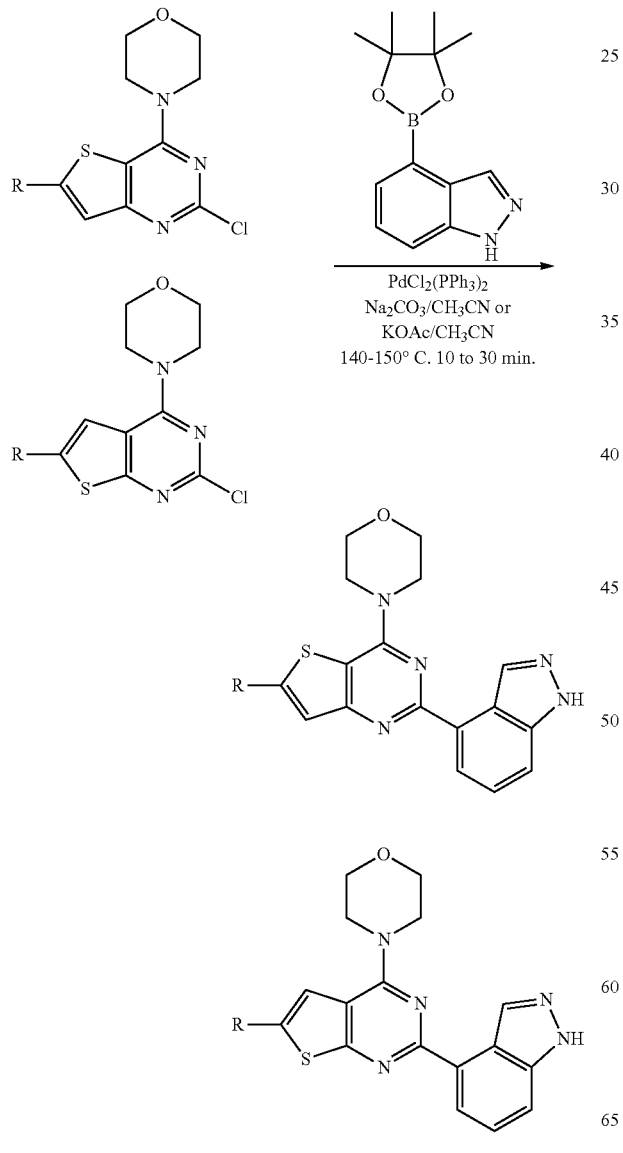

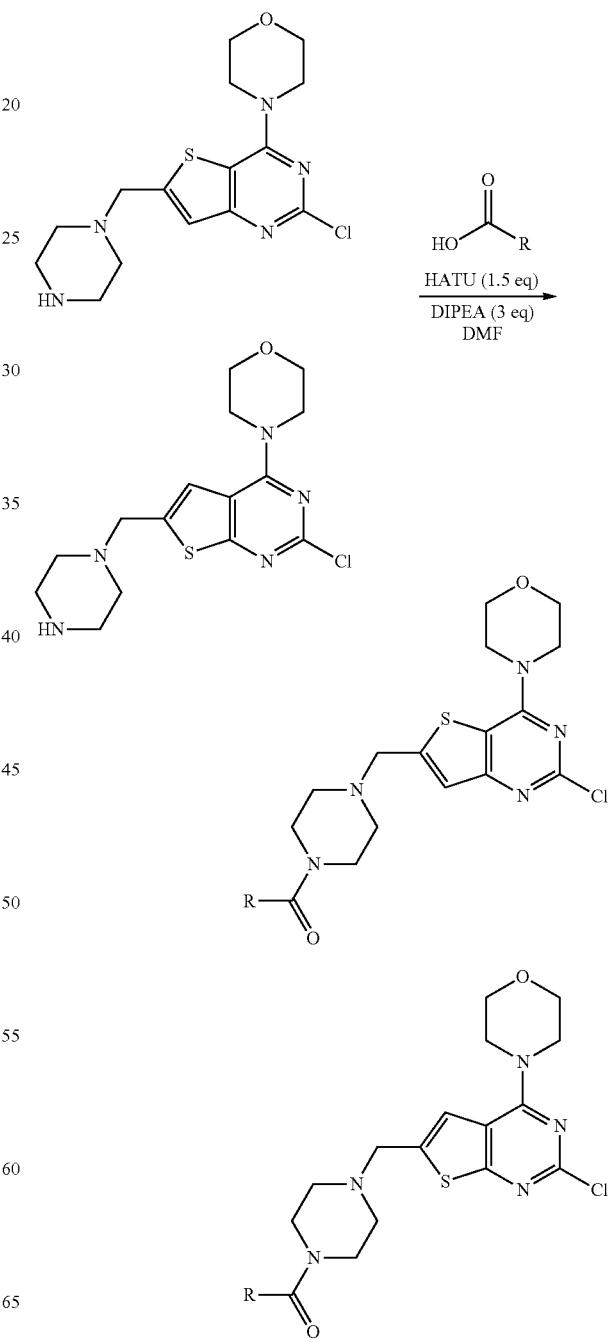

2-Chloro-4-morpholino-6-((piperazin-1-yl)methyl)thieno[3,2-d]pyrimidine or 2-chloro-4-morpholino-6-((piperazin-1-yl)methyl)thieno[2,3-d]pyrimidine is treated with 1.5 eq HATU, 3 eq of amine and 3 eq of DIPEA in DMF to approximately 0.1 M concentration. The reaction is stirred until complete and extracted in Ethyl Acetate with Saturated Bicarbonate Solution one time. The organic layer is dried, filtered and concentrated to yield the crude intermediate.

C) Reductive Amination

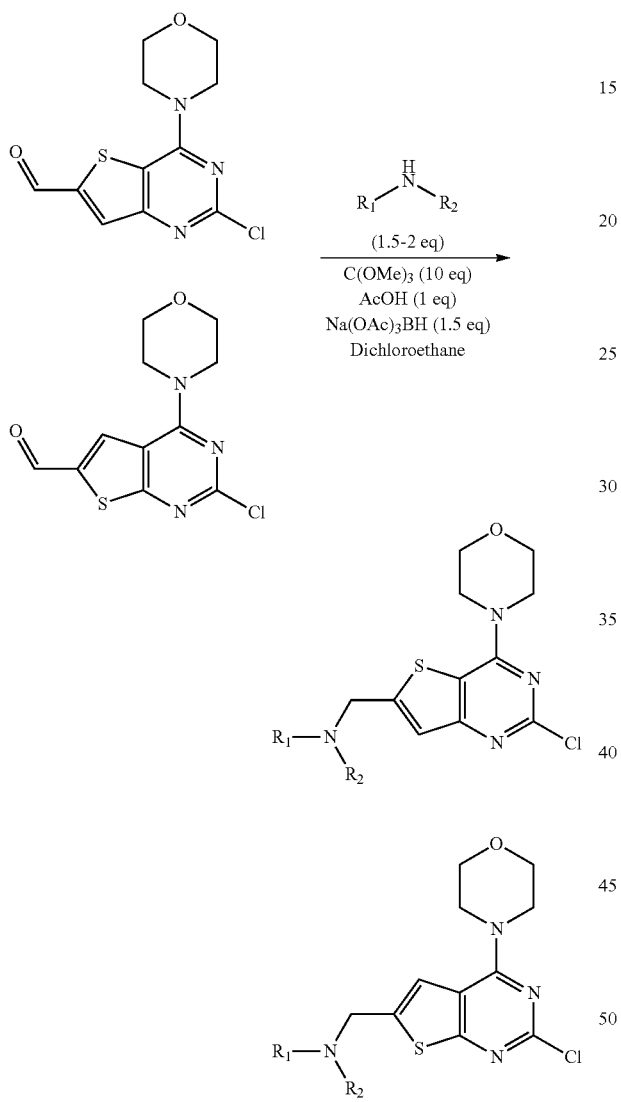

2-Chloro-4-morpholinothieno[3,2-d]pyrimidine-6-carbaldehyde or 2-chloro-4-morpholinothieno[2,3-d]pyrimidine-6-carbaldehyde was dissolved to a 0.2 M concentration in dichloroethane. To this solution was added 1.5 to 2.0 equivalents of an amine, 10 equivalents of trimethylorthoformate, and 1 equivalent of acetic acid. The mixture was allowed to stir for 2-6 hours prior to adding 1.5 equivalents of sodium triacetoxyborohydride. Following 12 to 16 hours of stirring the reaction was poured into saturated sodium bicarbonate and extracted several times with ethyl acetate. This intermediate was either purified on silica gel or used crude in the next reaction.

EXAMPLE 1B

Further General Synthetic Procedures

D) Removal of t-butoxylcarbonyl (BOC) Group

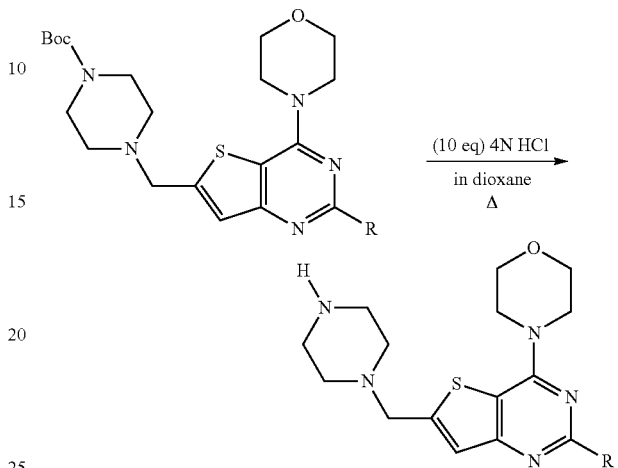

Ten or more equivalents of 4N HCl in Dioxane, with or without dichloromethane as a co-solvent, are added to the starting material (general scheme shown above but similar scaffolds also used). Heating up to 40° C. for several hours is occasionally required to remove the boc group. The reaction is concentrated to dryness and used crude in subsequent reaction.

E) Suzuki Coupling Reactions

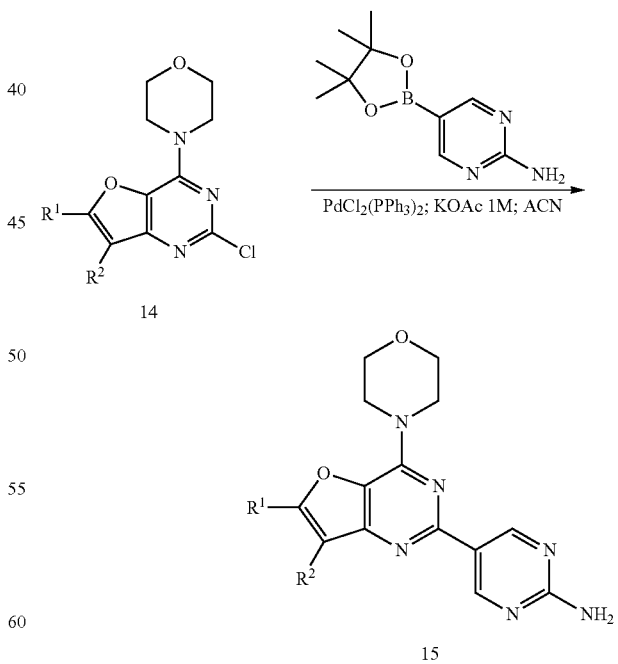

Generally, substituted 2-chloro-4-morpholinofuro[3,2-d]pyrimidine 14 (1 eq), 5-(4,4,5,5-tetramethyl-1,3,2-dioxaborolan-2-yl)pyrimidin-2-amine (1.7 eq) (or other boronic acid/ester) and bis(triphenylphosphine)palladium(II) dichloride (0.1 eq) in 1M KOAc aqueous solution (3 eq) and an equal volume of acetonitrile (3 eq) was heated to 100° C. in a sealed microwave reactor for 10-15 min. Upon completion, the contents are extracted with ethyl acetate, or another organic solvent. After evaporation of the organic layer the product 15, may be purified on silica or by reverse phase HPLC.

REFERENCE EXAMPLE 1

2,4-Dichloro-thieno[3,2-d]pyrimidine

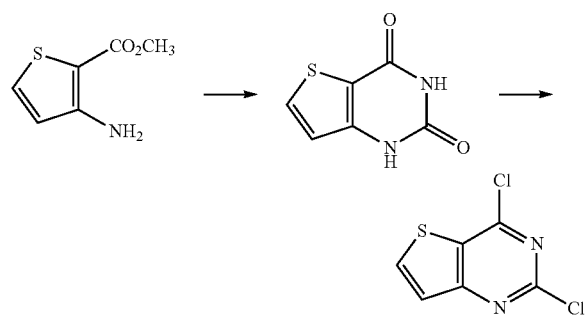

A mixture of methyl 3-amino-2-thiophenecarboxylate (13.48 g, 85.85 mmol) and urea (29.75 g, 5 eq.) was heated at 190° C. for 2 hours. The hot reaction mixture was then poured onto sodium hydroxide solution and any insoluble material removed by filtration. The mixture was then acidified (HCl, 2N) to yield 1H-thieno[3,2-d]pyrimidine-2,4-dione) as a white precipitate, which was collected by filtration and air dried (9.49 g, 66%).

$^1$H NMR (400 MHz, d$_6$-DMSO) 6.90 (1H, d, J=5.2 Hz), 8.10 (1H, d, J=5.2 Hz), 11.60-11.10 (2H, br, s).

A mixture of 1H-thieno[3,2-d]pyrimidine-2,4-dione (9.49 g, 56.49 mmol) and phosphorous oxychloride (150 mL) was heated at reflux for 6 hours. The reaction mixture was then cooled and poured onto ice/water with vigorous stirring yielding a precipitate. The mixture was then filtered to yield 2,4-dichloro-thieno[3,2-d]pyrimidine as a white solid (8.68 g, 75%).

$^1$H NMR (400 MHz, CDCl$_3$) 7.56 (1H, d, J=5.5 Hz). 8.13 (1H, d, J=5.5 Hz).

REFERENCE EXAMPLE 2

2-Chloro-4-morpholin-4-yl-thieno[3,2-d]pyrimidine

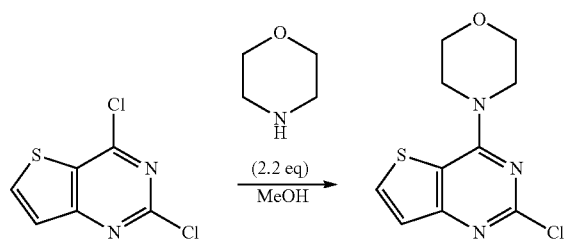 [SMILES: "MeOH" ; Clc1nc(Cl)c2sccc2n1 ; C1COCCN1 ; Clc1nc(N2CCOCC2)c2sccc2n1]

A mixture of 2,4-dichloro-thieno[3,2-d]pyrimidine (8.68 g, 42.34 mmol), morpholine (8.11 mL, 2.2 eq.) and methanol (150 mL) was stirred at room temperature for 1 hour. The reaction mixture was then filtered, washed with water and methanol, to yield the title compound as a white solid (11.04 g, 100%).

$^1$H NMR (400 MHz, d$_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

REFERENCES EXAMPLE 3

2-Chloro-4-morpholin-4-yl-thieno[3,2-d]pyrimidine-6-carbaldehyde

To a suspension of 2-chloro-4-morpholin-4-yl-thieno[3,2-d]pyrimidine (65) (1.75 g, 6.85 mmol) in dry THF (40 mL) at −78° C. was added a 2.5M solution of nBuLi in hexane (3.3 mL, 1.2 eq.). After stirring for 1 hour, dry N,N-dimethylformamide (796 µL, 1.5 eq.) was added. The reaction mixture was stirred for 1 hour at −78° C. and then warmed slowly to room temperature. After a further 2 hours at room temperature the reaction mixture poured onto ice/water yielding a yellow precipitate. This was collected by filtration and air-dried to yield the title compound (1.50 g, 77%).

$^1$H NMR (400 MHz, d$_6$-DMSO) 3.76 (4H, t, J=4.9 Hz), 3.95 (4H, t, J=4.9 Hz), 8.28 (1H, s), 10.20 (1H, s).

2-Chloro-4-morpholin-4-yl-thieno[2,3-d]pyrimidine-6-carbaldehyde was prepared in an analogous manner by commencing with methyl-2-aminothiophen-3-carboxylate.

2-Chloro-7-methyl-4-morpholin-4-yl-thieno[3,2-d]pyrimidine-6-carbaldehyde was also prepared in analogous manner by commencing with 3-amino-4-methyl-thiophene-2-carboxylic acid ethyl ester.

REFERENCE EXAMPLE 4

4-(4,4,5,5-Tetramethyl-[1,3,2]dioxaborolan-2-yl)-1H-indazole

Process 1

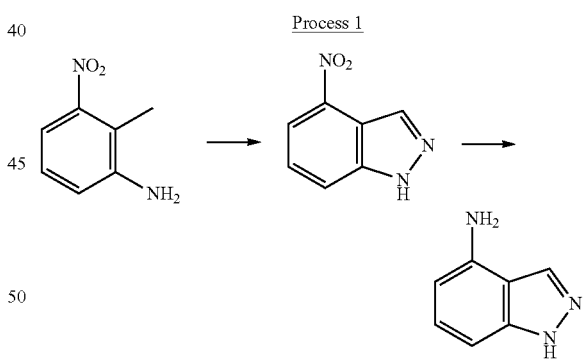

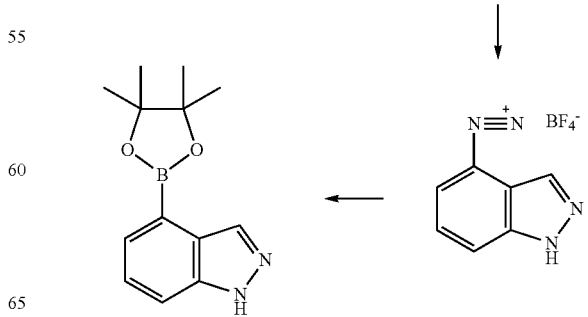

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 hours, the deep red solution was poured onto ice/water and the precipitate collected by filtration to yield 4-nitro-1H-indazole (1.98 g, 81%).

A mixture of 4-nitro-1H-indazole (760 mg, 4.68 mmol), palladium on charcoal (10%, cat.) and ethanol (30 mL) was stirred under a balloon of hydrogen for 4 hours. The reaction mixture was then filtered through celite, and the solvent removed in vacuo to yield 1H-indazol-4-ylamine (631 mg, 100%).

An aqueous solution of sodium nitrite (337 mg, 4.89 mmol) in water (2 mL) was added dropwise to a suspension of 1H-indazol-4-ylamine (631 mg, 4.74 mmol) in 6M hydrochloric acid (7.2 mL) at below 0° C. After stirring for 30 minutes sodium tetrafluorobrate (724 mg) was added. The reaction mixture became very thick and was filtered and washed briefly with water to yield 1H-indazole-4-diazonium, tetrafluoroborate salt (218 mg, 20%) as a deep red solid.

Dry methanol (4 mL) was purged with argon for 5 minutes. To this was added 1H-indazole-4-diazonium, tetrafluoroborate salt (218 mg, 0.94 mmol), bis-pinacolato diboron (239 mg, 1.0 eq.) and [1,1'-bis(diphenylphosphino)ferrocene]palladium (II) chloride (20 mg). The reaction mixture was stirred for 5 hours and then filtered through celite. The residue was purified using flash chromatography to yield the desired title compound (117 mg).

Process 2

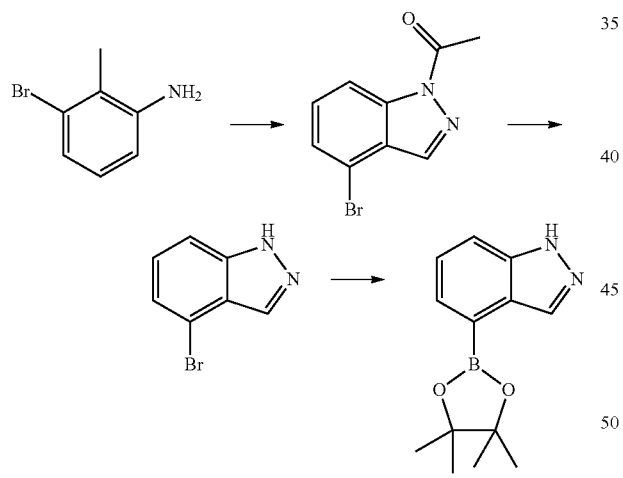

To a solution of 3-bromo-2-methyl aniline (5.0 g, 26.9 mmol) in chloroform (50 mL) was added potassium acetate (1.05 eq., 28.2 mmol, 2.77 g). Acetic anhydride (2.0 eq., 53.7 mmol, 5.07 mL) was added with concurrent cooling in ice-water. The mixture was then stirred at room temperature for 10 minutes after which time a white gelatinous solid formed. 18-Crown-6 (0.2 eq., 5.37 mmol, 1.42 g) was then added followed by iso-amyl nitrite (2.2 eq., 59.1 mmol, 7.94 mL) and the mixture was heated under reflux for 18 h. The reaction mixture was allowed to cool, and was partitioned between chloroform (3×100 mL) and saturated aqueous sodium hydrogen carbonate (100 mL). The combined organic extracts were washed with brine (100 mL), separated and dried (MgSO₄).

The crude product was evaporated onto silica and purified by chromatography eluting with 20%→40% EtOAc-petrol to give 1-(4-bromo-indazol-1-yl)-ethanone (A) (3.14 g, 49%) as an orange solid, and 4-bromo-1H-indazole (B)(2.13 g, 40%) as a pale orange solid.

A ¹H NMR (400 MHz, CDCl₃) 2.80 (3H, s), 7.41 (1H, t, J=7.8 Hz), 7.50 (1H, d, J=7.8 Hz), 8.15 (1H, s), 8.40 (1H, d, J=7.8 Hz).

B: ¹H NMR (400 MHz, CDCl₃) 7.25 (1H, t, J=7.3 Hz), 7.33 (1H, d, J=7.3 Hz), 7.46 (1H, d, J=7.3 Hz), 8.11 (1H, s), 10.20 (1H, br s),

To a solution of the 1-(4-bromo-indazol-1-yl)-ethanone (3.09 g, 12.9 mmol) in MeOH (50 mL) was added 6N aqueous HCl (30 mL) and the mixture was stirred at room temperature for 7 h. The MeOH was evaporated and the mixture partitioned between EtOAc (2×50 mL) and water (50 mL). The combined organic layers were washed with brine (50 mL), separated and dried (MgSO₄). The solvent was removed by evaporation under reduced pressure to give 4-bromo-1H-indazole (2.36 g, 93%).

To a solution of the 4-bromo-1H-indazole (500 mg, 2.54 mmol) and bis(pinacolato)diboron (1.5 eq., 3.81 mmol) in DMSO (20 mL) was added potassium acetate (3.0 eq., 7.61 mmol, 747 mg; dried in drying pistol) and PdCl₂(dppf)₂ (3 mol %, 0.076 mmol, 62 mg). The mixture was degassed with argon and heated at 80° C. for 40 h. The reaction mixture was allowed to cool and partitioned between water (50 mL) and ether (3×50 mL). The combined organic layers were washed with brine (50 mL), separated and dried (MgSO₄). The crude material was purified by chromatography eluting with 30%→40% EtOAc-petrol to give an inseparable 3:1 mixture of the 4-(4,4,5,5-tetramethyl-[1,3,2]dioxaborolan-2-yl)-1H-indazole (369 mg, 60%) and indazole (60 mg, 20%); this was isolated as a yellow gum which solidified upon standing to furnish as an off-white solid.

¹H NMR (400 MHz, d₆-DMSO) 1.41 (12H, s), 7.40 (1H, dd, J=8.4 Hz, 6.9 Hz), 7.59 (1H, d, J=8.4 Hz), 7.67 (1H, d, J=6.9 Hz), 10.00 (1H, br s), 8.45 (1H, s), and indazole: 7.40 (1H, t), 7.18 (1H, t, J=7.9 Hz), 7.50 (1H, d, J=9.1 Hz), 7.77 (1H, d, J=7.9 Hz), 8.09 (1H, s). Impurity at 1.25.

REFERENCE EXAMPLE 5

2-(1H-Indazol-4-yl)-4-morpholin-4-yl-thieno[3,2-d]pyrimidine-6-carbaldehyde

A mixture of 2-chloro-4-morpholin-4-yl-thieno[3,2-d]pyrimidine-6-carbaldehyde (100 mg, 0.35 mmol), 4-(4,4,5,5-tetramethyl-[1,3,2]dioxaborolan-2-yl)-1H-indazole (95 mg, 0.39 mmol) and sodium carbonate (112 mg) were suspended in toluene (2.5 mL), ethanol (1.5 mL) and water (0.7 mL). To this was added bis(triphenylphosphine)palladium(II) chloride (13.5 mg) and the reaction vessel was flushed with argon. The reaction mixture was microwaved at 120° C. for 1 hour and then partitioned between dichloromethane and water, the organic layer was washed with brine, dried over magnesium sulfate, filtered and evaporated in vacuo. The resulting residue was purified using flash chromatography to yield the title compound (97 mg).

REFERENCE EXAMPLE 6

Preparation of 2-(1H-Indazol-4-yl)-6-(4-methyl-piperazin-1-ylmethyl)-4-morpholin-4-yl-thieno[3,2-d]pyrimidine To a mixture of 2-(1H-Indazol-4-yl)-4-morpholin-4-yl-thieno[3,2-d]pyrimidine-6-carbaldehyde (91 mg, 0.26 mmol), 1-methylpiperazine (34 mg, 0.36 mmol) and acetic acid (15 uL) in 1,2-dichloroethane (2 mL) was added sodium triacetoxyborohydride (60 mg, 0.28 mmol). The reaction mixture was stirred at room temperature overnight and then basified (NaHCO$_3$, saturated), diluted with dichloromethane, washed with brine. Organic layer was separated, dried (MgSO$_4$), filtered and evaporated in vacuo. The residue was purified using flash chromatography to give the title compound (33 mg).

REFERENCE EXAMPLE 7

2-chloro-6-(4-methyl-piperazin-1-yl methyl)-4-morpholin-4-yl-thieno[3,2-d]pyrimidine

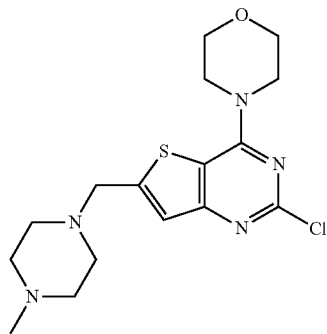 [SMILES: CN1CCN(Cc2cc3nc(Cl)nc(N4CCOCC4)c3s2)CC1]

To a mixture of 2-chloro-4-morpholin-4-yl-thieno[3,2-d]pyrimidine-6-carbaldehyde (66) (147 mg, 0.52 mmol), 1-methyl-piperazine (1.5 eq., 87 μL) and acetic acid (1.05 eq., 32 μL) in 1,2-dichloroethane (3 mL) was added sodium triacetoxyborohydride (1.1 eq., 121 mg) and then stirred at room temperature overnight. The reaction mixture was diluted with dichloromethane, washed with a saturated solution of sodium hydrogen carbonate, brine, separated and dried (MgSO$_4$). The crude product was evaporated in vacuo and purified by chromatography to give the title compound 72 as an off-white crystalline solid (51 mg, 45%).

REFERENCE EXAMPLE 8

(2-chloro-4-morpholinothieno[3,2-d]pyrimidin-6-yl)methanol

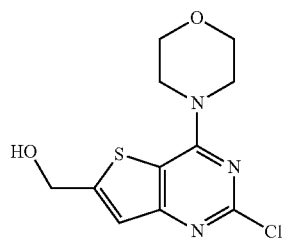 [SMILES: OCc1cc2nc(Cl)nc(N3CCOCC3)c2s1]

A solution of 2-chloro-4-morpholinothieno[3,2-d]pyrimidine-6-carbaldehyde (1.0 g, 3.5 mmol) in MeOH (30 mL) at 0° C. was treated with NaBH$_4$ (0.1 g, 3.5 mmol). The solution was allowed to warm to room temperature and stirred 15 min. The reaction mixture was quenched with a mixture of a saturated solution of sodium bicarbonate and water (1:1, v/v). The aqueous solution was extracted with EtOAc. The combined organic layers were dried over Na$_2$SO$_4$ and concentrated in vacuo. The crude material required no further purification (0.9 g, 90%). MS (Q1) 286 (M)+

REFERENCE EXAMPLE 9

6-(bromomethyl)-2-chloro-4-morpholinothieno[3,2-d]pyrimidine

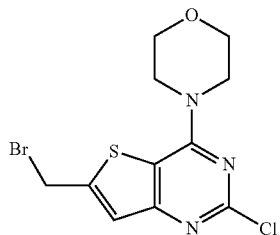 [SMILES: Clc1nc(N2CCOCC2)c2sc(CBr)cc2n1]

To a solution of (2-chloro-4-morpholinothieno[3,2-d]pyrimidin-6-yl)methanol (100 mg, 0.4 mmol) in benzene (3.0 mL) at 0° C. was added PBr$_3$ (30 μL, 0.4 mmol). The reaction was heated at reflux for 1 hour. After cooling to room temperature the reaction was quenched by the addition of water. The aqueous layer was extracted with EtOAc. The combined organics were dried over Na$_2$SO$_4$ and concentrated in vacuo. The crude material did not require further purification (115 mg, 94%). MS (Q1) 350 (M)+

REFERENCE EXAMPLE 10

1-(2-Chloro-4-morpholin-4-yl-thieno[3,2-d]pyrimidin-6-ylmethyl)-4-methanesulfonyl-piperazin-2-one

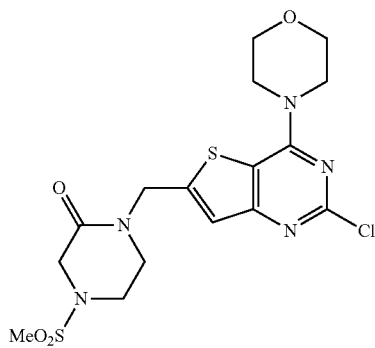 [SMILES: CS(=O)(=O)N1CCN(Cc2cc3nc(Cl)nc(N4CCOCC4)c3s2)C(=O)C1]

To a solution of 4-BOC-piperazinone (0.3 g, 1.6 mmol) in DMF (3 mL) at 0° C. was added NaH (60% in mineral oil, 1.9 mmol). Next, 6-(bromomethyl)-2-chloro-4-morpholinothieno[3,2-d]pyrimidine (0.6 g, 2 mmol) was added and the reaction stirred for 15 min. The reaction was quenched with saturated NH$_4$Cl and the aqueous layer was extracted with EtOAc. The combined organics were dried over Na$_2$SO$_4$ and concentrated in vacuo. This intermediate was dissolved in CH$_2$Cl$_2$ (40 mL) and MeOH (40 mL) and Et$_2$O (10 mL) and cooled to 0° C. To this solution was added 4 M HCl in dioxane (20 mL). The reaction was warmed to room temperature, stirred 18 h, then was concentrated in vacuo. To the residue was added CH$_2$Cl$_2$ (50 mL), Et$_3$N (1.5 mL, 11 mmol), and MeSO$_2$Cl (0.6 mL, 8 mmol). The reaction mixture stirred 42 h at room temperature. The reaction was quenched with water and extracted with EtOAc. The combined organics were dried over Na$_2$SO$_4$ and concentrated in vacuo (0.25 g, 28% over 3 steps). MS (Q1) 446 (M)+

REFERENCE EXAMPLE 11

2-Chloro-6-(4-methanesulfonyl-piperazin-1-ylmethyl)-4-morpholin-4-yl-thieno[3,2-d]pyrimidine

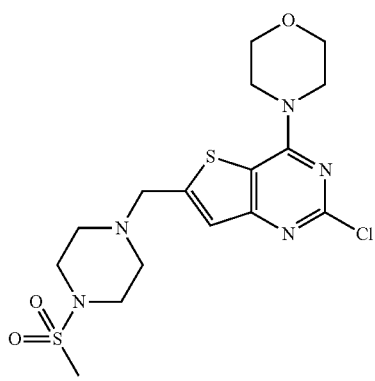 [SMILES: CS(=O)(=O)N1CCN(Cc2cc3nc(Cl)nc(N4CCOCC4)c3s2)CC1]

Reaction between N-BOC-piperazine and methane sulfonyl chloride in dichloromethane and triethylamine yielded 4-methanesulfonyl-piperazine-1-carboxylic acid tert-butyl ester. Cleavage of the BOC protecting group using HCl (2M) in dichloromethane yielded 1-methanesulfonyl-piperazine. HCl salt.

Reaction between 1-methanesulfonyl-piperazine. HCl salt and 2-chloro-4-morpholin-4-yl-thieno[3,2-d]pyrimidine-6-carbaldehyde using procedure C yielded the title compound.

REFERENCE EXAMPLE 12

2-Chloro-6-(4-methanesulfonyl-piperazin-1-ylmethyl)-4-morpholin-4-yl-thieno[2,3-d]pyrimidine

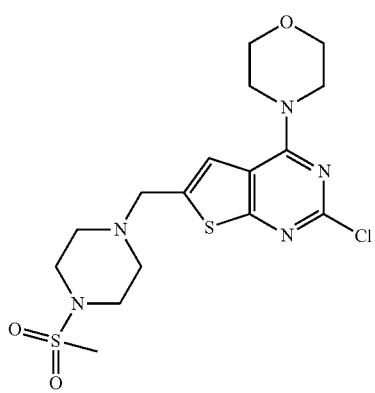 [SMILES: CS(=O)(=O)N1CCN(Cc2cc3c(N4CCOCC4)nc(Cl)nc3s2)CC1]

Reaction between 1-methanesulfonyl-piperazine. HCL salt and 2-chloro-4-morpholin-4-yl-thieno[2,3-d]pyrimidine-6-carbaldehyde using procedure C yielded the title compound

REFERENCE EXAMPLE 13

Tert-butyl furan-3-ylcarbamate

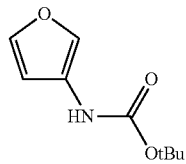 [SMILES: CC(C)(C)OC(=O)Nc1ccoc1]

3-Furoic acid (5.60 g, 1.0 eq) was dissolved in tert-butanol (200 ml) and treated with triethylamine (10 ml, 1.4 eq) and diphenyl phosphoryl azide (12 ml, 1.1 eq). Mixture was heated at reflux for 18 h. Reaction mixture was cooled to room temperature, then concentrated to 50 ml and poured into saturated aq. NaHCO$_3$. Mixture was stirred at 0° C. for 2 h. Solid was collected by filtration and dried under high vacuum. The crude reaction mixture was purified by flash chromatography to yield tert-butyl furan-3-ylcarbamate (6.95 g, 76%): $^1$H NMR (CDCl$_3$, 400 MHz) δ 7.71 (bs, 1H), 7.27 (m, 1H), 6.27 (bs, 1H), 6.20 (bs, 1H), 1.50 (s, 9H); MS (Q1) 184 (M)$^+$.

REFERENCE EXAMPLE 14

Tert-butyl 2-(methoxycarbonyl)furan-3-ylcarbamate

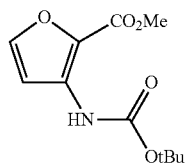

To a solution of tert-butyl furan-3-ylcarbamate (1.7 g, 1.0 eq) in THF (50 ml) at −30° C. was added TMEDA (1.75 ml, 1.3 eq) followed by 1.6M solution of n-butyllithium (8.4 ml, 2.25 eq, 1.6M in hexanes). Reaction mixture was allowed to warm up to 0° C. and stirred for 1 h, before being cooled back to −30° C. Dimethyl carbonate (2.4 ml, 3.0 eq) was quickly added, before the reaction mixture was allowed to warm up to room temperature for 1 hr. Reaction mixture was quenched with 2M HCl, followed by addition of saturated aq. NaCl. Mixture was extracted with ethyl acetate. The combined organic extracts were dried with Na$_2$SO$_4$ and concentrated. The crude reaction mixture was purified by flash chromatography to yield tert-butyl 2-(methoxycarbonyl)furan-3-ylcarbamate (1.14 g, 51%): MS (Q1) 242 (M)$^+$.

REFERENCE EXAMPLE 15

Methyl 3-aminofuran-2-carboxylate

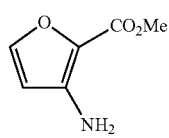

Tert-butyl 2-(methoxycarbonyl)furan-3-ylcarbamate (1.14 g, 1.0 eq) was dissolved in dichloromethane (8 ml) and treated with trifluoroacetic acid (5 ml). Reaction mixture was stirred at room temperature for 3 h, and was then concentrated. Residue was dissolved in dichloromethane and washed with saturated aq. NaHCO$_3$. The organic layer was dried (Na$_2$SO$_4$) and concentrated Mixture was extracted with ethyl acetate. The combined organic extracts were dried with Na$_2$SO$_4$ and concentrated. The crude reaction mixture was purified by flash chromatography to yield methyl 3-aminofuran-2-carboxylate (574 mg, 86%): MS (Q1) 142 (M)$^+$.

REFERENCE EXAMPLE 16

Ethyl 3-ureidofuran-2-carboxylate

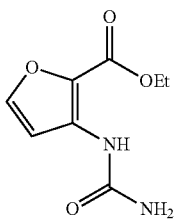 [SMILES: CCOC(=O)c1occc1NC(N)=O]

To a solution of methyl 3-aminofuran-2-carboxylate (100 mg, 1.0 eq) in dichloromethane (3 ml) at −78° C. was added chlorosulfonyl isocyanate (0.09 ml, 1.4 eq) dropwise. The reaction was slowly warmed to room temperature and stirred for 40 minutes. Reaction was concentrated. To the residue was added 6N HCl (3.5 ml) and mixture was heated to 100° C. for 20 minutes. Reaction mixture was allowed to cool down to room temperature, and was neutralized with saturated aq. NaHCO$_3$. Solid was collected by filtration to yield ethyl 3-ureidofuran-2-carboxylate (120 mg, 92%) as a beige solid which was used in the next reaction without further purification.

REFERENCE EXAMPLE 17

Furo[3,2-d]pyrimidine-2,4-diol

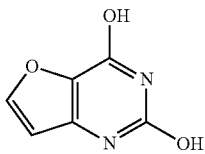

Ethyl 3-ureidofuran-2-carboxylate (120 mg, 1.0 eq) was suspended in methanol (6 ml) and treated with 1.5 M NaOH (1.5 ml). Reaction mixture was heated to reflux for 90 minutes. Reaction mixture was allowed to cool down to room temperature, and was acidified with 6N HCl up to pH 3. Mixture was concentrated. Methanol was added to residue and solid was filtered and dried at 95° C. under high vacuum for 24 h to yield furo[3,2-d]pyrimidine-2,4-diol (90 mg, 91%) which was used in the next reaction without further purification.

REFERENCE EXAMPLE 18

2,4-Dichlorofuro[3,2-d]pyrimidine

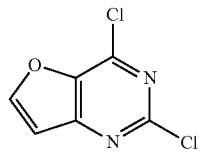

Furo[3,2-d]pyrimidine-2,4-diol (39 mg, 1.0 eq) was dissolved in POCl$_3$ (1.8 ml). Mixture was cooled to −40° C. and N,N-diisopropylethylamine (0.45 ml) wad slowly added. Reaction mixture was then heated to reflux for 48 h, then cooled to room temperature Reaction mixture was poured into ice/water. Mixture was extracted with ethyl acetate. The combined organic layers were washed with saturated aq. NaHCO$_3$, dried (Na$_2$SO$_4$) and concentrated to yield 2,4-dichlorofuro[3,2-d]pyrimidine (23 mg, 48%) which was used in the next reaction without further purification.

REFERENCE EXAMPLE 19

2-Chloro-4-morpholinofuro[3,2-d]pyrimidine

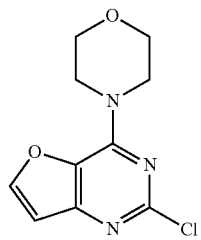 [SMILES: Clc1nc(N2CCOCC2)c2occc2n1]

2,4-Dichlorofuro[3,2-d]pyrimidine (23 mg, 1.0 eq) was suspended in methanol (1.7 ml) and treated with morpholine (0.09 ml, 4.0 eq). Reaction mixture was stirred at room temperature for 2 h, before being quenched with saturated aq. NaHCO$_3$. Mixture was extracted with dichloromethane. The combined organic layers were dried (Na$_2$SO$_4$) and concentrated to yield 2-chloro-4-morpholinofuro[3,2-d]pyrimidine (14 mg, 48%) which was used in the next reaction without further purification.

REFERENCE EXAMPLE 20

2-Chloro-4-morpholinofuro[3,2-d]pyrimidine-6-carbaldehyde

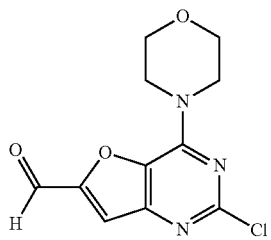 [SMILES: O=Cc1cc2nc(Cl)nc(N3CCOCC3)c2o1]

To a solution of 2-chloro-4-morpholinofuro[3,2-d]pyrimidine (40 mg, 1.0 eq) dissolved in THF (1.7 ml) at −78° C. was added 1.6M solution of n-butyllithium (0.14 ml, 1.3 eq, 1.6M in hexanes). Reaction mixture was stirred at −78° C. for 30 minutes. DMF (0.05 ml, 4.0 eq) was added and reaction mixture was allowed to slowly warm up to room temperature and stirred for 90 minutes. Reaction mixture was quenched with water, and extracted with dichloromethane. The combined organic layers were dried ($Na_2SO_4$) and concentrated. The crude reaction mixture was purified by flash chromatography to yield 2-chloro-4-morpholinofuro[3,2-d]pyrimidine-6-carbaldehyde (22 mg, 50%): $^1$H NMR ($CDCl_3$, 400 MHz) δ 9.92 (s, 1H), 7.48 (s, 1H), 4.12 (m, 4H), 3.86 (dd, 4H); MS (Q1) 268 (M)$^+$.

REFERENCE EXAMPLE 21

2-Chloro-64(4-(methylsulfonyl)piperazin-1-yl)methyl)-4-morpholinofuro[3,2-d]pyrimidine

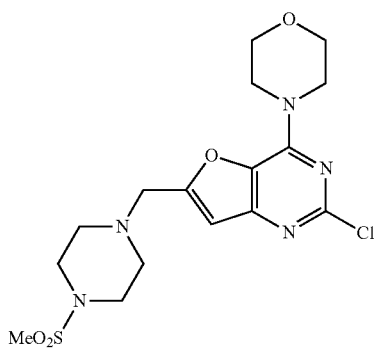 [SMILES: CS(=O)(=O)N1CCN(Cc2cc3nc(Cl)nc(N4CCOCC4)c3o2)CC1]

2-Chloro-4-morpholinofuro[3,2-d]pyrimidine-6-carbaldehyde (65 mg, 1.0 eq) was dissolved in 1,2-dichloroethane (9.7 ml) and treated with hydrochloride salt of 1-methanesulfonylpiperazine (69 mg, 1.4 eq), sodium acetate (28 mg, 1.4 eq) and trimethyl orthoformate (0.27 ml, 10 eq). Reaction mixture was stirred at room temperature for 12 h. Sodium triacetoxyborohydride (62 mg, 1.2 eq) was added and reaction mixture was stirred at room temperature for 8 h. Reaction mixture was quenched with saturated aq. $NaHCO_3$ and extracted with dichloromethane. The combined organic layers were dried ($Na_2SO_4$) and concentrated. The crude reaction mixture was purified by flash chromatography to yield 2-chloro-6-((4-(methylsulfonyl)piperazin-1-yl)methyl)-4-morpholinofuro[3,2-d]pyrimidine (70 mg, 68%): MS (Q1) 416 (M)$^+$.

EXAMPLE 2

Compounds of the Invention—Series A

The following compounds of the invention were prepared. The compound numbering corresponds to that used in Table 1A above.

14: 1-(2-Chloro-4-morpholin-4-yl-thieno[3,2-d]pyrimidin-6-ylmethyl)-4-methanesulfonyl-piperazin-2-one (100 mg, 0.2 mmol) was converted to 14 using General Procedure A (10 mg, 10%). MS (Q1) 528 (M)+

68: To 1 g of 2-chloro-4-morpholinothieno[3,2-d]pyrimidine-6-carbaldehyde was added 855 mg 1-BOC-piperazine via Procedure C to give 1.59 g of 2-chloro-4-morpholino-6-((Boc-piperazin-1-yl)methyl)thieno[3,2-d]pyrimidine. The crude HCl salt of 2-chloro-4-morpholino-6-((piperazin-1-yl)methyl)thieno[3,2-d]pyrimidine was then formed by treatment with 5 eq 4N HCl in dioxane in a solution of DCM and subsequent evaporation to dryness.

100 mg of crude HCl salt of 2-chloro-4-morpholino-6-((piperazin-1-yl)methyl)thieno[3,2-d]pyrimidine was treated with 135 mg of Boc-Glycine via Procedure B. This crude intermediate was then subjected to Procedure A to give 31.5 mg of 68. MS (Q1) 493.2 (M)+.

67: 25 mg of crude HCl salt of 2-chloro-4-morpholino-6-((piperazin-1-yl)methyl)thieno[3,2-d]pyrimidine was treated with 135 mg of N,N-Dimethylglycine via Procedure B. This crude intermediate was then subjected to Procedure A to give 7.4 mg of 67. MS (Q1) 521.2 (M)+.

66: 400 mg of crude HCl salt of 2-chloro-4-morpholino-6-((piperazin-1-yl)methyl)thieno[3,2-d]pyrimidine was treated with 175 mg of L-Lactic Acid via Procedure B. This crude intermediate was then subjected to Procedure A to give 212 mg of 66. MS (Q1) 508.2 (M)+.

56: The crude HCl salt of 2-chloro-4-morpholino-6-((piperazin-1-yl)methyl)thieno[3,2-d]pyrimidine (50 mg) was treated with 5 eq methyl chloroformate and 6 eq DIPEA in 1 mL of DMF. The reaction mixture was concentrated and extracted into Ethyl Acetate with Saturated Ammonium Chloride. The aqueous layer was back-extracted once with DCM. The organics were combined and concentrated to dryness. This crude intermediate was then subjected to Procedure A to give 3.7 mg of 56. MS (Q1) 494.2 (M)+.

55: The crude HCl salt of 2-chloro-4-morpholino-6-((piperazin-1-yl)methyl)thieno[3,2-d]pyrimidine (50 mg) was treated with 5 eq ethyl chloroformate and 6 eq DIPEA in 1 mL of DMF. The reaction mixture was concentrated and extracted into Ethyl Acetate with Saturated Ammonium Chloride. The aqueous layer was back-extracted once with DCM. The organics were combined and concentrated to dryness. This crude intermediate was then subjected to Procedure A to give 35.4 mg of 55. MS (Q1) 508.2 (M)+.

54: The crude HCl salt of 2-chloro-4-morpholino-6-((piperazin-1-yl)methyl)thieno[3,2-d]pyrimidine (50 mg) was treated with 3 eq Acetic Anhydride and 5 eq DIPEA in 1 mL of DCM. The reaction mixture was concentrated and extracted into Ethyl Acetate with Saturated Ammonium Chloride. The aqueous layer was back-extracted once with DCM. The organics were combined and concentrated to dryness. This crude intermediate was then subjected to Procedure A to give 20.2 mg of 54. MS (Q1) 478.2 (M)+.

53: The crude HCl salt of 2-chloro-4-morpholino-6-((piperazin-1-yl)methyl)thieno[3,2-d]pyrimidine (50 mg) was treated with 5 eq of Formic Acid, 5 eq EDC and 5 eq DIPEA in 1 mL of DMF. This crude intermediate was then subjected to Procedure A to give 5.1 mg of 53. MS (Q1) 464.2 (M)+.

52: The crude HCl salt of 2-chloro-4-morpholino-6-((piperazin-1-yl)methyl)thieno[3,2-d]pyrimidine (50 mg) was treated with 2.5 eq of pivaloyl chloride and 3 eq DIPEA in 1 mL of DCM. This crude intermediate was then subjected to Procedure A to give 36.7 mg of 52. MS (Q1) 520.3 (M)+.

48: The crude HCl salt of 2-chloro-4-morpholino-6-((piperazin-1-yl)methyl)thieno[3,2-d]pyrimidine (50 mg) was treated with 2.5 eq of cyclopropanecarbonyl chloride and 3 eq DIPEA in 1 mL of DCM. This crude intermediate was then subjected to Procedure A to give 27.2 mg of 48. MS (Q1) 504.2 (M)+.

107: The crude HCl salt of 2-chloro-4-morpholino-6-((piperazin-1-yl)methyl)thieno[3,2-d]pyrimidine (100 mg) was treated with 70 mg of D-Lactic Acid via Procedure B. This crude intermediate was then subjected to Procedure A to give (R)-1-(4-((2-(1H-indazol-4-yl)-4-morpholinothieno[3,2-d]pyrimidin-6-yl)methyl)piperazin-1-yl)-2-hydroxypropan-1-one. MS (Q1) 508.2 (M)+.

108: The crude HCl salt of 2-chloro-4-morpholino-6-((piperazin-1-yl)methyl)thieno[3,2-d]pyrimidine (100 mg) was treated with 75 mg of 2-Hydroxyisobutyric Acid via Procedure B. This crude intermediate was then subjected to Procedure A to give 1-(4-((2-(1H-indazol-4-yl)-4-morpholinothieno[3,2-d]pyrimidin-6-yl)methyl)piperazin-1-yl)-2-hydroxy-2-methylpropan-1-one. MS (Q1) 522.2 (M)+.

109: The crude HCl salt of 2-chloro-4-morpholino-6-((piperazin-1-yl)methyl)thieno[3,2-d]pyrimidine (100 mg) was treated with 55 mg of Glycolic Acid via Procedure B. This crude intermediate was then subjected to Procedure A to give 1-(4-((2-(1H-indazol-4-yl)-4-morpholinothieno[3,2-d]pyrimidin-6-yl)methyl)piperazin-1-yl)-2-hydroxyethanone. MS (Q1) 494.4 (M)+.

110: The crude HCl salt of 2-chloro-4-morpholino-6-((piperazin-1-yl)methyl)thieno[3,2-d]pyrimidine (100 mg) was treated with 55 mg of Methoxyacetic Acid via Procedure B. This crude intermediate was then subjected to Procedure A to give 1-(4-((2-(1H-indazol-4-yl)-4-morpholinothieno[3,2-d]pyrimidin-6-yl)methyl)piperazin-1-yl)-2-methoxyethanone. MS (Q1) 508 (M)+.

111: The crude HCl salt of 2-chloro-4-morpholino-6-((piperazin-1-yl)methyl)thieno[3,2-d]pyrimidine (100 mg) was treated with 70 µL of tetrahydro-2-furoic acid via Procedure B. This crude intermediate was then subjected to Procedure A to give (4-((2-(1H-indazol-4-yl)-4-morpholinothieno[3,2-d]pyrimidin-6-yl)methyl)piperazin-1-yl)(tetrahydrofuran-2-yl)methanone. MS (Q1) 534.3 (M)+.

112: The crude HCl salt of 2-chloro-4-morpholino-6-((piperazin-1-yl)methyl)thieno[3,2-d]pyrimidine (100 mg) was treated with 100 mg of Boc-amino-cyclopropanecarboxylic acid via Procedure B. This crude intermediate was then subjected to Procedure A to give (4-((2-(1H-indazol-4-yl)-4-morpholinothieno[3,2-d]pyrimidin-6-yl)methyl)piperazin-1-yl)(1-aminocyclopropyl)methanone. MS (Q1) 519.3 (M)+.

113: The crude HCl salt of 2-chloro-4-morpholino-6-((piperazin-1-yl)methyl)thieno[3,2-d]pyrimidine (100 mg) was treated with 140 mg of Boc-Alanine via Procedure B. This crude intermediate was then subjected to Procedure A to give (S)-1-(4-((2-(1H-indazol-4-yl)-4-morpholinothieno[3,2-d]pyrimidin-6-yl)methyl)piperazin-1-yl)-2-aminopropan-1-one. MS (Q1) 507.3 (M)+.

114: The crude HCl salt of 2-chloro-4-morpholino-6-((piperazin-1-yl)methyl)thieno[3,2-d]pyrimidine (100 mg) was treated with 140 mg of Boc-D-Alanine via Procedure B. This crude intermediate was then subjected to Procedure A to give (R)-1-(4-((2-(1H-indazol-4-yl)-4-morpholinothieno[3,2-d]pyrimidin-6-yl)methyl)piperazin-1-yl)-2-aminopropan-1-one. MS (Q1) 507.3 (M)+.

115: The crude HCl salt of 2-chloro-4-morpholino-6-((piperazin-1-yl)methyl)thieno[3,2-d]pyrimidine (100 mg) was treated with 100 mg of methanesulphonylacetic acid via Procedure B. This crude intermediate was then subjected to Procedure A to give 1-(4-((2-(1H-indazol-4-yl)-4-morpholinothieno[3,2-d]pyrimidin-6-yl)methyl)piperazin-1-yl)-2-(methylsulfonyl)ethanone. MS (Q1) 556.3 (M)+.

116: To 700 mg of 2-chloro-4-morpholinothieno[2,3-d]pyrimidine-6-carbaldehyde was added 645 mg 1-BOC-piperazine via Procedure C to give 1.12 g of 2-chloro-4-morpholino-6-((Boc-piperazin-1-yl)methyl)thieno[2,3-d]pyrimidine. The crude HCl salt of 2-chloro-4-morpholino-6-((piperazin-1-yl)methyl)thieno[2,3-d]pyrimidine was then formed by treatment with 5 eq 4N HCl in dioxane in a solution of DCM and subsequent evaporation to dryness.

The crude HCl salt of 2-chloro-4-morpholino-6-((piperazin-1-yl)methyl)thieno[2,3-d]pyrimidine (100 mg) was treated with 65 mg of L-Lactic Acid via Procedure B. This crude intermediate was then subjected to Procedure A to give (S)-1-(4-((2-(1H-indazol-4-yl)-4-morpholinothieno[2,3-d]pyrimidin-6-yl)methyl)piperazin-1-yl)-2-hydroxypropan-1-one. MS (Q1) 508.2 (M)+.

117: The crude HCl salt of 2-chloro-4-morpholino-6-((piperazin-1-yl)methyl)thieno[2,3-d]pyrimidine (75 mg) was treated with 51 mg of D-Lactic Acid via Procedure B. This crude intermediate was then subjected to Procedure A to give (R)-1-(4-((2-(1H-indazol-4-yl)-4-morpholinothieno[2,3-d]pyrimidin-6-yl)methyl)piperazin-1-yl)-2-hydroxypropan-1-one. MS (Q1) 508.2 (M)+.

118: The crude HCl salt of 2-chloro-4-morpholino-6-((piperazin-1-yl)methyl)thieno[2,3-d]pyrimidine (75 mg) was treated with 55 mg of 2-Hydroxyisobutyric Acid via Procedure B. This crude intermediate was then subjected to Procedure A to give 1-(4-((2-(1H-indazol-4-yl)-4-morpholinothieno[2,3-d]pyrimidin-6-yl)methyl)piperazin-1-yl)-2-hydroxy-2-methylpropan-1-one. MS (Q1) 522.2 (M)+.

119: The crude HCl salt of 2-chloro-4-morpholino-6-((piperazin-1-yl)methyl)thieno[2,3-d]pyrimidine (75 mg) was treated with 40 mg of Glycolic Acid via Procedure B. This crude intermediate was then subjected to Procedure A to give 1-(4-((2-(1H-indazol-4-yl)-4-morpholinothieno[2,3-d]pyrimidin-6-yl)methyl)piperazin-1-yl)-2-hydroxyethanone. MS (Q1) 494.4 (M)+.

120: The crude HCl salt of 2-chloro-4-morpholino-6-((piperazin-1-yl)methyl)thieno[2,3-d]pyrimidine (75 mg) was treated with 41 µL of methoxylacetic acid via Procedure B. This crude intermediate was then subjected to Procedure A to give 1-(4-((2-(1H-indazol-4-yl)-4-morpholinothieno[2,3-d]pyrimidin-6-yl)methyl)piperazin-1-yl)-2-methoxyethanone. MS (Q1) 508 (M)+.

121: The crude HCl salt of 2-chloro-4-morpholino-6-((piperazin-1-yl)methyl)thieno[2,3-d]pyrimidine (75 mg) was treated with 50 µL of Tetrahydro-2-furoic Acid via Procedure B. This crude intermediate was then subjected to Procedure A to give (4-((2-(1H-indazol-4-yl)-4-morpholinothieno[2,3-d]pyrimidin-6-yl)methyl)piperazin-1-yl)(tetrahydrofuran-2-yl)methanone. MS (Q1) 534.3 (M)+.

122: The crude HCl salt of 2-chloro-4-morpholino-6-((piperazin-1-yl)methyl)thieno[2,3-d]pyrimidine (75 mg) was treated with 100 mg of Boc-2-Aminoisobutyric Acid via Procedure B. This crude intermediate was then subjected to Procedure A to give 1-(4-((2-(1H-indazol-4-yl)-4-morpholinothieno[2,3-d]pyrimidin-6-yl)methyl)piperazin-1-yl)-2-amino-2-methylpropan-1-one. MS (Q1) 521.5 (M)+.

123: The crude HCl salt of 2-chloro-4-morpholino-6-((piperazin-1-yl)methyl)thieno[2,3-d]pyrimidine (75 mg) was treated with 100 mg of Boc-amino-cyclopropanecarboxylic acid via Procedure B. This crude intermediate was then subjected to Procedure A to give (4-((2-(1H-indazol-4-yl)-4-morpholinothieno[2,3-d]pyrimidin-6-yl)methyl)piperazin-1-yl)(1-aminocyclopropyl)methanone. MS (Q1) 519.3 (M)+.

124: The crude HCl salt of 2-chloro-4-morpholino-6-((piperazin-1-yl)methyl)thieno[2,3-d]pyrimidine (75 mg) was treated with 93 mg of Boc-Glycine Acid via Procedure B. This crude intermediate was then subjected to Procedure A to give 1-(4-((2-(1H-indazol-4-yl)-4-morpholinothieno[2,3-d]pyrimidin-6-yl)methyl)piperazin-1-yl)-2-aminoethanone. MS (Q1) 493.3 (M)+.

125: The crude HCl salt of 2-chloro-4-morpholino-6-((piperazin-1-yl)methyl)thieno[2,3-d]pyrimidine (75 mg) was treated with 100 mg of Boc-Alanine Acid via Procedure B. This crude intermediate was then subjected to Procedure A to give (S)-1-(4-((2-(1H-indazol-4-yl)-4-morpholinothieno[2,3-d]pyrimidin-6-yl)methyl)piperazin-1-yl)-2-aminopropan-1-one. MS (Q1) 507.3 (M)+.

126: The crude HCl salt of 2-chloro-4-morpholino-6-((piperazin-1-yl)methyl)thieno[2,3-d]pyrimidine (75 mg) was treated with 100 mg of N-Boc-D-alanine via Procedure B. This crude intermediate was then subjected to Procedure A to give (R)-1-(4-((2-(1H-indazol-4-yl)-4-morpholinothieno[2,3-d]pyrimidin-6-yl)methyl)piperazin-1-yl)-2-aminopropan-1-one. MS (Q1) 507.3 (M)+.

127: The crude HCl salt of 2-chloro-4-morpholino-6-((piperazin-1-yl)methyl)thieno[2,3-d]pyrimidine (75 mg) was treated with 100 mg of methanesulphonylacetic acid via Procedure B. This crude intermediate was then subjected to Procedure A to give 1-(4-((2-(1H-indazol-4-yl)-4-morpholinothieno[2,3-d]pyrimidin-6-yl)methyl)piperazin-1-yl)-2-(methylsulfonyl)ethanone. MS (Q1) 556.3 (M)+.

63: 2-Chloro-4-morpholinothieno[3,2-d]pyrimidine-6-carbaldehyde (50 mg) was reacted with 4-hydroxypiperidine following the protocol in general procedure C. The crude material was then used in general procedure A to give 3 mg of 63 following reversed phase HPLC purification. MS (Q1) 451 (M)+

64: 2-Chloro-4-morpholinothieno[3,2-d]pyrimidine-6-carbaldehyde (50 mg) was reacted with 3-hydroxypyrrolidine following the protocol in general procedure C. The crude material was then used following general procedure A to give 7 mg of 64 following reversed phase HPLC purification. MS (Q1) 437 (M)+

65: 2-Chloro-4-morpholinothieno[3,2-d]pyrimidine-6-carbaldehyde (50 mg) was dissolved in 2 mL dimethylformamide. To this solution was added 2.6 equivalents of 3-hydroxypiperidine, 3 equivalents of magnesium sulfate, and 0.04 mL of acetic acid. The mixture was allowed to stir for 6 hours prior to adding 2.5 equivalents of sodium triacetoxyborohydride. Following 12 to 16 hours of stirring the reaction was poured into saturated sodium bicarbonate and extracted several times with ethylacetate. This chloro intermediate used crude following the protocol for general procedure A to give 6 mg of 65 after reversed phase HPLC purification. MS (Q1) 451 (M)+

49: 2-Chloro-4-morpholinothieno[3,2-d]pyrimidine-6-carbaldehyde (175 mg) was reacted with 3-(methanesulfonyl)pyrrolidine following the protocol in general procedure C. The crude material was then used in general procedure A to give 177 mg of G-34670 following purification on silica (0 to 15% MeOH gradient in dichloromethane over 40 min, 40 g column). MS (Q1) 499.2 (M)+

50: 2-Chloro-4-morpholinothieno[3,2-d]pyrimidine-6-carbaldehyde (200 mg) was reacted according to procedure C with (S)-4-N-trityl-2-methyl-piperazine. The crude material was then dissolved in 10 mL of methanol and treated with 0.5 mL of concentrated HCl for several hours before basifying with NaOH and extracting into EtOAc. After evaporation the crude reaction mixture containing 2-chloro-6-(((S)-2-methylpiperazin-1-yl)methyl-4-morpholinothieno[3,2-d]pyrimidine was dissolved in 10 mL of dichloromethane and treated with 0.3 mL of diisopropylethylamine and 54 µL of methanesulfonyl chloride. After overnight stirring an additional 20 µL of methanesulfonyl chloride was added to convert remaining starting material to product. Upon completion the reaction was extracted with dichloromethane and water and then purified on silica gel using a MeOH gradient in dichloromethane to give 186 mg of 2-chloro-6-(((S)-4-N-sulfonyl-2-methylpiperazin-1-yl)methyl-4-morpholinothieno[3,2-d]pyrimidine. 160 mg of this material was used following general procedure SUZUKI and purified with reversed phase HPLC to give compound 50. MS (Q1) 528 (M)+

1: 2-Chloro-4-morpholinothieno[3,2-d]pyrimidine-6-carbaldehyde (100 mg) was reacted according to procedure C with (1S,4S)—N-Boc-2,5-diaza-bicyclo[2.2.1]heptane to give 140 mg of the Boc protected piperazine following silica gel purification (25% to 100% EtOAc gradient in hexanes, 12 g column). The Boc group was removed by treating the compound with 1.5 mmol of HCl in dioxane. After evaporation the free amine was sulfonylated in 3 mL of dichloromethane using 100 µL of triethylamine as a base and 35 µL of methanesulfonylchloride. After two hours the reaction was complete and extracted with dichloromethane and saturated NaCl. The crude material from this reaction was used following general procedure SUZUKI and purified with reversed phase HPLC to give 61 mg of compound 1. MS (Q1) 526 (M)+

75: N-Butyllithium (9.4 mL, 22.48 mmol, 2.5 M in hexane solution) was added to a mixture of 2-chloro-4-morpholinothieno[3,2-d]pyrimidine (3.0 g, 11.74 mmol) in 60 mL of THF at −78° C. The reaction mixture was allowed to warm to −40° C. and stirred for 30 min. A solution of iodine (6.0 g, 23.48 mmol) in 10 mL of THF was added dropwise. After the addition was completed. The reaction mixture was brought to room temperature and stirred for 2 h. The mixture was quenched by diluting with dichloromethane (300 mL) and extracting with H$_2$O (2×100 mL). The organic layer was washed with Na$_2$S$_2$O$_3$ (2×100 mL), H$_2$O (2×100 mL), dried over MgSO$_4$, filtered and evaporated to afford 2-chloro-6-iodo-4-morpholinothieno[3,2-d]pyrimidine (3.4 g, 75%).

2-Chloro-6-iodo-4-morpholinothieno[3,2-d]pyrimidine (150 mg), 2-oxazolidinone (103 mg), potassium phosphate tribasic (250 mg), copper iodide (7 mg), 4 µL of N,N-dimethylethylenediamine in 2 mL of 1,4-dioxane was heated to 100° C. for 15 hr. The reaction mixture was evaporated and the residue was diluted with ethyl acetate (50 mL), washed with brine (30 mL), dried over MgSO$_4$, filtered and evaporated. The crude product was purified on reverse phase HPLC to give 46 mg of 3-(2-chloro-4-morpholinothieno[3,2-d]pyrimidin-6-yl)oxazolidin-2-one.

3-(2-Chloro-4-morpholinothieno[3,2-d]pyrimidin-6-yl)oxazolidin-2-one (46 mg) was coupled to 4-(4,4,5,5-tetramethyl-1,3,2-dioxaborolan-2-yl)-1H-indazole via Procedure A. The product was purified by reverse phase HPLC to yield 8.6 mg of 3-(2-(1H-indazol-4-yl)-4-morpholinothieno[3,2-d]pyrimidin-6-yl)oxazolidin-2-one. MS (Q1) 423 (M)+

73: 2-Chloro-6-iodo-4-morpholinothieno[3,2-d]pyrimidine (150 mg), 90 µL of 2-pyrrolidinone, potassium phosphate tribasic (250 mg), copper iodide (7 mg), 4 µL of N,N-dimethylethylenediamine in 2 mL of 1,4-dioxane was heated to 100° C. for 16 h. The reaction mixture was evaporated and the residue was diluted with ethyl acetate (60 mL), washed with brine (30 mL), dried over MgSO$_4$, filtered and evaporated. The crude product was purified on reverse phase HPLC to give 53 mg of 1-(2-chloro-4-morpholinothieno[3,2-d]pyrimidin-6-yl)pyrrolidin-2-one. 1-(2-Chloro-4-morpholinothieno[3,2-d]pyrimidin-6-yl) pyrrolidin-2-one (35 mg) was coupled to 4-(4,4,5,5-tetramethyl-1,3,2-dioxaborolan-2-yl)-1H-indazole via Procedure A. The product was purified by reverse phase HPLC to yield 19.5 mg of 1-(1H-indazol-4-yl)-4-morpholinothieno[3,2-d] pyrimidin-6-yl)pyrrolidin-2-one. MS (Q1) 421 (M)$^+$ 81: 2-Chloro-6-(4-methylsulfonyl-piperazin-1-yl-methyl)-4-morpholin-4-yl-thieno[3,2-d]pyrimidine was reacted with 2-fluoropyridine-5-boronic acid in General Procedure A on a 18.5 mmol scale to give 34.2 mg. of the desired product after RP-HPLC purification. MS (Q1) 493.1 (M)+.

80: 2-Chloro-6-(4-methylsulfonyl-piperazin-1-yl-methyl)-4-morpholin-4-yl-thieno[3.2-d]pyrimidine was reacted with 3-fluorophenyl boronic acid in General Procedure A on a 18.5 mmol scale to give 20.8 mg. of the desired product after RP-HPLC purification. MS (Q1) 492.3 (M)+.

79: 2-Chloro-6-(4-methylsulfonyl-piperazin-1-yl-methyl)-4-morpholin-4-yl-thieno[3.2-d]pyrimidine was reacted with 3-(N-methylaminocarbonyl)phenyl boronic acid in General Procedure A on a 18.5 mmol scale to give 7.4 mg. of the desired product after RP-HPLC purification. MS (Q1) 531.3 (M)+.

78: 2-Chloro-6-(4-methylsulfonyl-piperazin-1-yl-methyl)-4-morpholin-4-yl-thieno[3.2-d]pyrimidine was reacted with 2-fluoropyridine-3-boronic acid in General Procedure A on a 18.5 mmol scale to give 23.5 mg. of the desired product after RP-HPLC purification. MS (Q1) 493.4 (M)+.

77: 2-Chloro-6-(4-methylsulfonyl-piperazin-1-yl-methyl)-4-morpholin-4-yl-thieno[3.2-d]pyrimidine was reacted with pyrimidine-5-boronic acid in General Procedure A on a 18.5 mmol scale to give 8.1 mg of the desired product after RP-HPLC purification. MS (Q1) 476.3 (M)+.

76: 2-Chloro-6-(4-methylsulfonyl-piperazin-1-yl-methyl)-4-morpholin-4-yl-thieno[3.2-d]pyrimidine was reacted with 3-methylsulfonylaminophenyl boronic acid in General Procedure A on a 18.5 mmol scale to give 76 mg. of the desired product after RP-HPLC purification. MS (Q1) 567.2 (M)+.

2: 2-Chloro-6-((4-(methylsulfonyl)piperazin-1-yl)methyl)-4-morpholinofuro[3,2-d]pyrimidine (40 mg, 1.0 eq) was dissolved in toluene/ethanol/water (4:2:1, 1.6 ml) and treated with 4-(4,4,5,5-tetramethyl-1,3,2-dioxaborolan-2-yl)-1H-indazole (59 mg, 2.5 eq), PdCl$_2$(PPh$_3$)$_2$ (6.8 mg, 0.10 eq) and sodium carbonate (36 mg, 3.5 eq). The vial was sealed and heated with stirring in the microwave to 150° C. for 15 minutes. The crude reaction mixture was concentrated and purified by reverse phase HPLC to afford 2-(1H-indazol-4-yl)-6-((4-(methylsulfonyl)piperazin-1-yl)methyl)-4-morpholinofuro[3,2-d]pyrimidine: MS (Q1) 498 (M)$^+$.

EXAMPLE 3

Further Compounds of the Invention—Series B

The following compounds of the invention were prepared. The compound numbering corresponds to that used in Table 1A above.

5: 2-Chloro-6-(4-methanesulfonyl-piperazin-1-ylmethyl)-4-morpholin-4-yl-thieno[2,3-d]pyrimidine was reacted with pyrimidine-5-boronic acid in General Procedure A. Purification on silica yielded the desired compound.
MS (Q1) 476.3 (M)+.
NMR (400 MHz CDCl3): 2.67 (4H, t (J 4.79), CH2), 2.81 (3H, s, CH3), 3.29 (4H, m, CH2), 3.83 (2H, s, CH2), 3.89-4.01 (8H, m, CH2), 7.18 (1H, s, ar), 9.28 (1H, s, ar), 9.67 (2H, s, ar)

11: 2-Chloro-6-(4-methylsulfonyl-piperazin-1-yl-methyl)-4-morpholin-4-yl-thieno[3,2-d]pyrimidine was reacted with benzenesulfonamide-3-boronic acid pinacol ester in General Procedure A. Purification on silica yielded the desired compound.
NMR: (CDCl3): 2.68-2.72 (4H, m), 2.82 (3H, s), 3.29-3.33 (4H, m), 3.90 (2H, s), 3.90-3.94 (4H, m), 4.05-4.10 (4H, m), 4.81 (211, br. s), 7.33 (1H, s), 7.62-7.66 (1H, m), 8.00 (1H, d, J=8.0), 8.68 (1H, d, J=8.0), 9.02 (1H, s)
(ESI+): MH+ 553.18

12: 2-Chloro-6-(4-methylsulfonyl-piperazin-1-yl-methyl)-4-morpholin-4-yl-thieno[3,2-d]pyrimidine was reacted with 4-(hydroxymethyl)phenyl boronic acid in General Procedure A. Purification on silica yielded the desired compound
NMR: (DMSO-d6): 2.58-2.62 (4H, m), 2.89 (3H, s), 3.13-3.18 (4H, m), 3.78-3.81 (4H, m), 3.92 (2H, s), 3.95-4.00 (4H, m), 4.56 (2H, d, J=5.7), 5.23 (1H, t, J=5.7), 7.40 (1H, s), 7.44 (2H, d, J=8.2), 8.38 (2H, d, J=8.2)
(ESI+): MH+ 504.18

13: 2-Chloro-6-(4-methylsulfonyl-piperazin-1-yl-methyl)-4-morpholin-4-yl-thieno[3,2-d]pyrimidine was reacted with 3-carbamoylphenyl boronic acid in General Procedure A. Purification on silica yielded the desired compound
(DMSO-d6): 2.58-2.62 (4H, m), 2.89 (3H, s), 3.13-3.18 (4H, m), 3.78-3.81 (4H, m), 3.92 (2H, s), 3.95-4.00 (4H, m), 7.40 (1H, br), 7.42 (1H, s), 7.53-7.58 (1H, m), 7.94 (1H, d, J=7.7), 8.09 (1H, br), 8.51 (1H, d, J=7.7), 8.38 (1H, s)
(ESI+): MH+ 517.24

84: 2-Chloro-6-(4-methylsulfonyl-piperazin-1-yl-methyl)-4-morpholin-4-yl-thieno[3,2-d]pyrimidine was reacted with pyridine-3-boronic acid in General Procedure A. Purification on silica yielded the desired compound.
NMR: (CDCl3): 2.68-2.72 (4H, m), 2.82 (3H, s), 3.29-3.33 (4H, m), 3.90 (2H, s), 3.90-3.94 (4H, m), 4.05-4.10 (4H, m), 7.33 (1H, s), 7.34-7.38 (1H, m), 8.68 (2H, d, J=5.6), 9.64 (1H, s)
(ESI+): MH+ 475.11

47: 2-Chloro-6-(4-methanesulfonyl-piperazin-1-ylmethyl)-4-morpholin-4-yl-thieno[2,3-d]pyrimidine was reacted with 3-formylphenylboronic acid in General Procedure A to yield 3-[6-(4-methanesulfonyl-piperazin-1-ylmethyl)-4-morpholin-4-yl-thieno[2,3-d]pyrimidin-2-yl]-benzaldehyde. Treatment of this aldehyde with sodium borohydride (2.5 equivalents) in ethanol yielded the desired compound.
1H NMR CDCL3
NMR: 1.67 (t, H, OH, J=6.08 Hz), 2.64-2.67 (m, 4H, 2×Ch2), 2.80 (s, 3H, Ch3), 3.27-3.29 (m, 4H, 2×CH2), 3.89-3.90 (m, 4H, 2×CH2), 3.96-3.98 (m, 4H, 2×Ch2), 4.80 (d, 2H, CH2, J=6.06 Hz), 7.14 (s, H, ArH), 7.46 (m, 2H, 2×ArH), 8.38 (m, H, ArH), 8.43 (s, H, ArH).
MH+=504.15

85: 2-Chloro-6-(4-methylsulfonyl-piperazine-1-yl-methyl)-4-morpholin-4-yl-thieno[3,2-d}pyrimidine was reacted with N-4-(4,4,5,5-tetramethyl-1,3,2-dioxaborolan-2-yl)

phenylmethanesulfonamide in General Procedure A. Purification on silica yielded the desired compound.

NMR: (CDCl3): 2.68-2.72 (4H, m), 2.82 (3H, s), 3.06 (3H, s), 3.29-3.33 (4H, m), 3.90 (2H, s), 3.90-3.94 (4H, m), 4.05-4.10 (4H, m), 6.45 (1H, br. s), 7.27 (2H, d, J=8.8), 7.32 (1H, s), 8.44 (2H, d, J=8.8)

MS: (ESI+): MH+ 567.20

86: 2-Chloro-6-(4-methylsulfonyl-piperazine-1-yl-methyl)-4-morpholin-4-yl-thieno[3.2-d}pyrimidine was reacted with 4-(4,4,5,5-tetramethyl-1,3,2-dioxaborolan-2-yl)aniline in General Procedure A. Purification on silica yielded 4-[6-(4-Methanesulfonyl-piperazin-1-ylmethyl)-4-morpholin-4-yl-thieno[3,2-d]pyrimidin-2-yl]aniline. This was then reacted with acetic anhydride in dichloromethane and triethylamine to give the desired compound.

NMR: (CDCl3): 2.20 (3H, s), 2.68-2.72 (4H, m), 2.82 (3H, s), 3.29-3.33 (4H, m), 3.90 (2H, s), 3.90-3.94 (4H, m), 4.05-4.10 (4H, m), 7.22 (1H, br. s), 7.32 (1H, s), 7.62 (2H, d, J=8.5), 8.42 (2H, d, J=8.5)

NMR: (ESI+): MH+ 531.19

89: 2-Chloro-6-(4-methylsulfonyl-piperazine-1-yl-methyl)-4-morpholin-4-yl-thieno[3.2-d}pyrimidine was reacted with 3-(4,4,5,5-tetramethyl-1,3,2-dioxaborolan-2-yl)quinoline in General Procedure A. Purification on silica yielded the desired compound.

NMR: (CDCl3): 2.68-2.72 (4H, m), 2.82 (3H, s), 3.29-3.33 (4H, m), 3.90 (2H, s), 3.90-3.94 (4H, m), 4.05-4.10 (4H, m), 7.49 (1H, s), 7.58 (1H, t, J=7.0), 7.75 (1H, t, J=7.0), 7.97 (1H, d, J=7.6), 8.29 (1H, d, J=8.4), 9.17 (1H, d, J=1.9), 9.96 (1H, d, J=2.1)

MS: (ESI+): MH+ 525.24

90: 2-Chloro-6-(4-methylsulfonyl-piperazine-1-yl-methyl)-4-morpholin-4-yl-thieno[3.2-d}pyrimidine was reacted with 4-(4,4,5,5-tetramethyl-1,3,2-dioxaborolan-2-yl)isoquinoline in General Procedure A. Purification on silica yielded the desired compound.

NMR: (CDCl3): 2.68-2.72 (4H, m), 2.82 (3H, s), 3.29-3.33 (4H, m), 3.90-3.94 (4H, m), 3.96 (2H, s), 4.05-4.10 (4H, m), 7.42 (1H, s), 7.64 (1H, t, J=7.0), 7.75 (1H, t, J=7.0), 8.06 (1H, d, J=8.0), 8.83 (1H, d, J=8.6), 9.13 (1H, s), 9.32 (1H, s)

MS: (ESI+): MH+ 525.23

87: 2-chloro-6-(4-methanesulfonyl-piperidin-1-ylmethyl)-4-morpholin-4-yl-thieno[2,3-d]pyrimidine was reacted with pyridine-3-boronic acid in General Procedure A. Purification on silica yielded the desired compound.

NMR: (CDCl$_3$): 2.65-2.67 (m, 4H, 2×CH2), 2.87 (s, 3H, CH3), 3.27-3.30 (m, 4H, 2×CH2), 3.82 (s, 2H, CH2), 3.88-3.90 (m, 4H, 2×CH2), 3.97-3.99 (m, 4H, 2×CH2), 7.16 (s, H, ArH), 7.36-7.39 (m, H, ArH), 8.66-8.69 (m, 2H, 2×ArH), 9.62 (d, H, ArH, J=1.28 Hz).

MS: (ESI+): MH+=475.18

91: 2-chloro-6-(4-methanesulfonyl-piperidin-1-ylmethyl)-4-morpholin-4-yl-thieno[2,3-d]pyrimidine was reacted 3-acetylphenylboronic acid in General Procedure A. Purification on silica yielded the desired compound.

NMR: (CDCl$_3$): 2.65-2.67 (m, 4H, 2×CH2), 2.70 (s, 3H, CH3), 2.80 (s, 3H, CH3), 3.27-3.30 (m, 4H, 2×CH2), 3.82 (s, 2H, CH2), 3.89-3.92 (m, 4H, 2×CH2), 3.98-4.00 (m, 4H, 2×CH2), 7.16 (s, H, ArH), 7.55 (t, H, ArH, J=7.75 Hz), 8.03 (d, H, ArH, J=7.73 Hz), 8.64 (d, H, ArH, J=7.78 Hz), 9.01 (s, H, ArH).

MS: (ESI+): MH+=516.19

93: 1-{3-[6-(4-Methanesulfonyl-piperazin-1-ylmethyl)-4-morpholin-4-yl-thieno[2,3-d]pyrimidin-2-yl]-phenyl}-ethanone was treated with sodium borohydride (2.8 eq.) in ethanol. Purification on silica yielded the desired compound.

NMR: (CDCl$_3$): 1.57 (d, 3H, CH3), 1.85 (d, H, OH), 2.64-2.67 (m, 4H, 2×CH2), 2.80 (s, 3H, CH3), 3.27-3.28 (m, 4H, 2×CH2), 3.81 (s, 2H, CH2), 3.88-3.91 (m, 4H, 2×CH2) 3.96-3.98 (m, 4H, 2×CH2), 5.00-5.03 (m, H, CH), 7.14 (s, H, ArH), 7.42-7.49 (m, 2H, 2×ArH), 8.35 (d, H, ArH, J=7.27 Hz), 8.43 (s, H, ArH).

MS: (ESI+): MH+=518.27

94: 2-chloro-6-(4-methanesulfonyl-piperidin-1-ylmethyl)-4-morpholin-4-yl-thieno[2,3-d]pyrimidine was reacted with 4-(4,4,5,5-tetramethyl-1,3,2-dioxaborolan-2-yl)isoquinoline in General Procedure A. Purification on silica yielded the desired compound.

NMR: (CDCl$_3$): 2.67-2.69 (m, 4H, 2×CH2), 2.80 (s, 3H, CH3), 3.29-3.31 (m, 4H, 2×CH2), 3.85 (s, 2H, CH2), 3.88-3.90 (m, 4H, 2×CH2), 3.99-4.01 (m, 4H, 2×CH2), 7.22 (s, H, ArH), 7.63 (t, ArH, J=7.53 Hz), 7.75 (t, H, ArH, J=8.31 Hz), 8.03 (d, H, ArH, J=8.1 Hz), 8.88 (d, H, ArH, J=8.61 Hz), 9.16 (s, H, ArH), 9.30 (s, H, ArH).

MS: (ESI+): MH+=525.23

95: 2-chloro-6-(4-methanesulfonyl-piperidin-1-ylmethyl)-4-morpholin-4-yl-thieno[2,3-d]pyrimidine was reacted with 3-(4,4,5,5-tetramethyl-1,3,2-dioxaborolan-2-yl)quinoline in General Procedure A. Purification on silica yielded the desired compound.

NMR: (CDCl$_3$): 2.66-2.69 (m, 4H, 2×CH2), 2.80 (s, 3H, CH3), 3.28-3.31 (m, 4H, 2×CH2), 3.83 (s, 2H, CH2), 3.91-3.91 (m, 4H, 2×CH2), 4.01-4.04 (m, 4H, 2×CH2), 7.18 (s, H, ArH), 7.57 (t, H, ArH, J=7.27 Hz), 7.74 (t, H, ArH, J=7.14 Hz), 7.96 (d, H, ArH, J=8.47 Hz), 9.15 (d, H, ArH, J=2.0 Hz), 9.94 (d, H, ArH, J=2.0 Hz).

MS: (ESI+): MH+=525.28

37: To a solution of 4-methoxybenzyl alcohol (1.73 g) in DMSO (10 mL) at room temperature was added sodium hydride (500 mg). The reaction mixture was stirred for 75 min and then a solution of 3,5-dibromopyridine (3.0 g) in DMSO (15 mL) was added. The reaction mixture was then heated at 90° C. for 2.5 h and then allowed to cool to room temperature, quenched with water (60 mL) and extracted into diethyl ether (3×60 mL). The combined organics were washed with brine (100 mL), dried (MgSO$_4$), reduced in vacuo and purified by column chromatography to give 3-bromo-5-(4-methoxy-benzyloxy)-pyridine as a white solid (1.76 g).

To a solution of 3-bromo-5-(4-methoxy-benzyloxy)-pyridine (300 mg) in THF (10 mL) was added triiospropyl borate (0.28 mL) and the mixture cooled to −78° C. Then n-butyl-lithium (0.49 mL of a 2.5 M solution in hexanes) was added maintaining the temperature below −65° C. The reaction mixture was then allowed to warm to −20° C. over 1 h and then quenched with 2 M aqueous hydrochloric acid (2 mL). The mixture was allowed to warm to room temperature over 1 h and then diluted with water (25 mL), the pH was adjusted to 7 and then extracted into ethyl acetate (3×25 mL). The combined organics were washed with brine (20 mL), dried (MgSO$_4$) and reduced in vacuo. A mixture of the crude product and pinacol (236 mg) in toluene (15 mL) was then heated at reflux for 4 h. The mixture was then reduced in vacuo, dissolved in ethyl acetate (30 mL) and washed with water (2×30 mL) and brine (30 mL). The combined organics were dried (MgSO$_4$) and reduced in vacuo to give 3-(4-methoxy-benzyloxy)-5-(4,4,5,5-tetramethyl-[1,3,2]dioxaborolan-2-yl)-pyridine as an off-white solid (162 mg).

2-Chloro-6-(4-methyl-piperazin-1-ylmethyl)-4-morpholin-4-yl-thieno[3,2-d]pyrimidine was reacted with 3-(4- methoxy-benzyloxy)-5-(4,4,5,5-tetramethyl-[1,3,2]dioxaborolan-2-yl)-pyridine in General Procedure A. Purification on silica yielded 2-[5-(4-methoxy-benzyloxy)-pyridin-3-yl]-6-(4-methyl-piperazin-1-ylmethyl)-4-morpholin-4-yl-thieno[3,2-d]pyrimidine. This was then reacted with trifluoroacetic acid in dichloromethane to give the desired compound.

NMR: (CDCl3): 2.31 (3H, s, Me), 2.46-2.68 (8H, m, CH2), 3.73 (2H, s, CH2), 3.74-3.82 (4H, m, CH2), 3.94-3.99 (4H, m, CH2), 7.20 (1H, s, Ar), 8.12 (1H, s, Ar), 8.22 (1H, s, Ar) and 9.07 (1H, s, Ar).

MS: (ESI+): MH+ 427.15

39: 2-Chloro-6-(4-methyl-piperazin-1-ylmethyl)-4-morpholin-4-yl-thieno[3,2-d]pyrimidine was reacted with 4-(4,4,5,5-tetramethyl-[1,3,2]dioxaborolan-2-yl)-pyrazole-1-carboxylic acid tert-butyl ester in General Procedure A. The BOC group was cleaved under the conditions of the Suzuki reaction. Purification on silica yielded the desired compound.

NMR: (DMSO): 13.05 (bs, 1H); 8.31 (bs, 2H); 7.26 (s, 1H); 3.92 (m, 4H); 3.85 (s, 2H); 3.77 (m, 4H); 2.41 (m, 8H); 2.15 (s, 3H).

MS: (ESI+): MH+ 400.21

40: 2-Chloro-6-(4-methyl-piperazin-1-ylmethyl)-4-morpholin-4-yl-thieno[3,2-d]pyrimidine was reacted with 3-formyl phenyl boronic acid in General Procedure A. Purification on silica yielded 3-[6-(4-methyl-piperazin-1-ylmethyl)-4-morpholin-4-yl-thieno[3,2-d]pyrimidin-2-yl]-benzaldehyde. This was then treated with methylmagnesium bromide in THF to give the desired compound.

NMR: (CDCl3): 1.49 (d, J=6.5, 3H), 2.10 (d, J=1.7, 1H), 2.25 (s, 3H), 2.46 (s, br, 4H), 2.54 (s, br, 4H), 3.74 (s, 2H), 3.82 (t, J=4.8, 4H), 3.98 (t, J=4.8, 4H), 4.94 (q, J=6.4, 1H), 7.23 (s, 1H), 7.35-7.42 (m, 2H), 8.27 (m, 1H), 8.35 (s, 1H).

MS: (ESI+): MH+ 454.27

41: 2-Chloro-6-(4-methyl-piperazin-1-ylmethyl)-4-morpholin-4-yl-thieno[3,2-d]pyrimidine was reacted with 3-formyl phenyl boronic acid in General Procedure A. Purification on silica yielded 3-[6-(4-methyl-piperazin-1-ylmethyl)-4-morpholin-4-yl-thieno[3,2-d]pyrimidin-2-yl]-benzaldehyde. This was then treated with sodium borohydride in methanol to give the desired compound.

NMR: (CDCl3): 2.25 (s, 3H), 2.47 (s, 4H), 2.54 (s, 4H), 3.75 (s, 2H), 3.80 (t, J=4.8, 4H), 3.98 (t, J=4.8, 4H), 4.71 (s, 2H), 7.23 (m, 1H), 7.38 (m, 2H), 8.28 (m, 1H), 8.34 (s, 1H).

MS: (ESI+): MH+ 440.23

35: A solution of 4-methoxybenzylalcohol (10 g) in ether (300 ml) was shaken with hydrobromic acid, 48%, (150 ml). The organic phase was washed with saturated sodium bromide, dried (K2CO3) and the solvents removed in vacuo to give 4-methoxybenzylbromide (13.17 g).

To a solution of 3-bromo-4-fluorophenol (0.59 g) in tetrahydrofuran (7 ml) under nitrogen was added sodium hydride, 60% dispersion in mineral oil (0.13 g). The solution was stirred at room temperature. After 30 minutes a solution of 4-methoxybenzylbromide (0.62 g) was added in tetrahydrofuran (5 ml). The reaction mixture was stirred at 50° C. overnight. The reaction mixture was partitioned between dichloromethane and brine, then dried (MgSO4), the solvents were removed in vacuo to give a crude residue. This crude residue was purified using flash chromatography to give 2-bromo-1fluoro-4-(4-methoxy-benzyloxy)-benzene (0.71 g). To a solution of 2-bromo-1fluoro-4-(4-methoxy-benzyloxy)-benzene (0.33 g) in tetrahydrofuran (10 ml) under nitrogen was added triiopropylborate (0.29 ml). The mixture was cooled to −78° C. and 2.5M n-butyllithium solution in hexanes was added. The reaction mixture was stirred at −40° C. for 1 hour, then warmed to 20° C. and quenched with 2M hydrochloric acid (aq) (2 ml). The reaction mixture was warmed to room temperature and stirred for 1 hour. The reaction mixture was adjusted to pH 7 using saturated sodium bicarbonate solution, then partitioned between ethyl acetate and water, dried (MgSO4) and the solvents removed in vacuo to yield a crude residue (0.31 g). A mixture of this crude residue and pinacol (0.25 g) in toluene (10 ml) were stirred under reflux overnight in a Dean-Stark apparatus. The solvents were removed in vacuo, the residue was then partitioned between ethyl acetate and water, the combined organics were washed with water then brine and dried (MgSO4), the solvents were removed in vacuo to yield 2-[2-fluoro-5-(4-methoxy-benzyloxy-phenyl]-4,4,5,5-tetramethyl-[1,3,2]dioxyborolane (0.28 g)

2-Chloro-6-(4-methyl-piperazin-1-ylmethyl)-4-morpholin-4-yl-thieno[3,2-d]pyrimidine was reacted with 2-[2-fluoro-5-(4-methoxy-benzyloxy-phenyl]-4,4,5,5-tetramethyl-[1,3,2]dioxyborolane in general procedure A. Purification on silica yielded 2-[2-fluoro-5-(4-methoxy-benzyloxy)-phenyl]-6-(4-methyl-piperazin-1-ylmethyl)-4-morpholin-4-yl-thieno[3,2-d]pyrimidine. This was then reacted with trifluoroacetic acid in dichloromethane to yield the desired compound.

NMR: 400 MHz; CDCl3: 2.34(3H, s); 2.58 (8H, m); 3.84 (2H, s); 3.90 (4H, t, J=4.8 Hz); 4.04 (4H, t, J=4.8 Hz); 6.84 (1H, m); 7.02 (1H, t, J=9.6 Hz); 7.30 (1H, s); 7.57 (1H, m).

MS: (ESI+): MH+ 444

36: A solution of 4-methoxybenzylalcohol (10 g) in ether (300 ml) was shaken with hydrobromic acid, 48%, (150 ml). The organic phase was washed with saturated sodium bromide, dried (K2CO3) and the solvents removed in vacuo to give 4-methoxybenzylbromide (13.17 g).

To a solution of 5-bromo-2,3-difluorophenol (1.0 g) in tetrahydrofuran (10 ml) under nitrogen was added sodium hydride, 60% dispersion in mineral oil (0.20 g). The solution was stirred at room temperature. After 30 minutes a solution of 4-methoxybenzylbromide (0.96 g) was added in tetrahydrofuran (7 ml). The reaction mixture was stirred at 50° C. overnight. The reaction mixture was partitioned between dichloromethane and brine, then dried (MgSO4), the solvents were removed in vacuo to give a crude residue. This crude residue was purified using flash chromatography to give 5-bromo-1,2-difluoro-3-(4-methoxy-benzyloxy)-benzene (0.76 g).

To a solution of 5-bromo-1,2-difluoro-3-(4-methoxy-benzyloxy)-benzene (0.35 g) in tetrahydrofuran (10 ml) under nitrogen was added triiopropylborate (0.29 ml). The mixture was cooled to −78° C. and 2.5M n-butyllithium solution in hexanes was added. The reaction mixture was stirred at −40° C. for 1 hour, then warmed to 20° C. and quenched with 2M hydrochloric acid (aq) (2 ml). The reaction mixture was warmed to room temperature and stirred for 1 hour. The reaction mixture was adjusted to pH 7 using saturated sodium bicarbonate solution, then partitioned between ethyl acetate and water, dried (MgSO4) and the solvents removed in vacuo to yield a crude residue (0.31 g). A mixture of this crude residue and pinacol (0.25 g) in toluene (10 ml) were stirred under reflux overnight in a Dean-Stark apparatus. The solvents were removed in vacuo, the residue was then partitioned between ethyl acetate and water, the combined organics were washed with water then brine and dried (MgSO4), the solvents were removed in vacuo to yield 2-[3,4-difluoro-5-(4-methoxy-benzyloxy)-phenyl]-4,4,5,5-tetramethyl-[1,3,2]dioxaborolane (0.28 g)

2-Chloro-6-(4-methyl-piperazin-1-ylmethyl)-4-morpholin-4-yl-thieno[3,2-d]pyrimidine was reacted with yield 2-[3,4-difluoro-5-(4-methoxy-benzyloxy)-phenyl]-4,4,5,5- tetramethyl-[1,3,2]dioxaborolane in general procedure A. Purification on silica yielded 2-[3,4-difluoro-5-(4-methoxy-benzyloxy)-phenyl]-6-(4-methyl-piperazin-1-ylmethyl)-4-morpholin-yl-thieno[3,2-d]pyrimidine. This was then reacted with trifluoroacetic acid in dichloromethane to yield the desired compound.

NMR: 400 MHz; CDCl3: 2.36(3H, s); 2.67 (8H, m); 3.84 (2H, s); 3.90 (4H, t, J=4.7 Hz); 4.00 (4H, t, J=4.7 Hz); 7.24 (1H, s); 7.80 (1H, m); 7.90 (1H, d, J=7.6 Hz).

MS: (ESI+): MH+ 462

33: A solution of 4-methoxybenzylalcohol (10 g) in ether (300 ml) was shaken with hydrobromic acid, 48%, (150 ml). The organic phase was washed with saturated sodium bromide, dried ($K_2CO_3$) and the solvents removed in vacuo to give 4-methoxybenzylbromide (13.17 g).

To a solution of 5-bromo-2-chlorophenol (1.0 g) in tetrahydrofuran (10 ml) under nitrogen was added sodium hydride, 60% dispersion in mineral oil (0.20 g). The solution was stirred at room temperature. After 30 minutes a solution of 4-methoxybenzylbromide (0.97 g) was added in tetrahydrofuran (7 ml). The reaction mixture was stirred at 50° C. overnight. The reaction mixture was partitioned between dichloromethane and brine, then dried ($MgSO_4$), the solvents were removed in vacuo to give a crude residue. This crude residue was purified using flash chromatography to give 4-bromo-1-chloro-2-(4-methoxy-benzyloxy)-benzene (0.96 g).

To a solution of 4-bromo-1-chloro-2-(4-methoxy-benzyloxy)-benzene (0.35 g) in tetrahydrofuran (10 ml) under nitrogen was added triiopropylborate (0.29 ml). The mixture was cooled to −78° C. and 2.5M n-butyllithium solution in hexanes was added. The reaction mixture was stirred at −40° C. for 1 hour, then warmed to 20° C. and quenched with 2M hydrochloric acid (aq) (2 ml). The reaction mixture was warmed to room temperature and stirred for 1 hour. The reaction mixture was adjusted to pH 7 using saturated sodium bicarbonate solution, then partitioned between ethyl acetate and water, dried ($MgSO_4$) and the solvents removed in vacuo to yield a crude residue (0.31 g). A mixture of this crude residue and pinacol (0.25 g) in toluene (10 ml) were stirred under reflux overnight in a Dean-Stark apparatus. The solvents were removed in vacuo, the residue was then partitioned between ethyl acetate and water, the combined organics were washed with water then brine and dried ($MgSO_4$), the solvents were removed in vacuo to yield 2-[4-chloro-3-(4-methoxy-benzyloxy)-phenyl]-4,4,5,5-tetramethyl-[1,3,2]dioxaborolane (0.28 g).

2-Chloro-6-(4-methyl-piperazin-1-ylmethyl)-4-morpholin-4-yl-thieno[3,2-d]pyrimidine was reacted with 2-[4-chloro-3-(4-methoxy-benzyloxy)-phenyl]-4,4,5,5-tetramethyl-[1,3,2]dioxaborolane in general procedure A. Purification on silica yielded 2-[4-chloro-3-(4-methoxy-benzyloxy)-phenyl]-6-(4-methyl-piperazin-1-ylmethyl)-4-morpholin-4-yl-thieno[3,2-d]pyrimidine. This was then reacted with trifluoroacetic acid in dichloromethane to yield the desired compound.

NMR: 400 MHz; CDCl3: 2.25(3H, s); 2.50 (8H, m); 3.77 (2H, s); 3.82 (4H, t, J=4.9 Hz); 3.98 (4H, t, J=5.0 Hz); 7.23 (1H, s); 7.32 (1H, d, J=8.4 Hz); 7.93 (1H, d, J=8.4 Hz); 8.04 (1H, s).

MS: (ESI+): MH+ 460

16: To 2-methylbenzimidazole (75 mg) in N,N-dimethylformamide (3 mL) was added sodium hydride (60% dispersion, 23 mg). After stirring for 30 mins, 2-chloro-6-(4-methanesulfonyl-piperazin-1-ylmethyl)-4-morpholin-4-yl-thieno[2,3-d]pyrimidine (242 mg) was added and the reaction mixture was heated to 90° C. After 16 hours the reaction mixture was cooled, diluted with ethyl acetate and washed with brine. The organic fraction was concentrated in vacuo and purified using flash chromatography to yield the title compound [M+H]+ 528.21

(400 MHz CDCl3): 2.68 (4H, t (J 4.80), CH2), 2.81 (3H, s, CH3), 2.94 (3H, s, CH3), 3.30 (4H, t (J 4.61), CH2), 3.83 (2H, s, CH2), 3.88-4.00 (8H, m, CH2), 7.19 (1H, s, ar), 7.31 (1H, m, ar), 7.70-7.73 (1H, m, ar), 8.10-8.12 (1H, m, ar)

88: 6-(4-Methanesulfonyl-piperazin-1-ylmethyl)-2-(2-methyl-imidazol-1-yl)-4-morpholin-4-yl-thieno[3,2-d]pyrimidine was made in a similar manner to the compound above using 2-methylimidazole and 2-chloro-6-(4-methanesulfonyl-piperazin-1-ylmethyl)-4-morpholin-4-yl-thieno[3,2-d]pyrimidine.

(CDCl3): 2.68-2.72 (4H, m), 2.82 (3H, s), 2.85 (3H, s), 3.29-3.33 (4H, m), 3.90 (2H, s), 3.90-3.94 (4H, m), 4.05-4.10 (4H, m), 6.93 (1H, d, J=1.6), 7.25 (1H, s), 7.82 (1H, d, J=1.6)

(ESI+): MH+ 478.17

101: 6-(4-Methanesulfonyl-piperazin-1-ylmethyl)-2-(2-methyl-benzoimidazol-1-yl)-4-morpholin-4-yl-thieno[3,2-d]pyrimidine was made in a similar manner to the compound above using 2-methylbenzimidazole and 2-chloro-6-(4-methanesulfonyl-piperazin-1-ylmethyl)-4-morpholin-4-yl-thieno[3,2-d]pyrimidine.

(ESI+): MH+

(CDCl3): 2.68-2.72 (4H, m), 2.82 (3H, s), 2.92 (3H, s), 3.29-3.33 (4H, m), 3.90 (2H, s), 3.90-3.94 (4H, m), 4.05-4.10 (4H, m), 7.27-7.30 (2H, m), 7.32 (1H, s), 7.71-7.75 (1H, m), 8.09-8.12 (1H, m)

EXAMPLE 4

Compounds of the Invention—Series C

The following compounds of the invention were prepared. The compound numbering corresponds to that used in Table 1A above.

3: To 1-Boc-4-piperidone (10 g) in ethanol stirring at 0° C. was added sodium borohydride (9.45 g) portionwise. The reaction mixture was stirred at 0° C. for 1 hour. The reaction mixture was then quenched with water and extracted with chloroform. The combined organic were washed with brine and dried ($MgSO_4$). The solvent was removed in vacuo to yield 9.2 g of 4-hydroxy-piperidine-1-carboxylic acid tert-butyl ester.

To 4-hydroxy-piperidine-1-carboxylic acid tert-butyl ester (9.2 g) in dichloromethane (170 ml), stirring at 0° C. was added methane sulphoyl chloride (5.33 ml) and triethylamine (10.24 ml). The reaction mixture was slowly warmed to room temperature and stirred overnight. The reaction mixture was partitioned between chloroform and water. The combined organics were washed with brine and dried ($MgSO_4$). The solvent was removed in vacuo to yield 14 g of 4-methanesulfonyl-piperidine-carboxylic acid tert-butyl ester. A mixture of 4-methanesulfonyl-piperidine-carboxylic acid tert-butyl ester (2.82 g) thioacetate (2.31 g) and DMF (40 ml) was stirred at 60° C. After 4 hours the reaction mixture was cooled and partitioned between ethyl acetate and brine. The combined organics were dried ($MgSO_4$) and the solvents removed in vacuo. The resulting crude mixture was purified by flash chromatography to yield 4-acetylsulfanyl-piperidine-1-carboxylic acid tert-butyl ester (1.8 g). 4-acetylsulfanyl-piperidine-1-carboxylic acid tert-butyl ester (400 mg) was stirred in acetic acid (3 ml) and water (3 ml) at 0° C. Chlorine gas was bubbled through the reaction mixture. The reaction mixture was stirred for 1.5 hours. The reaction mixture was then diluted with water to yield a precipitate which was collected by filtration to yield 4-chlorosulfonyl-piperidine-1-carboxylic acid tert-butyl ester (295 mg).

To a solution of 4-chlorosulfonyl-piperidine-1-carboxylic acid tert-butyl ester (295 mg) in dichloromethane stirring at 0° C. was added triethylamine (96 µL) and morpholine (55 µL). The reaction mixture was stirred overnight then quenched with water and extracted into dichloromethane. The combined organics were washed with brine and dried (MgSO4). The solvent was removed in vacuo to yield 4-(morpholine-4-sulfonyl)-piperidine-1-carboxylic acid tert-butyl ester (120 mg).

To a solution of 4-(morpholine-4-sulfonyl)-piperidine-1-carboxylic acid tert-butyl ester in dichloromethane (10 ml) and methanol (10 ml) was added 2M hydrogen chloride in ether (2 µL). The reaction mixture was stirred overnight. The solvents were removed in vacuo to yield 4-(piperidine-4-sulfonyl)-morpholine hydrochloride salt.

Reaction with 2-chloro-4-morpholin-4-yl-thieno[3,2-d]pyrimidine-6-carbaldehyde using procedure C yielded 1-(2-chloro-4-morpholin-4-yl-thieno[3,2-d]pyrimidin-6-ylmethyl)-piperidine-4-sulfonic acid dimethylamide. This compound was subjected to procedure A to yield the desired final compound which was purified using flash chromatography.

(M+H)+ 542.28

(400 MHz CDCl3): 1.95-2.04 (4H, m, CH2), 2.14 (2H, td (J 11.36, 2.99), CH2), 2.94 (6H, s, CH3), 2.99 (1H, m, CH), 3.13 (2H, d (J 11.59), CH2), 3.85 (2H, s, CH2), 3.92-3.95 (4H, m, CH2), 4.08-4.15 (4H, m, CH2), 7.36 (1H, s, ar), 7.50 (1H, t (J 7.73), ar), 7.58 (1H, d (J 8.34), ar), 8.27 (1H, d (J 7.52), 9.02 (1H, s, ar), 10.25 (1H, b, NH)

The following compounds were prepared in an analogous manner using the appropriate amine.

27: 1-[2-(1H-Indazol-4-yl)-4-morpholin-4-yl-thieno[3,2-d]pyrimidin-6-ylmethyl]-piperidine-4-sulfonic acid dimethylamide was prepared as above using piperidine-4-sulfonic acid dimethyl amide hydrochloride salt.

(M+H)+ 542.28

(400 MHz CDCl3): 1.95-2.04 (4H, m, CH2), 2.14 (2H, td (J 11.36, 2.99), CH2), 2.94 (6H, s, CH3), 2.99 (1H, m, CH), 3.13 (2H, d (J 11.59), CH2), 3.85 (2H, s, CH2), 3.92-3.95 (4H, m, CH2), 4.08-4.15 (4H, m, CH2), 7.36 (1H, s, ar), 7.50 (1H, t (J 7.73), ar), 7.58 (1H, d (J 8.34), ar), 8.27 (1H, d (J 7.52), 9.02 (1H, s, ar), 10.25 (1H, b, NH)

22: 1-[2-(1H-Indazol-4-yl)-4-morpholin-4-yl-thieno[3,2-d]pyrimidin-6-ylmethyl]-piperidine-4-sulfonic acid methylamide was prepared as above using piperidine-4-sulfonic acid methylamine hydrochloride salt.

MH+=528.24

400 MHz 1H NMR CDCl3

1.60-1.70 (m, 2H, CH2), 1.90-2.0 (m, 2H, CH2), 2.1-2.2 (m, 2H, CH2), 2.58 (d, 3H, CH3, J=4.76 Hz), 2.95-3.05 (m, 2H, CH2), 3.80-3.85 (m, 4H, 2×CH2), 3.88 (s, 2H, CH2), 3.95-4.05 (m, 4H, 2×CH2), 6.90 (m, H, ArH), 7.45 (m, H, ArH), 7.64 (d, H, ArH, J=8.21 Hz), 8.2 (d, H, ArH, J=7.2 Hz), 8.86 (s, H, ArH), 13.15 (sbr, H, NH).

24: 2-(1H-Indazol-4-yl)-6-[4-(4-methyl-piperazine-1-sulfonyl)-piperidin-1-ylmethyl]-4-morpholin-4-yl-thieno[3,2-d]pyrimidine was prepared as above using 1-methyl-4-(piperidine-4-sulphonyl)-piperizine hydrochloride salt.

400 MHz 1H NMR CDCl3

1.90-2.0 (m, 2H, CH2), 2.05-2.15 (m, 2H, CH2), 2.32 (s, 3H, CH3), 2.45-2.55 (m, 4H, 2×CH2), 2.90-3.09 (m, H, CH), 3.05-3.15 (m, 2H, CH2), 3.38-3.43 (m, 4H, 2×CH2), 7.35 (s, H, ArH), 7.49 (t, H, ArH, J=7.6 Hz), 7.58 (d, H, ArH, J=8.33 Hz), 8.27 (d, H, ArH, J=7.53 Hz), 9.00 (s, H, ArH, 10.15 (sbr, H, NH).

MH+=597.25

18: 1-[2-(1H-Indazol-4-yl)-4-morpholin-4-yl-thieno[3,2-d]pyrimidin-6-ylmethyl]-piperidine-4-sulfonic acid (2-methoxy-ethyl)-methyl-amide was prepared as above using piperidine-4-sulfonic acid (2-methoxy-ethyl)-methyl-amide hydrochloride salt.

(CDCl3): 1.98-2.10 (4H, m), 2.11-2.19 (2H, m), 2.99 (3H, s), 3.00-3.10 (1H, m), 3.12-3.18 (2H, m), 3.37 (3H, s), 3.41-3.45 (2H, m), 3.53-3.58 (2H, m), 3.84 (2H, s), 3.90-3.94 (4H, m), 4.10-4.14 (4H, m), 7.38 (1H, s), 7.48-7.52 (1H, m), 7.58 (1H, d, J=8.3), 8.38 (1H, d, J=7.6), 9.20 (1H, s), 10.10 (1H, br)

(ESI+): MH+ 586

19: 1-[2-(1H-Indazol-4-yl)-4-morpholin-4-yl-thieno[2,3-d]pyrimidin-6-ylmethyl]-piperidine-4-sulfonic acid dimethylamide was prepared as above using piperidine-4-sulfonic acid dimethyl amide hydrochloride salt.

NMR: 1.9-2.0 (m, 2H, CH2), 2.0-2.2 (m, 4h, 2×CH2), 2.94 (s, 6H, 2×CH3), 2.95-3.0 (m, H, CH), 3.05-3.10 (m, 2H, CH2), 3.79 (s, 2H, CH2), 3.92-3.94 (m, 4H, 2×CH2), 7.15 (s, H, ArH), 7.50 (t, H, ArH, J=7.79 Hz), 7.59 (d, H, ArH, J=8.23 Hz), 8.32 (d, H, ArH, J=7.34 Hz), 9.02 (s, H, ArH), 10.1 (sbr, H, NH).

MH+=542.19

20: 1-[2-(1H-Indazol-4-yl)-7-methyl-4-morpholin-4-yl-thieno[3,2-d]pyrimidin-6-ylmethyl]piperidine-4-sulfonic acid dimethylamide was prepared as above using piperidine-4-sulfonic acid dimethyl amide hydrochloride salt.

NMR: 1.98-2.08 (4H, m), 2.12-2.18 (2H, m), 2.54 (3H, s), 2.94 (6H, s), 2.98-3.06 (1H, m), 3.12-3.18 (2H, m), 3.84 (2H, s), 3.90-3.94 (4H, m), 4.10-4.14 (4H, m), 7.48-7.52 (1H, m), 7.58 (1H, d, J=8.3), 8.38 (1H, d, J=7.6), 9.20 (1H, s), 10.10 (1H, br)

(ESI+): MH+ 556

21: A mixture of 4-methanesulfonyloxy-piperidine-1-carboxylic acid tert-butyl ester (1.015 g) and sodium thiomethoxide (635 mg) was heated to 80° C. in dimethylformamide (10 mL). After 4h, the reaction mixture was diluted with water, extracted with ethyl acetate, dried (MgSO4), filtered and concentrated in vacuo and then purified by flash chromatography to give 4-methylsulfanyl-piperidine-1-carboxylic acid tert-butyl ester (600 mg). To a solution of 4-methylsulfanyl-piperidine-1-carboxylic acid tert-butyl ester (600 mg) in chloroform (15 mL) was added mCPBA (1.46 g). After stirring for 2 days, the reaction mixture was diluted with dichloromethane, washed with sodium bicarbonate solution, dried (MgSO4) and the solvent removed in vacuo to yield 4-methanesulfonyl-piperidine-1-carboxylic acid tert-butyl ester (505 mg) as a white solid.

Treatment of this compound with HCl in dichloromethane/methanol yielded 4-methanesulfonyl-piperidine, which was isolated as the hydrochloride salt.

Reaction with 2-chloro-4-morpholin-4-yl-thieno[2,3-d]pyrimidine-6-carbaldehydeusing procedure C yielded 2-chloro-6-(4-methanesulfonyl-piperidin-1-ylmethyl)-4-morpholin-4-yl-thieno[2,3-d]pyrimidine. This compound was subjected to procedure A to yield the desired final compound which was purified using flash chromatography.

1H NMR CDCL3

1.9-2.0 (m, 2H, Ch2), 2.1-2.2 (m, 4H, 2×CH2), 2.84 (m, 4H, 2×CH2), 3.15-3.20 (m, 2H, CH2), 3.90-3.95 (m, 4H, 2×CH2), 4.0-4.05 (m, 4H, 2×CH2), 7.15 (s, H, ArH), 7.50 (t,

H, ArH, J=7.78), 7.59 (d, H, ArH, J=8.32 Hz), 8.32 (d, H, ArH, J=7.21 Hz), 9.02 (s, H, ArH), 10.1 (sbr, H, NH).
MH+=513.19
The following compound was prepared in an analogous manner:
23: (ESI+): MH+ 527
(CDCl3): 1.94-2.03 (2H, m), 2.12-2.24 (4H, m), 2.55 (3H, s), 2.88 (3H, s), 2.88-2.95 (1H, m), 3.21-3.25 (2H, m), 3.84 (2H, s), 3.90-3.94 (4H, m), 4.10-4.14 (4H, m), 7.48-7.52 (1H, m), 7.58 (1H, d, J=8.3), 8.38 (1H, d, J=7.6), 9.20 (1H, s), 10.10 (1H, br)

45: Reaction between 2-chloro-4-morpholin-4-yl-thieno[3,2-d]pyrimidine-6-carbaldehyde and 1-methyl-4-(methylamino)piperidine using procedure C yielded (2-chloro-4-morpholin-4-yl-thieno[3,2-d]pyrimidin-6-ylmethyl)-methyl-(1-methyl-piperidin-4-yl)-amine. This compound was subjected to procedure A to yield the desired final compound which was purified using flash chromatography.
1H NMR 400 MHz DMSO
13.2 (bs, 1H); 8.87 (s, 1H); 8.21 (d, 1H); 7.65 (d, 1H, J=7.3 Hz); 7.46 (t, 2H, J=7.7 Hz); 3.90 (m, CH2×4); 3.93 (s, 2H); 2.79 (d, 2H, J=11.2); 2.40 (m, 1H); 2.25 (s, 3H); 2.12 (s, 3H); 1.68 (m, CH2×3).
M/S (m+1)=478.3; LC>/95% purity 9: To a solution of piperazine (1 g) and triethylamine (1.78 mL) in dichloromethane (20 mL) at 0° C. was added dropwise trifluoromethanesulfonyl chloride (1.24 mL). The reaction mixture was stirred at room temperature for 16 h and then quenched with water (20 mL) and extracted into dichloromethane (2×40 mL). The combined organic layers were washed with saturated aqueous brine solution (2×40 mL), dried (MgSO4) and concentrated to afford 1-trifluoromethanesulfonyl-piperazine as a pale yellow solid (1.92 g, 76%). Reaction between 2-chloro-4-morpholin-4-yl-thieno[3,2-d]pyrimidine-6-carbaldehyde and 1-trifluoromethanesulfonyl-piperazine using procedure C yielded 2-chloro-4-morpholin-4-yl-6-(4-trifluoromethanesulfonyl-piperazin-1-ylmethyl)-thieno[3,2-d]pyrimidine. This compound was subjected to procedure A to yield the desired final compound which was purified using flash chromatography
[M+H]+ 568.23
NMR: (400 MHz, CDCl3): 2.67-2.72 (4 H, m, CH2), 3.53-3.64 (4 H, m, CH2), 3.90-3.98 (6 H, m, CH2), 4.08-4.14 (4 H, m, CH2), 7.40 (1 H, s, Ar), 7.48 (1 H, t, J 8.23, Ar), 7.53 (1 H, d, J 8.28, Ar), 8.27 (1 H, d, J 7.33, Ar), 9.02 (1 H, s, Ar) and 10.11 (1 H, s, NH).

4: To a solution of (S)-methylpiperazine (400 mg) in dichloromethane (20 mL) at 0° C. was added di-tert-butyl dicarbonate (871 mg). The reaction was stirred at room temperature for 4 h and then quenched with water (20 mL) and extracted into dichloromethane (2×40 mL). The combined organics were washed with saturated aqueous brine solution (40 mL), dried (MgSO4) and concentrated to give (S)-3-methyl-piperazine-1-carboxylic acid tert-butyl ester as a white solid (669 mg, 84%).
To a solution of (S)-3-methyl-piperazine-1-carboxylic acid (669 mg) and triethylamine (0.56 mL) in dichloromethane (10 mL) at 0° C. was added dropwise methanesulfonyl chloride (0.28 mL). The reaction mixture was stirred at room temperature for 16 h and then quenched with water (10 mL) and extracted into dichloromethane (2×20 mL). The combined organic layers were washed with saturated aqueous brine solution (2×20 mL), dried (MgSO4) and concentrated to give (S)-4-methanesulfonyl-3-methyl-piperazine-1-carboxylic acid tert-butyl ester as a pale yellow solid (924 mg, 99%).

To a solution of (S)-4-methanesulfonyl-3-methyl-piperazine-1-carboxylic acid tert-butyl ester (924 mg) in dichloromethane (20 mL) at 0° C. was added dropwise HCl (6.65 mL of a 2 M solution in diethyl ether). The reaction mixture was stirred at room temperature for 2 h. The precipitate formed was then collected by filtration and dried to afford (S)-1-methanesulfonyl-2-methyl-piperazine hydrochloride salt as a white solid (583 mg, 82%).
Reaction between 2-chloro-4-morpholin-4-yl-thieno[3,2-d]pyrimidine-6-carbaldehyde and (S)-1-methanesulfonyl-2-methyl-piperazine hydrochloride salt using procedure C yielded 2-chloro-6-((S)-4-methanesulfonyl-3-methyl-piperazin-1-ylmethyl)-4-morpholin-4-yl-thieno[3,2-d]pyrimidine. This compound was subjected to procedure A to yield the desired final compound which was purified using flash chromatography.
NMR: (400 MHz, CDCl3): 1.42 (3 H, d, J 6.75, Me), 2.33 (1 H, td, J 11.42 and 3.45), 2.43 (1 H, dd, J 3.62 and 11.23), 2.76 (1 H, d, J 11.17), 2.88 (3 H, s, Me), 2.91 (1 H, d, J 11.54), 3.34 (1 H, td, J 12.01 and 3.04), 3.59 (1 H, d, J 12.81), 3.72-3.94 (6 H, m, CH2), 4.08-4.12 (6 H, m, CH2), 7.39 (1 H, s, Ar), 7.51 (1 H, t, J 8.19, Ar), 7.60 (1 H, t, J 8.29, Ar), 8.25 (1 H, d, J 6.96, Ar), 9.01 (1 H, s, Ar) and 10.12 (1 H, s, NH).
[M+H]+ 528.26
The following compound was prepared in an analogous manner using 2-chloro-4-morpholin-4-yl-thieno[2,3-d]pyrimidine-6-carbaldehyde.
96: (400 MHz, CDCl3): 1.34 (3H, d (J 6.77), CH3), 2.25-2.35 (2H, m, CH2), 2.70 (1H, d, CH), 2.80 (3H, s, CH3), 2.90 (1H, d, CH), 3.25-3.30 (1H, m, CH), 3.42 (1H, d, CH), 3.55 (1H, m, CH), 3.67 (1H, d, CH), 3.76 (1H, d, CH), 3.86-3.93 (8H, m, CH2), 7.09 (1H, s, ar), 7.44-7.46 (1H, m, ar), 7.52 (1H, d, ar), 8.25 (1H, d (J 7.56) ar), 8.96 (1H, s, ar), 10.00 (1H, b, NH)
(M+H)+ 528.24

10: This compound was prepared in an analogous manner to the compound above using (R)-methylpiperazine as the starting material.
NMR: (400 MHz, CDCl3): 1.42 (3 H, d, J 6.75, Me), 2.33 (1 H, td, J 11.42 and 3.45), 2.43 (1 H, dd, J 3.62 and 11.23), 2.76 (1 H, d, J 11.17), 2.88 (3 H, s, Me), 2.91 (1 H, d, J 11.54), 3.34 (1 H, td, J 12.01 and 3.04), 3.59 (1 H, d, J 12.81), 3.72-3.94 (6 H, m, CH2), 4.08-4.12 (6 H, m, CH2), 7.40 (1 H, s, Ar), 7.51 (1 H, t, J 8.22, Ar), 7.60 (1 H, t, J 8.31, Ar), 8.27 (1 H, d, J 6.79, Ar), 9.01 (1 H, s, Ar) and 10.20 (1 H, s, NH).
[M+H]+ 528.27
The following compound was prepared in an analogous manner using 2-chloro-4-morpholin-4-yl-thieno[2,3-d]pyrimidine-6-carbaldehyde.
98: (M+H)+ 528.23
NMR: (400 MHz CDCl3): 1.25-1.28 (1H, m, CH), 1.42 (3H, d (J 6.71), CH3), 1.54 (1H, s, CH), 2.29-2.40 (2H, m, CH), 2.77 (1H, d (J 11.1), CH), 2.87 (3H, s, CH3), 2.95 (1H, d (J 11.25), CH), 3.30-3.36 (1H, m, CH), 3.60 (1H, d, (J 12.75), CH), 3.72 (1H, d (J 14.18), CH), 3.85 (2H, d (J 14.13), CH2), 3.92-4.01 (8H, m, CH2), 4.12-4.13 (1H, m, CH), 7.16 (1H, s, ar), 7.51 (1H, t (J 7.75, ar), 7.60 (1H, d (J 8.29), ar), 8.32 (1H, d (J 7.29), ar), 9.04 (1H, s, ar), 10.10 (1H, b, NH)

8: To a solution of piperazine (1 g) and triethylamine (1.78 mL) in dichloromethane (20 mL) at 0° C. was added dropwise 2-propanesulfonyl chloride (1.30 mL). The reaction mixture was stirred at room temperature for 16 h and then quenched with water (20 mL) and extracted into dichloromethane (2×40 mL). The combined organic layers were washed with saturated aqueous brine solution (2×40 mL), dried (MgSO$_4$) and concentrated to afford 1-(propane-2-sulfonyl)-piperazine as a white solid (1.87 g, 84%).

Reaction between 2-chloro-4-morpholin-4-yl-thieno[3,2-d]pyrimidine-6-carbaldehyde and 1-(propane-2-sulfonyl)-piperazine using procedure C yielded 2-chloro-4-morpholin-4-yl-6-[4-(propane-2-sulfonyl)-piperazin-1-ylmethyl]-thieno[3,2-d]pyrimidine. This compound was subjected to procedure A to yield the desired final compound which was purified using flash chromatography.

[M+H]+ 542.22

NMR: (400 MHz, CDCl3): 1.28 (6 H, d, J 6.84, Me), 2.51-2.61 (4 H, m, CH2), 3.13 (1 H, septet, J 6.93, CH), 3.35-3.60 (4 H, m, CH2), 3.81 (2 H, s, CH2), 3.83-3.90 (4 H, m, CH2), 3.96-4.04 (4 H, m, CH2), 7.32 (1 H, s, Ar), 7.40 (1 H, t, J 8.20, Ar), 7.48 (1 H, d, J 8.22, Ar), 8.20 (1 H, d, J 7.32, Ar), 8.92 (1 H, s, Ar) and 10.26 (1 H, s, Ar).

The following compound was prepared in an analogous manner using 2-chloro-4-morpholin-4-yl-thieno[2,3-d]pyrimidine-6-carbaldehyde.

97: NMR: (400 MHz, CDCl3): 1.24 (1H, m, CH), 1.36 (6H, d (J 6.84), CH3), 2.62 (4H, m, CH2), 3.44-3.49 (4H, m, CH2), 3.82 (2H, s, CH2), 3.93-4.00 (8H, m, CH2), 7.17 (1H, s, ar), 7.51-7.53 (1H, m, ar), 7.59 (1H, m, ar), 8.32 (1H, d (J 6.69), ar), 9.04 (1H, s, ar), 10.05 (1H, b, NH) (M+H)+ 542.24

7: To a solution of cis-2,6-dimethyl-piperazine (600 mg) and triethylamine (0.80 mL) in dichloromethane (10 mL) at 0° C. was added dropwise methanesulfonyl chloride (0.43 mL). The reaction mixture was stirred at room temperature for 16 h and then quenched with water (10 mL) and extracted into dichloromethane (2×20 mL). The combined organic layers were washed with saturated aqueous brine solution (2×20 mL), dried (MgSO$_4$) and concentrated to afford (3S,5R)-1-methanesulfonyl-3,5-dimethyl-piperazine as a white solid (817 mg, 81%).

Reaction between 6-(bromomethyl)-2-chloro-4-morpholinothieno[3,2-d]pyrimidine and (3S,5R)-1-methanesulfonyl-3,5-dimethyl-piperazine using potassium carbonate and acetonitrile yielded 2-chloro-6-((2S,6R)-4-methanesulfonyl-2,6-dimethyl-piperazin-1-ylmethyl)-4-morpholin-4-yl-thieno[3,2-d]pyrimidine. This compound was subjected to procedure A to yield the desired final compound which was purified using flash chromatography.

[M+H]+ 542.24

NMR: (400 MHz, CDCl3): 1.18 (6 H, d, J 6.90, Me), 2.48-2.52 (2 H, m, CH2), 2.72 (3 H, s, SO2Me), 2.78-2.88 (2 H, m, CH2), 3.51-3.56 (2 H, m, CH2), 3.81-3.88 (4 H, m, CH2), 3.96-4.02 (4 H, m, CH2), 4.12 (2 H, s, CH2), 7.28 (1 H, s, Ar), 7.42 (1 H, t, J 8.22, Ar), 7.49 (1 H, d, J 8.31, Ar), 8.20 (1 H, d, J 7.26, Ar) 8.94 (1 H, s, Ar) and 10.08 (1 H, s, NH).

The following compound was prepared in an analogous manner using 2-chloro-4-morpholin-4-yl-thieno[2,3-d]pyrimidine-6-carbaldehyde.

102: NMR: (400 Mhz, CDCl3): 1.19-1.24 (6H, m, CH3), 2.61 (2H, t (J 10.72), CH2), 2.80 (3H, s, CH3), 2.88-2.90 (2H, m, CH2), 3.59 (2H, d (J 10.46), CH2), 3.93-4.00 (8H, m, CH2) 4.14 (2H, s, CH2), 7.12 (1H, s, ar), 7.51 (1H, t (J 7.80), ar), 7.60 (1H, d (J 8.29), ar), 8.32 (1H, d (J 6.73), ar), 9.04 (1H, s, ar), 10.10 (1H, b, NH)

6: Reaction between 2-chloro-4-morpholin-4-yl-thieno[3,2-d]pyrimidine-6-carbaldehyde and cis-2,6-dimethyl-piperazine using procedure C yielded 2-chloro-6-((3R,5S)-3,5-dimethyl-piperazin-1-ylmethyl)-4-morpholin-4-yl-thieno[3,2-d]pyrimidine. This compound treated with methane sulphonyl chloride using standard conditions to yield 2-chloro-6-((3R,5S)-4-methanesulfonyl-3,5-dimethyl-piperazin-1-ylmethyl)-4-morpholin-4-yl-thieno[3,2-d]pyrimidine. This compound was subjected to procedure A to yield the desired final compound which was purified using flash chromatography.

[M+H]+ 542.25

(400 MHz, CDCl3): 1.52 (6 H, d, J 6.93, Me), 2.33 (2 H, dd, J 11.37 and 4.34, CH2), 2.81 (2 H, d, J 11.15, CH2), 2.89 (3 H, s, SO2Me), 3.86 (2 H, s, CH2), 3.88-3.94 (4 H, m, CH2), 4.05-4.13 (6 H, m, CH2), 7.40 (1 H, s, Ar), 7.51 (1 H, t, J 8.20, Ar), 7.58 (1 H, d, J 8.29, Ar), 8.27 (1 H, d, J 7.32, Ar), 9.02 (1 H, s, Ar) and 10.14 (1 H, s, Ar).

92: To 1-BOC-homopiperizine (0.8 ml) was added methane sulphonyl chloride (0.34 ml) and triethylamine (0.68 ml). The reaction mixture was stirred at room temperature for 4 hours. The reaction mixture was then partitioned between dichloromethane and water. The combined organic extracts were then washed with brine and dried (MgSO$_4$). The solvent was removed in vacuo to yield 1.23 g crude 4-methanesulfonyl-[1,4]diazepane-1-carboxylic acid tert-butyl ester.

Crude 4-Methanesulfonyl-[1,4]diazepane-1-carboxylic acid tert-butyl ester (1.23 g) was stirred in anhydrous methanol (10 ml). 2M hydrogen chloride in ether (22 ml) was added. The reaction mixture was stirred at room temperature. After 5 minutes a precipitate formed, addition of anhydrous methanol (5 ml) caused this to dissolve. The reaction mixture was stirred overnight at room temperature. The solvents were removed in vacuo to yield 1.06 g of 1-methanesulfonyl-[1,4]diazepane hydrochloride salt.

Reaction between 2-chloro-4-morpholin-4-yl-thieno[3,2-d]pyrimidine-6-carbaldehyde and 1-methanesulfonyl-[1,4]diazepane hydrochloride salt using procedure C yielded 2-chloro-6-(4-methanesulfonyl-[1,4]diazepan-1-ylmethyl)-4-morpholin-4-yl-thieno[3,2-d]pyrimidine. This compound was subjected to procedure A to yield the desired final compound which was purified using flash chromatography.

NMR: (400 MHz, CDCl3): 1.26 (3H, s, CH3), 1.96 (2H, m, CH2), 2.86-2.88 (4H, m, CH2), 3.49-3.52 (4H, m, CH2), 3.92-3.94 (4H, m, CH2), 4.03 (2H, s, CH2), 4.08-4.11 (4H, m, CH2), 7.38 (1H, s, ar), 7.51-7.53 (1H, m, ar), 7.58 (1H, d, ar), 8.28 (1H, d, J (7.41), ar), 9.02 s, ar), 10.05 (1H, b, NH) (M+H)+ 528.23

94: To a mixture of isobutyraldehyde (9.5 mL) and dioxane (0.38 mL) in diethyl ether (40 mL) at room temperature was added bromine (0.11 mL). The reaction mixture was cooled to 0° C. and bromine (5.1 mL) was added dropwise. The reaction mixture was stirred for 10 min and then poured into ice water (250 mL). Sodium carbonate (6 g) was added gradually to the mixture with vigorous stirring. Then, the organic phase was separated, dried (MgSO$_4$) and distilled using Kugelrohr apparatus to give 2-bromo-2-methyl-propionaldehyde as a colourless oil (3.794 g).

To a solution of ethylene diamine (8.40 mL) in toluene (20 mL) at 0° C. was added 2-bromo-2-methyl-propionaldehyde (3.794 g). The reaction mixture was stirred vigorously at room temperature for 1 h and then at reflux for 30 min. After cooling to room temperature the two phases were separated and the lower phase was extracted with toluene (2×30 mL). The toluene phase was then concentrated and distilled using Kugelrhor apparatus to give 6,6-dimethyl-1,2,3,6-tetrahydro-pyrazine (1.56 g).

To a solution of 6,6-dimethyl-1,2,3,6-tetrahydro-pyrazine (1.56 g) in ethanol (100 mL) was added Pd/C (300 mg). The reaction mixture was stirred for 16 h with a hydrogen balloon. The mixture was then filtered through Celite and the filtrate concentrated and distilled using kugelrohr apparatus to afford 2,2-dimethyl-piperazine as a colourless oil which solidified on standing (1.23 g).

To a solution of 2,2-dimethypiperazine (400 mg) and triethylamine (0.59 mL) in dichloromethane (10 mL) at 0° C. was added dropwise methanesulfonyl chloride (0.30 mL). The reaction mixture was stirred at room temperature for 16 h and then quenched with water (10 mL) and extracted into dichloromethane (2×20 mL). The combined organic layers were washed with saturated aqueous brine solution (2×20 mL), dried ($MgSO_4$) and concentrated to afford 1-methanesulfonyl-3,3-dimethyl-piperazine as a white solid (412 mg, 61%).

Reaction between 2-chloro-4-morpholin-4-yl-thieno[3,2-d]pyrimidine-6-carbaldehyde and 1-methanesulfonyl-3,3-dimethyl-piperazine using procedure C yielded 2-chloro-6-(4-methanesulfonyl-2,2-dimethyl-piperazin-1-ylmethyl)-4-morpholin-4-yl-thieno[3,2-d]pyrimidine. This compound was subjected to procedure A to yield the desired final compound which was purified using flash chromatography.

(400 MHz, CDCl3): 1.15 (6 H, s, Me), 2.62-2.68 (2 H, m, CH2), 2.72 (3 H, s, Me), 2.95 (2 H, s, CH2), 3.12-3.18 (2 H, m, CH2), 3.81-3.90 (6 H, m, CH2), 3.98-4.04 (4 H, m, CH2), 7.32 (1 H, s, Ar), 7.42 (1 H, t, J 8.22, Ar), 7.50 (1 H, d, J 8.23, Ar), 8.20 (1 H, d, J 7.18, Ar), 8.92 (1 H, s, Ar) and 9.98 (1 H, s, NH).

[M+H]+ 542.25

100: To a solution of 2,2-dimethypiperazine (400 mg) in dichloromethane (20 mL) at 0° C. was added di-tert-butyl dicarbonate (766 mg). The reaction was stirred at room temperature for 4 h and then quenched with water (20 mL) and extracted into dichloromethane (2×40 mL). The combined organics were washed with saturated aqueous brine solution (40 mL), dried ($MgSO_4$) and concentrated to give 3,3-diemethyl-piperazine-1-carboxylic acid tert-butyl ester as a white solid (720 mg, 96%).

To a solution of 3,3-diemethyl-piperazine-1-carboxylic acid tert-butyl ester (720 mg) and triethylamine (0.59 mL) in dichloromethane (10 mL) at 0° C. was added dropwise methanesulfonyl chloride (0.30 mL). The reaction mixture was stirred at room temperature for 16 h and then quenched with water (10 mL) and extracted into dichloromethane (2×20 mL). The combined organic layers were washed with saturated aqueous brine solution (2×20 mL), dried ($MgSO_4$) and concentrated to give 4-methanesulfonyl-3,3-dimethyl-piperazine-1-carboxylic acid tert-butyl ester as a white solid (914 mg, 93%).

To a solution of 4-methanesulfonyl-3,3-dimethyl-piperazine-1-carboxylic acid tert-butyl ester (914 mg) in dichloromethane (20 mL) at 0° C. was added dropwise HCl (6.65 mL of a 2 M solution in diethyl ether). The reaction mixture was stirred at room temperature for 2 h. The precipitate formed was then collected by filtration and dried to afford 1-methanesulfonyl-2,2-dimethyl-piperazine hydrochloride salt as a white solid (540 mg, 75%).

Reaction between 2-chloro-4-morpholin-4-yl-thieno[3,2-d]pyrimidine-6-carbaldehyde and 1-methanesulfonyl-2,2-dimethyl-piperazine hydrochloride salt using procedure C yielded 2-chloro-6-(4-methanesulfonyl-3,3-dimethyl-piperazin-1-ylmethyl)-4-morpholin-4-yl-thieno[3,2-d]pyrimidine. This compound was subjected to procedure A to yield the desired final compound which was purified using flash chromatography.

(400 MHz, CDCl3): 1.49 (6 H, s, Me), 2.28 (2 H, s, CH2), 2.55-2.58 (2 H, m, CH2), 2.88 (3 H, s, Me), 3.44-3.48 (2 H, m, CH2), 3.76 (2 H, s, CH2), 3.82-3.89 (4 H, m, CH2), 4.01-4.08 (4 H, m, CH2), 7.29 (1 H, s, Ar), 7.41 (1 H, t, J 8.22, Ar), 7.52 (1 H, d, J 8.24, Ar), 8.20 (1 H, d, J 7.21, Ar), 8.96 (1 H, s, Ar) and 10.02 (1 H, s, NH).

[M+H]+ 542.27

29: Reaction between N-BOC-piperazine and methane sulfonyl chloride in dichloromethane and triethylamine yielded 4-methanesulfonyl-piperazine-1-carboxylic acid tert-butyl ester. Cleavage of the BOC protecting group using HCl (2M) in dichloromethane yielded 1-methanesulfonyl-piperazine. HCl salt.

Reaction between 1-methanesulfonyl-piperazine. HCL salt and 2-chloro-7-methyl-4-morpholin-4-yl-thieno[3,2-d]pyrimidine-6-carbaldehyde using procedure C yielded 2-chloro-6-(4-methanesulfonyl-piperazin-1-ylmethyl)-7-methyl-4-morpholin-4-yl-thieno[3,2-d]pyrimidine. This compound was subjected to procedure A to yield the desired final compound which was purified using flash chromatography.

NMR: (CDCl3): 2.55 (3H, s), 2.71-2.75 (4H, m), 2.82 (3H, s), 3.30-3.33 (4H, m), 3.89 (2H, s), 3.90-3.93 (4H, m), 4.06-4.10 (4H, m), 7.51-7.54 (1H, m), 7.60 (1H, d, J=8.3), 8.37 (1H, d, J=6.8), 9.18 (1H, s), 10.05 (1H, br)

(ESI+): MH+ 528 (100%)

31: Reaction between 1-methylpiperazine and 2-chloro-4-morpholin-4-yl-thieno[2,3-d]pyrimidine-6-carbaldehyde using Procedure C yielded 2-chloro-6-(4-methyl-piperazin-1-ylmethyl)-4-morpholin-4-yl-thieno[2,3-d]pyrimidine. This compound was subjected to procedure A to yield the desired final compound which was purified using flash chromatography.

400 MHz 1H NMR CDCl3

2.31 (s, 3H, CH3), 2.50 (m, 4H, 2×CH2), 2.60 (m, 4H, 2×CH2), 3.78 (s, 2H, CH2), 3.91-3.94 (m, 4H, 2×CH2), 3.98-4.00 (m, 4H, 2×CH2), 7.16 (s, H, ArH), 7.50 (t, H, ArH, J=7.39 Hz), 7.58 (d, H, ArH, J=8.29 Hz), 8.32 (d, H, ArH, J=7.37 Hz), 9.03 (s, H, ArH), 10.15 (sbr, H, NH).

MH+=450.18

57: 2-Chloro-6-(4-methanesulfonyl-piperazin-1-ylmethyl)-4-morpholin-4-yl-thieno[2,3-d]pyrimidine (see intermediates) was subjected to procedure A. The final compound was purified using flash chromatography.

400 MHz 1H NMR CDCl3

2.67 (m, 4H, 2×CH2), 2.81 (s, 3H, CH3), 3.30 (m, 4H, 2×CH2), 3.83 (s, 2H, CH2), 3.92-3.94 (m, 4H, 2×CH2), 3.98-4.00 (m, 4H, 2×CH2), 7.17 (s, H, ArH), 7.50 (t, H, ArH, J=7.81 Hz), 7.59 (d, H, ArH, J=8.31 Hz), 8.31 (d, H, ArH, J=6.98 Hz), 10.12 (sbr, H, NH).

MH+=514.10

43: To a solution of N-BOC-piperazine (1.06 g) in $CH_2Cl_2$/MeOH (20 mL) at 0° C. was added 2M HCl in ether (3.14 mL). After 1 h the solvent was removed in vacuo to give a white solid. This was dissolved in water and NaCN was added (280 mg). To this mixture was added a solution of acetone (4204) in water (2 mL). The resultant was stirred at room temperature for 72 h then diluted with water and extracted with ethyl acetate. Combined extracts were dried ($Na_2SO_4$), filtered and concentrated to give 4-(cyano-dimethyl-methyl)-piperazine-1-carboxylic acid tert-butyl ester (77%).

To a solution of 4-(cyano-dimethyl-methyl)-piperazine-1-carboxylic acid tert-butyl ester (1 g) and $K_2CO_3$ (100 mg) in dry DMSO (20 mL) at 0° C. was added a 27.5% hydrogen peroxide (2 mL) dropwise. The resulting mixture was heated at 40° C. overnight then diluted with water give a solid. This was collected, washed and dried to give 4-(1-carbamoyl-1-methyl-ethyl)-piperazine-1-carboxylic acid tert-butyl ester (806 mg). Subsequent treatment with 2M HCl in ether gave 2-piperazin-1-yl-isobutyramide dihydrochloride (100%).

Reductive amination of 2-chloro-4-morpholin-4-yl-thieno[3,2-d]pyrimidine-6-carbaldehyde with 2-piperazin-1-yl-isobutyramide dihydrochloride according General Procedure C gave 2-[4-(2-chloro-4-morpholin-4-yl-thieno[3,2-d]pyrimidin-6-ylmethyl)-piperazin-1-yl]isobutyramide after purification on silica.

2-[4-(2-Chloro-4-morpholin-4-yl-thieno[3,2-d]pyrimidin-6-ylmethyl)-piperazin-1-yl]-isobutyramide was reacted with 4-(4,4,5,5-tetramethyl-[1,3,2]dioxaborolan-2-yl)-1H-indazole in General Procedure A. Purification on silica yielded the desired compound.

NMR: (CDCl$_3$): 1.24 (s, 6H, 2×CH2), 2.55-2.65 (m, 8H, 4×CH2), 3.85 (s, 2H, CH2), 3.90-3.92 (m, 4H, 2×CH2), 4.07-4.09 (m, 4H, 2×CH2), 5.35 (m, H, NH), 7.09 (m, H, NH), 7.37 (s, H, ArH), 7.48 (t. H, ArH, J=7.72 Hz), 7.57 (d, H, ArH, J=8.22 Hz), 8.26 (d, H, ArH, J=7.14 Hz), 9.0 (s, H, ArH0, 10.4 (sbr, H, NH).

MS: (ESI+): MH+=521.27

44: To a solution of piperidone (317 mg) and potassium carbonate (530 mg) in acetonitrile at room temperature (20 mL) was added 2-bromoethyl methyl ether (0.48 mL). The reaction mixture was heated at reflux for 16 h, allowed to cool to room temperature and then reduced in vacuo. The residue was then redissolved in dichloromethane (20 mL) and washed with water (20 mL) and brine (20 mL), dried (MgSO$_4$) and reduced in vacuo to give 1-(2-methoxy-ethyl)-piperidin-4-one as colourless oil (171 mg).

To a suspension of 2-chloro-4-morpholin-4-yl-thieno[3,2-d]pyrimidine-6-carbaldehyde (1.0 g) and molecular sieves in methanol (20 mL) at room temperature was added acetic acid (0.1 mL) and a solution of methylamine (219 mg) in methanol (1 ml). The reaction mixture was stirred at room temperature for 24 h. Then sodium borohydride (542 mg) was added portionwise and the reaction stirred at room temperature for a further 30 min. The reaction was then quenched with saturated aqueous sodium hydrogen carbonate solution (10 mL) and extracted into dichloromethane (2×10 mL). The combined organics were washed with brine (20 mL), dried (MgSO4) and reduced in vacuo to give (2-chloro-4-morpholin-4-yl-thieno[3,2-d]pyrimidin-6-ylmethyl)-methyl-amine as a white solid (0.95 g).

(2-chloro-4-morpholin-4-yl-thieno[3,2-d]pyrimidin-6-ylmethyl)-methyl-amine was then reacted with 1-(2-methoxy-ethyl)-piperidin-4-one in general procedure C. Purification on silica yielded (2-chloro-4-morpholin-4-yl-thieno[3,2-d]pyrimidin-6-ylmethyl)-[1-(2-methoxy-ethyl)-piperidin-4-yl]-methyl-amine.

(2-Chloro-4-morpholin-4-yl-thieno[3,2-d]pyrimidin-6-ylmethyl)-[1-(2-methoxy-ethyl)-piperidin-4-yl]-methyl-amine was then reacted with 4-(4,4,5,5-tetramethyl-[1,3,2]dioxaborolan-2-yl)-1H-indazole in general procedure A. Purification on silica yielded the title compound.

NMR: DMSO: 13.15 (bs, 1H); 8.86 (s, 1H); 8.21 (d, 1H, J=7.3 Hz); 7.65 (d, 1H, J=8.2 Hz); 7.45 (m, 2H); 3.99 (m, 4H); 3.94 (s, 2H); 3.82 (m, 4H); 3.38 (m, 2H); 3.22 (s, 3H); 2.94 (m, 2H); 2.49 (m, 2H); 2.48 (m, 1H); 2.22 (s, 3H); 1.94 (m, 2H); 1.74 (m, 2H); 1.35 (m, 2H).

32: Hydrogen chloride gas (4 g) was bubbled through methanol (120 mL) at 0° C. Proline (3.80 g) was then added and the mixture was stirred at room temperature for 4.5 h and then reduced in vacuo to give pyrrolidine-2-carboxylic acid methyl ester hydrochloride salt as a white solid (5.5 g).

To a suspension of pyrrolidine-2-carboxylic acid methyl ester hydrochloride salt (5.5 g) in acetonitrile (90 mL) was added triethylamine (10.2 mL) and di-tert-butyldicarbonate (8.0 g). The reaction mixture was stirred at room temperature for 16 h and then reduced in vacuo. The residue was redissolved in dichloromethane (40 mL) and washed with brine (40 mL), dried (MgSO4), reduced in vacuo and purified by column chromatography to give pyrrolidine-1,2-dicarboxylic acid 1-tert-butyl ester 2-methyl ester as a yellow oil (6.33 g).

To a solution of pyrrolidine-1,2-dicarboxylic acid 1-tert-butyl ester 2-methyl ester (3.5 g) in toluene (40 mL) at −78° C. was added dropwise diisobutylaluminium hydride (20 mL of a 1.5 M solution in toluene) maintaining the temperature below −65° C. The reaction mixture was stirred at −78° C. for 2 h and then quenched with methanol (10 mL). The mixture was then diluted with diethyl ether (50 mL), potassium sodium tartrate tetrahydrate was added and the mixture stirred vigorously for 20 min at room temperature. The two phases were then separated and the aqueous layer extracted with dichloromethane (2×50 mL). The combined organics were then washed with brine (100 mL), dried (MgSO$_4$), reduced in vacuo and purified by column chromatography to give 2-formyl-pyrrolidine-1-carboxylic acid tert-butyl ester as a pale yellow oil (2.687 g).

To a suspension of 2-formyl-pyrrolidine-1-carboxylic acid tert-butyl ester (2.68 g) in methanol (30 mL) at room temperature was added a solution of methylamine (831 mg) in methanol (3 mL). The reaction mixture was stirred at room temperature for 72 h and then sodium borohydride (760 mg) and molecular sieves were added. After stirring at room temperature for 2 h, the reaction mixture was filtered and the filtrate reduced in vacuo. The residue was redissolved in dichloromethane (30 mL) and washed with saturated sodium bicarbonate solution (30 mL). The combined organics were washed with brine (30 mL), dried (MgSO$_4$) and reduced in vacuo to give 2-methylaminomethyl-pyrrolidine-1-carboxylic acid tert-butyl ester as a pale yellow oil (2.56 g).

To a solution of 2-methylaminomethyl-pyrrolidine-1-carboxylic acid tert-butyl ester (500 mg) in dichloromethane (10 mL) at room temperature was added triethylamine (0.36 mL) and methanesulphonyl chloride (0.20 mL). The reaction mixture was stirred at room temperature for 4 h and then partitioned between dichloromethane (20 mL) and saturated aqueous sodium bicarbonate solution (30 mL). The combined organics were washed with brine (30 mL), dried (MgSO$_4$), reduced in vacuo and purified by column chromatography to give 2-[(methanesulfonyl-methyl-amino)-methyl]-pyrrolidine-1-carboxylic acid tert-butyl ester as a white solid (0.63 g).

To a solution of 2-[(methanesulfonyl-methyl-amino)-methyl]-pyrrolidine-1-carboxylic acid tert-butyl ester (0.63 g) in dichloromethane (10 mL) at room temperature was added hydrogen chloride (3.0 mL of a 2 M solution in diethyl ether). The reaction mixture was stirred at room temperature for 72 h and then reduced in vacuo to give N-methyl-N-pyrrolidin-2-ylmethyl-methanesulfonamide as a crystalline solid (0.49 g).

To a mixture of 6-bromomethyl-2-chloro-4-morpholin-4-yl-thieno[3,2-d]pyrimidine (0.50 g) and N-methyl-N-pyrrolidin-2-ylmethyl-methanesulfonamide (390 mg) in acetonitrile (10 mL) was added potassium carbonate (490 mg). The reaction mixture was heated at 80° C. for 16 h and then allowed to cool to room temperature. The reaction mixture was then partitioned between dichloromethane (20 mL) and saturated aqueous sodium bicarbonate solution (20 mL). The combined organics were washed with brine (30 mL), dried (MgSO$_4$), reduced in vacuo and purified by column chromatography to give N-[1-(2-chloro-4-morpholin-4-yl-thieno

[3,2-d]pyrimidin-6-ylmethyl)-pyrrolidin-2-ylmethyl]-N-methyl-methanesulfonamide as a pale yellow solid (580 mg).

N-[1-(2-Chloro-4-morpholin-4-yl-thieno[3,2-d]pyrimidin-6-ylmethyl)-pyrrolidin-2-ylmethyl]-N-methyl-methanesulfonamide was reacted with 4-(4,4,5,5-tetramethyl-[1,3,2]dioxaborolan-2-yl)-1H-indazole in general procedure A. Purification on silica yielded the title compound.

NMR: CDCl$_3$: 1.80 (3H, m); 2.02 (1H, m); 2.40 (1H, m); 2.80 (3H, s); 2.97 (4H, m); 3.18 (3H, m); 3.90 (4H, m); 4.10 (4H, t, J=4.7 Hz); 4.30 (1H, d, J=14.6 Hz); 7.37 (1H, s); 7.50 1H, t, J=7.7 Hz); 7.58 (1H, d, J=8.2 Hz); 8.28 (1H, d, J=7.1 Hz); 9.02 (1H, s); 10.00 (1H, br s).

MS: (ESI+): MH+ 542

42: To a solution of tetrahydrothiopyran-4-one (400 mg) stirring in acetonitrile (5 ml) and Na2.EDTA (0.0004 M aq, 3 ml) was added potassium peroxymonosulphate (Oxone™, 6.34 g) and NaHCO3 (2.69 g) in several aliquots over 30 minutes. The reaction mixture was stirred at room temperature for a further 2 hours, then diluted with water (40 ml), extracted into dichloromethane, and dried (MgSO4) to give 1,1-dioxo-tetrahydro-thiopyran-4-one (330 mg) as a white solid. To this compound (75 mg) stirring in anhydrous 1,2-dichloroethane (6 ml) was added 2-chloro-4-morpholin-4-yl-thienopyrimidine-6-yl methyl methylamine (150 mg, as previously prepared from 2-chloro-4-morpholin-4-yl-thienopyrimidine-6-carbaldehyde and methylamine under reductive amination conditions), followed by glacial acetic acid (31 µl) and sodium triacetoxy borohydride (138 mg). The reaction mixture was stirred for 24 hours at room temperature, and the product isolated by extraction into dichloromethane, followed by purification by flash chromatography to give (2-chloro-4-morpholin-4-yl-thienopyrimidine-6-ylmethyl)-(1,1-dioxo-hexahydro-thiopyran-4-yl)-methyl-amine (115 mg) as a yellow solid, which was used in a Suzuki coupling with 4-(4,4,5,5-tetramethyl-[1,3,2]dioxaborolan-2-yl)-1H-indazole, to give, after flash silica purification the title compound (38 mg) as a white solid.

1H NMR 400 MHz DMSO 13.18 (bs, 1H); 8.87 (s, 1H); 8.21 (d, 1H, J=7.2 Hz); 7.65 (d, 1H, J=8.2 Hz)

7.45 (m, 2H); 3.98 (m, 6H) 3.82 (m, 4H); 3.26-3.06 (m, CH2×2)

2.91 (m, 1H); 2.28 (s, 3H); 2.04 (m, CH2×2)

M/S ESI (m+1)=513.1

LC>/95% purity

34: To a solution of 1-methanesulphonyl-piperidine-4-one (182 mg; prepared from N-BOC-piperidone by reaction of piperidone-4-one TFA salt with methane sulphonyl chloride), stirring in anhydrous 1,2-dichloroethane (6 ml) was added 2-methoxyethylamine (90 µl) followed by glacial acetic acid (62 µl). Sodium triacetoxy borohydride (284 mg), was added in aliquots over 30 minutes and the reaction mixture stirred for 12 hours at room temperature, then diluted with dichloromethane (40 ml), washed with 50% NaHCO3 solution and dried (MgSO4). The solvents were removed in vacuo to give a residue which was purified by silica flash chromatography to give 1-methanesulphonyl-piperidin-4-yl-2-methoxy-ethylamine (148 mg), as a white solid.

To a solution of 1-methanesulphonyl-piperidin-4-yl-2-methoxy-ethylamine (146 mg), stirring in 1,2-dichloroethane (10 ml), was added 2-chloro-4-morpholin-4-yl-thieno[3,2-d]pyrimidine-6-carbaldehyde (176 mg), followed by glacial acetic acid (38 µl), and sodium triacetoxy borohydride (171 mg). The reaction mixture was stirred for 12 hours at room temperature. The product was isolated by extraction into dichloromethane, followed by purification by flash silica chromatography, to give (2-chloro-4-morpholino-4-yl-thieno[3,2-d]pyrimidin-6-ylmethyl)-(1-methanesulphonyl-piperidin-4-yl)-(2-methoxyethylamine), (103 mg) as a white solid, which was used in a Suzuki coupling with 4-(4,4,5,5-tetramethyl-[1,3,2]dioxaborolan-2-yl)-1H-indazole, to give, after flash silica purification the title compound (72 mg) as a white solid.

1H NMR 400 MHz d6 DMSO 13.15 (bs, 1H); 8.87 (s, 1H); 8.21 (d, 1H, J=8.3 Hz)

7.65 (d, 1H, J=8.3 Hz); 7.46 (t, 1H); 4.08 (s, 2H)

4.01 (m, 4H+CH2); 3.83 (m, 4H); 3.60 (m, 2H); 3.22 (s, 3H);

2.81 (s, 3H); 2.75 (m, CH2×2); 2.67 (m, CH); 1.86 (m, CH2)

LC-MS (m+1) 586.2

Purity>95%

30: To a solution of 4-(2-aminoethyl)-morpholine (600 mg) stirring in anhydrous 1,2-dichloroethane (40 ml), was added 2-chloro-4-morpholin-4-yl-thieno[3,2-d]pyrimidine-6-carbaldehyde (1.31 g), followed by glacial acetic acid (277 µl) and sodium triacetoxy borohydride (1.27 g) added in several aliquots over 30 minutes. The reaction mixture was stirred for 12 hours at room temperature, then diluted with chloroform (50 ml), washed with 50% NaHCO3 solution and dried (MgSO4). The solvents were removed in vacuo to give a residue which was purified by flash silica chromatography to give (2-chloro-4-morpholin-4-yl-thieno[3,2-d]pyrimidine-6-ylmethyl)-(2-morpholin-4-yl-ethyl)-amine (398 mg), as a white solid.

To this compound (172 mg), stirring in anhydrous 1,2-dichloroethane (8 ml), was added 1-methanesulphonyl-piperidine-4-one, (77 mg; prepared from N-BOC-piperidone by reaction of piperidone-4-one TFA salt with methane sulphonyl chloride), followed by glacial acetic acid (26 µl), and sodium triacetoxy borohydride (129 mg). The reaction mixture was stirred for 12 hours at room temperature and then diluted with chloroform (30 ml), washed with 50% NaHCO3 solution and dried (MgSO4). The solvents were removed in vacuo to give a residue which was purified by silica flash chromatography to give (2-chloro-4-morpholin-4-yl-thieno[3,2-d]pyrimidin-6-ylmethyl)-(1-methanesulphonyl-piperidine-4-yl)-(2-morpholin-4-yl-ethyl)-amine, (123 mg) as an off-white solid, which was used in a Suzuki coupling with 4-(4,4,5,5-tetramethyl-[1,3,2]dioxaborolan-2-yl)-1H-indazole, to give, after flash silica purification the title compound (6 mg) as a white solid.

1H NMR 400 MHz DMSO 13.15 (bs, 1H); 8.87 (s, 1H); 8.30 (s, 1H); 8.21 (d, 1H, J=6.9 Hz);

7.65 (d, 1H, J=8.2 Hz); 7.46 (m, 1H); 4.02 (m, 4H+CH2), 3.83 (m, 4H);

3.61 (m, CH2×2); 3.53 (m, CH2×2); 2.81 (s, 3H); 2.68 (m, CH2×2);

2.40 (m, CH+CH2×2); 1.86 (m, CH2); 1.56 (m, CH2).

71: To a solution of 1-methyl-piperidone (1.00 g) in 1,2-dichloroethane (20 ml) was added 2-methoxyethylamine (0.77 ml), followed by sodium triacetoxyborohydride (2.62 g) and acetic acid (0.53 g). The reaction mixture was stirred at room temperature overnight. Dichloromethane/aqueous sodium hydrogen carbonate extraction and purification on silica gave (2-methoxy-ethyl)-(1-methyl-piperidin-4-yl)-amine (1.52 g).

2-Chloro-4-morpholin-4-yl-thieno[3,2-d]pyrimidine-6-carbaldehyde (150 mg) and (2-methoxy-ethyl)-(1-methyl-piperidin-4-yl)-amine (128 mg) were stirred together in 1,2-dichloroethane (8 ml) and acetic acid (32 mg) with sodium triacetoxyborohydride (146 mg) at room temperature overnight. Dichloromethane/aqueous sodium hydrogen carbonate extraction and purification on silica yielded (2-chloro-4-morpholin-4-yl-thieno[3,2-d]pyrimidin-6-ylmethyl)-(2-methoxy-ethyl)-(1-methyl-piperidin-4-yl)-amine (97 mg). (96 mg), 4-indazole-boronate ester (107 mg), sodium carbonate (70 mg) and PdCl$_2$(PPh$_3$)$_2$ (8 mg) in toluene (2 ml), ethanol (1 ml) and water (0.5 ml) were heated in a microwave at 120° C. for 60 min. Dichloromethane/water extraction and purification on silica gave the title compound (64 mg).

NMR: (DMSO) 13.15 (bs, 1H); 8.86 (s, 1H); 8.21 (d, 1H, J=7.0 Hz); 7.65 (d, 1H, J=8.0 Hz); 7.45 (t, 2H, J=7.7 Hz); 4.05 (s, 2H); 3.99 (m, CH2×2); 3.82 (m, CH2×2); 3.39 (m, 2H); 3.21 (s, 3H); 2.79 (m, 2H); 2.73 (m, 2H); 2.49 (m, 1H); 2.12 (s, 3H); 1.89-1.49 (m, CH2×3)

MS: MH+=522.31

59: Hydrogen chloride gas (4 g) was bubbled through methanol (120 mL) at 0° C. Proline (3.80 g) was then added and the mixture was stirred at room temperature for 4.5 h and then reduced in vacuo to give pyrrolidine-2-carboxylic acid methyl ester hydrochloride salt as a white solid (5.5 g).

To a suspension of pyrrolidine-2-carboxylic acid methyl ester hydrochloride salt (5.5 g) in acetonitrile (90 mL) was added triethylamine (10.2 mL) and di-tert-butyldicarbonate (8.0 g). The reaction mixture was stirred at room temperature for 16 h and then reduced in vacuo. The residue was redissolved in dichloromethane (40 mL) and washed with brine (40 mL), dried (MgSO$_4$), reduced in vacuo and purified by column chromatography to give pyrrolidine-1,2-dicarboxylic acid 1-tert-butyl ester 2-methyl ester as a yellow oil (6.33 g).

To a solution of pyrrolidine-1,2-dicarboxylic acid 1-tert-butyl ester 2-methyl ester (3.5 g) in toluene (40 mL) at −78° C. was added dropwise diisobutylaluminium hydride (20 mL of a 1.5 M solution in toluene) maintaining the temperature below −65° C. The reaction mixture was stirred at −78° C. for 2 h and then quenched with methanol (10 mL). The mixture was then diluted with diethyl ether (50 mL), potassium sodium tartrate tetrahydrate was added and the mixture stirred vigorously for 20 min at room temperature. The two phases were separated and the aqueous layer extracted with dichloromethane (2×50 mL). The combined organics were then washed with brine (100 mL), dried (MgSO$_4$), reduced in vacuo and purified by column chromatography to give 2-formyl-pyrrolidine-1-carboxylic acid tert-butyl ester as a pale yellow oil (2.687 g).

To a suspension of 2-formyl-pyrrolidine-1-carboxylic acid tert-butyl ester (2.68 g) in methanol (30 mL) at room temperature was added a solution of methylamine (831 mg) in methanol (3 mL). The reaction mixture was stirred at room temperature for 72 h and then sodium borohydride (760 mg) and molecular sieves were added. After stirring at room temperature for 2 h, the reaction mixture was filtered and the filtrate reduced in vacuo. The residue was redissolved in dichloromethane (30 mL) and washed with saturated sodium bicarbonate solution (30 mL). The combined organics were washed with brine (30 mL), dried (MgSO$_4$) and reduced in vacuo to give 2-methylaminomethyl-pyrrolidine-1-carboxylic acid tert-butyl ester as a pale yellow oil (2.56 g).

To a solution of 6-bromomethyl-2-chloro-4-morpholin-4-yl-thieno[3,2-d]pyrimidine (420 mg) and 2-methylaminomethyl-pyrrolidine-1-carboxylic acid tert-butyl ester (310 mg) in acetonitrile (10 mL) was added potassium carbonate (250 mg). The reaction mixture was heated at 80° C. for 4 h and then allowed to cool to room temperature. The mixture was then partitioned between dichloromethane (20 mL) and saturated aqueous sodium bicarbonate solution (20 mL) and the organic layer washed with brine (20 mL), dried (MgSO4), reduced in vacuo and purified on column chromatography to give 2-{[(2-chloro-4-morpholin-4-yl-thieno [3,2-d]pyrimidin-6-ylmethyl)-methyl-amino]-methyl}-pyrrolidine-1-carboxylic acid tert-butyl ester as a white solid (487 mg).

To a solution of 2-{[(2-chloro-4-morpholin-4-yl-thieno[3,2-d]pyrimidin-6-ylmethyl)-methyl-amino]-methyl}-pyrrolidine-1-carboxylic acid tert-butyl ester (480 mg) in dichloromethane (10 mL) was added hydrogen chloride (3 mL of a 2.0 M solution in diethyl ether). The mixture was stirred at room temperature for 16 h and then reduced in vacuo to give (2-chloro-4-morpholin-4-yl-thieno[3,2-d]pyrimidin-6-ylmethyl)-methyl-pyrrolidin-2-ylmethyl-amine hydrochloride salt as a yellow solid (380 mg).

To a stirring solution of (2-chloro-4-morpholin-4-yl-thieno [3,2-d]pyrimidin-6-ylmethyl)-methyl-pyrrolidin-2-ylmethyl-amine hydrochloride salt (380 mg) in dichloromethane (10 mL) was added triethylamine (0.30 mL) and methane sulfonyl chloride (71 μL). The mixture was stirred at room temperature for 2 h and then partitioned between dichloromethane (20 mL) and saturated aqueous sodium bicarbonate solution (20 mL). The organics were washed with brine (20 mL), dried, reduced in vacuo and purified by column chromatography to give (2-chloro-4-morpholin-4-yl-thieno [3,2-d]pyrimidin-6-ylmethyl)-(1-methanesulfonyl-pyrrolidin-2-ylmethyl)-methyl-amine as an off-white solid (124 mg).

(2-Chloro-4-morpholin-4-yl-thieno[3,2-d]pyrimidin-6-ylmethyl)-(1-methanesulfonyl-pyrrolidin-2-ylmethyl)-methylamine was reacted with 4-(4,4,5,5-tetramethyl-[1,3,2]dioxaborolan-2-yl)-1H-indazole in general procedure A. Purification on silica yielded the title compound.

NMR: CDCl$_3$: 1.88-1.96 (2H, m); 1.99-2.03 (1H, m); 2.04-2.12 (1H, m); 2.40 (3H, s); 2.52 (1H, dd, J=12.50 and 9.21); 2.72 (1H, dd, J=12.52 and 4.55); 2.88 (3H, s); 3.28-3.41 (2H, m); 3.84-3.92 (7H, m); 4.02-4.10 (4H, m); 7.46 (1H, s); 7.49 (1H, t, J=8.14); 7.62 (1H, d, J=8.28); 8.28 (1H, d, J=7.26); 9.01 (1H, s); 10.10 (1H, s).

MS: ESI+: MH+ 542

58: To a solution of 1-N-BOC-3-pyrrolidinone (3.0 g) in methanol (30 ml) was added a solution of freshly prepared methylamine (0.75 g) in methanol (3.1 ml). The reaction mixture was stirred for 1 hour and then sodium borohydride (0.61 g) was added. After stirring for 4 hours the reaction mixture was then diluted with dichloromethane, washed with sodium bicarbonate solution, dried (Mg$_2$SO$_4$) and the solvent removed in vacuo to give 3-methylamino-pyrrolidine-1-carboxylic acid tert-butyl ester (3.18 g).

To a solution of 3-methylamino-pyrrolidine-1-carboxylic acid tert-butyl ester (0.50 g) in dichloromethane (10 ml) was added triethylamine (0.38 ml) followed by methanesulfonic acid (0.21 ml). After stirring for 24 hours, the reaction mixture was diluted with dichloromethane, washed with sodium bicarbonate solution, dried (MgSO$_4$) and the solvent removed in vacuo. The residue was purified by flash chromatography to yield 3-(methanesulfonyl-methyl-amino)-pyrrolidine-1-carboxylic acid tert-butyl ester (0.52 g). Treatment of this compound with HCl in dichloromethane/methanol yielded N-Methyl-N-pyrrolidin-3-yl-methanesulfonamide hydrochloride salt (0.41 g).

To a solution of 6-bromomethyl-2-chloro-4-morpholin-4-yl-thieno[3,2-d]pyrimidine (500 mg) and N-Methyl-N-pyrrolidin-3-yl-methanesulfonamide hydrochloride salt (370 mg) in acetonitrile (10 mL) was added potassium carbonate (490 mg). The reaction mixture was heated at 80° C. for 16 h and then allowed to cool to room temperature. The mixture was then partitioned between dichloromethane (20 mL) and saturated aqueous sodium bicarbonate solution (20 mL) and the organic layer washed with brine (20 mL), dried (MgSO$_4$), reduced in vacuo and purified on column chromatography to give N-methyl-N-[1-(2-methyl-4-morpholin-4-yl-thieno[3,2-d]pyrimidin-6-ylmethyl)-pyrrolidin-3-yl]-methanesulfonamide as a pale yellow solid (395 mg).

N-methyl-N-[1-(2-methyl-4-morpholin-4-yl-thieno[3,2-d]pyrimidin-6-ylmethyl)-pyrrolidin-3-yl]-methanesulfonamide was reacted with 4-(4,4,5,5-tetramethyl-[1,3,2]dioxaborolan-2-yl)-1H-indazole in general procedure A. Purification on silica yielded the title compound.

NMR: CDCl$_3$: 1.88-1.98 (1H, m); 2.12-2.26 (1H, m); 2.44 (1H, q, J=8.28); 2.62-2.70 (1H, m); 2.89 (3H, s); 2.86 (1H, dd, J=10.24 and 3.98); 2.92 (3H, s); 2.96-3.01 (1H, m); 3.84-3.98 (6H, m); 4.02-4.10 (4H, m); 4.52-4.63 (1H, m); 7.34 (1H, s); 7.50 (1H, t, J=8.20); 7.61 (1H, d, J=8.21); 8.26 (1H, d, J=7.23); 9.01 (1H, s); 10.11 (1H, s).

MS: ESI+: MH+ 528

60: To a solution of 1-N-BOC-3-pyrrolidinone (3.0 g) in methanol (30 ml) was added a solution of freshly prepared methylamine (0.75 g) in methanol (3.1 ml). The reaction mixture was stirred for 1 hour and then sodium borohydride (0.61 g) was added. After stirring for 4 hours the reaction mixture was then diluted with dichloromethane, washed with sodium bicarbonate solution, dried (Mg$_2$SO$_4$) and the solvent removed in vacuo to give 3-methylamino-pyrrolidine-1-carboxylic acid tert-butyl ester (3.18 g).

To a mixture of 6-bromomethyl-2-chloro-4-morpholino-4-yl-thieno[3,2,-d]pyrimidine (0.50 g) and 3-methylamino-pyrrolidine-1-carboxylic acid tert-butyl ester (0.34 g) in acetonitrile (10 ml) was added potassium carbonate (0.30 g) and heated to 80° C. for 3 hours. The reaction mixture was then diluted with dichloromethane, washed with sodium bicarbonate solution, dried (Mg$_2$SO$_4$) and the solvent removed in vacuo. The residue was purified by flash chromatography to yield 3-[(2-Chloro-4-morpholin-4-yl-thieno[3,2,-d]pyrimidin-6-ylmethyl)-amino]-pyrrolidine-1-carboxylic acid tert-butyl ester (0.65 g). Treatment of this compound with HCl in dichloromethane/methanol yielded (2-chloro-4-morpholin-4-yl-thieno[3,2,-d]pyrimidin-6-ylmethyl)-amino-pyrrolidin-3-amine hydrochloride salt (0.56 g).

To a suspension of (2-chloro-4-morpholin-4-yl-thieno[3,2,-d]pyrimidin-6-ylmethyl)-amino-pyrrolidin-3-amine hydrochloride salt (0.56 g) in dichloromethane (10 ml) was added triethylamine (0.42 ml) followed by methanesulfonyl chloride (0.12 ml). After stirring for 3 hours the reaction mixture was diluted with dichloromethane, washed with sodium bicarbonate solution, dried (Mg$_2$SO$_4$) and the solvent removed in vacuo. The residue was purified by flash chromatography to yield (2-chloro-4-morpholin-4-yl-thieno[3,2,-d]pyrimidin-6-ylmethyl)-(1-methanesulfonyl-pyrrolidin-3-yl)-methyl-amine (0.25 g). (2-Chloro-4-morpholin-4-yl-thieno[3,2,-d]pyrimidin-6-ylmethyl)-(1-methanesulfonyl-pyrrolidin-3-yl)-methyl-amine was reacted with 4-(4,4,5,5-tetramethyl-[1,3,2]dioxaborolan-2-yl)-1H-indazole in general procedure A. Purification on silica yielded the title compound.

NMR: CDCl$_3$: 1.94-2.01 (1H, m); 2.20-2.28 (1H, m); 2.36 (3H, s); 2.85 (3H, s); 3.20-3.38 (3H, m); 3.52-3.65 (2H, m); 3.72-3.95 (6H, m); 4.02-4.07 (4H, m); 7.33 (1H, s); 7.49 (1H, t, J=8.21); 7.60 (1H, d, J=8.22); 8.24 (1H, d, J=7.20); 9.01 (1H, s); 10.12 (1H, s).

MS: ESI+: MH+ 528

74: Reductive amination of 1-Methanesulfonyl-piperidin-4-one (150 mg) with (2-Chloro-4-morpholin-4-yl-thieno[3,2-d]pyrimidin-6-ylmethyl)-methyl-amine (250 mg) under standard conditions followed by aqueous work-up and purification on silica gave (2-chloro-4-morpholin-4-yl-thieno[3,2-d]pyrimidin-6-ylmethyl)-(1-methanesulfonyl-piperidin-4-yl)-methyl-amine (279 mg).

(2-Chloro-4-morpholin-4-yl-thieno[3,2-d]pyrimidin-6-ylmethyl)-(1-methanesulfonyl-piperidin-4-yl)-methyl-amine was reacted with 4-(4,4,5,5-tetramethyl-[1,3,2]dioxaborolan-2-yl)-1H-indazole in General Procedure A. Purification on silica yielded the desired compound.

NMR: (DMSO): 13.16 (bs, 1H); 8.87 (s, 1H); 8.21 (d, 1H, J=7.3 Hz); 7.65 (d, 1H, J=8.3 Hz); 7.46 (m, 2H); 3.99 (m, 4H); 3.95 (s, 2H); 3.82 (m, 4H); 3.61 (m, 2H); 2.84 (s, 3H); 2.72 (m, 2H); 2.62 (m, 1H); 2.29 (s, 3H); 1.87 (m, 2H); 1.58 (m, 2H)

MS: (ESI+): MH+=542.3

72: To a suspension of piperazine-2-carboxylic acid dihydrochloride (10 g) in 1,4-dioxane (100 mL) and water (50 mL) at 0° C. was added 17M NaOH solution in portions followed by di-tert-butyldicarbonate (11.8 g). The resulting mixture was warmed to R.T. and stirred for 5 h. Triethylamine (13.7 mL) and methanesulfonyl chloride (3.8 mL) were added this mixture was stirred overnight at R.T. The reaction mixture was concentrated in vacuo, diluted with 2M HCl and extracted with EtOAC. Combined extracts were dried (MgSO4), filtered and concentrated to give 4-methanesulfonyl-piperazine-1,3-dicarboxylic acid 1-tert-butyl ester (8.46 g).

To a solution of 4-methanesulfonyl-piperazine-1,3-dicarboxylic acid 1-tert-butyl ester (8.4 g, crude) in DMF (50 mL) was added K$_2$CO$_3$ (7.5 g) and iodomethane (8.5 mL) The mixture was stirred overnight at R.T. An aqueous work-up followed by purification on silica gave 4-methanesulfonyl-piperazine-1,3-dicarboxylic acid 1-tert-butyl ester 3-methyl ester (3.267 g). A solution of 4-methanesulfonyl-piperazine-1,3-dicarboxylic acid 1-tert-butyl ester 3-methyl ester (3.2 g) in dry THF (20 mL) was added via cannular to a mixture of lithium aluminium hydride (0.75 g) in THF (30 mL0 at 0° C. and under N$_2$ atmosphere. The resultant mixture was then warmed to R.T. and stirred for 2.5 h. The reaction was carefully quenched with aqueous ammonium chloride (5 mL) then filtered over Celite. An aqueous work-up followed by purification on silica gave 3-hydroxymethyl-4-methanesulfonyl-piperazine-1-carboxylic acid tert-butyl ester (1.13 g).

3-Formyl-4-methanesulfonyl-piperazine-1-carboxylic acid tert-butyl ester was prepared from 3-hydroxymethyl-4-methanesulfonyl-piperazine-1-carboxylic acid tert-butyl ester following a procedure in J. Med. Chem. 2005, 48(2), pp 4009-4024.

Reductive amination of 3-formyl-4-methanesulfonyl-piperazine-1-carboxylic acid tert-butyl ester (160 mg) with dimethylamine hydrochloride (67 mg) according to General Procedure C followed by an aqueous work-up and purification on silica gave 3-dimethylaminomethyl-4-methanesulfonyl-piperazine-1-carboxylic acid tert-butyl ester (160 mg). This was treated with 2M HCl to give desired (1-methanesulfonyl-piperazin-2-ylmethyl)-dimethyl-amine dihydrochloride (140 mg).

To a mixture of 6-bromomethyl-2-chloro-4-morpholin-4-yl-thieno[3,2-d]pyrimidine (140 mg) and (1-methanesulfonyl-piperazin-2-ylmethyl)-dimethyl-amine dihydrochloride (140 mg) in dry MeCN (6 mL) was added $K_2CO_3$ (190 mg). The mixture was stirred at 80° C. for 4 h. An aqueous work-up followed by purification on silica gave [4-(2-chloro-4-morpholin-4-yl-thieno[3,2-d]pyrimidin-6-ylmethyl)-1-methanesulfonyl-piperazin-2-ylmethyl]-dimethyl-amine (115 mg).

[4-(2-Chloro-4-morpholin-4-yl-thieno[3,2-d]pyrimidin-6-ylmethyl)-1-methanesulfonyl-piperazin-2-ylmethyl]dimethyl-amine was reacted with 4-(4,4,5,5-tetramethyl-[1,3,2]dioxaborolan-2-yl)-1H-indazole in General Procedure A. Purification on silica yielded the desired compound.

400 MHz; CDCl3

2.30(7H, m); 2.37(2H, m); 2.53(1H, m); 2.83-3.07(6H, m); 3.27(1H, m); 3.68(1H, d, J=12.6 Hz); 3.84(3.84(2H, m); 3.94(4H, t, J=4.7 Hz); 4.10(4H, t, J=4.7 Hz); 7.40(1H, s); 7.52(1H, t, J=7.7 Hz); 7.60(1H, d, J=8.3 Hz); 8.28(1H, d, J=7.4 Hz); 9.02(1H, s); 10.15(1H, br s).

MS: (ESI+) M+H (571)

70: 2-Chloro-6-(4-methyl-piperazin-1-ylmethyl)-4-morpholin-4-yl-thieno[3,2-d]pyrimidine was reacted with 3-amino-4-methylbenzeneboronic acid in general procedure A. Purification by flash chromatography on silica yielded 2-Methyl-5-[6-(4-methyl-piperazin-1-ylmethyl)-4-morpholin-4-yl-thieno[3,2-d]pyrimidin-2-yl]-phenylamine. To a solution of 2-Methyl-5-[6-(4-methyl-piperazin-1-ylmethyl)-4-morpholin-4-yl-thieno[3,2-d]pyrimidin-2-yl]-phenylamine (154 mg) in chloroform (10 ml) and acetic acid (2 ml) was added isoamyl nitrite (55 µL). The reaction mixture was stirred at room temperature for 3 days. The reaction mixture was diluted with chloroform and washed with a 50/50 mixture of saturated sodium bicarbonate solution and brine, dried ($MgSO_4$) and the solvents were removed in vacuo to give a crude residue. This was purified by flash chromatography to yield the desired product.

NMR: 400 MHz 1H NMR DMSO: 13.15 (bs, 1H); 8.57 (s, 1H); 8.20 (d, 1H); 8.10 (s, 1H) 7.81 (d, 1H); 7.40 (s, 1H); 3.99 (m, 4H); 3.82 (m, 4H+CH2); 2.35 (m, 8H), 2.16 (s, 3H)

MS: (ESI+): 450.2

62: To a solution of 4-hydroxymethyl-piperidine-1-carboxylic acid tert-butyl ester (2.0 g) in anhydrous tetrahyrofuran (50 ml) was added carbon tetrabromide (6.2 g) and triphenylphosphine (4.88 g). the reaction mixture was stirred at room temperature for 3 dayss. The reaction mixture was filtered through celite. The filtrate was taken up in ethyl actetate, washed with water then brine, dried (MgSO4) and the solvent removed in vacuo give a crude product. This was purified using flash chromatography which yielded Bromomethyl-piperidine-1-carboxylic acid tert-butyl ester (1.287 g).

To a solution of pyrazole (68 mgs) in anhydrous dimethylformamide was added sodium hydride (44 mgs). The reaction mixture was stirred at 50° C. for 25 minutes. 4-Bromomethyl-piperidine-1-carboxylic acid tert-butyl ester (280 mgs) in anhydrous dimethylformamide was added. The reaction mixture was stirred at 70° C. under argon for 2.5 hours. The reaction mixture was quenched with water (1 ml) and the solvents were removed in vacuo. The crude residue was partitioned between dichloromethane and water, dried ($MgSO_4$) and the solvents removed in vacuo to give a crude product. This was purified using flash chromatography to yield 4-Pyrazol-1-ylmethyl-piperidine-1-carboxylic acid tert-butyl ester (148 mg).

To a solution of 4-Pyrazol-1-ylmethyl-piperidine-1-carboxylic acid tert-butyl ester (215 mg) in anhydrous dichloromethane (5 ml) was added 2M hydrogen chloride in ether (4.1 ml). The reaction mixture was stirred at room temperature for 6 hours. The solvents were removed in vacuo to yield 4-Pyrazol-1-ylmethyl-piperidine hydrochloride salt.

To a solution of 4-Pyrazol-1-ylmethyl-piperidine hydrochloride salt in 1,2-dichloroethane (5 ml) was added 2-Chloro-4-morpholin-4-yl-thieno[3,2-d]pyrimidine-6-carbaldehyde (230 mg) and glacial acetic acid (50 µL). The reaction mixture was stirred at room temperature for 6 hours. Sodium triacetoxyborohydride (224 mg) and triethylamine (113 µL) were added. The reaction mixture was stirred at room temperature overnight. The reaction mixture was diluted with dichloromethane, washed with a 50/50 mixture of saturated sodium bicarbonate solution and brine, dried ($MgSO_4$) and the solvents removed in vacuo to give a crude product. This was purified by flash chromatography to yield 2-Chloro-4-morpholin-4-yl-6-(4-pyrazol-1-ylmethyl-piperidin-1-ylmethyl)-thieno[3,2-d]pyrimidine (154 mg).

2-Chloro-4-morpholin-4-yl-6-(4-pyrazol-1-ylmethyl-piperidin-1-ylmethyl)-thieno[3,2-d]pyrimidine was reacted with 4-(4,4,5,5-Tetramethyl-[1,3,2]dioxaborolan-2-yl)-1H-indazole in general procedure A. Purification by flash chromatography on silica yielded the desired product.

NMR: 400 MHz 1H NMR in DMSO: 13.15 (bs, 1H); 8.87 (s, 1H); 8.21 (d, 1H, J=6.7 HZ); 7.67 (d, 1H, J=6.2 Hz); 7.64 (s, 1H); 7.44 (m, 3H); 6.20 (t, 1H); 4.01 (m, 4H+CH2); 3.83 (m, 4H+CH2); 2.91 (m, 2H); 2.04 (m, 2H); 1.98 (m, 2H); 1.45 (m, 2H); 1.25 (m, 2H)

MS: (ESI+): 512.2

61: To a solution of 4-hydroxymethyl-piperidine-1-carboxylic acid tert-butyl ester (2.0 g) in anhydrous tetrahyrofuran (50 ml) was added carbon tetrabromide (6.2 g) and triphenylphosphine (4.88 g). the reaction mixture was stirred at room temperature for 3 days. The reaction mixture was filtered through celite. The filtrate was taken up in ethyl actetate, washed with water then brine, dried (MgSO4) and the solvent removed in vacuo give a crude product. This was purified using flash chromatography which yielded Bromomethyl-piperidine-1-carboxylic acid tert-butyl ester (1.287 g).

To a solution of 2-pyrrolidone (86 mg) in anhydrous dimethylormamide (5 ml) was added sodium hydride (45 mg). the reaction mixture was stirred under nitrogen at 50° C. for 35 minutes. 4-Bromomethyl-piperidine-1-carboxylic acid tert-butyl ester (86 mg) in anhydrous dimethylformamide (5 ml) was added. The reaction mixture was stirred at 70° C. overnight. The solvents were removed in vacuo and the crude residue was partitioned between dichloromethane and water, the combined organic extracts were washed with brine, dried (MgSO4) and the solvents removed in vacuo to give a crude product. This was purified using flash chromatography to yield 4-(2-Oxo-pyrrolidin-1-ylmethyl)-piperidine-1-carboxylic acid tert-butyl ester (99 mg).

To a solution of 4-(2-Oxo-pyrrolidin-1-ylmethyl)-piperidine-1-carboxylic acid tert-butyl ester in dichloromethane was added 2M hydrogen chloride in ether (1.78 ml). The reaction mixture was stirred at room temperature for 6 hours. The solvents were removed in vacuo to yield 1-Piperidin-4-ylmethyl-pyrrolidin-2-one hydrochloride salt.

To a solution of 1-Piperidin-4-ylmethyl-pyrrolidin-2-one hydrochloride salt in anhydrous 1,2-dichloroethane was added triethyamine (47 µL), the reaction mixture was stirred at room temperature for 2 hours. 2-Chloro-4-morpholin-4-yl-thieno[3,2-d]pyrimidine-6-carbaldehyde (99 mg) and glacial acetic acid were added, the reaction mixture was stirred at room temperature for 4 hours. Sodium triacetoxyborohydride (96 mg) was added. The reaction mixture was stirred at room temperature overnight. The reaction mixture was diluted with dichloromethane, washed with a 50/50 mixture of saturated sodium bicarbonate solution and brine, dried (MgSO4) and the solvents removed in vacuo to give a crude residue. This was purified using column chromatography to give 2-[1-(2-Chloro-4-morpholin-4-yl-thieno[3,2-d]pyrimidin-6-ylmethyl)-piperidin-4-ylmethyl]-cyclopentanone (73 mg).

2-[1-(2-Chloro-4-morpholin-4-yl-thieno[3,2-d]pyrimidin-6-ylmethyl)-piperidin-4-ylmethyl]-cyclopentanone was reacted with 4-(4,4,5,5-Tetramethyl-[1,3,2]dioxa borolan-2-yl)-1H-indazole in procedure A. Purification by flash chromatography on silica yielded the desired product.

NMR: 1H NMR 400 MHz, d6 DMSO: 13.15 (bs, 1H); 8.87 (s, 1H); 8.21 (d, 1H, J=7.4 Hz); 7.65 (d, 1H, J=8.3 Hz); 7.46 (t, 1H, J=8.3 Hz); 4.01 (m, 4H); 3.83 (m, 4H+CH2); 3.06 (m, 2H); 2.91 (m, 2H); 2.20 (t, 1H, J=7.8 Hz); 2.06 (t, 1H, J=11.2 Hz); 1.90 (m, 2H); 1.56 (m, 3H); 1.19 (m, 2H).

MS: (ESI+): 532.3

82: 2-chloro-6-(4-methanesulfonyl-piperidin-1-ylmethyl)-4-morpholin-4-yl-thieno[2,3-d]pyrimidine was reacted with 2-methoxy-5-pyrimidine-boronic acid in General Procedure A. Purification on silica yielded the desired compound.

NMR: (CDCl$_3$): 2.64-2.67 (m, 4H, 2×CH2), 2.80 (s, 3H, CH3), 3.27-3.30 (m, 4H, 2×CH2), 3.81 (s, 2H, CH2), 3.87-3.89 (m, 4H, 2×CH2), 3.95-3.97 (m, 4H, 2×CH2), 4.09 (s, 3H, CH3), 7.14 (s, H, ArH), 9.45 (s, 2H, 2×ArH).

MS: (ESI+): MH+=506.16

83: 2-chloro-6-(4-methanesulfonyl-piperidin-1-ylmethyl)-4-morpholin-4-yl-thieno[2,3-d]pyrimidine was reacted with 2-dimethylamino-pyrimidine-5-boronic acid in General Procedure A. Purification on silica yielded the desired compound.

NMR: (CDCl$_3$): 2.63-2.66 (m, 4H, 2×CH2), 2.79 (s, 3H, CH3), 3.25-3.28 (m, 10H, 2×CH2+2×CH3), 3.79 (s, 2H, CH2), 3.84-3.87 (m, 4H, 2×CH2), 3.91-3.94 (m, 4H, 2×CH2), 7.101 (s, H, ArH), 9.28 (s, 2H, 2×ArH).

MS: (ESI+): MH+=519.27

EXAMPLE 5

Further Compounds of the Invention

The following further compounds of the invention were prepared. The compound numbering corresponds to that used in Table 1B.

140: To 190 mg of 2-Chloro-6-(4-methanesulfonyl-piperazin-1-ylmethyl)-4-morpholin-4-yl-thieno[2,3-d]pyrimidine in 1 mL 1M KOAc and 2 mL acetonitrile was added 109.8 mg (1.02 eq) of 7-azaindole-5-boronic acid pinacol ester and 50.8 mg (0.1 eq) of Pd(PPh$_3$)$_4$ as per General Procedure A to give 170.7 mg of the desired product after RP-HPLC purification (75% yield). MS (Q1) 514.2 (M)+.

152: To 200 mg of 2-Chloro-6-(4-methanesulfonyl-piperazin-1-ylmethyl)-4-morpholin-4-yl-thieno[2,3-d]pyrimidine in 2 mL 1M Sodium carbonate in water and 2 mL acetonitrile was added 270 mg (1.5 eq) of 3-((2-(trimethylsilyl)ethoxy)methyl)-2-methyl-6-(4,4,5,5-tetramethyl-1,3,2-dioxaborolan-2-yl)-3H-imidazo[4,5-b]Pyridine and 54 mg (0.05 eq) of Pd (PPh$_3$)$_4$ as per General Procedure A. This insoluble intermediate was filtered off, washed with water, concentrated in vacuo and dissolved in 20 mL THF followed by the addition of 2.8 mL (6.0 eq) of 1.0 M Tetra-n-butylammonium fluoride in THF. After heating the reaction to 80° C. with a reflux condenser attached overnight, complete reaction was confirmed by LCMS. The reaction was diluted with water, extracted with EtOAc, concentrated in vacuo and gave 55.2 mg of the desired product after RP-HPLC purification (21% yield). MS (Q1) 529.2 (M)+.

132: To 96 mg (0.23 mM) of 2-chloro-6-(4-methyl-piperazin-1-yl methyl)-4-morpholin-4-yl-thieno[3,2-d]pyrimidine in 1 mL 1M KOAc and 1.5 mL acetonitrile was added 73.2 mg (1.3 eq) of 4-(4,4,5,5-Tetramethyl-[1,3,2]dioxaborolan-2-yl)-1H-indazole and 26.6 mg (0.1 mM) of Pd (PPh$_3$)$_4$ as per General Procedure A to Give 23.4 mg of the desired product after RP-HPLC purification (17% yield). MS (Q1) 492.4 (M)+.

131: 590 mg of crude HCl salt of 2-chloro-7-methyl-4-morpholino-6-((piperazin-1-yl)methyl)thieno[3,2-d]pyrimidine was treated with 430 mg of L-Lactic Acid via Procedure B. 60 mg of this crude intermediate was reacted with 4-(4,4,5,5-tertamethyl-1,3,2-dioxaborolan-2-yl)1H-indazole via Procedure A to give 32.5 mg of the desired product after reverse phase HPLC purification. MS (Q1) 522.3 (M)+.

134: 200 mg of 2-chloro-4-morpholinothieno[3,2-d]pyrimidine-6-carbaldehyde was used according to procedure C with (S)-4-N-trityl-2-methyl-piperazine. The crude material was then dissolved in 10 mL of methanol and reacted with 0.5 mL of concentrated HCl for several hours before basifying with NaOH and extracting into EtOAc. After evaporation the crude reaction mixture containing 200 mg of 2-chloro-6-(((S)-2-methylpiperazin-1-yl)methyl-4-morpholinothieno[3,2-d]pyrimidine was reacted with lactic acid via Procedure B. 120 mg of (S)-1-((S)-4-((2-chloro-4-morpholinothieno[3,2-d]pyrimidin-6-yl) methyl)-3-methylpiperazin-1-yl)-2-hydroxypropan-1-one was reacted with 4-(4,4,5,5-tertamethyl-1,3,2-dioxaborolan-2-yl)1H-indazole via Procedure A to give 47.5 mg of the desired product after reverse phase HPLC purification. MS (Q1) 522.3 (M)+.

148: 250 mg of tert-butyl 4-((2-chloro-7-methyl-4-morpholinothieno[3,2-d]pyrimidin-6-yl)methyl)piperazine-1-carboxylate was reacted with 5-(4,4,5,5-tetramethyl-1,3,2-dioxaborolan-2-yl)-1H-pyrrolo[2,3-b]pyridine via Procedure A. This crude intermediate was subjected to Procedure D.

The crude HCl salt of 7-methyl-4-morpholino-6-((piperazin-1-yl)methyl)-2-(1H-pyrrolo[2,3-b]pyridin-5-yl)thieno[3,2-d]pyrimidine was reacted with L-Lactic acid via Procedure B to give 86.7 mg of the desired product after reverse phase HPLC purification. MS (Q1) 522.2 (M)+.

150: 100 mg of tert-butyl 4-((2-chloro-7-methyl-4-morpholinothieno[3,2-d]pyrimidin-6-yl)methyl)piperazine-1-carboxylate was reacted with quinolin-3-yl-3-boronic ester via Procedure A. This crude intermediate was subjected to Procedure D.

The crude HCl salt of 3-(7-methyl-4-morpholino-6-((piperazin-1-yl)methyl)thieno[3,2-d]pyrimidin-2-yl)quinoline was reacted with L-Lactic acid via Procedure B to give 21.6 mg of the desired product after reverse phase HPLC purification. MS (Q1) 533.2 (M)+.

149: 250 mg of tert-butyl 4-((2-chloro-4-morpholinothieno[2,3-d]pyrimidin-6-yl)methyl)piperazine-1-carboxylate was reacted with 5-(4,4,5,5-tetramethyl-1,3,2-dioxaborolan-2-yl)-1H-pyrrolo[2,3-b]pyridine via Procedure A. This crude intermediate was subjected to Procedure D.

The crude HCl salt of 4-morpholino-6-((piperazin-1-yl)methyl)-2-(1H-pyrrolo[2,3-b]pyridin-5-yl)thieno[2,3-d]pyrimidine was reacted with L-Lactic acid via Procedure B to give 58.5 mg of the desired product after reverse phase HPLC purification. MS (Q1) 508.2 (M)+.

151: 100 mg of tert-butyl 4-((2-chloro-4-morpholinothieno[2,3-d]pyrimidin-6-yl)methyl)piperazine-1-carboxylate was reacted with quinolin-3-yl-3-boronic ester via Procedure A. This crude intermediate was subjected to Procedure D.

The crude HCl salt of 3-(4-morpholino-6-((piperazin-1-yl)methyl)thieno[2,3-d]pyrimidin-2-yl)quinoline reacted with L-Lactic acid via Procedure B to give 68 mg of the desired product after reverse phase HPLC purification. MS (Q1) 519.2 (M)+.

153: 100 mg of tert-butyl 4-((2-chloro-4-morpholinothieno[2,3-d]pyrimidin-6-yl)methyl)piperazine-1-carboxylate was reacted with 3-((2(trimethylsilyl)ethoxy)methyl)-2-methyl-6-(4,4,5,5-tetramethyl-1,3,2-dioxaborolan-2-yl)-3H-imidazo[4,5-b]pyridine via Procedure A. Crude intermediate tert-butyl 4-((2-(1-((2-(trimethylsilyl)ethoxy)methyl)-2-methyl-1H-benzo[d]imidazol-6-yl)-4-morpholinothieno[2,3-d]pyrimidin-6-yl)methyl) piperazine-1-carboxylate was then refluxed overnight with 2 equivalents of tetrabutylammoniumfloride in THF to remove the SEM protecting group. The crude material was then extracted with water and ethyl acetate. The organic layer was concentrated to dryness and then subjected to Procedure D.

The crude HCl salt of 2-(2-methyl-1H-benzo[d]imidazol-5-yl)-4-morpholino-6-((piperazin-1-yl)methyl)thieno[2,3-d]pyrimidine was reacted with L-Lactic Acid via Procedure B to give 14.1 mg of the desired product after reverse phase HPLC purification. MS (Q1) 523.2 (M)+.

142: 2-chloro-6-((4-(methylsulfonyl)piperazin-1-yl)methyl)-4-morpholinofuro[3,2-d]pyrimidine (1 eq), azaindole boronic ester (1.7 eq) and bis(triphenylphosphine)palladium(II) dichloride (0.1 eq) in 1M Na$_2$CO$_3$ aqueous solution (3 eq) and an equal volume of acetonitrile (3 eq) was heated to 130° C. in a sealed microwave reactor for 10 min. Upon completion, the reaction mixture was concentrated and crude mixture was purified by reverse phase HPLC to yield 12 mg of 5-(4-morpholinofuro[2,3-d]pyrimidin-2-yl)pyrimidin-2-amine. MS (Q1) 498 (M)$^+$.

141: 2-chloro-6-((4-(methylsulfonyl)piperazin-1-yl)methyl)-4-morpholinofuro[2,3-d]pyrimidine (1 eq), 4-(4,4,5,5-tetramethyl-1,3,2-dioxaborolan-2-yl)-1H-indazole (1.7 eq) and bis(triphenylphosphine)palladium(II) dichloride (0.1 eq) in 1M KOAc aqueous solution (3 eq) and an equal volume of acetonitrile (3 eq) was heated to 140° C. in a sealed microwave reactor for 10 min. Upon completion, the reaction mixture was concentrated and crude mixture was purified by reverse phase HPLC to yield 16 mg of 2-(1H-indazol-4-yl)-6-((4-methylsulfonylpiperazin-1-yl)methyl)-4-morpholinofuro[2,3-d]pyrimidine. MS (Q1) 498 (M)$^+$.

128: 2-chloro-6-((4-(methylsulfonyl)piperazin-1-yl)methyl)-4-morpholinofuro[3,2-d]pyrimidine (1 eq), indole boronic ester (1.7 eq) and bis(triphenylphosphine)palladium(II) dichloride (0.1 eq) in 1M Na$_2$CO$_3$ aqueous solution (3 eq) and an equal volume of acetonitrile (3 eq) was heated to 140° C. in a sealed microwave reactor for 10 min. Upon completion, the reaction mixture was concentrated and crude mixture was purified by reverse phase HPLC to yield 12 mg of 5-(4-morpholinofuro[2,3-d]pyrimidin-2-yl)pyrimidin-2-amine. MS (Q1) 497 (M)$^+$.

133: Prepared from the appropriate intermediate according to General Procedure A using 5-(4,4,5,5-tetramethyl-1,3,2-dioxaborolan-2-yl)-1H-pyrrolo[2,3-b]pyridine. The compound is obtained after reverse phase HPLC purification (49 mg). MS (Q1) 514 (M)+

130: To 2-chloro-4-morpholinothieno[3,2-d]pyrimidine-6-carbaldehyde (100 mg, 0.35 mmol) in 1,2-dichloroethane (2 mL) was added AcOH (20 µL, 0.35 mmol) and 4-Amino-1-BOC-piperidine (210 mg, 1.05 mmol). The resulting solution stirred overnight at room temperature then Na(OAc)$_3$BH (90 mg, 0.42 mmol) was added and the reaction stirred 4 h at room temperature. The reaction was quenched with water and extracted with DCM then EtOAc. The combined organics were dried over Na$_2$SO$_4$, filtered, and concentrated in vacuo. The crude product was dissolved in MeOH (5 mL) and AcOH (80 µL), then formaldehyde (37%, 31 µL) and NaCNBH$_3$ (26 mg, 0.42 mmol) were added. The reaction mixture was allowed to stir overnight then additional formaldehyde (37%, 56 µL) was added to drive the reaction to completion.

After 1 h at room temperature the reaction was complete and quenched with saturated aqueous K$_2$CO$_3$ and diluted with EtOAc. The aqueous layer was extracted with EtOAc and the combined organics were dried over Na$_2$SO$_4$, filtered, and concentrated in vacuo. The crude product was dissolved in CH$_2$Cl$_2$ (10 mL), MeOH (10 mL), and Et$_2$O (5 mL) and 4 M HCl in dioxane (10 mL) was added. The resulting mixture stirred at room temperature for 3 days then was concentrated in vacuo. The residue was dissolved in CH$_2$Cl$_2$ (20 mL) and Et$_3$N (5 mL) was added. Excess water was added to the solution. The organic phase was separated and the aqueous layer was extracted with EtOAc. The combined organics were dried over Na$_2$SO$_4$, filtered, and concentrated in vacuo. The crude material was carried onto the next step without purification. Compound 130 was produced by Suzuki coupling with 4(4,4,5,5-tetramethyl-1,3,2-dioxaborolan-2-yl)-1H-indazole according to General Procedure A (6 mg). MS (Q1) 464 (M)+

EXAMPLE 6

Additional Compounds of the Invention

The following additional compounds of the invention were prepared. The compound numbering corresponds to that used in Table 1B above.

129: To N-BOC-piperazine (1.3 g) in dry DCM (10 ml) was added triethylamine (1.2 mL) and cyclopropanesulphonyl chloride (1.04 g) and the reaction mixture was stirred at room temperature for 16 hours. The reaction mixture was then diluted with DCM, washed with water, dried (MgSO$_4$) and reduced in vacuo. The residue was dissolved in methanol (10 mL) and 4M HCL in dioxane was added (20 mL). After stirring overnight the solvent was reduced in vacuo to yield 1-cyclopropanesulfonyl-piperazine hydrochloride.

2-chloro-4-morpholin-4-yl-thieno[3,2-d]pyrimidine-6-carbaldehyde was treated with 1-cyclopropanesulfonyl-piperazine hydrochloride using General Procedure C (reductive amination) to yield 2-chloro-6-(4-cyclopropanesulfonyl-piperazin-1-ylmethyl)-4-morpholin-4-yl-thieno[3,2-d]pyrimidine.

2-chloro-6-(4-cyclopropanesulfonyl-piperazin-1-ylmethyl)-4-morpholin-4-yl-thieno[3,2-d]pyrimidine was reacted with 4-(4,4,5,5-tetramethyl-[1,3,2]dioxaborolan-2-yl)-1H-indazole in general procedure A. Purification by column chromatography yielded the title compound.

(400 Mhz, CDCl3): 1.00-1.02 (2H, m, CH2), 1.19-1.23 (2H, m, CH2), 2.29 (1H, m, CH), 2.69 (4H, m, CH2), 3.40 (4H, m, CH2), 3.91-3.94 (6H, m, CH2), 4.08-4.11 (4H, m,

CH2), 7.41 (1H, s, ar), 7.49-7.53 (1H, m, ar), 7.60 (1H, d (J8.30), ar), 8.29 (1H, d J (7.05), ar), 9.02 (1H, s, ar), 10.10 (1H, b, NH)

(M+H)+ 540.34

137: 2-Chloro-6-(4-methanesulfonyl-piperazin-1-ylmethyl)-4-morpholin-4-yl-thieno[3,2-d]pyrimidine was reacted with 5-(4,4,5,5-tetramethyl-[1.3.2]dioxaborolan-2-yl)-1H-indazole (commercially available) in general procedure A. Purification by column chromatography yielded the title compound.

NMR: CDCl$_3$: 2.58-2.62 (4 H, m, CH$_2$), 2.74 (1 H, s, Me), 3.22-3.25 (4 H, m, CH$_2$), 3.82 (2 H, s, CH$_2$), 3.82-3.86 (4 H, m, CH$_2$), 4.00-4.02 (4 H, m, CH$_2$), 7.28 (1 H, s, Ar), 7.48 (1 H, d, J 8.2, Ar), 8.09 (1 H, s, Ar), 8.48 (1 H, d, J 8.2, Ar), 8.82 (1 H, d, J 7.5, Ar) and 10.01 (1 H, s, NH).

MS: (ESI+): MH+ 514.17

143: (2-chloro-4-morpholin-4-yl-thieno[3,2-d]pyrimidin-6-ylmethyl)-methyl-amine was made by treating 2-chloro-4-morpholin-4-yl-thieno[3,2-d]pyrimidine-6-carbaldehyde (intermediate 10) and 40% methylamine in water according to General Procedure C (reductive amination).

(2-Chloro-4-morpholin-4-yl-thieno[3,2-d]pyrimidin-6-ylmethyl)-(1-isopropyl-piperidin-4-yl)-methyl-amine was made by treating (2-chloro-4-morpholin-4-yl-thieno[3,2-d]pyrimidin-6-ylmethyl)-methyl-amine and 1-isopropyl-4-piperidone according to the General Procedure C (reductive amination).

A suspension of (2-chloro-4-morpholin-4-ylthieno[3,2-d]pyrimidin-6-ylmethyl)-(1-isopropyl-piperidin-4-yl)-methyl-amine (63 mg, 0.149 mmol), 4-(4,4,5,5-tetramethyl-[1,3,2]dioxaborolan-2-yl)-1H-indazole (44 mg, 0.179 mmol), 1M Na$_2$CO$_3$ (0.5 ml, 0.5 mmol) and Pd(PPh$_3$)$_2$Cl$_2$ (11 mg, 0.015 mmol) in acetonitrile (3 ml) was heated in a microwave at 140° C. for 25 mins. The reaction was then acidified with 2N HCl (aq) extracted with ethyl acetate, the water layer separated and basified with K$_2$CO$_3$ (sat. aq) resulting in an impure precipitate. This was purified on alumina using 5% methanol in dichloromethane as the eluent, (11 mg, 15%).

NMR (CDCl3, 400 MHz), 0.96 (6H, d, J=6.4), 1.54-1.60 (2H, m), 1.77-1.80 (2H, m), 2.04-2.09 (2H, m), 2.30 (3H, s), 2.40-2.46 (1H, m), 2.62-2.68 (1H, m), 2.88-2.92 (2H, m), 3.84 (4H, t, J=4.4), 3.87 (2H, s), 4.02 (4H, t, J=4.8), 7.19 (1H, s), 7.43 (1H, t, J=7.6), 7.50 (1H, d, J=8.4), 8.20 (1H, dd, J=7.2, 0.8), 8.95 (1H, d, J=0.8), 10.2 (1H, br s).

MS: (ESI+): MH+=506.

145: Intermediate F (1.00 g) was reacted with tert-butyl-1-piperazine carboxylate (0.85 g) in General Procedure Z. Aqueous work-up and purification on silica gave 4-(2-chloro-4-morpholin-4-yl-thieno[2,3-d]pyrimidine-6-ylmethyl0-piperazine-1-carboxylic acid tert-butyl ester (1.61 g).

4-(2-Chloro-4-morpholin-4-yl-thieno[2,3-d]pyrimidine-6-ylmethyl0-piperazine-1-carboxylic acid tert-butyl ester (1.61 g) was treated with an excess of hydrogen chloride in diethyl ether at room temperature overnight. Removal of volatiles and basification with aqueous sodium hydrogen chloride afforded 2-chloro-4-morpholin-4-yl-6-piperazin-1-ylmethyl-thieno[2,3-d]pyrimidine (0.90 g).

To 2-chloro-4-morpholin-4-yl-6-piperazin-1-ylmethyl-thieno[2,3-d]pyrimidine (187 mg) in anhydrous DCM (5 ml) and triethylamine (111 ul) was added cyclopropanesulfonyl chloride (65 ul) at 0° C. The reaction mixture was allowed to warm up to room temperature over 4 hours. Aqueous work-up and purification on silica gave 2-chloro-4-morpholin-4-yl-6-[4-(cyclopropane-2-sulfonyl)-piperazin-1-ylmethyl]-thieno[2,3-d]pyrimidine (159 mg). 2-Chloro-4-morpholin-4-yl-6-[4-(cyclopropane-2-sulfonyl)-piperazin-1-ylmethyl]thieno[2,3-d]pyrimidine was reacted with 7-azaindole-5-boronic acid pinacol ester in General Procedure A. Purification on silica yielded the desired compound.

NMR (CDCl3): 1.00-1.05 (2H, m), 1.18-1.22 (2H, m), 2.28-2.32 (1H, m), 2.65-2.69 (4H, m), 3.37-3.41 (4H, m), 3.83 (2H, s), 3.92-3.96 (4H, m), 4.00-4.04 (4H, m), 6.62-6.64 (1H, m), 7.18 (1H, s), 7.37-7.39 (1H, m), 9.02 (1H, d), 9.37 (1H, br), 9.46 (1H, d)

MS (ESI+): MH+ 540.21 (15%)

146: To 2-chloro-4-morpholin-4-yl-6-piperazin-1-ylmethyl-thieno[2,3-d]pyrimidine (150 mg) in anhydrous DCM (4 ml) and triethylamine (90 ul) was added 2-thiophenesulfonyl chloride (101 ul) at 0° C. The reaction mixture was allowed to warm up to room temperature over 4 hours. Aqueous work-up and purification on silica gave 2-chloro-4-morpholin-4-yl-6-[4-(thiophene-2-sulfonyl)-piperazin-1-ylmethyl]-thieno[2,3-d]pyrimidine (208 mg). 2-Chloro-4-morpholin-4-yl-6-[4-(thiophene-2-sulfonyl)-piperazin-1-ylmethyl]-thieno[2,3-d]pyrimidine was reacted with 7-azaindole-5-boronic acid pinacol ester in General Procedure A. Purification on silica yielded the desired compound.

NMR (CDCl3): 2.67-2.70 (4H, m), 3.15-3.18 (4H, m), 3.79 (2H, s), 3.91-3.95 (4H, m), 3.99-4.03 (4H, m), 6.61-6.63 (1H, m), 7.15 (1H, s), 7.18-7.20 (1H, m), 7.33-7.36 (1H, m), 7.54-7.57 (1H, m), 7.66-7.68 (1H, m), 8.91 (1H, br), 8.99 (1H, d), 9.44 (1H, d)

MS (ESI+): MH+582 (10%)

138: 4-[6-(4-Methanesulfonyl-piperazin-1-ylmethyl)-4-morpholin-4-yl-thieno[3,2-d]pyrimidin-2-yl]-benzene-1,2-diamine (150 mg, described above)) was heated in dry THF (4 ml) with CDI (195 mg) at 40° C. for 5 hours and then stirred at room temperature overnight. Added water, precipitate was filtered, washed with water and dried. The residue was purified by flash chromatography to give the title compound (43 mg).

NMR (DMSO): 2.49-2.52 (4H, m), 2.90 (3H, s), 3.15-3.18 (4H, m), 3.80-3.83 (4H, m), 3.92 (2H, s), 3.95-3.97 (4H, m), 7.00 (1H, d, J=8.2), 7.39 (1H, s), 7.99 (1H, s), 8.12 (1H, d, J=8.2), 10.65 (1H, br), 10.80 (1H, br)

MS (ESI+): MH+ 530.36

139: A solution of (3-acetamido-2-nitrophenyl)boronic acid (300 mg) in 2M aqueous hydrochloric acid solution (4 mL) was heated at 80° C. for 20 min. After cooling to room temperature, the solvent was reduced in vacuo to give a brown solid which was redissolved in 1,4-dioxane (5 mL). Pinacol (316 mg) was added and the mixture heated at 100° C. for 30 min. After cooling to room temperature the solvent was reduced in vacuo to give a beige solid which was dissolved in acetic acid (5 mL). Palladium on carbon (100 mg) was added and the mixture stirred under an atmosphere of hydrogen at 40° C. for 1 h. The reaction mixture was then filtered through Celite and the filtrate reduced in vacuo. Purification by column chromatography gave 2-amino-3-(4,4,5,5-tetramethyl-1,3,2-dioxaborolan-2-yl)aniline.

2-Chloro-6-(4-methanesulfonyl-piperazin-1-ylmethyl)-4-morpholin-4-yl-thieno[3,2-d]pyrimidine was reacted with 2-amino-3-(4,4,5,5-tetramethyl-1,3,2-dioxaborolan-2-yl) aniline in general procedure A. Purification by column chromatography yielded 3-[6-(4-methanesulfonyl-piperazin-1-ylmethyl)-4-morpholin-4-yl-thieno[3,2-d]pyrimidin-2-yl]-benzene-1,2-diamine which was heated in formic acid at reflux for 4 h. After cooling to room temperature, the solution was poured into saturated aqueous sodiumhydrogen carbonate solution (20 mL) and extracted into dichloromethane (3×20 mL). The combined organics were washed with aqueous brine solution (2×20 mL), dried (MgSO$_4$), reduced in vacuo and purified by column chromatography to give the title compound.

NMR: CDCl$_3$: 2.62-2.65 (4 H, m, CH$_2$), 2.74 (3 H, s, Me), 3.24-3.27 (4 H, m, CH$_2$), 3.84 (2 H, s, CH$_2$), 3.85-3.87 (4 H, m, CH$_2$), 4.01-4.05 (4 H, m, CH$_2$), 7.30-7.32 (2 H, m, Ar), 7.86 (1 H, d, J 7.9, Ar), 8.10 (1 H, s, Ar) and 8.32 (1 H, d, J 7.9, Ar).

MS: (ESI+): MH+ 514.22

144: A solution of 2,3-diamino-5-bromopyridine (1.34 g) in formic acid (7 mL) was heated at reflux for 3 h. After cooling to room temperature, the solvent was reduced in vacuo to give an off-white solid which was recrystallised from methanol-water to give 6-bromo-3H-imidazo[4,5-b]pyridine as a pale orange solid.

To a solution of 6-bromo-3H-imidazo[4,5-b]pyridine (1.0 g) in THF (20 mL) at 0° C. was added sodium hydride (187 mg) and the reaction stirred at 0° C. for 1 h. Then, 2-(trimethylsilyl)ethoxymethyl chloride (0.94 mL) was added and the reaction stirred at room temperature for 16 h. The reaction was quenched with water (20 mL) and extracted into ethyl acetate (2×20 mL). The combined organics were washed with aqueous brine solution (2×20 mL), dried (MgSO$_4$), reduced in vacuo and purified by column chromatography to give 6-bromo-3-(2-trimethylsilanyl-ethoxymethyl)-3H-imidazo[4,5-b]pyridine.

To a solution of 6-bromo-3-(2-trimethylsilanyl-ethoxymethyl)-3H-imidazo[4,5-b]pyridine (350 mg) in 1,4-dioxane (10 mL) was added bis(tributyltin) (1.08 mL), tetrakis(triphenylphosphine)palladium (0) (62 mg) and lithium chloride (136 mg) and the reaction heated at reflux for 16 h. After cooling to room temperature, the reaction mixture was filtered through Celite, washing with ethyl acetate. The filtrate was washed with water (2×30 mL), aqueous brine solution (2×20 mL), dried (MgSO$_4$), reduced in vacuo and purified by column chromatography to give 6-tributylstannanyl-3-(2-trimethylsilanyl-ethoxymethyl)-3H-imidazo[4,5-b]pyridine as a colourless oil.

To a solution of 2-chloro-6-(4-methanesulfonyl-piperazin-1-ylmethyl)-4-morpholin-4-yl-thieno[3,2-d]pyrimidine (450 mg) in DMF (6 mL) was added sodium thiomethoxide (183 mg) and the reaction heated at 100° C. for 16 h. After cooling to room temperature the reaction mixture was poured into ice water and the resulting precipitate filtered and air dried to give 6-(4-methanesulfonyl-piperazin-1-ylmethyl)-2-methylsulfanyl-4-morpholin-4-yl-thieno[3,2-d]pyrimidine as a white solid.

To a solution of 6-(4-methanesulfonyl-piperazin-1-ylmethyl)-2-methylsulfanyl-4-morpholin-4-yl-thieno[3,2-d]pyrimidine (90 mg) in 1,2-dimethoxyethane (10 mL) was added 6-tributylstannanyl-3-(2-trimethylsilanyl-ethoxymethyl)-3H-imidazo[4,5-]pyridine (219 mg) and copper(I) bromide-dimethylsulfide (84 mg) and the reaction stirred at room temperature for 10 min. Then, tetrakis(triphenylphosphine)palladium (0) (12 mg) was added and the reaction heated at reflux for 16 h. After cooling to room temperature, the reaction mixture was diluted with ethyl acetate (20 mL) and washed with water (2×30 mL), aqueous brine solution (2×20 mL), dried (MgSO$_4$), reduced in vacuo and purified by column chromatography to give 6-(4-methanesulfonyl-piperazin-1-ylmethyl)-4-morpholin-4-yl-2-[3-(2-trimethylsilanyl-ethoxymethyl)-3H-imidazo[4,5-b]pyridin-6-yl]-thieno[3,2-d]pyrimidine as a white solid.

To a solution of 6-(4-methanesulfonyl-piperazin-1-ylmethyl)-4-morpholin-4-yl-2-[3-(2-trimethylsilanyl-ethoxymethyl)-3H-imidazo[4,5-b]pyridin-6-yl]-thieno[3,2-d]pyrimidine (70 mg) in THF (10 mL) was added tetrabutylammonium fluoride (0.16 mL of a 1 M solution in THF) and the reaction heated at reflux for 1 h. After cooling to room temperature, the reaction was diluted with dichloromethane (20 mL) and washed with water (2×30 mL), aqueous brine solution (2×20 mL), dried (MgSO$_4$), reduced in vacuo and purified by column chromatography to give the title compound.

NMR: CDCl$_3$: 2.61-2.64 (4 H, m, CH$_2$), 2.76 (3 H, s, Me), 3.22-3.25 (4 H, m, CH$_2$), 3.80 (2 H, s, CH$_2$), 3.81-3.84 (4 H, m, CH$_2$), 4.02-4.05 (4 H, m, CH$_2$), 7.31 (1 H, s, Ar), 8.21 (1 H, s, Ar), 9.09 (1 H, s, Ar) and 9.50 (1 H, s, Ar).

MS: (ESI+): MH+ 515.19

147: To a solution 2-chloro-6-(4-methanesulfonyl-piperazin-1-ylmethyl)-4-morpholin-4-yl-thieno[2,3-d]pyrimidine (450 mg) in DMF (6 mL) was added sodium thiomethoxide (183 mg) and the reaction heated at 100° C. for 16 h. After cooling to room temperature the reaction mixture was poured into ice water and the resulting precipitate filtered and air dried to give 6-(4-methanesulfonyl-piperazin-1-ylmethyl)-2-methylsulfanyl-4-morpholin-4-yl-thieno[2,3-d]pyrimidine as a white solid.

To a solution of 6-(4-methanesulfonyl-piperazin-1-ylmethyl)-2-methylsulfanyl-4-morpholin-4-yl-thieno[2,3-d]pyrimidine (90 mg) in 1,2-dimethoxyethane (10 mL) was added 6-tributylstannanyl-3-(2-trimethylsilanyl-ethoxymethyl)-3H-imidazo[4,5-]pyridine (219 mg) and copper(I) bromide-dimethylsulfide (84 mg) and the reaction stirred at room temperature for 10 min. Then, tetrakis(triphenylphosphine)palladium (0) (12 mg) was added and the reaction heated at reflux for 16 h. After cooling to room temperature, the reaction mixture was diluted with ethyl acetate (20 mL) and washed with water (2×30 mL), aqueous brine solution (2×20 mL), dried (MgSO$_4$), reduced in vacuo and purified by column chromatography to give 6-(4-methanesulfonyl-piperazin-1-ylmethyl)-4-morpholin-4-yl-2-[3-(2-trimethylsilanyl-ethoxymethyl)-3H-imidazo[4,5-b]pyridin-6-yl]-thieno[2,3-d]pyrimidine as a white solid.

To a solution of 6-(4-methanesulfonyl-piperazin-1-ylmethyl)-4-morpholin-4-yl-2-[3-(2-trimethylsilanyl-ethoxymethyl)-3H-imidazo[4,5-b]pyridin-6-yl]-thieno[2,3-d]pyrimidine (70 mg) in THF (10 mL) was added tetrabutylammonium fluoride (0.16 mL of a 1 M solution in THF) and the reaction heated at reflux for 1 h. After cooling to room temperature, the reaction was diluted with dichloromethane (20 mL) and washed with water (2×30 mL), aqueous brine solution (2×20 mL), dried (MgSO$_4$), reduced in vacuo and purified by column chromatography to give the title compound.

NMR: CDCl$_3$: 2.58-2.61 (4 H, m, CH$_2$), 2.72 (3 H, s, Me), 3.21-3.23 (4 H, m, CH$_2$), 3.76 (2 H, s, CH$_2$), 3.80-3.82 (4 H, m, CH$_2$), 3.92-3.94 (4 H, m, CH$_2$), 7.10 (1 H, s, Ar), 8.15 (1 H, s, Ar), 9.09 (1 H, s, Ar) and 9.49 (1 H, s, Ar).

MS: (ESI+): MH+ 515.14

135: Intermediate G (500 mg) was reacted with 2-nitro-4-(4,4,5,5-tetramethyl-1,3,2-dioxaborolan--yl)aniline (613 mg) in a General Procedure A. Aqueous work-up and purification by flash chromatography gave 4-[6-(4-methanesulfonyl-piperazin-1-ylmethyl)-4-morpholin-4-yl-thieno[3,2-d]pyrimidin-2-yl]-2-nitro-phenylamine (633 mg).

4-[6-(4-Methanesulfonyl-piperazin-1-ylmethyl)-4-morpholin-4-yl-thieno[3,2-d]pyrimidin-2-yl]-2-nitro-phenylamine (200 mg) was stirred under hydrogen balloon with palladium on carbon (10%, 70 mg) in a mixture of MeOH and DCM (1:1, 10 ml) at room temperature overnight. The reaction mixture was then filtered through celite, volatiles removed in vacuo, and the residue purified by flash chromatography to give 4-[6-(4-methanesulfonyl-piperazin-1-ylmethyl)-4-morpholin-4-yl-thieno[3,2-d]pyrimidin-2-yl]-benzene-1,2-diamine (99 mg).

4-[6-(4-Methanesulfonyl-piperazin-1-ylmethyl)-4-morpholin-4-yl-thieno[3,2-d]pyrimidin-2-yl]-benzene-1,2-diamine (95 mg) was refluxed in formic acid (1 mL) for 1 hour. The reaction mixture was basified with aqueous sodium hydrogen carbonate and extracted into DCM. Flash chromatography and recrystallisation from hot DCM/hexane gave the title compound (32 mg).

NMR (CDCl3): 2.67-2.71 (4H, m), 2.81 (3H, s), 3.29-3.33 (4H, m), 3.89 (2H, s), 3.89-3.93 (4H, m), 4.08-4.12 (4H, m), 7.35 (1H, s), 7.70-7.80 (1H, br), 8.10 (1H, s), 8.48 (1H, d, J=8.6), 8.80 (1H, br)

MS (ESI+): MH+ 514.20 (100%)

136: 2-Nitro-4-(4,4,5,5-tetramethyl-1,3,2-dioxaborolan-2-yl)aniline (1.00 g) was stirred under hydrogen balloon with palladium on carbon (10%, 150 mg) in a mixture of MeOH and DCM (1:1, 10 ml) at room temperature overnight. The reaction mixture was then filtered through celite, volatiles removed in vacuo, and the residue purified by flash chromatography to give 4-(4,4,5,5-tetramethyl-1,3,2-dioxaborolan-2-yl)benzene-1,2-diamine (890 mg).

Intermediate G (750 mg) was reacted with 4-(4,4,5,5-tetramethyl-1,3,2-dioxaborolan-2-yl)benzene-1,2-diamine (815 mg) in a General Procedure A. Purification by flash chromatography afforded 4-[6-(4-methanesulfonyl-piperazin-1-ylmethyl)-4-morpholin-4-yl-thieno[3,2-d]pyrimidin-2-yl]-benzene-1,2-diamine (535 mg).

4-[6-(4-Methanesulfonyl-piperazin-1-ylmethyl)-4-morpholin-4-yl-thieno[3,2-d]pyrimidin-2-yl]-benzene-1,2-diamine (102 mg) was refluxed in acetic acid (1 mL) for 1 hour. The reaction mixture was basified with aqueous sodium hydrogen carbonate and extracted into DCM. Flash chromatography and diethyl ether trituration gave the title compound (47 mg).

NMR (CDCl3/MeOD): 2.56 (3H, s), 2.63-2.66 (4H, m), 2.78 (3H, s), 3.24-3.27 (4H, m), 3.85 (2H, s), 3.85-3.87 (4H, m), 4.02-4.05 (4H, m), 7.29 (1H, s), 7.60 (1H, br), 8.22 (1H, d, J=1.5), 8.30 (1H, br)

MS (ESI+): MH+ 528.33

154: 2-Chloro-6-(4-methanesulfonyl-piperazin-1-ylmethyl)-4-morpholin-4-yl-thieno[2,3-d]pyrimidine was reacted with 2-aminopyrimidine-5-boronic acid pinacol ester in general procedure A. Purification by column chromatography yielded 5-[6-(4-methanesulfonyl-piperazin-1-ylmethyl)-4-morpholin-4-yl-thieno[2,3-d]pyrimidin-2-yl]-pyrimidin-2-ylamine.

To a solution of 5-[6-(4-methanesulfonyl-piperazin-1-ylmethyl)-4-morpholin-4-yl-thieno[2,3-d]pyrimidin-2-yl]pyrimidin-2-ylamine (70 mg) in chloroacetaldehyde (2 mL) was added sodium hydrogen carbonate (300 mg) and the mixture was stirred at room temperature for 72 h. The mixture was then diluted with dichloromethane (10 mL) and washed with aqueous brine solution (2×10 mL), dried (MgSO4), reduced in vacuo and purified by column chromatography to give the title compound.

NMR: CDCl3: 2.60-2.63 (4 H, m), 2.54 (3 H, s), 3.21-3.24 (4 H, m), 3.76 (2 H, s), 3.83-3.85 (4 H, m), 3.91-3.94 (4 H, m), 7.53 (1 H, s, Ar), 7.78 (1 H, s, Ar), 9.36 (1 H, d, J 2.2, Ar) and 9.50 (1 H, d, J 2.2, Ar).

MS: (ESI+): MH+ 515.19

155: To 1-BOC-homopiperizine (0.8 ml) was added methane sulphonyl chloride (0.34 ml) and triethylamine (0.68 ml). The reaction mixture was stirred at room temperature for 4 hours. The reaction mixture was then partitioned between dichloromethane and water. The combined organic extracts were then washed with brine and dried (MgSO4). The solvent was removed in vacuo to yield 1.23 g of crude 4-methanesulfonyl-[1,4]diazepane-1-carboxylic acid tert-butyl ester.

Crude 4-methanesulfonyl-[1,40diazepane-1-carboxylic acid tert-butyl ester (1.23 g) was stirred in anhydrous methanol (10 ml). 2M hydrogen chloride in ether (22 ml) was added. The reaction mixture was stirred at room temperature. After 5 minutes a precipitate formed, addition of anhydrous methanol (5 ml) caused this to dissolve. The reaction mixture was stirred overnight at room temperature. The solvents were removed in vacuo to yield 1.06 g of 1-methanesulfonyl-[1,4]diazepane hydrochloride salt.

Reaction between 2-chloro-4-morpholin-4-yl-thieno[2,3-d]pyrimidine-6-carbaldehyde and 1-methanesulfonyl-[1,4]diazepane hydrochloride salt using General Procedure C (reductive amination) yielded 2-chloro-6-(4-methanesulfonyl-[1,4]diazepan-1-ylmethyl)-4-morpholin-4-yl-thieno[2,3-d]pyrimidine.

2-Chloro-6-(4-methanesulfonyl-[1,4]diazepan-1-ylmethyl)-4-morpholin-4-yl-thieno[2,3-d]pyrimidine was reacted with 4-(4,4,5,5-tetramethyl-[1,3,2]dioxaborolan-2-yl)-1H-indazole in general procedure A. Purification by column chromatography yielded the title compound.

(400 MHz CDCl3): 3.38-3.44 (4H, m, CH2), 3.86-3.92 (10H, m, CH2), 7.10 (1H, s, ar), 7.42-7.46 (1H, m, ar), 7.53 (1H, d (J=8.33), ar), 8.25 (1H, d (J=6.65), ar), 8.96 (1H, s, ar), 10.00 (1H, b, NH)

MH+=528.24

156: To 1-BOC-homopiperizine (0.8 ml) was added methane sulphonyl chloride (0.34 ml) and triethylamine (0.68 ml). The reaction mixture was stirred at room temperature for 4 hours. The reaction mixture was then partitioned between dichloromethane and water. The combined organic extracts were then washed with brine and dried (MgSO4). The solvent was removed in vacuo to yield 1.23 g crude 4-methanesulfonyl-[1,4]diazepane-1-carboxylic acid tert-butyl ester.

Crude 4-Methanesulfonyl-[1,4]diazepane-1-carboxylic acid tert-butyl ester (1.23 g) was stirred in anhydrous methanol (10 ml). 2M hydrogen chloride in ether (22 ml) was added. The reaction mixture was stirred at room temperature. After 5 minutes a precipitate formed, addition of anhydrous methanol (5 ml) caused this to dissolve. The reaction mixture was stirred overnight at room temperature. The solvents were removed in vacuo to yield 1.06 g of 1-methanesulfonyl-[1,4]diazepane hydrochloride salt.

Reaction between 2-chloro-4-morpholin-4-yl-thieno[3,2-d]pyrimidine-6-carbaldehyde and 1-methanesulfonyl-[1,4]diazepane hydrochloride salt using procedure C yielded 2-chloro-6-(4-methanesulfonyl-[1,4]diazepan-1-ylmethyl)-4-morpholin-4-yl-thieno[3,2-d]pyrimidine. This compound was subjected to procedure A to yield the desired final compound which was purified using flash chromatography.

NMR: (400 MHz, CDCl3): 1.26 (3H, s, CH3), 1.96 (2H, m, CH2), 2.86-2.88 (4H, m, CH2), 3.49-3.52 (4H, m, CH2), 3.92-3.94 (4H, m, CH2), 4.03 (2H, s, CH2), 4.08-4.11 (4H, m, CH2), 7.38 (1H, s, ar), 7.51-7.53 (1H, m, ar), 7.58 (1H, d, ar), 8.28 (1H, d, J (7.41), ar), 9.02 (1H, s, ar), 10.05 (1H, b, NH)

(M+H)+ 528.23

157: 2-Nitro-4-(4,4,5,5-tetramethyl-1,3,2-dioxaborolan-2-yl)aniline (1.00 g) was stirred under hydrogen balloon with palladium on carbon (10%, 150 mg) in a mixture of MeOH and DCM (1:1, 10 ml) at room temperature overnight. The reaction mixture was then filtered through celite, volatiles removed in vacuo, and the residue purified by flash chromatography to give 4-(4,4,5,5-tetramethyl-1,3,2-dioxaborolan-2-yl)benzene-1,2-diamine (890 mg).

Intermediate G (750 mg) was reacted with 4-(4,4,5,5-tetramethyl-1,3,2-dioxaborolan-2-yl)benzene-1,2-diamine (815 mg) in a General Procedure A. Purification by flash chromatography afforded 4-[6-(4-methanesulfonyl-piperazin-1-ylmethyl)-4-morpholin-4-yl-thieno[3,2-d]pyrimidin-2-yl]-benzene-1,2-diamine (535 mg).

4-[6-(4-Methanesulfonyl-piperazin-1-ylmethyl)-4-morpholin-4-yl-thieno[3,2-d]pyrimidin-2-yl]-benzene-1,2-diamine (102 mg) was refluxed in acetic acid (1 mL) for 1 hour. The reaction mixture was basified with aqueous sodium hydrogen carbonate and extracted into DCM. Flash chromatography and diethyl ether trituration gave the title compound (47 mg).

NMR (CDCl3/MeOD): 2.56 (3H, s), 2.63-2.66 (4H, m), 2.78 (3H, s), 3.24-3.27 (4H, m), 3.85 (2H, s), 3.85-3.87 (4H, m), 4.02-4.05 (4H, m), 7.29 (1H, s), 7.60 (1H, br), 8.22 (1H, d, J=1.5), 8.30 (1H, br)

MS (ESI+): MH+ 528.33

158: 2-Chloro-6-(4-methanesulfonyl-piperazin-1-ylmethyl)-4-morpholin-4-yl-thieno[3,2-d]pyrimidine was reacted with 5-(4,4,5,5-tetramethyl-[1.3.2]dioxaborolan-2-yl)-1H-indazole (commercially available) in general procedure A. Purification by column chromatography yielded the title compound.

NMR: CDCl3: 2.58-2.62 (4 H, m, CH$_2$), 2.74 (1 H, s, Me), 3.22-3.25 (4 H, m, CH$_2$), 3.82 (2 H, s, CH$_2$), 3.82-3.86 (4 H, m, CH$_2$), 4.00-4.02 (4 H, m, CH$_2$), 7.28 (1 H, s, Ar), 7.48 (1 H, d, J 8.2, Ar), 8.09 (1 H, s, Ar), 8.48 (1 H, d, J 8.2, Ar), 8.82 (1 H, d, J 7.5, Ar) and 10.01 (1 H, s, NH).

159: A solution of 4-(6-((4-methylsulfonyl)piperazin-1-yl)methyl)-4-morpholinothieno[2,3-d]pyrimidin-2-yl)benzene-1,2-diamine (87.5 mg, 0.20 mMol) in 1 mL of formic acid was refluxed for several hours, then cooled to room temperature and concentrated in vacuo to give a dark solid. This residue was taken into DMF at 100 mM, and purified by prep RP-HPLC to give 36.5 mg of the desired product in a 36.5% yield MS (Q1) 514.0 (M)+

160: A solution of 4-(6-((4-methylsulfonyl)piperazin-1-yl)methyl)-4-morpholinothieno[2,3-d]pyrimidin-2-yl)benzene-1,2-diamine (87.5 mg, 0.20 mMol) in 1 mL of acetic acid was refluxed for several hours, then cooled to room temperature and concentrated in vacuo to give a dark solid. This residue was taken into DMF at 100 mM, and purified by prep RP-HPLC to give 31.5 mg of the desired product in a 30% yield MS (Q1) 528.5 (M)+

161: 12-chloro-6-((4-(methylsulfonyl)piperazin-1-yl)methyl)-4-morpholinothieno[2,3-d]pyrimidine and 3,5-diaminophenyl boronic acid were used in General procedure A Suzuki Coupling to produce 4-(6-((4-methylsulfonyl)piperazin-1-yl)methyl)-4-morpholinothieno[2,3-d]pyrimidin-2-yl)benzene-1,2-diamine in 78% yield MS (Q1) 514.2 (M)+

EXAMPLE 7

Biological Testing

Compounds of the invention, prepared as described in the preceding Examples, were submitted to the following series of biological assays:

(i) PI3K Biochemical Screening

Compound inhibition of PI3K was determined in a radiometric assay using purified, recombinant enzyme and ATP at a concentration of 1 uM. All compounds were serially diluted in 100% DMSO. The kinase reaction was incubated for 1 hour at room temperature, and the reaction was terminated by the addition of PBS. IC$_{50}$ values were subsequently determined using sigmoidal dose-response curve fit (variable slope). All of the compounds tested had an IC$_{50}$ against PI3K of 50 uM or less.

(ii) Cellular Proliferation Inhibition

Cells were seeded at optimal density in a 96 well plate and incubated for 4 days in the presence of test compound. Alamar Blue™ was subsequently added to the assay medium, and cells were incubated for 6 hours before reading at 544 nm excitation, 590 nm emission. EC$_{50}$ values were calculated using a sigmoidal dose response curve fit. All the compounds tested had an EC$_{50}$s of 50 uM or less in the range of cell lines utilized.

(iii) Caco-2 Permeability

Caco-2 cells were seeded onto Millipore Multiscreen plates at $1\times10^5$ cells/cm$^2$, and were cultured for 20 days. Assessment of compound permeability was subsequently conducted. The compounds were applied to the apical surface (A) of cell monolayers and compound permeation into the basolateral (B) compartment was measured. This was performed in the reverse direction (B–A) to investigate active transport. A permeability coefficient value, P$_{app}$, for each compound, a measure of the rate of permeation of the compound across the membrane, was calculated. Compounds were grouped into low (P$_{app}$</=1.0×10$^6$ cm/s) or high (P$_{app}$>/=1.0×10$^6$ cm/s) absorption potential based on comparison with control compounds with established human absorption.

For assessment of a compound's ability to undergo active efflux, the ratio of basolateral (B) to apical (A) transport compared with A to B was determined. Values of B–A/A–B>/=1.0 indicated the occurrence of active cellular efflux. All of the compounds tested through the Caco-2 permeability screen had P$_{app}$ values >/=1.0×10$^6$ cm/s. One compound assessed through the bidirectional assay, PI540, had an B–A/A–B asymmetry index of less than 1.0, indicating that the compound does not undergo active cellular efflux.

(iv) Hepatocyte Clearance

Suspensions of cryopreserved human hepatocytes were used. Incubations were performed at compound concentration of 1 mM or 3 µM at a cell density of 0.5×10$^6$ viable cells/mL. The final DMSO concentration in the incubation was 0.25%. Control incubations were also performed in the absence of cells to reveal any non-enzymatic degradation. Duplicate samples (50 µL) were removed from the incubation mixture at 0, 5, 10, 20, 40 and 60 minutes (control sample at 60 minutes only) and added to methanol—containing internal standard (100 µL)—to terminate the reaction. Tolbutamide, 7-hydroxycoumarin, and testosterone were used as control compounds. Samples were centrifuged and the supernatants at each time point pooled for analysis by LC-MSMS. From a plot of ln peak area ratio (parent compound peak area/internal standard peak area) against time, intrinsic clearance (CL$_{int}$) was calculated as follows: CL$_{int}$ (µl/min/million cells)=V×k, where k is the elimination rate constant, obtained from the gradient of ln concentration plotted against time; V is a volume term derived from the incubation volume and is expressed as uL 10$^6$ cells$^{-1}$.

Compounds were classified with low (CL</=4.64 µL/min/10$^6$ cells), medium (CL>/=4.6; </=25.2 µl/min/10$^6$ cells) and high (>/=25.2 µl/min/10$^6$ cells) clearance. The majority of the tested compounds of the invention were determined to have low hepatocyte clearance.

(v) Cytochrome P450 Inhibition

Compounds of the invention were screened against five CYP450 targets (1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) were used as controls. Plates were read using a BMG LabTechnologies PolarStar in fluorescence mode. The majority of the tested compounds assessed in this assay displayed weak activity ($IC_{50}>/=5$ uM) against all isoforms of CYP450.

(vi) Cytochrome P450 Induction

Freshly isolated human hepatocytes from a single donor were cultured for 48 hours prior to addition of test compound at three concentrations and were incubated for 72 hours. Probe substrates for CYP3A4 and CYP1A2 were added for 30 minutes and 1 hour before the end of the incubation. At 72 hours, cells and media were removed and the extent of metabolism of each probe substrate quantified by LC-MS/MS. The experiment was controlled by using inducers of the individual P450s incubated at one concentration in triplicate. The compounds of the invention assessed in this assay showed negligible effects on induction of cytochrome P450 enzymes.

(vii) Plasma Protein Binding

Solutions of test compound (5 um, 0.5% final DMSO concentration) were prepared in buffer and 10% plasma (v/v in buffer). A 96 well HT dialysis plate was assembled so that each well was divided in two by a semi-permeable cellulose membrane. The buffer solution was added to one side of the membrane and the plasma solution to the other side; incubations were then conducted at 37° C. over 2 hours in triplicate. The cells were subsequently emptied, and the solutions for each batch of compounds were combined into two groups (plasma-free and plasma-containing) then analysed by LC-MSMS using two sets of calibration standards for plasma-free (6 points) and plasma-containing solutions (7 points). The fraction unbound value for each compound was calculated: highly protein bound compounds ($>/=90\%$ bound) had an $Fu</=0.1$. The compounds of the invention assessed in this assay had Fu values$>/=0.1$.

(viii) hERG channel blockage

Compounds of the invention were evaluated for their ability to modulate rubidium efflux from HEK-294 cells stably expressing hERG potassium channels using established flux methodology. Cells were prepared in medium containing RbCl and were plated into 96-well plates and grown overnight to form monolayers. The efflux experiment was initiated by aspirating the media and washing each well with 3×100 µL of pre-incubation buffer (containing low $[K^+]$) at room temperature. Following the final aspiration, 50 µL of working stock (2×) compound was added to each well and incubated at room temperature for 10 minutes. 50 µL of stimulation buffer (containing high [K+]) was then added to each well giving the final test compound concentrations. Cell plates were then incubated at room temperature for a further 10 minutes. 80 µL of supernatant from each well was then transferred to equivalent wells of a 96-well plate and analysed via atomic emission spectroscopy. Compounds were screened as 10 pt duplicate $IC_{50}$ curves, n=2, from a top concentration of 100 µM.

EXAMPLE 8 p110 Isoform Selectivity Scintillation Proximity Binding Assay

The ability of representative compounds from Tables 1a and 1b to inhibit the lipid kinase activity of purified preparations of human PI3K isoforms alpha, beta, delta, and gamma was determined by a radiometric scintillation proximity assay (SPA, GE Healthcare, Amersham Biosciences). Concentration dependent inhibition at 50% ($IC_{50}$ µMol) was determined for all four isoforms (alpha) and fold potency over beta, delta, and gamma relative to alpha was calculated for a selection of compounds in Table 2. Each compound has a p110 alpha $IC_{50}<1$ µMol.

TABLE 2

| Compound | alpha/beta | alpha/delta | alpha/gamma |
|---|---|---|---|
| 2 | >10 | <10 | >10 |
| 4 | >10 | <10 | >10 |
| 7 | >10 | <10 | >10 |
| 16 | >10 | <10 | >10 |
| 23 | >10 | <10 | >10 |
| 24 | >10 | <10 | >10 |
| 27 | >10 | <10 | >10 |
| 28 | >10 | <10 | >10 |
| 29 | >10 | <10 | >10 |
| 34 | >10 | <10 | >10 |
| 54 | <10 | <10 | >10 |
| 57 | >10 | <10 | >10 |
| 58 | >10 | <10 | >10 |
| 59 | >10 | <10 | >10 |
| 60 | >10 | <10 | >10 |
| 62 | >10 | <10 | >10 |
| 65 | <10 | <10 | >10 |
| 66 | <10 | <10 | >10 |
| 89 | >10 | >10 | >10 |
| 90 | >10 | <10 | >10 |
| 94 | >10 | <10 | >10 |
| 95 | >10 | >10 | >10 |
| 133 | >10 | <10 | >10 |
| 139 | <10 | <10 | <10 |
| 140 | >10 | >10 | >10 |
| 141 | <10 | <10 | >10 |
| 142 | >10 | <10 | >10 |
| 144 | <10 | <10 | >10 |
| 147 | >10 | >10 | >10 |
| 157 | >10 | <10 | >10 |

EXAMPLE 9

Tablet Composition

Tablets, each weighing 0.15 g and containing 25 mg of a compound of the invention are manufactured as follows:
Composition for 10,000 tablets
Active compound (250 g)
Lactose (800 g)
Corn starch (415 g)
Talc powder (30 g)
Magnesium stearate (5 g)

The active compound, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

EXAMPLE 10

Injectable Formulation

Formulation A

| Active compound | 200 mg |
|---|---|
| Hydrochloric Acid Solution 0.1M or | 4.0 to 7.0 |
| Sodium Hydroxide Solution 0.1M q.s. to pH | |
| Sterile water q.s. to | 10 ml |

The compound of the invention is dissolved in most of the water (35° 40° C.) and the pH adjusted to between 4.0 and 7.0 with the hydrochloric acid or the sodium hydroxide as appropriate. The batch is then made up to volume with water and filtered through a sterile micropore filter into a sterile 10 ml amber glass vial (type 1) and sealed with sterile closures and overseals.

Formulation B

| Active Compound | 125 mg |
| Sterile, Pyrogen-free, pH 7 Phosphate Buffer, q.s. to | 25 ml |
| Active compound | 200 mg |
| Benzyl Alcohol | 0.10 g |
| Glycofurol 75 | 1.45 g |
| Water for injection q.s to | 3.00 ml |

The active compound is dissolved in the glycofurol. The benzyl alcohol is then added and dissolved, and water added to 3 ml. The mixture is then filtered through a sterile micropore filter and sealed in sterile 3 ml glass vials (type 1).

EXAMPLE 11

Syrup Formulation

| Active compound | 250 mg |
| Sorbitol Solution | 1.50 g |
| Glycerol | 2.00 g |
| Sodium benzoate | 0.005 g |
| Flavour | 0.0125 ml |
| Purified Water q.s. to | 5.00 ml |

The compound of the invention is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:
1. A compound selected from:
(1S,4S)-2-((2-(1H-indazol-4-yl)-4-morpholinothieno[3,2-d]pyrimidin-6-yl)methyl)-5-methylsulfonyl-2,5-diaza-bicyclo[2.2.1]heptane;
2-(1H-indazol-4-yl)-6-((4-methylsulfonylpiperazin-1-yl)methyl)-4-morpholinofuro[3,2-d]pyrimidine;
2-(1H-indazol-4-yl)-6-((4-(N-morpholino)sulfonylpiperazin-1-yl)methyl)-4-morpholinothieno[3,2-d]pyrimidine;
2-(1H-indazol-4-yl)-6-(((3S,5R)-3-methyl-4-methylsulfonylpiperazin-1-yl)methyl)-4-morpholinothieno[3,2-d]pyrimidine;
2-(1H-indazol-4-yl)-6-(((3S,5R)-3,5-dimethyl-4-methylsulfonylpiperazin-1-yl)methyl)-4-morpholinothieno[3,2-d]pyrimidine;
6-(((2R,6S)-4-methylsulfonyl-2,6-dimethylpiperazin-1-yl)methyl)-2-(1H-indazol-4-yl)-4-morpholinothieno[3,2-d]pyrimidine;
6-(((2R,6S)-4-isopropylsulfonyl-2,6-dimethylpiperazin-1-yl)methyl)-2-(1H-indazol-4-yl)-4-morpholinothieno[3,2-d]pyrimidine;
6-(((2R,6S)-4-trifluoromethylsulfonyl-2,6-dimethylpiperazin-1-yl)methyl)-2-(1H-indazol-4-yl)-4-morpholinothieno[3,2-d]pyrimidine;
6-(((R)-4-methylsulfonyl-3-methylpiperazin-1-yl)methyl)-2-(1H-indazol-4-yl)-4-morpholinothieno[3,2-d]pyrimidine;
1-((2-(1H-indazol-4-yl)-4-morpholinothieno[3,2-d]pyrimidin-6-yl)methyl)-4-methylsulfonylpiperazin-2-one;
1-(4-((2-(1H-indazol-4-yl)-4-morpholinothieno[3,2-d]pyrimidin-6-yl)methyl)piperazin-1-yl)-2-amino-2-methylpropan-1-one;
2-(1H-indazol-4-yl)-6-((4-N-methyl-N-methoxyethylaminosulfonylpiperidin-1-yl)methyl)-4-morpholinothieno[3,2-d]pyrimidine;
2-(1H-indazol-4-yl)-6-((4-N,N-dimethylaminosulfonylpiperidin-1-yl)methyl)-7-methyl-4-morpholinothieno[3,2-d]pyrimidine;
2-(1H-indazol-4-yl)-6-((4-N-methylaminosulfonylpiperidin-1-yl)methyl)-4-morpholinothieno[3,2-d]pyrimidine;
2-(1H-indazol-4-yl)-7-methyl-6-((4-(methylsulfonylpiperidin-1-yl)methyl)-4-morpholinothieno[3,2-d]pyrimidine;
2-(1H-indazol-4-yl)-6-((4-N-4-methylpiperazinosulfonylpiperidin-1-yl)methyl)-4-morpholinothieno[3,2-d]pyrimidine;
2-(1H-imidazol-1-yl)-6-((4-methylsulfonylpiperazin-1-yl)methyl)-4-morpholinothieno[3,2-d]pyrimidine;
2-(1H-benzo[d]imidazol-1-yl)-6-((4-methylsulfonylpiperazin-1-yl)methyl)-4-morpholinothieno[3,2-d]pyrimidine;
2-(1H-indazol-4-yl)-6-((4-N,N-dimethylaminosulfonylpiperidin-1-yl)methyl)-4-morpholinothieno[3,2-d]pyrimidine;
2-(1H-indazol-4-yl)-6-((4-N-morpholinosulfonylpiperazin-1-yl)methyl)-4-morpholinothieno[3,2-d]pyrimidine;
2-(1H-indazol-4-yl)-7-methyl-6-((4-(methylsulfonyl)piperazin-1-yl)methyl)-4-morpholinothieno[3,2-d]pyrimidine;
N-((2-(1H-indazol-4-yl)-4-morpholinothieno[3,2-d]pyrimidin-6-yl)methyl)-1-methylsulfonyl-N-(2-morpholinoethyl)piperidin-4-amine;
(1-((2-(1H-indazol-4-yl)-4-morpholinothieno[3,2-d]pyrimidin-6-yl)methyl)pyrrolidin-2-yl)-N-methylsulfonylmethanamine;
N-((2-(1H-indazol-4-yl)-4-morpholinothieno[3,2-d]pyrimidin-6-yl)methyl)-N-(2-methoxyethyl)-1-methylsulfonylpiperidin-4-amine;
5-(6-((4-methylpiperazin-1-yl)methyl)-4-morpholinothieno[3,2-d]pyrimidin-2-yl)pyridin-3-ol;
2-(1H-indazol-4-yl)-6-((1-methylpiperidin-4-yl)methyl)-4-morpholinothieno[3,2-d]pyrimidine;
N-((2-(1H-indazol-4-yl)-4-morpholinothieno[3,2-d]pyrimidin-6-yl)methyl)-tetrahydro-N-methyl-2H-sulfonylpyran-4-amine;
2-(4-((2-(1H-indazol-4-yl)-4-morpholinothieno[3,2-d]pyrimidin-6-yl)methyl)piperazin-1-yl)-2-methylpropanamide;
N-((2-(1H-indazol-4-yl)-4-morpholinothieno[3,2-d]pyrimidin-6-yl)methyl)-1-(2-methoxyethyl)-N-methylpiperidin-4-amine;
N-((2-(1H-indazol-4-yl)-4-morpholinothieno[3,2-d]pyrimidin-6-yl)methyl)-N,1-dimethylpiperidin-4-amine;
(4-((2-(1H-indazol-4-yl)-4-morpholinothieno[3,2-d]pyrimidin-6-yl)methyl)piperazin-1-yl)(cyclopropyl)methanone;
2-(1H-indazol-4-yl)-6-((3-(methylsulfonyl)pyrrolidin-1-yl)methyl)-4-morpholinothieno[3,2-d]pyrimidine;
2-(1H-indazol-4-yl)-6-(((S)-2-methyl-4-methylsulfonylpiperazin-1-yl)methyl)-4-morpholinothieno[3,2-d]pyrimidine;

1-(4-((2-(1H-indazol-4-yl)-4-morpholinothieno[3,2-d]pyrimidin-6-yl)methyl)piperazin-1-yl)-2,2-dimethylpropan-1-one;
4-((2-(1H-indazol-4-yl)-4-morpholinothieno[3,2-d]pyrimidin-6-yl)methyl)piperazine-1-carbaldehyde;
1-(4-((2-(1H-indazol-4-yl)-4-morpholinothieno[3,2-d]pyrimidin-6-yl)methyl)piperazin-1-yl)ethanone;
ethyl 4-((2-(1H-indazol-4-yl)-4-morpholinothieno[3,2-d]pyrimidin-6-yl)methyl)piperazine-1-carboxylate;
methyl 4-((2-(1H-indazol-4-yl)-4-morpholinothieno[3,2-d]pyrimidin-6-yl)methyl)piperazine-1-carboxylate;
1-((2-(1H-indazol-4-yl)-4-morpholinothieno[3,2-d]pyrimidin-6-yl)methyl)-N-methyl-N-methylsulfonylpyrrolidin-3-amine;
N-((2-(1H-indazol-4-yl)-4-morpholinothieno[3,2-d]pyrimidin-6-yl)methyl)-N-methyl(1-methylsulfonylpyrrolidin-2-yl)methanamine;
N-((2-(1H-indazol-4-yl)-4-morpholinothieno[3,2-d]pyrimidin-6-yl)methyl)-N-methyl-(1-methylsulfonylpyrrolidin)-3-amine;
1-((2-(1H-indazol-4-yl)-4-morpholinothieno[3,2-d]pyrimidin-6-yl)methyl)piperidin-4-ol;
1-((2-(1H-indazol-4-yl)-4-morpholinothieno[3,2-d]pyrimidin-6-yl)methyl)pyrrolidin-3-ol;
1-((2-(1H-indazol-4-yl)-4-morpholinothieno[3,2-d]pyrimidin-6-yl)methyl)piperidin-3-ol;
(S)-1-(4-((2-(1H-indazol-4-yl)-4-morpholinothieno[3,2-d]pyrimidin-6-yl)methyl)piperazin-1-yl)-2-hydroxypropan-1-one;
1-(4-((2-(1H-indazol-4-yl)-4-morpholinothieno[3,2-d]pyrimidin-6-yl)methyl)piperazin-1-yl)-2-(dimethylamino)ethanone;
1-(4-((2-(1H-indazol-4-yl)-4-morpholinothieno[3,2-d]pyrimidin-6-yl)methyl)piperazin-1-yl)-2-aminoethanone;
2-(1H-indazol-6-yl)-6-((4-methylpiperazin-1-yl)methyl)-4-morpholinothieno[3,2-d]pyrimidine;
N-((2-(1H-indazol-4-yl)-4-morpholinothieno[3,2-d]pyrimidin-6-yl)methyl)-N-(2-methoxyethyl)-1-methylpiperidin-4-amine;
(4-((2-(1H-indazol-4-yl)-4-morpholinothieno[3,2-d]pyrimidin-6-yl)methyl)-1-methylsulfonylpiperazin-2-yl)-N,N-dimethylmethanamine;
N-((2-(1H-indazol-4-yl)-4-morpholinothieno[3,2-d]pyrimidin-6-yl)methyl)-N,1-dimethylpiperidin-4-amine;
3-[6-(4-Methanesulfonyl-piperazin-1-ylmethyl)-4-morpholin-4-yl-thieno[3,2-d]pyrimidin-2-yl]-quinoline;
4-[6-(4-Methanesulfonyl-piperazin-1-ylmethyl)-4-morpholin-4-yl-thieno[3,2-d]pyrimidin-2-yl]-isoquinoline;
2-(1H-Indazol-4-yl)-6-(4-methanesulfonyl-3,3-dimethyl-piperazin-1-ylmethyl)-4-morpholin-4-yl-thieno[3,2-d]pyrimidine;
6-(4-Methanesulfonyl-piperazin-1-ylmethyl)-2-(2-methyl-benzoimidazol-1-yl)-4-morpholin-4-yl-thieno[3,2-d]pyrimidine;
(R)-1-(4-((2-(1H-indazol-4-yl)-4-morpholinothieno[3,2-d]pyrimidin-6-yl)methyl)piperazin-1-yl)-2-hydroxypropan-1-one;
1-(4-((2-(1H-indazol-4-yl)-4-morpholinothieno[3,2-d]pyrimidin-6-yl)methyl)piperazin-1-yl)-2-hydroxy-2-methylpropan-1-one;
1-(4-((2-(1H-indazol-4-yl)-4-morpholinothieno[3,2-d]pyrimidin-6-yl)methyl)piperazin-1-yl)-2-hydroxyethanone;
1-(4-((2-(1H-indazol-4-yl)-4-morpholinothieno[3,2-d]pyrimidin-6-yl)methyl)piperazin-1-yl)-2-methoxyethanone;
(4-((2-(1H-indazol-4-yl)-4-morpholinothieno[3,2-d]pyrimidin-6-yl)methyl)piperazin-1-yl)(tetrahydrofuran-2-yl)methanone;
(4-((2-(1H-indazol-4-yl)-4-morpholinothieno[3,2-d]pyrimidin-6-yl)methyl)piperazin-1-yl)(1-aminocyclopropyl)methanone;
(S)-1-(4-((2-(1H-indazol-4-yl)-4-morpholinothieno[3,2-d]pyrimidin-6-yl)methyl)piperazin-1-yl)-2-aminopropan-1-one;
(R)-1-(4-((2-(1H-indazol-4-yl)-4-morpholinothieno[3,2-d]pyrimidin-6-yl)methyl)piperazin-1-yl)-2-aminopropan-1-one;
1-(4-((2-(1H-indazol-4-yl)-4-morpholinothieno[3,2-d]pyrimidin-6-yl)methyl)piperazin-1-yl)-2-(methylsulfonyl)ethanone; and
2-(1H-Indazol-4-yl)-6-(4-methanesulfonyl-[1,4]diazepan-1-ylmethyl)-4-morpholin-4-yl-thieno[3,2-d]pyrimidine;
and the pharmaceutically acceptable salts thereof.

2. A pharmaceutical composition which comprises a pharmaceutically acceptable carrier or diluent and, as an active ingredient, a compound as described in claim 1, or a pharmaceutically acceptable salt thereof.

3. A composition according to claim 2, further comprising a chemotherapeutic agent.

4. A composition according to claim 2, which is formulated for oral administration.

5. A kit, comprising:
(a) a first pharmaceutical composition comprising a compound as defined in claim 1, or a pharmaceutically acceptable salt thereof; and
(b) instructions for use in the therapeutic treatment of a PI3K-mediated condition.

* * * * *